United States Patent
Gaul et al.

(10) Patent No.: US 10,815,210 B2
(45) Date of Patent: Oct. 27, 2020

(54) BENZOCYCLOBUTANE DERIVATIVES USEFUL AS DUAL SGLT1 / SGLT2 MODULATORS

(71) Applicant: Janssen Pharmaceutica NV, Beerse (BE)

(72) Inventors: Micheal Gaul, Yardley, PA (US); Gee-Hong Kuo, Scotch Plains, NJ (US); Guozhang Xu, Chesterbrook, PA (US); Yin Liang, Ambler, PA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 16/348,304

(22) PCT Filed: Nov. 8, 2017

(86) PCT No.: PCT/US2017/060576
§ 371 (c)(1),
(2) Date: May 8, 2019

(87) PCT Pub. No.: WO2018/089449
PCT Pub. Date: May 17, 2018

(65) Prior Publication Data
US 2019/0367469 A1    Dec. 5, 2019

Related U.S. Application Data

(60) Provisional application No. 62/419,993, filed on Nov. 10, 2016.

(51) Int. Cl.
*C07D 309/10*    (2006.01)

(52) U.S. Cl.
CPC .................. *C07D 309/10* (2013.01)

(58) Field of Classification Search
CPC ........ C07D 309/10; A61K 31/351; A61P 3/10
USPC .......................................... 549/417; 514/460
See application file for complete search history.

(56) References Cited

U.S. PATENT DOCUMENTS

2016/0222047 A1    8/2016    Zhong et al.

FOREIGN PATENT DOCUMENTS

| CN | 104327027 A | 2/2015 |
|---|---|---|
| WO | WO 2008/116195 A3 | 11/2008 |
| WO | WO 2011/048112 A1 | 4/2011 |
| WO | WO 2012/165914 A3 | 3/2013 |
| WO | WO 2015/032272 A1 | 3/2015 |

OTHER PUBLICATIONS

Kuo, G-H. et al.: Synthesis and biological evaluation of benzocyclobutane-C-glycosides as potent and orally active SGLT1/SGLT2 dual inhibitors. Bioorganic & Medicinal Chem. Lett., vol. 28, pp. 1182-1187, 2018.*
Chen et al., "Quantitative PCR Tissue Expression Profiling of the Human SGLT2 Gene and Related Family Members", *Diabetes Ther.*, Dec. 2010, pp. 57-92, vol. 1(2).
Derdau et al., "Synthesis of isotopically labelled SGLT inhibitors and their metabolites", *Tetrahedron*, Feb. 13, 2010, pp. 1472-1482, vol. 66(7), XP026874135.
Georgescu, E.F., "Angiotensin Receptor Blockers in the Treatment of NASH/NAFLD: Could They Be a First-Class Option?", *Advances in Therapy*, 2008, pp. 1141-1174, vol. 25, Issue 11.
Hediger et al., "Expression cloning and cDNA sequencing of the Na+/glucose co-transporter.". *Nature*, Nov. 26-Dec. 2, 1987, pp. 37-381, vol. 330(6146).
Imamura et al., "Discovery of Ipragliflozin (ASP1941): A novel-glucoside with benzothiophene structure as a potent and selective sodium glucose co-transporter 2 (SGLT2) inhibitor for the treatment of type 2 diabetes mellitus" *Bioorganic & Medicinal Chemistry*, Mar. 22, 2012, pp. 3263-3279, vol. 20, (10), XP028422762.
Lee et al., "The High Affinity Na+/Glucose Cotransporter. Re-evaluation of Function and Distribution of Expression", *J. Biol. Chem.*, Apr. 22, 1994, pp. 12032-12039, vol. 269(16).
Scafoglio et al., "Functional expression of sodium-glucose transporters in cancer", *PNAS*, 2015, pp. E4111-E4119, vol. 112(3).
You et al., "Molecular Characteristic of Na(+)-coupled Glucose Transporters in Adult and Embryonic Rat Kidney", *J. Biol. Chem.*, Dec. 8, 1995, pp. 29365-29371, vol. 270(49).
International Search Report relating to International Patent Application No. PCT/US2017/060576, filed Nov. 8, 2017. dated Mar. 9, 2018.
Written Opinion of the International Searching Authority relating to International Patent Application No. PCT/US2017/060576, filed Nov. 8, 2017. dated Mar. 9, 2018.
Marsenic, O., "Glucose Control by the Kidney: An Emerging Target in Diabetes", *Am. J. Kidney Dis.*, May 2009, pp. 875-883, vol. 53(5).
Wright, E.M., "Renal Na(+)-glucose cotransporters" *Am J Physiol, Renal Physiol*, Jan. 2001, pp. F10-F18, vol. 280(1).
Wright, E.M., et al., "Biology of Human Sodium Glucose Transporters", *Physiol. Rev.*, Apr. 2011, pp. 733-794, vol. 91(2).

* cited by examiner

*Primary Examiner* — Charanjit Aulakh

(57) ABSTRACT

The present invention is directed to benzocyclobutane derivatives, pharmaceutical compositions containing them and their use in the treatment of disorders and conditions modulated by SGLT activity, more particularly dual SGLT1/2 activity. More particularly, the compounds of the present invention are useful in the treatment of for example, Type II diabetes mellitus, Syndrome X, and complications and symptoms associated with said disorders.

14 Claims, No Drawings

BENZOCYCLOBUTANE DERIVATIVES USEFUL AS DUAL SGLT1 / SGLT2 MODULATORS

CROSS-REFERENCE TO RELATED APPLICATIONS

This application is a U.S. national stage of PCT Application No. PCT/US2017/060576, filed on Nov. 8, 2017, and claims the benefit of U.S. Provisional Application 62/419,993, filed on Nov. 10, 2016, which is incorporated by reference herein in its entirety.

FIELD OF THE INVENTION

The present invention is directed to benzocyclobutane derivatives, pharmaceutical compositions containing them and their use in the treatment of disorders and conditions modulated by SGLT activity, more particularly dual SGLT1/2 activity. More particularly, the compounds of the present invention are useful in the treatment of for example, Type II diabetes mellitus, Syndrome X, and complications and symptoms associated with said disorders.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus (IDDM) or juvenile onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Therapy for IDDM patients has consistently focused on administration of exogenous insulin, which may be derived from various sources (e.g., human, bovine, porcine insulin). The use of heterologous species material gives rise to formation of anti-insulin antibodies which have activity limiting effects and result in progressive requirements for larger doses in order to achieve desired hypoglycemic effects.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction. Typical treatment of Type II diabetes mellitus focuses on maintaining the blood glucose level as near to normal as possible with lifestyle modification relating to diet and exercise, and when necessary, the treatment with antidiabetic agents, insulin or a combination thereof. NIDDM that cannot be controlled by dietary management is treated with oral antidiabetic agents.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperinsulinemia, insulin resistance, dyslipidemia (e.g., high triglycerides, low HDL), hypertension and obesity. Although insulin resistance is not always treated in all Syndrome X patients, those who exhibit a prediabetic state (e.g., IGT, IFG), where fasting glucose levels may be higher than normal but not at the diabetes diagnostic criterion, is treated in some countries (e.g., Germany) with metformin to prevent diabetes. The anti-diabetic agents may be combined with pharmacological agents for the treatment of the concomitant co-morbidities (e.g., antihypertensives for hypertension, hypolipidemic agents for lipidemia).

Hyperglycemia is one common characteristic of these diabetic disorders. Treatments of hyperglycemia are focused on excretion of excessive glucose directly into urine, which involves sodium-glucose cotransporters (SGLTs), primarily found in the chorionic membrane of the intestine and kidney. In particular, renal reabsorption of glucose is mediated by SGLT1 and SGLT2 (MARSENIC, O., "Glucose Control by the Kidney: An Emerging Target in Diabetes", AM. J. Kidney Dis., 2009 May, pp 875-883, Vol. 53(5); WRIGHT, E. M., et al., "Biology of Human Sodium Glucose Transporters", Physiol. Rev., 2011 April, pp 733-794, Vol. 91(2)). SGLT1, a high-affinity low-capacity transporter with a $Na^+$:glucose transport ratio of 2:1, is present in intestinal and renal epithelial cells (LEE, W. S., et al., "The High Affinity Na+/Glucose Cotransporter. Re-evaluation of Function and Distribution of Expression", J. Biol. Chem., 1994 April 22, pp 12032-12039, Vol. 269(16)). On the other hand, SGLT2, also known as SAAT1, a low-affinity high-capacity transporter with a $Na^+$:glucose transport ratio of 1:1, is found in the epithelium of the kidney (YOU, G., et al., "Molecular Characteristic of Na(+)-coupled Glucose Transporters in Adult and Embryonic Rat Kidney", J. Biol. Chem., 1995 Dec. 8, pp 29365-29371, Vol. 270(49); CHEN, J., et al., "Quantitative PCR Tissue Expression Profiling of the Human SGLT2 Gene and Related Family Members", Diabetes Ther., 2010 December, pp 57-92, Vol. 1(2)). In addition, glucose absorption in the intestine is primarily mediated by SGLT1 and SGLT2. Thus, inhibition of SGLT1 and SGLT2 reduces plasma glucose through suppression of glucose reabsorption in the kidney, which was demonstrated in rodent models of IDDM and NIDDM by increasing the excretion of glucose in urine and lowering blood glucose levels.

Non-alcoholic fatty liver disease (NAFLD) is one cause of a fatty liver, occurring when fat is deposited (steatosis) in the liver. NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. Non-alcoholic steatohepatitis (NASH) is a progressive, severe form of NAFLD. Over a 10-year period, up to 20% of patients with NASH will develop cirrhosis of the liver, and 10% will suffer death related to liver disease. The exact cause of NAFLD is still unknown, however, both obesity and insulin resistance are thought to play a strong role in the disease process. The exact reasons and mechanisms by which the disease progresses from one stage to the next are not known.

NAFLD has been linked to insulin resistance (IR) and the metabolic syndrome (MS). As the renin-angiotensin system (RAS) plays a central role in insulin resistance, and subsequently in NAFLD and NASH, an attempt to block the deleterious effects of RAS overexpression has been proposed a target for treatment. While many potential therapies tested in NASH target only the consequences of this condition, or try to "get rid" of excessive fat, angiotensin receptor blockers (ARBs) may act as a tool for correction of the various imbalances that act in harmony in NASH/NAFLD. Indeed, by inhibiting RAS the intracellular insulin signaling pathway may be improved, resulting in better control of adipose tissue proliferation and adipokine production, as well as more balanced local and systemic levels of various cytokines. At the same time, by controlling the local RAS in the liver fibrosis may be prevented and the cycle that links steatosis to necroinflammation slowed down. (GEORGESCU, E. F., in Advances in Therapy, 2008, pp 1141-1174, Vol. 25, Issue 11)

SCAFOGLIO, C., et al., in "Functional expression of sodium-glucose transporters in cancer", PNAS, 2015, pp E41111-E4119, Vol 112(3), describe the role of sodium-dependent glucose transporters (SGLTs) in pancreatic and prostate adenocarcinomas, and their role in cancer cell survival. SGLT2 was found to be functionally expressed in pancreatic and prostate adenocarcinomas and further found to block glucose uptake and reduce tumor growth and survival in a xenograft model of pancreatic cancer, suggesting that SGLT2 inhibitors.

There remains a need for SGLT inhibitor compounds that have pharmacokinetic and pharmacodynamic properties suitable for use as human pharmaceuticals.

SUMMARY OF THE INVENTION

The present invention is directed to compounds of formula (I)

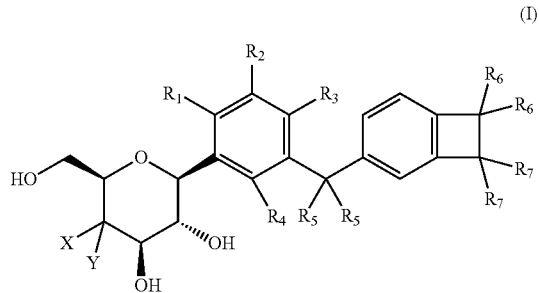

(I)

wherein
X is hydrogen and Y is selected from the group consisting of fluoro and (S)—OH; alternatively, X is fluoro and Y is fluoro;
$R^1$ is selected from the group consisting of hydrogen, halogen, —OH, $C_{1-4}$alkyl, fluorinated $C_{1-4}$alkyl, $C_{1-4}$alkoxy, fluorinated $C_{1-2}$alkoxy, —O-cylopropyl, —O-phenyl and —O-benzyl;

$R^2$ is selected from the group consisting of hydrogen, halogen and $C_{1-4}$alkyl;
$R^3$ is selected from the group consisting of hydrogen, halogen, $C_{1-4}$alkyl, $C_{1-4}$alkoxy, cyano, $NR^AR^B$, and $C_{3-5}$cycloalkyl; wherein $R^A$ and $R^B$ are each independently selected from the group consisting of hydrogen, methyl and ethyl;
$R^4$ is selected from the group consisting of hydrogen and $C_{1-4}$alkyl;
the two $R^5$ groups are the same and are selected from the group consisting of hydrogen and fluoro; alternatively, the two $R^5$ groups are taken together with the carbon atom to which they are bound to form carbonyl;
each $R^6$ is hydrogen;
each $R^7$ is hydrogen;
and isotopologues and pharmaceutically acceptable salts thereof.

The present invention is further directed to processes for the preparation of the compounds of formula (I). The present invention is further directed to a product prepared according to any of the process(es) described herein.

Illustrative of the invention are pharmaceutical compositions comprising a pharmaceutically acceptable carrier and a compound of formula (I) as described herein. An illustration of the invention is a pharmaceutical composition made by mixing a compound of formula (I) as described herein and a pharmaceutically acceptable carrier. Illustrating the invention is a process for making a pharmaceutical composition comprising mixing a compound of formula (I) as described herein and a pharmaceutically acceptable carrier.

Exemplifying the invention are methods of treating a disease, disorder, or condition mediated by SGLT activity (preferably, dual SGLT1 and SGLT2 activity) selected from the group consisting of impaired glucose tolerance (IGT), impaired fasting glucose (IFT), gestational diabetes, Type I diabetes mellitus, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer), comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated SGLT activity (preferably dual SGLT1 and SGLT2 activity) selected from the group consisting impaired glucose tolerance (IGT), impaired fasting glucose (IFT), gestational diabetes, Type I diabetes mellitus, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer). In another embodiment, the present invention is directed to a composition comprising a compound of formula (I) for the treatment of a disorder mediated by SGLT activity (preferably dual SGLT1 and SGLT2 activity) selected from the group consisting impaired glucose tolerance (IGT), impaired fasting glucose (IFT), gestational diabetes, Type II diabetes mellitus, Syndrome X (also known as Metabolic Syndrome), obesity, nephropathy, neuropathy, retinopathy, hypertension, angina, atherosderosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer).

Another example of the invention is the use of any of the compounds described herein in the preparation of a medicament for treating: (a) impaired glucose tolerance (IGT), (b) impaired fasting glucose (IFT), (c) gestational diabetes, (d) Type II diabetes mellitus, (e) Syndrome X (also known as Metabolic Syndrome), (f) obesity, (g) nephropathy, (h) neuropathy, (i) retinopathy, (j) hypertension, (k) angina, (l) atherosclerosis, (m) heart disease, (n) heart attack, (o) ischemia, (p) stroke, (q) nerve damage or poor blood flow in the feet, (r) non-alcoholic steatohepatitis (NASH), (s) non-alcoholic fatty liver disease (NAFLD), (t) liver fibrosis, (u) cataracts, (v) polycystic ovarian syndrome, (w) irritable bowel syndrome, (x) inflammation (y) cancer (preferably prostate cancer or pancreatic cancer), and (z) Type I diabetes mellitus, in a subject in need thereof. In another example, the present invention is directed to a compound as described herein for use in a methods for treating a disorder selected from the group consisting of impaired glucose tolerance (IGT), impaired fasting glucose (IFT), gestational diabetes, Type I diabetes mellitus, Type II diabetes mellitus, Syndrome X (also known as Metabolic Syndrome), obesity, nephropathy, neuropathy, retinopathy, hypertension, angina, atherosderosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer), in a subject in need thereof.

DETAILED DESCRIPTION OF THE INVENTION

The present invention is directed to compounds of formula (I)

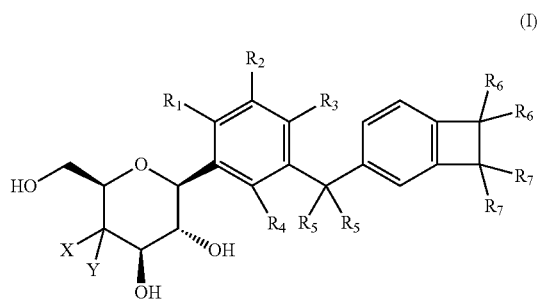

(I)

wherein X, Y, $R^1$, $R^2$, $R^3$, $R^4$, $R^5$, $R^6$ and $R^7$ are as herein defined; and isotopologues and pharmaceutically acceptable salts thereof. The compounds of the present invention are useful in the treatment of diseases, disorders and complications associated with SGLT activity (preferably dual SGLT1 and SGLT2 activity) selected from the group of impaired glucose tolerance (IGT), impaired fasting glucose (IFT), gestational diabetes, Type I diabetes mellitus, Type II diabetes mellitus, Syndrome X (also known as Metabolic Syndrome), obesity, nephropathy, neuropathy, retinopathy, hypertension, angina, atherosclerosis, heart disease, heart attack, ischemia, stroke, nerve damage or poor blood flow in the feet, non-alcoholic steatohepatitis (NASH), non-alcoholic fatty liver disease (NAFLD), liver fibrosis, cataracts, polycystic ovarian syndrome, irritable bowel syndrome, inflammation and cancer (preferably prostate cancer or pancreatic cancer).

In an embodiment, the present invention is directed to compounds of formula (I) wherein X is hydrogen and Y is selected from the group consisting of fluoro and (S)—OH. In another embodiment, the present invention is directed to compounds of formula (I) wherein X is hydrogen and Y is (S)—OH. In another embodiment, the present invention is directed to compounds of formula (I) wherein X is hydrogen and Y is fluoro. In another embodiment, the present invention is directed to compounds of formula (I) wherein X is fluoro and Y is fluoro.

In an embodiment, the present invention is directed to compounds of formula (I) wherein $R^1$ is selected from the group consisting of hydrogen, halogen, —OH, $C_{1-2}$alkyl, fluorinated $C_{1-2}$alkyl, $C_{1-4}$alkoxy, fluorinated $C_{1-2}$alkoxy, —O-cylopropyl and —O-benzyl. In another embodiment, the present invention is directed to compounds of formula (I) wherein $R^1$ is selected from the group consisting of hydrogen, halogen, —OH, $C_{1-2}$alkoxy, fluorinated $C_{1-2}$alkoxy, —O-cyclopropyl and —O-benzyl. In another embodiment, the present invention is directed to compounds of formula (I) wherein $R^1$ is selected from the group consisting of hydrogen, fluoro, —OH, methoxy, ethoxy, fluoromethoxy, difluoromethoxy, trifluoromethoxy, —O-cyclopropyl and —O-benzyl.

In another embodiment, the present invention is directed to compounds of formula (I) wherein $R^1$ is selected from the group consisting of hydrogen, fluoro, —OH, methoxy, —OCD$_3$, ethoxy, fluoromethoxy, difluoromethoxy, trifluoromethoxy, —O-cyclopropyl and —O-benzyl. In another embodiment, the present invention is directed to compounds of formula (I) wherein $R^1$ is selected from the group consisting of hydrogen, fluoro, —OH, methoxy, —OCD$_3$, ethoxy, fluoromethoxy and —O-cyclopropyl. In another embodiment, the present invention is directed to compounds of formula (I) wherein $R^1$ is selected from the group consisting of hydrogen, fluoro, —OH, methoxy, —OCD$_3$, ethoxy and —O-cyclopropyl.

In an embodiment, the present invention is directed to compounds of formula (I) wherein $R^2$ is selected from the group consisting of hydrogen, halogen and $C_{1-4}$alkyl. In another embodiment, the present invention is directed to compounds of formula (I) wherein $R^2$ is selected from the group consisting of hydrogen halogen and $C_{1-2}$alkyl. In another embodiment, the present invention is directed to compounds of formula (I) wherein $R^2$ is selected from the group consisting of hydrogen, bromo, iodo and methyl. In another embodiment, the present invention is directed to compounds of formula (I) wherein $R^2$ is selected from the group consisting of hydrogen, deuterium, bromo, iodo and methyl. In another embodiment, the present invention is directed to compounds of formula (I) wherein $R^2$ is selected from the group consisting of hydrogen, deuterium, iodo and methyl. In another embodiment, the present invention is directed to compounds of formula (I) wherein $R^2$ is selected from the group consisting of hydrogen, deuterium and iodo.

In an embodiment, the present invention is directed to compounds of formula (I) wherein $R^3$ is selected from the group consisting of hydrogen, halogen, $C_{1-4}$alkyl, $C_{1-4}$alkoxy, cyano, $NR^AR^B$, and $C_{3-4}$cycloalkyl; wherein $R^A$ and $R^B$ are each independently selected from the group consisting of hydrogen, methyl and ethyl. In another embodiment, the present invention is directed to compounds of formula (I) wherein $R^3$ is selected from the group consisting of hydrogen, halogen, $C_{1-2}$alkyl, $C_{1-2}$alkoxy, cyclopropyl, cyano, and $NR^AR^B$; wherein $R^A$ and $R^B$ are each independently selected from the group consisting of hydrogen and methyl.

In another embodiment, the present invention is directed to compounds of formula (I) wherein $R^3$ is selected from the group consisting of hydrogen, fluoro, chloro, methyl, ethyl, methoxy, cyano, dimethylamino and cyclopropyl. In another embodiment, the present invention is directed to compounds of formula (I) wherein $R^3$ is selected from the group consisting of hydrogen, chloro, methyl, ethyl, methoxy, dimethylamino and cyclopropyl. In another embodiment, the present invention is directed to compounds of formula (I) wherein $R^3$ is selected from the group consisting of chloro, methyl, ethyl, methoxy, dimethylamino and cyclopropyl.

In an embodiment, the present invention is directed to compounds of formula (I) wherein $R^4$ is selected from the group consisting of hydrogen and $C_{1-4}$alkyl. In another embodiment, the present invention is directed to compounds of formula (I) wherein $R^4$ is selected from the group consisting of hydrogen and $C_{1-2}$alkyl. In another embodiment, the present invention is directed to compounds of formula (I) wherein $R^4$ is selected from the group consisting of hydrogen and methyl. In another embodiment, the present invention is directed to compounds of formula (I) wherein $R^4$ is hydrogen.

In an embodiment, the present invention is directed to compounds of formula (I) wherein the two $R^5$ groups are the same and are selected from the group consisting of hydrogen, deuterium and fluoro. In another embodiment, the present invention is directed to compounds of formula (I) wherein the two $R^5$ groups are the same and are selected from the group consisting of hydrogen and deuterium. In another embodiment, the present invention is directed to compounds of formula (I) wherein the two $R^5$ groups are the same and are fluoro. In another embodiment, the present invention is directed to compounds of formula (I) wherein the two $R^5$ groups are taken together with the carbon atom to which they are bound to form carbonyl.

In an embodiment, the present invention is directed to compounds of formula (I) wherein both $R^6$ groups are the same and are hydrogen. In another embodiment, the present invention is directed to compounds of formula (I) wherein both $R^6$ groups are the same and are deuterium.

In an embodiment, the present invention is directed to compounds of formula (I) wherein both $R^7$ groups are the same and are hydrogen. In another embodiment, the present invention is directed to compounds of formula (I) wherein both $R^7$ groups are the same and are deuterium.

In another embodiment, the present invention is directed to compounds of formula (I) wherein both $R^6$ groups are the same and are hydrogen; and wherein both $R^7$ groups are the same and are deuterium. In another embodiment, the present invention is directed to compounds of formula (I) wherein both $R^6$ groups are the same and are deuterium; and wherein both $R^7$ groups are the same and are hydrogen.

In another embodiment, the present invention is directed to compounds of formula (I) wherein both $R^6$ groups are the same and are hydrogen; and wherein both $R^7$ groups are the same and are hydrogen. In another embodiment, the present invention is directed to compounds of formula (I) wherein both $R^6$ groups are the same and are deuterium; and wherein both $R^7$ groups are the same and are deuterium.

In another embodiment, the present invention is directed to compounds of formula (I) wherein X is hydrogen and Y is (S)—OH; $R^1$ is selected from the group consisting of hydrogen, fluoro, —OH, methoxy, —OCD$_3$, ethoxy, fluoromethoxy, difluoromethoxy, trifluoromethoxy and —O-cyclopropyl; $R^2$ is selected from the group consisting of hydrogen, deuterium, bromo, iodo and methyl; $R^3$ is selected from the group consisting of hydrogen, fluoro, chloro, methyl, ethyl, methoxy, cyano, dimethylamino and cyclopropyl; $R^4$ is selected from the group consisting of hydrogen and methyl; the two $R^5$ groups are the same and are selected from the group consisting of hydrogen, deuterium and fluoro; the two $R^6$ groups are the same and are selected from the group consisting of hydrogen and deuterium; the two $R^7$ groups are the same and are selected from the group consisting of hydrogen and deuterium; and isotopologues and pharmaceutically acceptable salts thereof.

In another embodiment, the present invention is directed to compounds of formula (I) wherein X is fluoro; Y is fluoro; $R^1$ is selected from the group consisting of hydrogen, —OH, methoxy and ethoxy; $R^2$ is hydrogen, $R^3$ is selected from the group consisting of chloro, methyl and methoxy; $R^4$ is hydrogen; each $R^5$ is hydrogen; each $R^6$ is hydrogen; each $R^7$ is hydrogen; and isotopologues and pharmaceutically acceptable salts thereof.

In another embodiment, the present invention is directed to compounds of formula (I) wherein X is hydrogen; Y is fluoro; $R^1$ is selected from the group consisting of hydrogen, fluoro, —OH, methoxy, ethoxy and —O-benzyl; $R^2$ is hydrogen, $R^3$ is selected from the group consisting of chloro, methyl, ethyl and methoxy; $R^4$ is hydrogen; the two $R^5$ groups are the same and are selected from the group consisting of hydrogen and fluoro; each $R^6$ is hydrogen; each $R^7$ is hydrogen; and isotopologues and pharmaceutically acceptable salts thereof.

In another embodiment, the present invention is directed to a compound selected from the group consisting of (2S,3R,4R,5S,6R)-2-(3-((1,2-dihydrocyclobutabenzen-4-yl)methyl)-4-methylphenyl)-6-(hydroxymethyl)-tetrahydro-2H-pyran-3,4,5-triol;

(2S,3R,4R,5S,6R)-2-(4-chloro-3-((1,2-dihydrocyclobutabenzen-4-yl)methyl)phenyl)-6-(hydroxymethyl)-tetrahydro-2H-pyran-3,4,5-triol;

(2S,3R,4R,5S,6R)-2-(3-((1,2-dihydrocyclobutabenzen-4-yl)methyl)-4-methoxyphenyl)-6-(hydroxymethyl)-tetrahydro-2H-pyran-3,4,5-triol;

(2S,3R,4R,5S,6R)-2-(5-((1,2-dihydrocyclobutabenzen-4-yl)methyl)-2-hydroxy-4-methylphenyl)-6-(hydroxymethyl)-tetrahydro-2H-pyran-3,4,5-triol;

2S,3R,4R,5S,6R)-2-(4-chloro-5-((1,2-dihydrocyclobutabenzen-4-yl)methyl)-2-methoxyphenyl)-6-(hydroxymethyl)-tetrahydro-2H-pyran-3,4,5-triol;

(2S,3R,4R,5S,6R)-2-(5-((1,2-dihydrocyclobutabenzen-4-yl)methyl)-2,4-dimethoxyphenyl)-6-(hydroxymethyl)-tetrahydro-2H-pyran-3,4,5-triol;

(2S,3R,4R,5S,6R)-2-(5-{bicyclo[4.2.0]octa-1(6),2,4-trien-3-ylmethyl}-4-ethyl-2-hydroxyphenyl)-6-(hydroxymethyl)oxane-3,4,5-triol;

(2S,3R,4R,5S,6R)-2-(5-((1,2-dihydrocyclobutabenzen-4-yl)methyl)-4-ethyl-2-methoxyphenyl)-6-(hydroxymethyl)-tetrahydro-2H-pyran-3,4,5-triol;

and isotopologues and pharmaceutically acceptable salts thereof.

Additional embodiments of the present invention, include those wherein the substituents selected for one or more of the variables defined herein (i.e. X, Y, $R^1$, $R^2$, $R^3$, $R^4$, $R^5$, $R^6$ and $R^7$) are independently selected to be any individual substituent or any subset of substituents selected from the complete list as defined herein. Additional embodiments of the present invention, include those wherein the substituents selected for one or more of the variables defined herein (i.e. X, Y, $R^1$, $R^2$, $R^3$, $R^4$, $R^5$, $R^6$ and $R^7$) are independently selected to correspond to any of the embodiments as defined herein.

In another embodiment of the present invention is any single compound or subset of compounds selected from the representative compounds listed in Tables 1-8 below. Representative compounds of the present invention are as listed in Table 1 to 8 below.

TABLE 1

Representative Compounds of Formula (I)

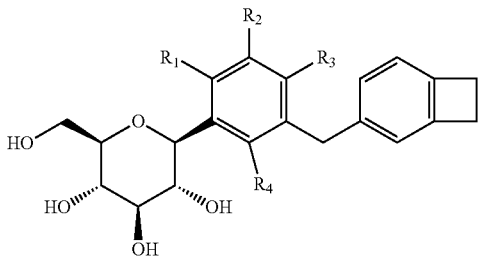

| Cmpd No. | $R^1$ | $R^2$ | $R^3$ | $R^4$ |
|---|---|---|---|---|
| 1 | H | H | —$CH_3$ | H |
| 2 | H | H | Cl | H |
| 3 | H | H | —$OCH_3$ | H |
| 4 | H | H | —$CH_2CH_3$ | H |
| 5 | H | H | cyclopropyl | H |
| 6 | —OH | H | —$CH_3$ | H |
| 7 | —$OCH_3$ | H | —$CH_3$ | H |
| 8 | —OH | H | Cl | H |
| 9 | —$OCH_3$ | H | Cl | H |
| 10 | —OH | H | —$OCH_3$ | H |
| 11 | —$OCH_3$ | H | —$OCH_3$ | H |
| 12 | —OH | H | —$CH_2CH_3$ | H |
| 13 | —$OCH_3$ | H | —$CH_2CH_3$ | H |
| 14 | —OH | H | cyclopropyl | H |
| 15 | —$OCH_3$ | H | cyclopropyl | H |
| 16 | H | H | —CN | H |
| 17 | —OH | H | —CN | H |
| 18 | —$OCH_3$ | H | —CN | H |
| 19 | —OH | H | F | H |
| 20 | —$OCH_3$ | H | F | H |
| 21 | H | H | —$N(CH_3)_2$ | H |
| 22 | —OH | H | —$N(CH_3)_2$ | H |
| 23 | —$OCH_3$ | H | —$N(CH_3)_2$ | H |
| 24 | H | H | H | H |
| 25 | —OH | H | H | H |
| 26 | —$OCH_3$ | H | H | H |
| 27 | —OH | —$CH_3$ | H | H |
| 28 | —OH | H | H | $CH_3$ |
| 29 | F | H | —$CH_3$ | H |
| 30 | F | H | Cl | H |
| 31 | F | H | —$OCH_3$ | H |
| 32 | F | H | —$CH_2CH_3$ | H |
| 33 | —$OCF_3$ | H | —$CH_3$ | H |
| 34 | —$OCF_3$ | H | —$OCH_3$ | H |
| 35 | —$OCF_3$ | H | —$CH_2CH_3$ | H |
| 36 | —$OCF_2H$ | H | —$CH_3$ | H |
| 37 | —$OCF_2H$ | H | Cl | H |
| 38 | —$OCF_2H$ | H | —$OCH_3$ | H |
| 39 | —$OCH_2F$ | H | —$CH_3$ | H |
| 40 | —$OCH_2F$ | H | Cl | H |
| 41 | —$OCH_2F$ | H | —$OCH_3$ | H |
| 42 | —$OCH_2F$ | H | —$CH_2CH_3$ | H |
| 100 | —OH | Br | —$CH_2CH_3$ | H |
| 101 | H | H | F | H |

TABLE 1-continued

Representative Compounds of Formula (I)

| Cmpd No. | $R^1$ | $R^2$ | $R^3$ | $R^4$ |
|---|---|---|---|---|
| 105 | —$OCH_2CH_3$ | H | —$CH_2CH_3$ | H |
| 113 | —$OCH_2CH_3$ | H | —$CH_3$ | H |
| 114 | —$OCH_2CH_3$ | H | —$OCH_3$ | H |
| 115 | —$OCH_2CH_3$ | H | Cl | H |
| 116 | —O-cyclo-propyl | H | —$CH_2CH_3$ | H |
| 117 | —O-cyclo-propyl | H | Cl | H |
| 118 | —O-cyclo-propyl | H | —$CH_3$ | H |
| 120 | —OH | I | —$CH_3$ | H |
| 121 | —OH | D | —$CH_3$ | H |
| 122 | —$OCF_2H$ | H | —$CH_2CH_3$ | H |

TABLE 2

Representative Compounds of Formula (I)

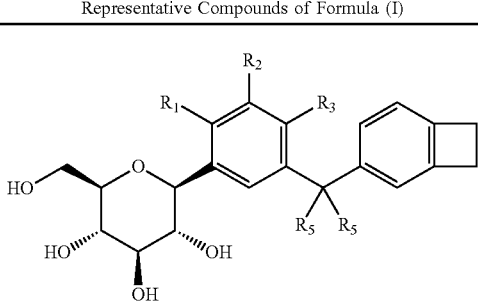

| Cmpd No. | $R^1$ | $R^2$ | $R^3$ | $R^5, R^5$ |
|---|---|---|---|---|
| 51 | H | H | —$CH_3$ | D, D |
| 52 | —OH | H | —$CH_3$ | D, D |
| 53 | —$OCH_3$ | H | —$CH_3$ | D, D |
| 54 | H | H | Cl | D, D |
| 55 | —OH | H | Cl | D, D |
| 56 | —$OCH_3$ | H | Cl | D, D |
| 57 | H | H | —$OCH_3$ | D, D |
| 58 | H | H | —$CH_2CH_3$ | D, D |
| 59 | —$OCH_3$ | H | —$OCH_3$ | D, D |
| 60 | —$OCH_3$ | H | —$CH_2CH_3$ | D, D |
| 139 | H | H | Cl | =O |
| 140 | H | H | Cl | F, F |
| 141 | H | H | —$CH_3$ | F, F |
| 144 | F | H | —$OCH_3$ | F, F |

TABLE 3

Representative Compounds of Formula (I)

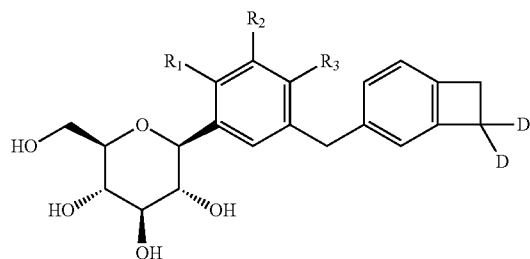

| Cmpd No. | R¹ | R² | R³ |
|---|---|---|---|
| 61 | —OH | H | —CH₃ |
| 62 | H | H | Cl |
| 63 | —OCH₃ | H | —CH₃ |
| 64 | H | H | —OCH₃ |
| 65 | H | H | CH₃ |
| 66 | H | H | —CH₂CH₃ |
| 67 | —OCH₃ | H | Cl |
| 68 | —OCH₃ | H | —OCH₃ |
| 69 | —OCH₃ | H | —CH₂CH₃ |
| 70 | F | H | —CH₃ |
| 71 | F | H | Cl |
| 72 | F | H | —OCH₃ |
| 73 | F | H | —CH₂CH₃ |
| 74 | F | H | cyclopropyl |

TABLE 4

Representative Compounds of Formula (I)

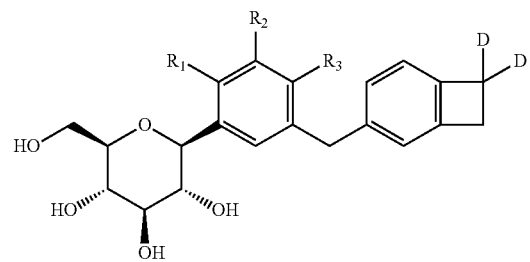

| Cmpd No. | R¹ | R² | R³ |
|---|---|---|---|
| 81 | H | H | Cl |
| 82 | H | H | —OCH₃ |
| 83 | —OCH₃ | H | Cl |
| 84 | —OCH₃ | H | —OCH₃ |
| 85 | H | H | —CH₃ |
| 86 | —OCH₃ | H | —CH₃ |
| 87 | H | H | —CH₂CH₃ |

TABLE 5

Representative Compounds of Formula (I)

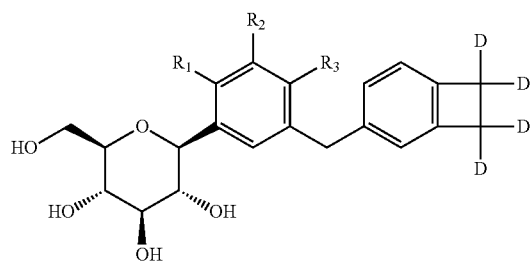

TABLE 5-continued

| Cmpd No. | R¹ | R² | R³ |
|---|---|---|---|
| 123 | H | H | Cl |

TABLE 6

Representative Compounds of Formula (I)

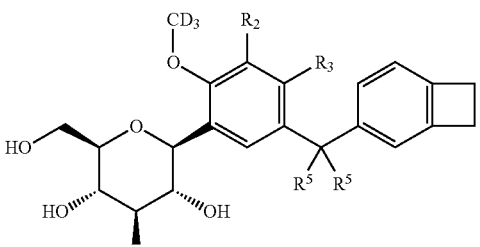

| Cmpd No. | R² | R³ | R⁵, R⁵ |
|---|---|---|---|
| 110 | H | —CH₃ | H, H |
| 111 | H | —CH₂CH₃ | H, H |
| 112 | H | —OCH₃ | H, H |
| 119 | H | —CH₃ | D, D |

TABLE 7

Representative Compounds of Formula (I)

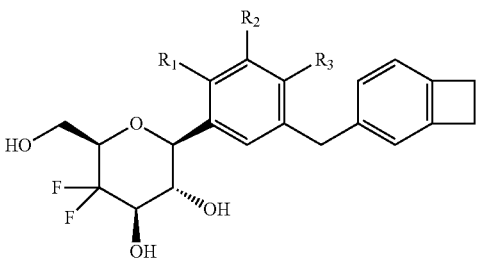

| Cmpd No. | R¹ | R² | R³ |
|---|---|---|---|
| 91 | H | H | —CH₃ |
| 92 | —OH | H | —CH₃ |
| 93 | —OCH₃ | H | —CH₃ |
| 102 | —OH | H | Cl |
| 103 | —OCH₃ | H | Cl |
| 104 | —OCH₂CH₃ | H | Cl |
| 106 | H | H | Cl |
| 107 | —OH | H | —OCH₃ |
| 108 | —OCH₃ | H | —OCH₃ |
| 109 | —OCH₂CH₃ | H | —OCH₃ |

TABLE 8

Representative Compounds of Formula (I)

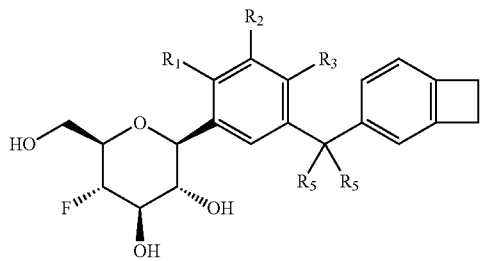

| Cmpd No. | R¹ | R² | R³ | R⁵, R⁵ |
| --- | --- | --- | --- | --- |
| 125 | —O-benzyl | H | —CH$_3$ | H, H |
| 126 | H | H | —CH$_3$ | H, H |
| 127 | —OH | H | —CH$_2$CH$_3$ | H, H |
| 128 | H | H | —CH$_2$CH$_3$ | H, H |
| 129 | —OH | H | Cl | H, H |
| 130 | —OH | H | —CH$_3$ | H, H |
| 131 | —OCH$_2$CH$_3$ | H | —CH$_3$ | H, H |
| 132 | —OCH$_2$CH$_3$ | H | Cl | H, H |
| 133 | —OCH$_3$ | H | Cl | H, H |
| 134 | H | H | Cl | H, H |
| 135 | —OH | H | —OCH$_3$ | H, H |
| 136 | —OCH$_3$ | H | —OCH$_3$ | H, H |
| 137 | —OCH$_2$CH$_3$ | H | —OCH$_3$ | H, H |
| 142 | H | H | —CH$_3$ | F, F |
| 143 | F | H | —OCH$_3$ | F, F |

As used herein, "halogen" shall mean chlorine, bromine, fluorine and iodine. Preferably, the halogen is selected from the group consisting of bromine, fluorine and iodine, more preferably fluorine.

As used herein, the term "C$_{X-Y}$alkyl" wherein X and Y are integers, whether used alone or as part of a substituent group, include straight and branched chains containing between X and Y carbon atoms. For example, C$_{1-4}$ alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the term "fluorinated C$_{1-4}$alkyl" shall mean any C$_{1-4}$alkyl group as defined above substituted with at least one fluorine atom, preferably one to three fluorine atoms. Suitable examples include but are not limited to —CH$_2$F, —CF$_2$H, —CF$_3$, —CH$_2$—CF$_3$, —CF$_2$—CF$_2$—CF$_2$—CF$_3$, and the like.

As used herein, unless otherwise noted, "C$_{1-4}$alkoxy" shall denote an oxygen ether radical of the above described straight or branched chain alkyl groups containing one to four carbon atoms. For example, methoxy, ethoxy, n-propoxy, isopropoxy, sec-butoxy, t-butoxy, and the like.

As used herein, unless otherwise noted, the term "fluorinated C$_{1-4}$alkoxy" shall mean any C$_{1-4}$alkoxy group as defined above substituted with at least one fluorine atom, preferably one to three fluorine atoms. Suitable examples include but are not limited to —OCH$_2$F, —OCF$_2$H, —OCF$_3$, —OCH$_2$—CF$_3$, —OCF$_2$—CF$_2$—CF$_2$—CF$_3$, and the like.

As used herein, unless otherwise noted, the term "C$_{X-Y}$cycloalkyl", wherein X and Y are integers, shall mean any stable X- to Y-membered monocyclic, saturated ring system. For example, the term "C$_{3-5}$cycloalkyl" shall include cyclopropyl, cyclobutyl and cyclopentyl.

When a particular group is "substituted" (e.g. alkyl, alkoxy, cycloalkyl, etc.), that group may have one or more substituents, preferably from one to five substituents, more preferably from one to three substituents, most preferably from one to two substituents, independently selected from the list of substituents.

With reference to substituents, the term "Independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "Isotopologues" shall mean molecules that differ only in their isotopic composition. More particularly, an isotopologue of a molecule differs from the parent molecule in that it contains at least one atom which is an isotope (i.e. has a different number of neutrons from its parent atom).

For example, isotopologues of water include, but are not limited to, "light water" (HOH or H$_2$O), "semi-heavy water" with the deuterium isotope in equal proportion to protium (HDO or $^1$H$^2$HO), "heavy water" with two deuterium isotopes of hydrogen per molecule (D$_2$O or $^2$H$_2$O), "superheavy water" or tritiated water (T$_2$O or $^3$H$_2$O), where the hydrogen atoms are replaced with tritium ($^3$H) isotopes, two heavy-oxygen water isotopologues (H$_2$$^{18}$O and H$_2$$^{17}$O) and isotopologues where the hydrogen and oxygen atoms may each independently be replaced by isotopes, for example the doubly labeled water isotopologue D$_2$$^{18}$O.

It is intended that within the scope of the present invention, any one or more element(s), in particular when mentioned in relation to a compound of formula (I), shall comprise all isotopes and isotopic mixtures of said element(s), either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{18}$O and $^{18}$O. The isotopes may be radioactive or non-radioactive. Radiolabelled compounds of formula (I) may comprise one or more radioactive isotope(s) selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

In certain embodiments, the present invention is directed to compounds of formula (I) wherein the two $R^5$ groups are the same and are both deuterium (D). In certain embodiments, the present invention is directed to compounds of formula (I) wherein the two $R^6$ groups are the same and are both deuterium (D). In certain embodiments, the present invention is directed to compounds of formula (I) wherein the two $R^7$ groups are the same and are both deuterium (D). In certain embodiments, the present invention is directed to compounds of formula (I) wherein the two $R^6$ groups and the two $R^7$ groups are the same and are each deuterium (D).

In certain embodiments, the present invention is directed to compounds of formula (I) wherein any $C_{1-4}$alkyl or $C_{1-4}$alkoxy substituent is deuterated (i.e. wherein one or more hydrogen atoms on the substituent group are replaced with a deuterium atom (D), preferably one to three hydrogen atoms are each replaced with a deuterium atom), for example —$CD_3$, —$CH_2CD_3$, $OCD_3$, and the like.

Under standard nomenclature used throughout this disclosure, the terminal portion of the designated side chain is described first, followed by the adjacent functionality toward the point of attachment Thus, for example, a "phenyl$C_1$-$C_6$alkylaminocarbonyl$C_1$-$C_6$alkyl" substituent refers to a group of the formula

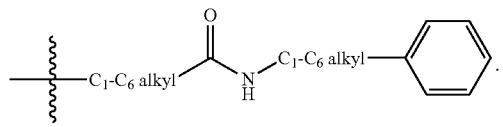

Abbreviations used in the specification, particularly the Schemes and Examples, are as follows:
AcOH or HOAc=Acetic acid
AMG=Alpha-Methyl Glucopyranoside
aq.=aqueous
$BF_3$·$Et_2$O Boron trifluoride diethyl etherate
BnBr=Benzylbromide
n-$Bu_4$NF Tetra-n-butylammonium fluoride
n-BuLi=n-Butyl lithium
sec-BuLi=sec-Butyl lithium
t-BuLi=tert-Butyl lithium
t-BuONa or NaOt-Bu=Sodium tert-butoxide
n-$Bu_3$SnH=Tri-n-butyl tin hydride
CSA=Camphorsulfonic acid
conc.=concentrated
DAST=Diethylaminosulfur trifluoride
DCM=Dichloromethane
Dess-Martin Reagent or Dess-Martin Periodinane 1,1,1-Triacetoxy-1,1-dihydro-1,2-benziodoxol-3(1H)-one
DCl=Deuterated hydrochloric acid
DIPEA or DIEA=Diisopropylethylamine
DMF=N,N-Dimethylformamide
DMSO=Dimethylsulfoxide $D_2$O=Deuterated water
EDCl=1-Ethyl-3-(3-dimetylaminopropyl)carbodiimide
$Et_3$B=Triethyl borane
$Et_3$N or TEA=Triethylamine
$Et_3$SiH=Triethylsilane
EtOAc or EA=Ethyl acetate
EtOH=Ethanol
GCMS=Gas chromatography-mass spectrometry
HATU=O-(7-Azabenzotriazol-1-yl)-N,N,N",N"-Tetramethyl Uronium Hexafluorophosphate
HDL=High density lipoprotein
HEPES=4-(2-Hydroxyethyl)-1-Piperizine Ethane Sulfonic Acid
HOBT=1-Hydroxybenzotriazole
HPLC=High Pressure Liquid Chromatography
IDDM=Insulin-dependent Diabetes Mellitus
IFG=Impaired fasting glucose
IGT=Impaired glucose tolerance
IRS=Insulin resistance syndrome
LAH=Lithium aluminum hydride
LC-MS or LCMS=Liquid chromatography-mass spectrometry
Me=Methyl (i.e. —$CH_3$)
MeCN=Acetonitrile
MeI=Methyl iodide
MeOH=Methanol
Mesyl=Methylsulfonyl
MOM=methoxy methyl
MS=Molecular Sieves
MsCl=Mesyl chloride
MTBE=Methyl t-butyl ether
NBS=N-Bromosuccinimide
NCS=N-Chlorosuccinimide
NIDDM=Non-insulin-dependent Diabetes Mellitus
NMP=N-methyl-2-pyrrolidinone
NMR=Nuclear magnetic resonance
PCC=Pyridinium chlorochromate
PDC=Pyridinium Dichromate
Pd(dppf)$Cl_2$=[1,1'-Bis(diphenylphosphino)ferrocene]dichloropalladium(II)
Pd(OAc)$_2$=Palladium acetate
Pd(PPh$_3$)$_4$=Tetrakistriphenylphosphine palladium (0)
PE=Petroleum ether
PMHS=Polymethylhydrosiloxane
PPHF=Poly(pyridine hydrogen fluoride)
SGLT=Sodium glucose transport
SGLT1 Sodium glucose transport-1
SGLT2 Sodium glucose transport-2
Sn(n-butyl)$_3$=Tri-n-butyl tin
TBDMS=tert-Butyldimethylsilyl
TEA=Triethylamine
TFA=Trifluoroacetic Acid
Tf$_2$O=Triflic anhydride
THF=Tetrahydrofuran
THP=Tetrahydropyran
TLC=Thin Layer Chromatography
TMS=Trimethylsilyl
TMSCl=Trimethylsilyl chloride
TMSI=Trimethylsilyl iodide
Tosyl or Ts=p-Toluenesulfonyl
TsCl=Tosyl chloride
TsOH or p-TsOH=p-Toluenesulfonic acid
Tris HCl or Tris-Cl or Tris buffer=Tris[hydroxymethyl]aminomethyl hydrochloride As used herein, unless otherwise noted, the term "Isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, Protective Groups in Organic Synthesis, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyldimethylsilyl, trimethylsilyl (TMS), MOM, THP, and the like. Other suitable oxygen protecting groups may be found in texts such as T. W. Greene & P. G. M. Wuts, Protective Groups in Organic Synthesis, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) of the present invention may be synthesized according to the general synthesis schemes described below. The preparation of the various starting materials used in the synthesis schemes which follow hereinafter is well within the skill of persons versed in the art.

Compounds of formula (I) wherein X is H and Y is (S)—OH, and wherein both $R^5$ groups are hydrogen, may be prepared according to the process as described in Scheme 1, below.

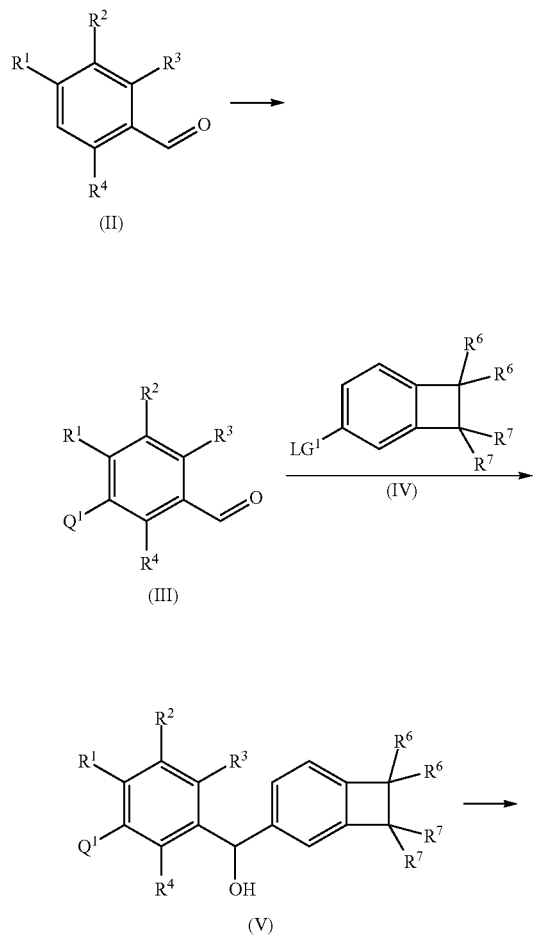

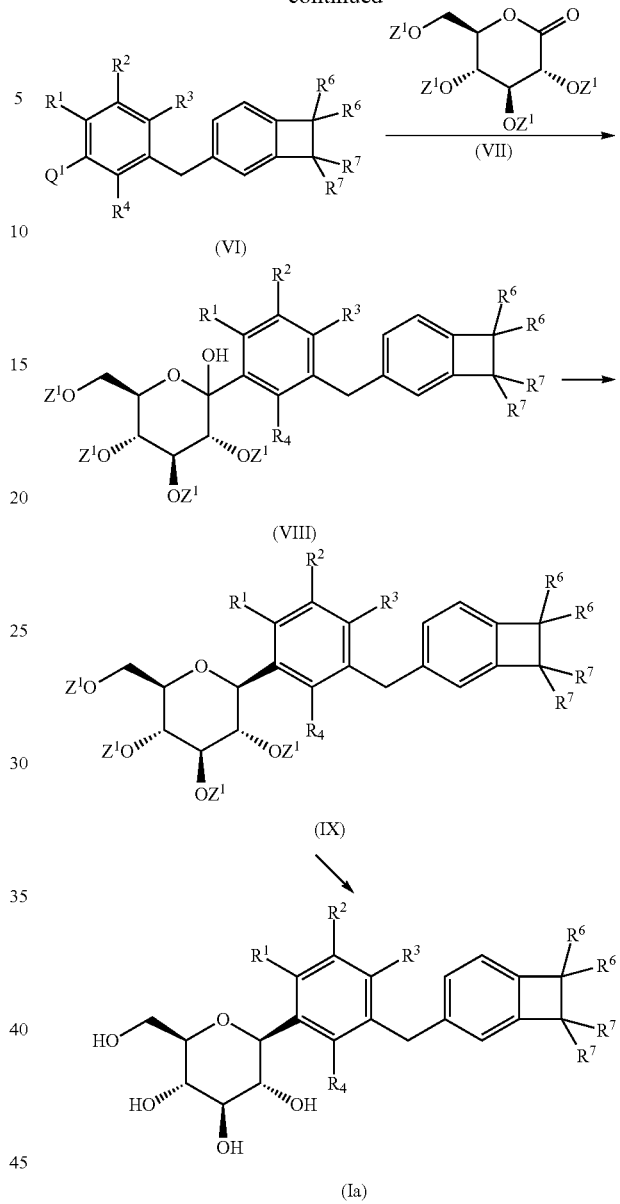

Accordingly, a suitably substituted compound of formula (II), a known compound or compound prepared by known methods, is reacted with a suitably selected halogenating (preferably brominating) agent such as $Br_2$, NBS, I, and the like; in a suitably selected organic solvent such as DCM, diethyl ether, and the like; to yield the corresponding compound of formula (III), wherein $Q^1$ represents the corresponding halogen (e.g. Br, I, etc.)

The compound of formula (III) is reacted with a suitably substituted compound of formula (IV), wherein $LG^1$ is a suitably selected leaving group such as Br, I, and the like, a known compound or compound prepared by known methods; wherein the compound of formula (IV) is pre-treated (and admixed with) with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; to yield the corresponding compound of formula (V).

The compound of formula (V) is reacted with a suitably selected reducing agent such as triethylsilane, Pd/C, LAH, and the like; in the presence of a suitably selected Lewis acid such as $BF_3.Et_2O$, TFA, acetic acid, $AlCl_3$, and the like; in a suitably selected organic solvent such as DCM, EtOAc, diethyl ether, and the like; to yield the corresponding compound of formula (VI).

The compound of formula (VI) is pre-treated with a suitably selected base such as n-BuLi, t-BuLi, sec-BuLi, and the like; in a suitably selected organic solvent such as THF, diethyl ether, and the like; at a temperature in the range of from about about −78° C. to about 20° C., preferably at about −78° C.; and then reacted with a suitably substituted compound of formula (VII), wherein each $Z^1$ is the same and is a suitably selected oxygen protecting group such as benzyl, trialkylsilane (e.g., triethylsilane, trimethylsilane, and the like), acetyl, and the like; to yield the corresponding compound of formula (VIII).

The compound of formula (VIII) is reacted with a suitably selected reducing agent such as triethylsilane, phenylsilane, n-$Bu_3SnH$, and the like; in the presence of a suitably selected Lewis acid such as $BF_3.Et_2O$, TFA, and the like; in a suitably selected organic solvent such as DCM, $CH_3CN$, toluene, and the like; to yield the corresponding compound of formula (IX).

The compound of formula (IX) is de-protected according to known methods; to yield the corresponding compound of formula (Ia). For example, wherein the $Z^1$ groups are each benzyl, the compound of formula (IX) is reacted with Pd/C/$H_2$ or $BCl_3$. In another example, wherein the $Z^1$ groups are each acetyl, the compound of formula (IX) is reacted with NaOH/water.

Compounds of formula (I) wherein X is H and Y is (S)—OH, and wherein both $R^5$ groups are hydrogen, may alternatively be prepared according to the process as described in Scheme 2, below.

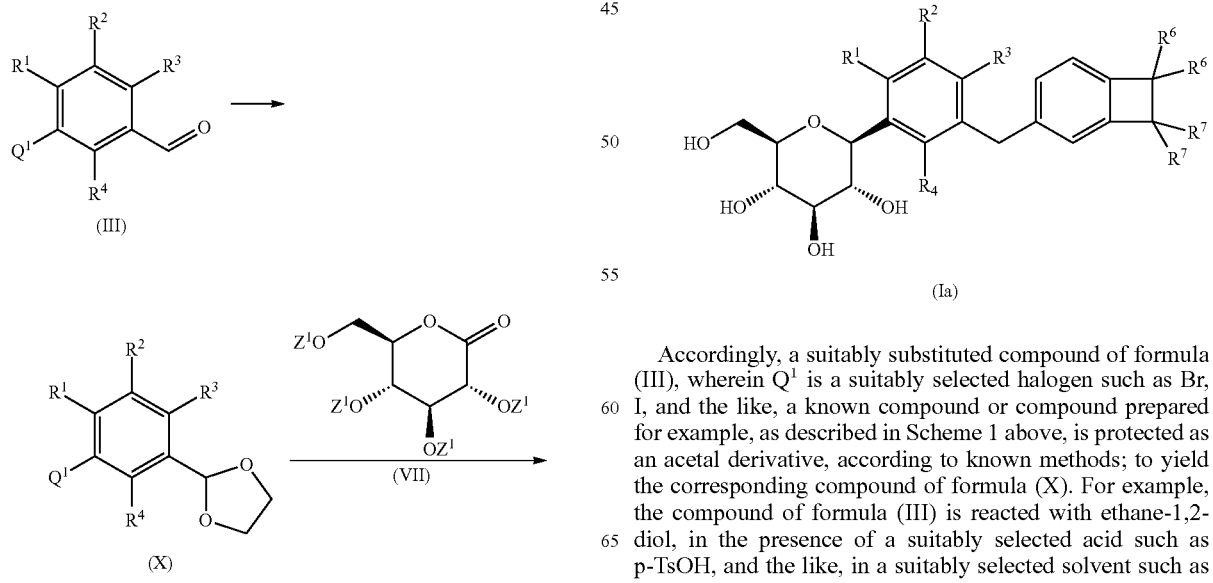

Accordingly, a suitably substituted compound of formula (III), wherein $Q^1$ is a suitably selected halogen such as Br, I, and the like, a known compound or compound prepared for example, as described in Scheme 1 above, is protected as an acetal derivative, according to known methods; to yield the corresponding compound of formula (X). For example, the compound of formula (III) is reacted with ethane-1,2-diol, in the presence of a suitably selected acid such as p-TsOH, and the like, in a suitably selected solvent such as benzene or toluene, and the like.

The compound of formula (X) is pre-treated with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; and then reacted with a suitably substituted compound of formula (VII), wherein each $Z^1$ is the same and is a suitably selected oxygen protecting group such as benzyl, trialkylsilane (e.g., triethylsilane, trimethylsilane, and the like), acetyl, and the like; to yield the corresponding compound of formula (XI).

The compound of formula (XI) is reacted with a suitably selected acid such as HCl, $H_2SO_4$, p-TsOH, and the like; in a suitably selected organic solvent such as acetone, 1,4-dioxane, water, and the like; to yield the corresponding compound of formula (XII).

The compound of formula (XII) is reacted with a suitably substituted compound of formula (IV), wherein $LG^1$ is a suitably selected leaving group such as Br, I, and the like; a known compound or compound prepared by known methods; wherein the compound of formula (IV) is pre-treated (and admixed with) with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably preferably at about −78° C.; to yield the corresponding compound of formula (XIII).

The compound of formula (XIII) is reacted with a suitably selected reducing agent such as triethylsilane, phenylsilane, n-$Bu_3$SnH, and the like; in the presence of a suitably selected Lewis acid such as $BF_3.Et_2O$, TFA, and the like; in a suitably selected organic solvent such as DCM, $CH_3CN$, toluene, and the like, to yield the corresponding compound of formula (IX).

The compound of formula (IX) is de-protected according to known methods (as described in Scheme 1 above); to yield the corresponding compound of formula (Ia).

Compounds of formula (I) wherein X is H and Y is (S)—OH, and wherein both $R^5$ groups are hydrogen, may alternatively be prepared according to the process as described in Scheme 3, below.

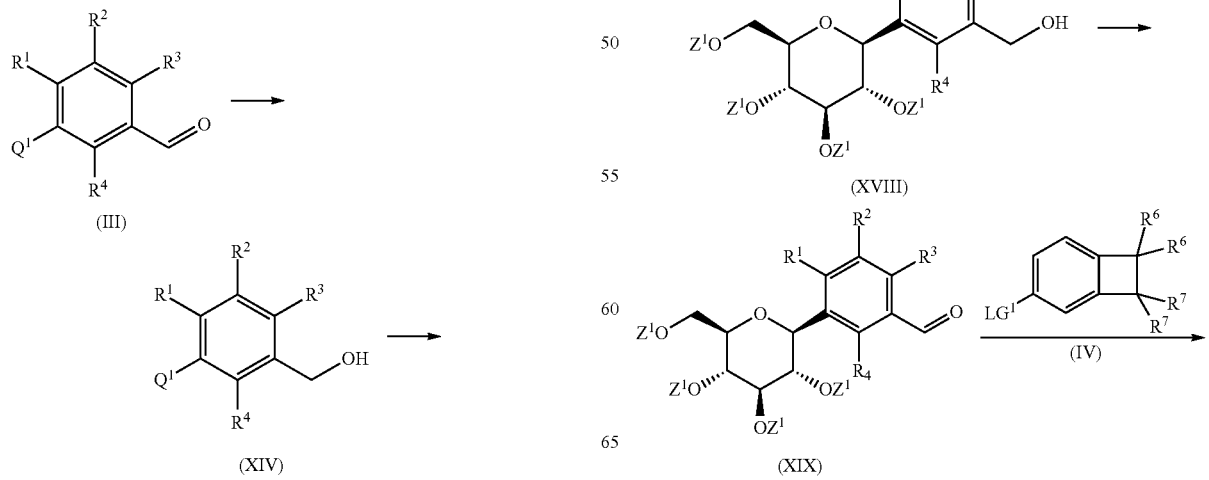

Scheme 3

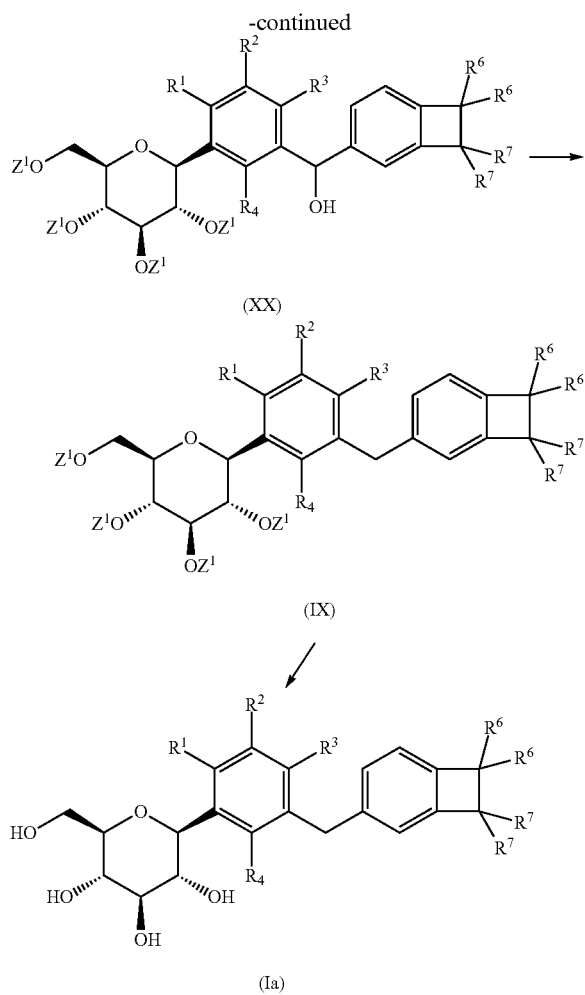

Accordingly, a suitably substituted compound of formula (III) wherein $Q^1$ is a suitably selected halogen such as Br, I, and the like, a known compound or compound prepared for example, as described in Scheme 1 above, is reacted with a suitably selected reducing agent such as $NaBH_4$, LAH, and the like; in a suitably selected organic solvent such as $CH_3OH$, THF, diethyl ether, and the like; to yield the corresponding compound of formula (XIV).

The compound of formula (XIV) is reacted to protect the hydroxyl group, according to known methods, to yield the corresponding compound of formula (XV), wherein $Z^2$ is the corresponding oxygen protecting group, such as TMS, TBDMS, benzyl, and the like. For example, the compound of formula (XIV) may be reacted with TMSCl to yield the corresponding compound of formula (XV), wherein $Z^2$ is TMS. In another example, the compound of formula (XIV) may be reacted with benzyl chloride to yield the corresponding compound of formula (XV), wherein $Z^2$ is benzyl.

The compound of formula (XV) is pre-treated with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; and then reacted with a suitably substituted compound of formula (VII), wherein each $Z^1$ is the same and is a suitably selected oxygen protecting group such as benzyl, trialkylsilane (e.g., triethylsilane, trimethylsilane, and the like), acetyl, and the like; to yield the corresponding compound of formula (XVI).

The compound of formula (XVI) is reacted with a suitably selected reducing agent such as triethylsilane, phenylsilane, $n-Bu_3SnH$, and the like; in the presence of a suitably selected Lewis acid such as $BF_3 \cdot Et_2O$, TFA, and the like; in a suitably selected organic solvent such as DCM, $CH_3CN$, toluene, and the like; to yield the corresponding compound of formula (XVII).

The compound of formula (XVII) is reacted to remove the $Z^2$ protecting groups, according to known methods, to yield the corresponding compound of formula (XVIII). For example, wherein $Z^2$ is TMS, the compound of formula (XVII) is reacted with $n-Bu_4NF$ In another example, wherein the $Z^2$ is acetyl, the compound of formula (XVII) is reacted with NaOH.

The compound of formula (XVIII) is reacted with a suitably selected oxidizing agent such as PCC, PDC, $MnO_2$, and the like; in a suitably selected organic solvent such as $CH_2Cl_2$, THF, 1,4-dioxane, and the like; to yield the corresponding compound of formula (XIX).

The compound of formula (XIX) is reacted with a suitably substituted compound of formula (IV), wherein $LG^1$ is a suitably selected leaving group such as Br, I, and the like; a known compound or compound prepared by known methods; wherein the compound of formula (IV) is pre-treated (and admixed with) with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; to yield the corresponding compound of formula (XX).

The compound of formula (XX) is reacted with a suitably selected reducing agent such as triethylsilane, Pd/C/$H_2$, and the like; in the presence of a suitably selected Lewis acid such as $BF_3 \cdot Et_2O$, TFA, acetic acid, and the like; in a suitably selected organic solvent such as DCM, EtOAc, and the like; to yield the corresponding compound of formula (IX).

The compound of formula (IX) is de-protected according to known methods (as described in Scheme 1 above); to yield the corresponding compound of formula (Ia).

Compounds of formula (I) wherein X is H and Y is (S)—OH, and wherein both $R^5$ groups are hydrogen, may alternatively be prepared according to the process as described in Scheme 4, below.

Scheme 4

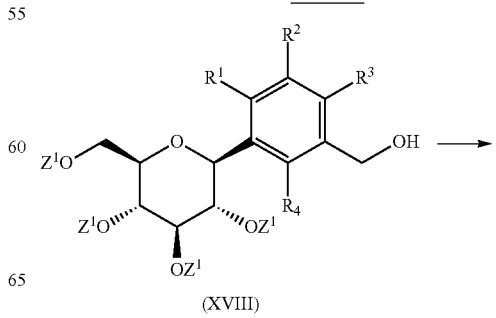

(XVIII)

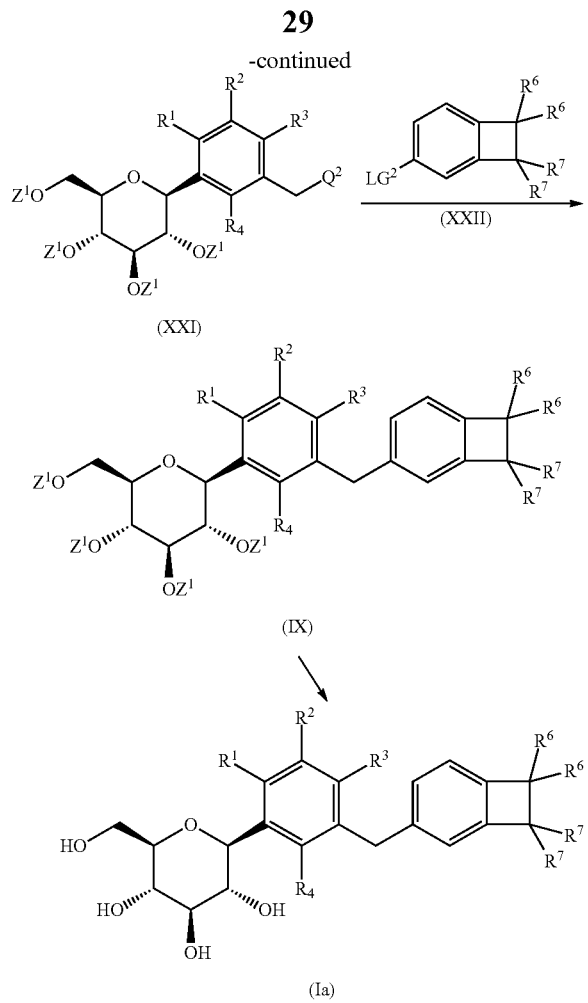

(XXI)

(IX)

(Ia)

Accordingly, a suitably substituted compound of formula (XVIII), prepared for example as described in Scheme 3 above, is reacted with a suitably selected halogenating agent such as a suitably selected brominating agent such as $PBr_3$, $Br_2$, $(COBr)_2$, and the like, or a suitably selected chlorinating agent such as $(COCl)_2$, $PCl_5$, thionyl chloride, and the like; in a suitably selected organic solvent such as $CCl_4$, $CH_2Cl_2$, and the like; to yield the corresponding compound of formula (XXI), where $Q^2$ is the corresponding halogen. For example wherein the compound of formula (XVIII) is reacted with $PBr_3$, then in the compound of formula (XXI) $Q^2$ is Br. Alternatively, when the compound of formula (XVIII) is reacted with thionyl chloride, then in the compound of formula (XXI) $Q^2$ is Cl.

The compound of formula (XXI) is reacted with a suitably substituted compound of formula (XXII), wherein $LG^2$ is $Sn(n-butyl)_3$, ZnBr, ZnCl, $B(OH)_2$,

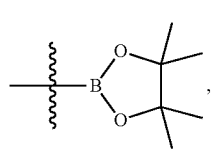 [SMILES: *B1OC(C)(C)C(C)(C)O1]

and the like; in the presence of a suitably selected palladium catalyst; according to known methods; to yield the corresponding compound of formula (IX).

For example, wherein $LG^2$ is $B(OH)_2$ or

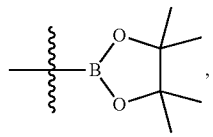 [SMILES: *B1OC(C)(C)C(C)(C)O1]

the compound of formula (XXI) is reacted with the compound of formula (XXII) in the presence of a suitably selected coupling agent such as $Pd(PPh_3)_4$, and the like, in the presence of a suitably selected base such as $Cs_2CO_3$, $K_2CO_3$, NaOH, and the like; in a suitably selected organic solvent such as DMF, acetonitrile, NMP (N-methyl-2-pyrrolidone), and the like.

Alternatively, wherein $LG^2$ is $Sn(n-butyl)_3$, and the like, the compound of formula the compound of formula (XXI) is reacted with the compound of formula (XXII) in the presence of a suitably selected coupling agent such as $Pd(PPh_3)_4$, $Pd(OAc)_2$, and the like; in the presence of a suitably selected base, such as $NaOCH_3$, TEA, $Cs_2CO_3$, and the like; in a suitably selected organic solvent such as THF, 1,4-dioxane, DMF, and the like.

Alternatively still, wherein $LG^2$ is ZnBr, ZnCl, and the like, the compound of formula (XXI) is reacted with the compound of formula (XXII) in the presence of a suitably selected coupling agent such as $Pd(PPh_3)_4$, $Pd(OAc)_2$, and the like; in the presence of a suitably selected base, such as $Cs_2CO_3$, CsF, t-BuONa, and the like; in a suitably selected organic solvent such as DMF, toluene, THF, and the like.

The compound of formula (IX) is de-protected according to known methods (as described in Scheme 1 above); to yield the corresponding compound of formula (Ia).

Compounds of formula (VI) may alternatively be prepared according to the process as described in Scheme 5, below.

Scheme 5

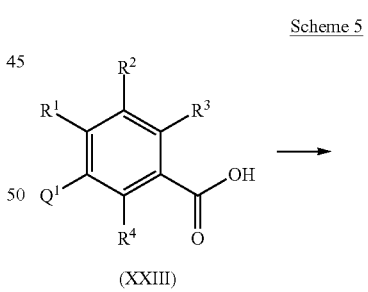

(XXIII)

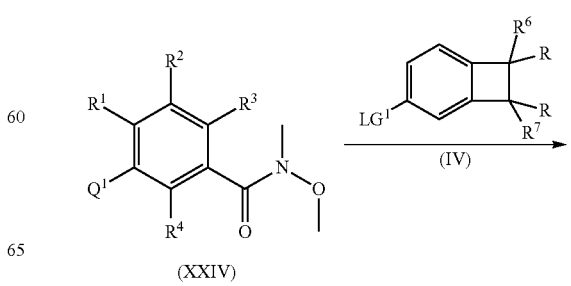

(XXIV)

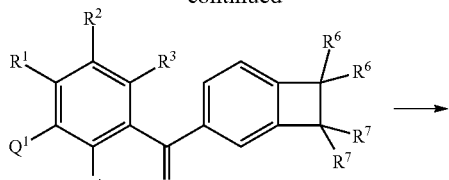

(XXV)

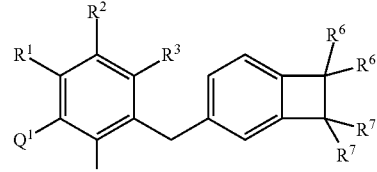

(VI)

Accordingly, a suitably substituted compound of formula (XXIII), wherein $Q^1$ is a suitably selected halogen, such as Br, Cl, I, and the like, a known compound or compound prepared by known methods, is reacted to convert the carboxylic acid to the Weinreb amide according to known methods, to yield the corresponding compound of formula (XXIV). For example, the compound of formula (XXIII) may be reacted with a suitably selected coupling reagent such as HATU, EDCl/HOBT, and the like; in the presence of a suitably selected base such as $Et_3N$, DIPEA, and the like; in a suitably selected organic solvent such as $CH_2Cl_2$, DMF, and the like.

The compound of formula (XXIV) is reacted with a suitably substituted compound of formula (IV), wherein $LG^1$ is a suitably selected leaving group such as Br, I, and the like; a known compound or compound prepared by known methods; wherein the compound of formula (IV) is pre-treated (and admixed with) with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; to yield the corresponding compound of formula (XXV).

The compound of formula (XXV) is reacted with a suitably selected reducing agent such as triethylsilane, LAH, and the like; in the presence of a suitably selected Lewis acid such as $BF_3.Et_2O$, TFA, $AlCl_3$, and the like; in a suitably selected organic solvent such as DCM, diethyl ether, and the like; to yield the corresponding compound of formula (VI).

The compound of formula (VI) is then reacted according to the procedure as described in Scheme 1 above, to yield the corresponding compound of formula (Ia).

Compounds of formula (I) wherein X is H or F, wherein Y is F, and wherein both $R^5$ groups are hydrogen, may alternatively be prepared according to the process as described in Scheme 6, below.

Scheme 6

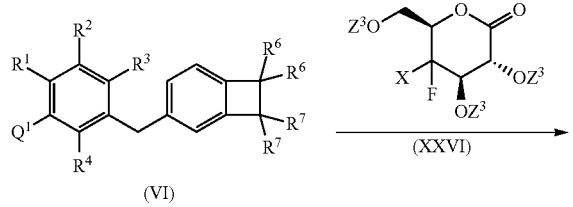

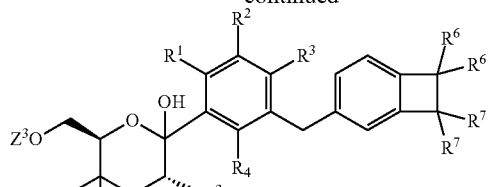

(XXVII)

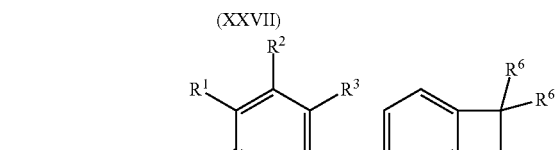

(XXVIII)

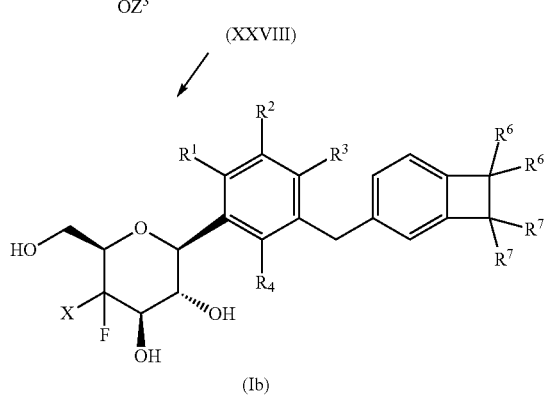

(Ib)

Accordingly, a suitably substituted compound of formula (VI), prepared for example as described in Scheme 1 or Scheme 5 above, is pre-treated with a suitably selected base such as n-BuLi, t-BuLi, sec-BuLi, and the like; in a suitably selected organic solvent such as THF, diethyl ether, and the like; at a temperature in the range of from about −78° C. to about 20° C., preferably at about −78° C.; and then reacted with a suitably substituted compound of formula (XXVI), wherein X is H or F and wherein each $Z^3$ is the same and is a suitably selected oxygen protecting group such as benzyl, trialkylsilane (e.g., triethylsilane, trimethylsilane, and the like), acetyl, and the like, a known compound or compound prepared by known methods; to yield the corresponding compound of formula (XXVII).

The compound of formula (XXVII) is reacted with a suitably selected reducing agent such as triethylsilane, phenylsilane, $n-Bu_3SnH$, and the like; in the presence of a suitably selected Lewis acid such as $BF_3.Et_2O$, TFA, and the like; in a suitably selected organic solvent such as DCM, $CH_3CN$, toluene, and the like; to yield the corresponding compound of formula (XXVIII).

The compound of formula (XXVIII) is de-protected according to known methods, to yield the corresponding compound of formula (Ib). For example, wherein the $Z^1$ groups are each benzyl, the compound of formula (XXVIII) is reacted with $BCl_3$. In another example, wherein the $Z^1$ groups are each acetyl, the compound of formula (XXVIII) is reacted with NaOH.

Compounds of formula (I) wherein each $R^5$ is deuterium may be prepared as described in Scheme 7, below.

Scheme 7

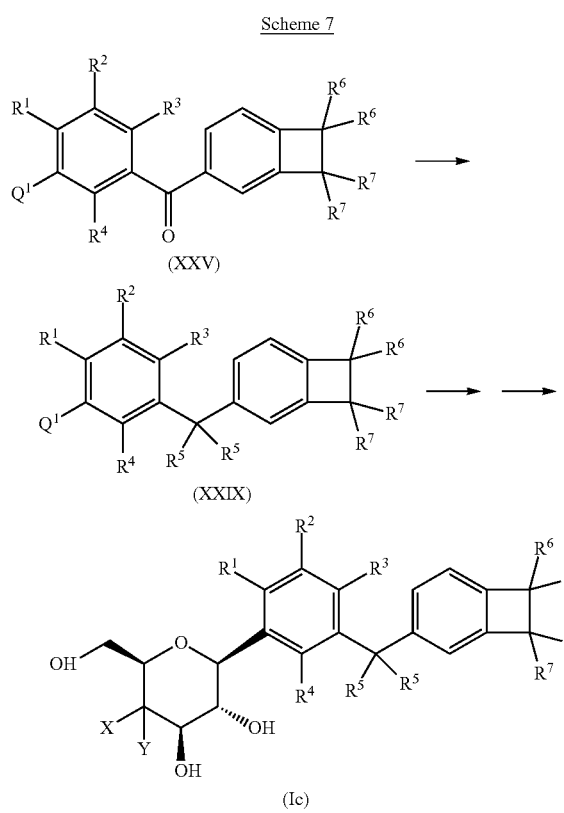

Accordingly, a suitably substituted compound of formula (XXV) wherein $Q^1$ is a suitably selected halogen such as Br, Cl, I, and the like, prepared for example as described in Scheme 5 above, is reacted with a suitably selected deuterated reducing agent such as $NaBD_4$, and the like; in the presence of a suitably selected Lewis acid such as $BF_3.Et_2O$, TFA, $AlCl_3$, and the like; in a suitably selected organic solvent such as DCM, diethyl ether, and the like; at a temperature in the range of from about 0° C. to about 40° C., preferably at about reflux temperature; to yield the corresponding compound of formula (XXIX).

The compound of formula (XXIX) is then substituted for the compound of formula (VI) in Scheme 1 or Scheme 6, and reacted as described therein, to yield the corresponding compound of formula (Ic).

Compounds of formula (I) wherein each $R^6$ is deuterium may be prepared as described in Scheme 8, below.

Scheme 8

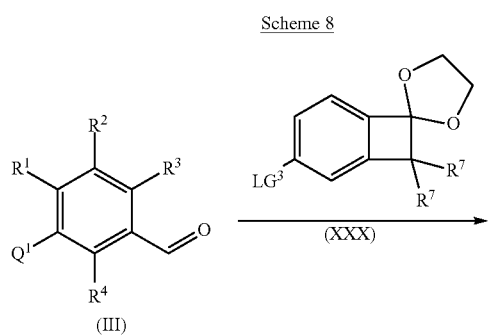

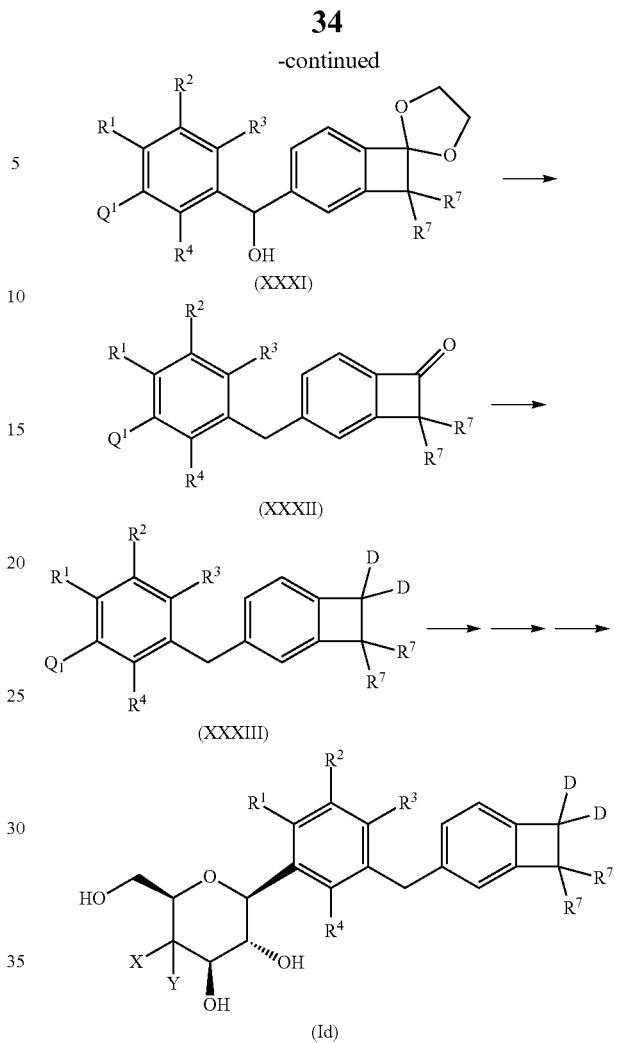

Accordingly, a suitably substituted compound of formula (III), wherein $Q^1$ is a suitably selected halogen such as Br, I, Cl, and the like, a known compound or compound prepared by known methods, is reacted with a suitably substituted compound of formula (XXX), wherein $LG^3$ is a suitably selected leaving group such as Br, I, and the like, a known compound or compound prepared by known methods; wherein the compound of formula (XXX) is pre-treated with a suitably selected base such as n-BuLi, t-BuLi, sec-BuLi, and the like; in a suitably selected solvent such as THF, diethyl ether, and the like; at a temperature in the range of from about −78° C. to about 20° C., preferably at about −78° C.; to yield the corresponding compound of formula (XXXI).

The compound of formula (XXXI) is reacted with a suitably selected reducing/de-protecting agent such as TMSI, a mixture of TFA and $Et_3SiH$, a mixture of $BF_3.Et_2O$ and $Et_3SiH$, and the like; in a suitably selected organic solvent such as DCM, $CH_3CN$, and the like; to yield the corresponding compound of formula (XXXII).

The compound of formula (XXXII) is reacted with a suitably selected reducing agent such as $HgCl_2$ in the presence of Zn, a mixture of $NaBD_4$ and $AlCl_3$, a mixture of $N_2H_4$ and KOH, and the like; in the presence of a suitably selected acid such as DCl, $CD_3COOD$, $CF_3COOD$, and the like; in a suitably selected deuterated alcohol or mixture of deuterated water and deuterated alcohol, such as a mixture of $D_2O$ and $CH_3CH_2OD$, a mixture of $D_2O$ and $CH_3OD$, a mixture of $D_2O$ and $(CH_3)_2CH-OD$, and the like; to yield the corresponding compound of formula (XXXIII).

The compound of formula (XXXIII) is then substituted for the compound of formula (VI) in Scheme 1 or Scheme 6, and reacted as described therein, to yield the corresponding compound of formula (Id).

Compounds of formula (I) wherein each $R^7$ is deuterium may be similarly prepared as described in Scheme 9, below.

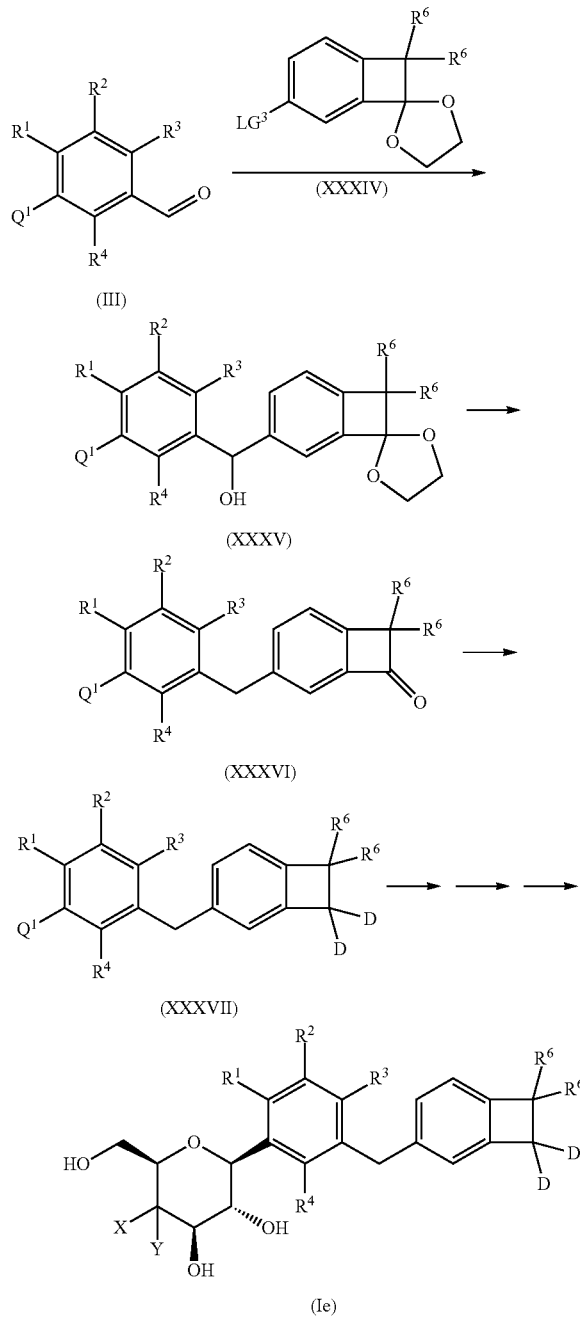

(Ie)

Accordingly, a suitably substituted compound of formula (III), wherein $Q^1$ is a suitably selected halogen such as Br, I, Cl, and the like, a known compound or compound prepared by known methods, is reacted with a suitably substituted compound of formula (XXXIV), wherein $LG^3$ is a suitably selected leaving group such as Br, I, and the like, a known compound or compound prepared by known methods; wherein the compound of formula (XXXIV) is pretreated with a suitably selected base such as n-BuLi, t-BuLi, sec-BuLi, and the like; in a suitably selected solvent such as THF, diethyl ether, and the like; at a temperature in the range of from about −78° C. to about 20° C., preferably at about −78° C.; to yield the corresponding compound of formula (XXXV).

The compound of formula (XXXV) is reacted with a suitably selected reducing/de-protecting agent such as TMSI, a mixture of TFA and $Et_3SiH$, a mixture of $BF_3.Et_2O$ and $Et_3SiH$, and the like; in a suitably selected organic solvent such as DCM, $CH_3CN$, and the like; to yield the corresponding compound of formula (XXXVI).

The compound of formula (XXXVI) is reacted with a suitably selected reducing agent such as $HgCl_2$ in the presence of Zn, a mixture of $NaBD_4$ and $AlCl_3$, a mixture of $LiAlD_4$ and $AlCl_3$, and the like; in the presence of a suitably selected acid such as DCl, $CD_3COOD$, $CF_3COOD$, and the like; in a suitably selected deuterated alcohol or mixture of deuterated water and deuterated alcohol, such as a mixture of $D_2O$ and $CH_3CH_2OD$, a mixture of $D_2O$ and $CH_3OD$, a mixture $D_2O$ and $(CH_3)_2CH-OD$, and the like; to yield the corresponding compound of formula (XXXVII).

The compound of formula (XXXVII) is then substituted for the compound of formula (VI) in Scheme 1 or Scheme 6, and reacted as described therein, to yield the corresponding compound of formula (Ie).

Compounds of formula (I) wherein each $R^6$ and each $R^7$ is deuterium may be prepared as described in Scheme 10, below.

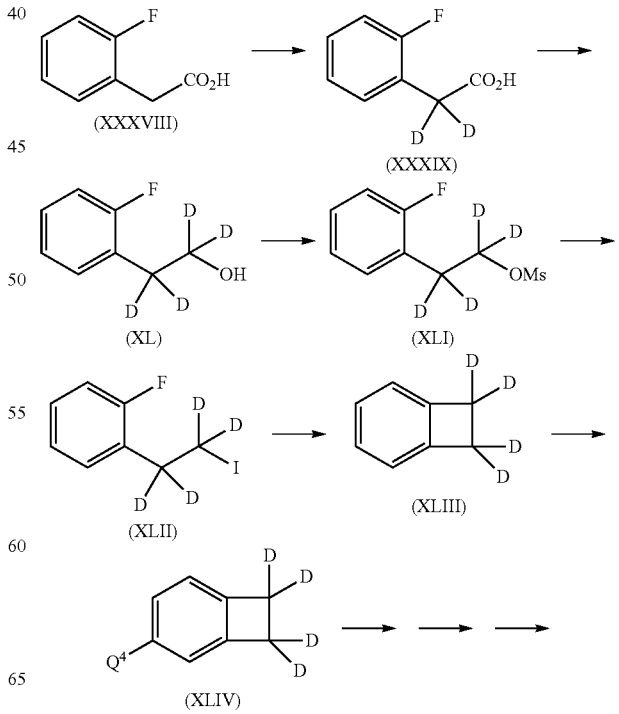

-continued

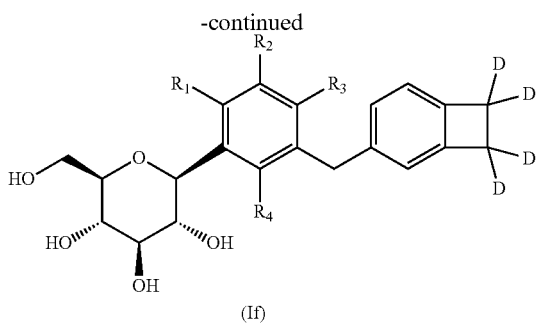

(If)

Accordingly, a compound of formula (XXXVIII), a known compound is reacted with a suitably selected base such as $K_2CO_3$, NaOH, KOH, and the like; in the presence of deuterated water; to yield the corresponding compound of formula (XXXIX).

The compound of formula (XXXIX) is reacted with a suitably selected deuterated reducing agent such as $NaBD_4$, $LiAlD_4$, $BD_3 \cdot THF$, and the like; in the presence of a suitably selected Lewis acid such as $BF_3 \cdot Et_2O$, TFA, $AlCl_3$, and the like; in a suitably selected organic solvent such as DCM, diethyl ether, and the like; at a temperature in the range of from about 0° C. to about 78° C., preferably at about reflux temperature; to yield the corresponding compound of formula (XL).

The compound of formula (XL) is reacted with a suitably selected sulfonylating agent such as MsCl, TsCl, $Tf_2O$, and the like; in the presence of a suitably selected base such as TEA, DIPEA, pyridine, and the like; in a suitably selected solvent such as DCM, THF, $CH_3CN$, and the like; to yield the corresponding compound of formula (XLI).

The compound of formula (XLI) is reacted with a suitably selected iodinating agent such as NaI, KI, LiI, and the like; in a suitably selected solvent such as acetone, THF, $CH_3CN$, and the like; to yield the corresponding compound of formula (XLII).

The compound of formula (XLII) is reacted with a suitably selected base such as n-BuLi, t-BuLi, sec-BuLi, and the like; in a suitably selected solvent such as THF, diethyl ether, and the like; at a temperature in the range of from about −78° C. to about 20° C., preferably at about −78° C.; to yield the corresponding compound of formula (XLIII).

The compound of formula (XLIII) is reacted with a suitably selected halogenating agent, for example a suitably selected brominating agent such as $Br_2$, NBS, and the like, or a suitably selected chlorinating agent such as $Cl_2$, NCS, and the like; in the presence of a suitably selected acid such as acetic acid, TFA, $H_2SO_4$, and the like; in a suitably selected solvent such as DCM, methanol, $CH_3CN$, and the like; to yield the corresponding compound of formula (XLIV), wherein $Q^4$ is the corresponding halogen.

The compound of formula (XLIV) is then substituted for the compound of formula (IV) in Scheme 1-3, or the compound of formula (XXII) in Scheme 4-5, and reacted as described in Schemes 1-6 above, to yield the corresponding compound of formula (If).

Compounds of formula (I) wherein each $R^5$ is fluoro may be prepared as described in Scheme 11.

Scheme 11

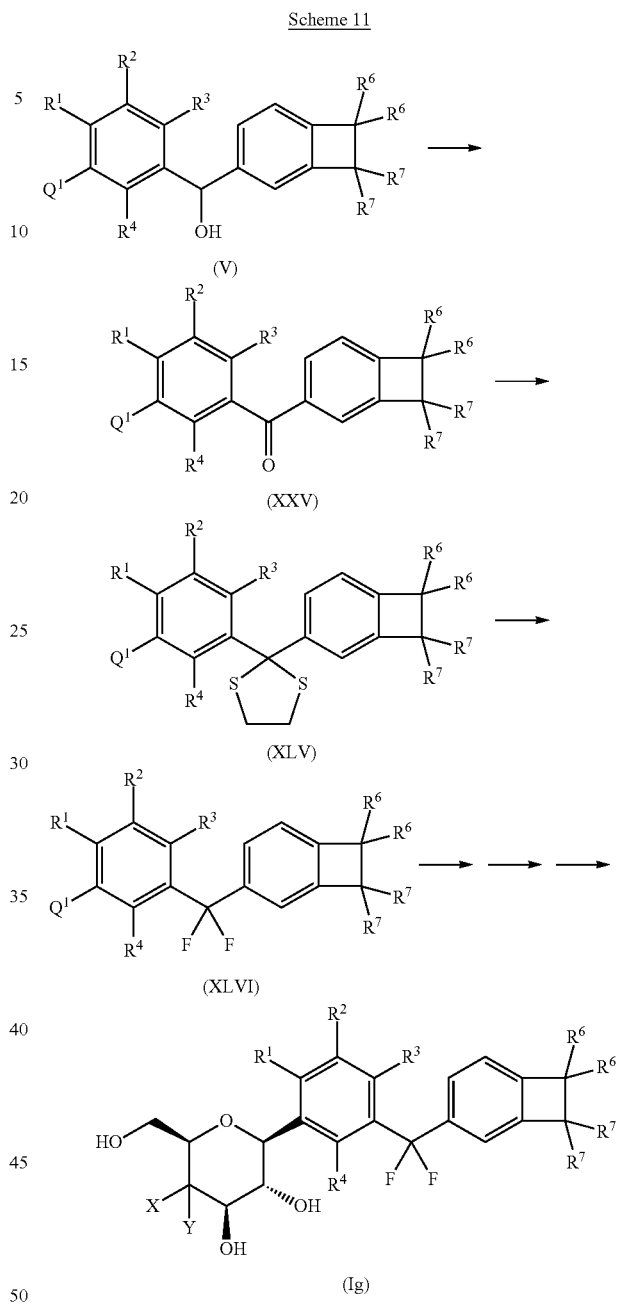

Accordingly, a suitably substituted compound of formula (V), prepared for example as described in Scheme 1 above, is reacted with a suitably selected oxidizing agent such as Dess-Martin periodinane (also known as Dess-Martin Reagent), $MnO_2$, PCC, and the like; in a suitably selected organic solvent such as DCM, DCE, and the like; to yield the corresponding compound of formula (XXV).

The compound of formula (XXV) is reacted with ethane-1,2-dithiol, a known compound; in the presence of a suitably selected Lewis acid such as $BF_3 \cdot Et_2O$, $AlCl_3$, $BF_3 \cdot AcOH$, and the like; in a suitably selected organic solvent such as DCM, AcOH, $CHCl_3$, and the like; to yield the corresponding compound of formula (XLV).

The compound of formula (XLV) is reacted with a suitably selected fluorinating agent such as PPHF, DAST, and the like; in a suitably selected organic solvent such as DCM, diethyl ether, CH$_3$CN, and the like; to yield the corresponding compound of formula (XLVI).

The compound of formula (XLVI) is then substituted for the compound of formula (VI) in Scheme 1 or Scheme 6, and reacted as described therein, to yield the corresponding compound of formula (Ig).

Compounds of formula (I) wherein for example, R$^1$ is OCD$_3$ may be prepared by reacting the corresponding compound of formula (I) wherein R$^1$ is OH with a suitably substituted deuterated methylhalide such as CD$_3$I, and the like; in the presence of a suitably selected base such as K$_2$CO$_3$, Cs$_2$CO$_3$, NaOH, and the like; in a suitably selected organic solvent such as acetonitrile, acetone, DMF, and the like.

One skilled in the art will recognize that additional isotopically substituted compounds of formula (I) may be prepared by reacting any of the intermediates or compounds of formula (I) described herein with a suitably substituted, isotopically labelled reagent, according to methods known in the art; and then reacting the resulting isotopically substituted compound or intermediate, as necessary, according to the schemes described herein, to yield the corresponding isotopically substituted compound of formula (I) (i.e. the corresponding isotopologue).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.05 mg/day to about 300 mg/day, or any amount or range therein, preferably from about 0.1 mg/day to about 100 mg/day, or any amount or range therein, preferably from about 1 mg/day to about 50 mg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders mediated by SGLT activity, preferably dual SGLT1 and SGLT2 activity, described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Compounds of this invention may be administered in any of the foregoing compositions and according to dosage regimens established in the art whenever treatment of disorders mediated by SGLT activity, preferably dual SGLT1 and SGLT2 activity, is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example A (3R,4R,6R)-3,4-bis(benzyloxy)-6-((benzyloxy)methyl)-5,5-difluorotetrahydro-2H-pyran-2-one

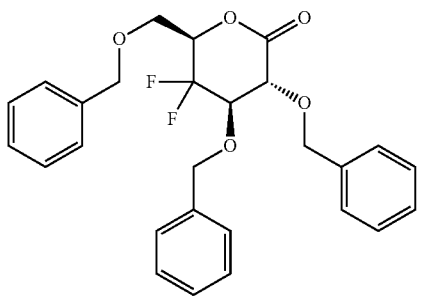 [SMILES: O=C1O[C@H](COCc2ccccc2)C(F)(F)[C@H](OCc2ccccc2)[C@H]1OCc1ccccc1]

Step 1: (4aR,6S,7R,8R,8aR)-6-(allyloxy)-2-phenyl-hexahydropyrano[3,2-d][1,3]dioxine-7,8-diol Into a 3-L 3-necked round-bottom flask purged and maintained with an inert atmosphere of nitrogen, was placed (2R,3R,4S,5R,6S)-2-(hydroxymethyl)-6-(prop-2-en-1-yloxy)oxane-3,4,5-triol (80 g, 363.27 mmol, 1.00 equiv), CSA (250 mg), (dimethoxymethyl)benzene (82 g, 538.80 mmol, 1.48 equiv), $CHCl_3$ (1.2 L). The resultant suspension was placed in a preheated oil bath (bath temp. 90° C.), and the distillate was collected. After approximately 15 mL was collected, the same volume of $CHCl_3$ was added. This process was repeated. The reaction progress was monitored by TLC. The resulting mixture was washed with 1×500 mL of water and 1×500 mL of saturated aqueous sodium bicarbonate. The resulting mixture was washed with 1×500 mL of brine. The mixture was dried over anhydrous sodium sulfate and concentrated under vacuum. The resulting residue was washed with PE/EA (20:1) to yield (4aR,6S,7R,8R,8aR)-2-phenyl-6-(prop-2-en-1-yloxy)-hexahydro-2H-pyrano[3,2-d][1,3]dioxine-7,8-diol as a white solid. $^1$H NMR: (300 MHz, $CDCl_3$): δ 7.54-7.47 (m, 2H), 7.41-7.34 (m, 3H), 5.99-5.86 (m, 1H), 5.55 (s, 1H), 5.34-5.21 (m, 2H), 5.09 (s, 1H), 4.29-4.21 (m, 3H), 4.11-4.05 (m, 2H), 3.93 (s, 2H), 3.74 (s, 1H). LC-MS (ES, m/z): 634.2 $[2M+NH_4]^+$

Step 2: (4aR,6S,7R,8S,8aS)-6-(allyloxy)-7,8-bis(benzyloxy)-2-phenylhexahydropyrano[3,2-d][1,3]dioxine Into a 3-L 3-necked round-bottom flask purged and maintained with an inert atmosphere of nitrogen, was placed (4aR,6S,7R,8R,8aR)-2-phenyl-6-(prop-2-en-1-yloxy)-hexahydro-2H-pyrano[3,2-d][1,3]dioxine-7,8-diol (100 g, 324.33 mmol, 1.00 equiv), N,N-dimethylformamide (1 L). This was followed by the addition of sodium hydride (39 g, 1.62 mol, 3.00 equiv, 60%), in portions at 0-10° C. The resulting solution was stirred for 30 minutes. To the resulting mixture was then added benzylbromide (166 g, 970.57 mmol, 2.99 equiv) dropwise with stirring at 0-10° C. The resulting solution was stirred overnight at room temperature. The reaction mixture was then poured into 3 L of water/ice. The resulting solution was extracted with 2×1 L of ethyl acetate and the organic layers combined. The resulting mixture was washed with 5×1 L of water and 2×1 L of brine. The mixture was dried over anhydrous sodium sulfate and concentrated under vacuum. The resulting mixture was washed with PE/EA (50:1) to yield (4aR,6S,7R,8S,8aS)-7,8-bis(benzyloxy)-2-phenyl-6-(prop-2-en-1-yloxy)-hexahydro-2H-pyrano[3,2-d][1,3]dioxine as a white solid. $^1$H NMR: (300 MHz, $CDCl_3$): δ 7.46-7.43 (m, 2H), 7.35-7.18 (m, 13H), 5.86-8.80 (m, 1H), 5.41 (s, 1H), 5.27-5.12 (m, 2H), 4.90 (s, 1H), 4.81-4.75 (m, 2H), 4.69-4.58 (m, 2H), 4.16-3.91 (m, 7H), 3.57 (s, 1H). LC-MS (ES, m/z): 506.2 $[M+NH_4]^+$

Step 3: (2R,3S,4S,5R,6S)-6-(allyloxy)-4,5-bis(benzyloxy)-2-((benzyloxy)methyl)tetrahydro-2H-pyran-3-ol Into a 3-L 3-necked round-bottom flask purged and maintained with an inert atmosphere of nitrogen, was placed (4aR,6S,7R,8S,8aS)-7,8-bis(benzyloxy)-2-phenyl-6-(prop-2-en-1-yloxy)-hexahydro-2H-pyrano[3,2-d][1,3]dioxine (128.3 g, 262.60 mmol, 1.00 equiv), dry dichloromethane (1.8 L), 4 Å molecular sieve (MS) (120 g). This was followed by the addition of triethylsilane (91.5 g, 786.92 mmol, 3.00 equiv) at −78° C. To the resulting mixture was then added trifluoromethanesulfonic acid (78.9 g, 525.73 mmol, 2.00 equiv) dropwise with stirring at −78° C. The resulting solution was stirred at −78° C. for 1 h. The reaction mixture was then quenched by the addition of 1.5 L of water. The resulting solution was extracted with 2×1.5 L of dichloromethane and the organic layers combined. The resulting mixture was washed with 1×1.5 L of saturated aqueous sodium bicarbonate and 2×1.5 L of brine. The mixture was dried over anhydrous sodium sulfate and concentrated under vacuum. The residue was applied onto a silica gel column with ethyl acetate/petroleum ether (0:1-1:3) to yield (2R,3S,4S,5R,6S)-4,5-bis(benzyloxy)-2-[(benzyloxy)methyl]-6-(prop-2-en-1-yloxy)oxan-3-ol as light yellow oil. LC-MS (ES, m/z): 508.2 $[M+NH_4]^+$

Step 4: (2R,4R,5R,6S)-6-(allyloxy)-4,5-bis(benzyloxy)-2-((benzyloxy)methyl)dihydro-2H-pyran-3 (4H)-one Into a 3-L 3-necked round-bottom flask purged and maintained with an inert atmosphere of nitrogen, was placed (2R,3S, 4S, 5R, 6S)-4,5-bis(benzyloxy)-2-[(benzyloxy)methyl]-6-(prop-2-en-1-yloxy)oxan-3-ol (85 g, 173.26 mmol, 1.00 equiv), DMSO (850 mL). This was followed by the addition of $Ac_2O$ (420 mL) dropwise with stirring at 10° C. The resulting solution was stirred for 1 h at 30° C. The resulting solution was allowed to react, with stirring, for an additional 1 h at 60° C. The reaction mixture was then quenched by the addition of 1.5 L of water/ice. The resulting solution was extracted with 2×1 L of ethyl acetate and the organic layers combined. The resulting mixture was washed with 5×1 L of water and 1×1 L of saturated aqueous sodium bicarbonate. The resulting mixture was washed with 2×1 L of brine. The mixture was dried over anhydrous sodium sulfate and concentrated under vacuum. The residue was applied onto a silica gel column with ethyl acetate/petroleum ether (0:1-1:4) to yield (2R,4R,5R,6S)-4,5-bis(benzyloxy)-

2-[(benzyloxy)methyl]-6-(prop-2-en-1-yloxy)oxan-3-one as light yellow oil. LC-MS (ES, m/z): 506.2 [M+NH$_4$]$^+$ Step 5: (2R,4R,5R,6S)-6-(allyloxy)-4,5-bis(benzyloxy)-2-((benzyloxy)methyl)-3,3-difluorotetrahydro-2H-pyran Into a 1-L 3-necked round-bottom flask purged and maintained with an inert atmosphere of nitrogen, was placed (2R,4R,5R,6S)-4,5-bis(benzyloxy)-2-[(benzyloxy)methyl]-6-(prop-2-en-1-yloxy)oxan-3-one (50 g, 102.34 mmol, 1.00 equiv), dichloromethane (500 mL), DAST (66 g, 409.94 mmol, 4.01 equiv). The resulting solution was stirred overnight at room temperature. The reaction mixture was then quenched by the addition of 1 L of water/ice. The resulting solution was extracted with 2×500 mL of dichloromethane and the organic layers combined. The resulting mixture was washed with 1×500 mL of saturated aqueous sodium bicarbonate and 2×500 mL of brine. The mixture was dried over anhydrous sodium sulfate and concentrated under vacuum. The residue was applied onto a silica gel column with ethyl acetate/petroleum ether (0:1-1:20) to yield (2R,4R,5R,6S)-4,5-bis(benzyloxy)-2-[(benzyloxy)methyl]-3,3-difluoro-6-(prop-2-en-1-yloxy)oxane as colorless oil. LC-MS (ES, m/z): 508.2

Step 6: (3R,4R,6R)-3,4-bis(benzyloxy)-6-((benzyloxy)methyl)-5,5-difluorotetrahydro-2H-pyran-2-ol Into a 1-L 3-necked round-bottom flask purged and maintained with an inert atmosphere of nitrogen, was placed (2R,4R,5R,6S)-4,5-bis(benzyloxy)-2-[(benzyloxy)methyl]-3,3-difluoro-6-(prop-2-en-1-yloxy)oxane (53 g, 103.81 mmol, 1.00 equiv), polymethylhydrosiloxane (PMHS) (101.6 g, 311.66 mmol, 3.00 equiv), ZnCl$_2$ (14.1 g, 103.44 mmol, 1.00 equiv), tetrakis(triphenylphosphane) palladium (12 g, 10.38 mmol, 0.10 equiv), THF (530 mL). The resulting solution was stirred overnight at room temperature. The reaction mixture was then quenched by the addition of 1 L of water. The resulting solution was extracted with 2×500 mL of ethyl acetate and the organic layers combined. The resulting mixture was washed with 2×500 mL of brine. The mixture was dried over anhydrous sodium sulfate and concentrated under vacuum. The residue was applied onto a silica gel column with ethyl acetate/petroleum ether (0:1-1:5) to yield (3R,4R,6R)-3,4-bis(benzyloxy)-6-[(benzyloxy) methyl]-5,5-difluorooxan-2-ol as a white solid. LC-MS (ES, m/z): 488.2 [M+NH$_4$]$^+$ Step 7: (3R,4R,6R)-3,4-bis(benzyloxy)-6-((benzyloxy)methyl)-5,5-difluorotetrahydro-2H-pyran-2-one Into a 500-mL round-bottom flask purged and maintained with an inert atmosphere of nitrogen, was placed a solution of (2S,3R, 4R, 6R)-3,4-bis(benzyloxy)-6-[(benzyloxy) methyl]-5,5-difluorooxan-2-ol (10 g, 21.25 mmol, 1.00 equiv) in DMSO (100 mL). This was followed by the addition of acetic anhydride (25 mL) at 0-10° C. The resulting solution was stirred overnight at room temperature. The reaction mixture was then quenched by the addition of 100 mL of water. The resulting solution was extracted with 3×100 mL of ethyl acetate and the organic layers combined. The resulting mixture was washed with 3×300 mL of H$_2$O. The resulting mixture was washed with 3×300 mL of aqueous sodium bicarbonate. The resulting mixture was concentrated under vacuum. The residue was applied onto a silica gel column with ethyl acetate/petroleum ether (1:5) to yield (3R,4R,6R)-3,4-bis(benzyloxy)-6-[(benzyloxy) methyl]-5,5-difluorooxan-2-one as a white solid.

Example 1: Compound #1

(2S,3R,4R,5S,6R)-2-(3-((1,2-dihydrocyclobutabenzen-4-yl)methyl)-4-methylphenyl)-6-(hydroxymethyl)-tetrahydro-2H-pyran-3,4,5-triol

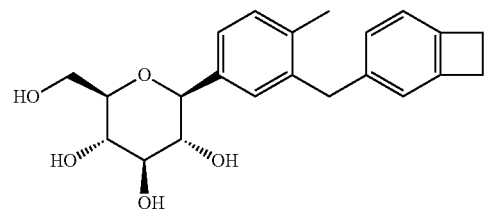 [SMILES: Cc1ccc([C@@H]2O[C@H](CO)[C@@H](O)[C@H](O)[C@H]2O)cc1Cc1ccc2c(c1)CC2]

To a mixture of 3-bromobicyclo[4.2.0]octa-1,3,5-triene (10 g, 54.63 mmol, 1.00 equiv) in THF (100 mL) was added n-BuLi (2.5 M in hexane, 21.9 mL, 1.00 equiv) dropwise with stirring at −78° C. The reaction mixture was stirred for 20 min at −78° C. To the resulting mixture was then added a solution of 5-bromo-2-methylbenzaldehyde (11.4 g, 57.27 mmol, 1.05 equiv) in THF (10 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (20:1 PE/EA) to yield (5-bromo-2-methylphenyl)(1,2-dihydrocyclobutabenzen-4-yl)methanol as colorless oil. $^1$H NMR (400 MHz, Chloroform-d) δ 7.83 (d, J=2.2 Hz, 1H), 7.34 (dd, J=8.0, 2.2 Hz, 1H), 7.17 (dd, J=7.5, 1.5 Hz, 1H), 6.96-7.07 (m, 3H), 5.89 (s, 1H), 3.16 (s, 5H), 2.15 (s, 3H).

To a mixture of (5-bromo-2-methylphenyl)(1,2-dihydrocyclobutabenzen-4-yl)methanol (14 g, 46.18 mmol, 1.00 equiv) in dichloromethane (100 mL) with Et$_3$SiH (11 g, 94.60 mmol, 2.00 equiv) was added CF$_3$COOH (11 g, 97.31 mmol, 2.00 equiv) at 0° C. The reaction mixture was stirred for 3 h at 0° C. Sodium bicarbonate was added and the mixture was extracted with DCM thrice. The combined extracts were washed with brine and dried over Na$_2$SO$_4$, concentrated and purified by chromatography on silica gel (5:1 PE/EA) to yield 4-(5-bromo-2-methylbenzyl)-1,2-dihydrocyclobutabenzene as colorless oil. $^1$H NMR (300 MHz, Chloroform-d) δ 7.20-7.32 (m, 2H), 7.03 (d, J=8.0 Hz, 1H), 6.97 (d, J=1.2 Hz, 2H), 6.81 (s, 1H), 3.92 (s, 2H), 3.15 (s, 4H), 2.21 (s, 3H).

To a mixture of 4-(5-bromo-2-methylbenzyl)-1,2-dihydrocyclobutabenzene (8.86 g, 30.85 mmol, 1.10 equiv) in tetrahydrofuran/toluene (37.5/75 mL) was added n-BuLi (2.5 M in hexane, 11.8 mL, 29.50 mmol, 1.05 equiv) dropwise with stirring at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (15.1 g, 28.03 mmol, 1.00 equiv) in tetrahydrofuran/toluene (7.5/15 mL) dropwise with stirring at −78° C. The reaction mixture was stirred for 2 h at −78° C. NH$_4$Cl/H$_2$O was added and the mixture was extracted with EtOAc thrice. The combined extracts were washed with brine and dried over Na$_2$SO$_4$, then concentrated to yield (3R,4S,5R,6R)-3,4,5-tris(benzyloxy)-6-(benzyloxymethyl)-2-(3-((1,2-dihydrocyclobut-abenzen-4-yl)methyl)-4-methylphenyl)-tetrahydro-2H-pyran-2-ol as yellow oil.

To a mixture of (3R,4S,5R,6R)-3,4,5-tris(benzyloxy)-6-(benzyloxymethyl)-2-(3-((1,2-dihydrocyclobutabenzen-4-yl)methyl)-4-methylphenyl)-tetrahydro-2H-pyran-2-ol (22.2 g, 29.72 mmol, 1.00 equiv) in dichloromethane (250 mL) with Et$_3$SiH (6.89 g, 59.25 mmol, 2.00 equiv) was added BF$_3$.Et$_2$O (8.43 g, 59.36, 2.00 equiv) dropwise at 0° C. The reaction mixture was stirred for 1.5 h at 0° C. Sodium bicarbonate was added and the mixture was extracted with DCM thrice. The combined extracts were washed with brine and dried over Na$_2$SO$_4$, then concentrated and purified by chromatography on silica gel (10:1 PE/EA) to yield (2R,3R,4R,5S,6S)-3,4,5-tris(benzyloxy)-2-(benzyloxymethyl)-6-(3-((1,2-dihydrocyclobutabenzen-4-yl)methyl)-4-methylphenyl)-tetrahydro-2H-pyran as light yellow oil. MS (ES) m/z: 731.3 [M+H]$^+$.

To a mixture of (2R,3R,4R,5S,6S)-3,4,5-tris(benzyloxy)-2-(benzyloxymethyl)-6-(3-((1,2-dihydrocyclobutabenzen-4-yl)methyl)-4-methylphenyl)-tetrahydro-2H-pyran (10 g, 13.68 mmol, 1.00 equiv) in dichloromethane (120 mL) with 1,2,3,4,5-pentamethylbenzene (18.22 g, 122.90 mmol, 9.00 equiv) was added BCl$_3$ (95.8 mL, 95.80 mmol, 7.00 equiv) dropwise at −78° C. The reaction mixture was stirred for 1 h at −78° C. Methanol was added. The resulting mixture was then concentrated and purified by chromatography on C18 (10%-50% CH$_3$CN/H$_2$O) to yield the title compound as a white solid.

$^1$H NMR (400 MHz, Methanol-d$_4$) δ 7.21 (d, J=6.6 Hz, 2H), 7.14 (d, J=7.3 Hz, 1H), 6.98 (d, J=7.2 Hz, 1H), 6.90 (d, J=7.6 Hz, 1H), 6.80 (s, 1H), 4.10 (d, J=9.3 Hz, 1H), 3.97 (d, J=2.0 Hz, 2H), 3.90 (d, J=12.4 Hz, 1H), 3.70 (dd, J=12.0, 4.7 Hz, 1H), 3.48 (dd, J=11.1, 5.8 Hz, 1H), 3.36-3.44 (m, 3H), 3.11 (s, 4H), 2.20 (s, 3H). MS (ES) m/z: 369.1 [M−H]$^−$.

Example 2: Compound #2

(2S,3R,4R,5S,6R)-2-(4-chloro-3-((1,2-dihydrocyclobutabenzen-4-yl)methyl)phenyl)-6-(hydroxymethyl)-tetrahydro-2H-pyran-3,4,5-triol

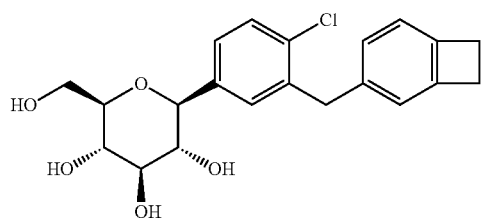 [SMILES: OC[C@H]1O[C@@H](c2ccc(Cl)c(Cc3ccc4c(c3)CC4)c2)[C@H](O)[C@@H](O)[C@@H]1O]

To a mixture of 3-bromobicyclo[4.2.0]octa-1,3,5-triene (10 g, 54.63 mmol, 1.10 equiv) in THF (100 mL) was added n-BuLi (2.5 M in hexane, 21.9 mL, 1.10 equiv) dropwise with stirring at −78° C. The reaction mixture was stirred for 20 min at −78° C. To the resulting mixture was then added a solution of 5-bromo-2-chlorobenzaldehyde (10.9 g, 49.67 mmol, 1.00 equiv) in THF (20 mL) dropwise at −78° C. The reaction mixture was stirred for 2 h at −78° C. NH$_4$Cl/H$_2$O was added and the mixture was extracted with EtOAc thrice, then concentrated and purified by chromatography on silica gel (10:1 PE/EA) to yield (5-bromo-2-chlorophenyl)(1,2-dihydrocyclobutabenzen-4-yl)methanol as light brown oil. MS (ES) m/z: 305.0, 307.0 [M-OH].

To a mixture of (5-bromo-2-chlorophenyl)(1,2-dihydrocyclobutabenzen-4-yl)methanol (11.61 g, 35.88 mmol, 1.00 equiv) in dichloromethane (100 mL) with Et$_3$SiH (8.31 g, 71.47 mmol, 2.00 equiv) was added BF$_3$.Et$_2$O (10.18 g, 71.69 mmol, 2.00 equiv) dropwise at 0° C. The reaction mixture was stirred for 1.5 h at 0° C. Sodium bicarbonate was added and the mixture was extracted with DCM thrice, then concentrated and purified by chromatography on silica gel (10:1 PE/EA) to yield 4-(5-bromo-2-chlorobenzyl)-1,2-dihydrocyclobutabenzene as light yellow oil. $^1$H NMR (300 MHz, DMSO-d$_6$) δ 7.51 (d, J=2.3 Hz, 1H), 7.49-7.34 (m, 2H), 7.10-6.97 (m, 2H), 6.93 (s, 1H), 4.01 (s, 2H), 3.08 (s, 4H).

To a mixture of 4-(5-bromo-2-chlorobenzyl)-1,2-dihydrocyclobutabenzene (7.76 g, 25.23 mmol, 1.10 equiv) in tetrahydrofuran/toluene (40/80 mL) was added n-BuLi (9.8 mL, 2.5 M in hexane, 24.51 mmol, 1.07 equiv) dropwise with stirring at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (12.35 g, 22.93 mmol, 1.00 equiv) in tetrahydrofuran/toluene (10/20 mL) dropwise with stirring at −78° C. The reaction mixture was stirred for 2 h at −78° C. NH$_4$Cl/H$_2$O was added and the mixture was extracted with EtOAc thrice, then concentrated and purified by chromatography on silica gel (15:1 PE/EA) to yield (3R,4S,5R,6R)-3,4,5-tris(benzyloxy)-6-(benzyloxymethyl)-2-(4-chloro-3-((1,2-dihydrocyclobutabenzen-4-yl)methyl) phenyl)-tetrahydro-2H-pyran-2-ol as yellow oil. MS (ES) m/z: 749.3 [M−OH]$^+$.

To a mixture of (3R,4S,5R,6R)-3,4,5-tris(benzyloxy)-6-(benzyloxymethyl)-2-(4-chloro-3-((1,2-dihydrocyclobutabenzen-4-yl)methyl)phenyl)-tetrahydro-2H-pyran-2-ol (19.68 g, 25.65 mmol, 1.00 equiv) in dichloromethane (200 mL) with Et$_3$SiH (5.95 g, 51.17 mmol, 2.00 equiv) was added BF$_3$.Et$_2$O (7.29 g, 51.34 mmol, 2.00 equiv) dropwise at 0° C. The reaction mixture was stirred for 1.5 h at 0° C. Sodium bicarbonate was added and the mixture was extracted with DCM thrice, then concentrated and purified by chromatography on silica gel (15:1 PE/EA) to yield (2R,3R,4R,5S,6S)-3,4,5-tris(benzyloxy)-2-(benzyloxymethyl)-6-(4-chloro-3-((1,2-dihydrocyclobutabenzen-4-yl)methyl)phenyl)-tetrahydro-2H-pyranas yellow oil. MS (ES) m/z: 773.3 [M+Na]$^+$.

To a mixture of (2R,3R,4R,5S,6S)-3,4,5-tris(benzyloxy)-2-(benzyloxymethyl)-6-(4-chloro-3-((1,2-dihydrocyclobutabenzen-4-yl)methyl)phenyl)-tetrahydro-2H-pyran (15.6 g, 20.76 mmol, 1.00 equiv) in dichloromethane (200 mL) with 1,2,3,4,5-pentamethylbenzene (27.67 g, 186.65 mmol, 9.00 equiv) was added BCl$_3$ (145.4 mL, 1 M in DCM, 145.40 mmol, 7.00 equiv) dropwise at −78° C. The reaction mixture was stirred for 1 h at −78° C. Methanol was added, and the resulting mixture concentrated and purified by chromatography on C18 reverse phase column (10%-50% CH3CN/H2O) to yield the title compound as a white solid.

$^1$H NMR (400 MHz, Methanol-d$_4$) δ 7.39-7.27 (m, 3H), 7.04 (d, J=7.6 Hz, 1H), 6.93 (d, J=7.6 Hz, 1H), 6.88 (s, 1H), 4.01-4.12 (m, 3H), 3.89 (d, J=11.2 Hz, 1H), 3.67-3.74 (m, 1H), 3.38-3.50 (m, 3H), 3.29 (d, J=9.0 Hz, 1H), 3.12 (s, 4H); MS (ES) m/z: 389.0 [M−H]$^−$.

Example 3: Compound #3

(2S,3R,4R,5S,6R)-2-(3-((1,2-dihydrocyclobutaben-zen-4-yl)methyl)-4-methoxyphenyl)-6-(hydroxymethyl)-tetrahydro-2H-pyran-3,4,5-triol

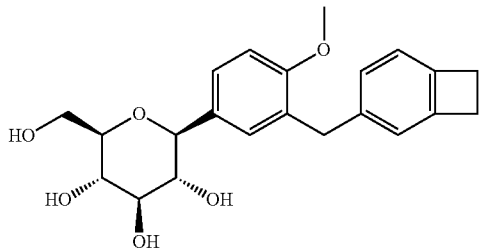 [SMILES: COc1ccc([C@@H]2O[C@H](CO)[C@@H](O)[C@H](O)[C@H]2O)cc1Cc1ccc2c(c1)CC2]

To a mixture of 3-bromobicyclo[4.2.0]octa-1,3,5-triene (80 g, 437.05 mmol, 1.05 equiv) in THF (800 mL) was added n-BuLi (2.5M in hexane, 180 mL, 1.10 equiv) dropwise at −78° C., and the reaction mixture was stirred at −78° C. for 30 min. 5-Bromo-2-methoxybenzaldehyde (89.5 g, 416.19 mmol, 1.00 equiv) in THF (800 mL) was then added to the solution dropwise at −78° C. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated and purified by chromatography on silica gel (10:1 PE/EA) to yield (5-bromo-2-methoxyphenyl)(1,2-dihydrocyclobutabenzen-4-yl)methanol as a colorless oil.

To a mixture of (5-bromo-2-methoxyphenyl)(1,2-dihydrocyclobutabenzen-4-yl)methanol (140 g, 438.61 mmol, 1.00 equiv) in DCM (1000 mL) with $Et_3SiH$ (102 g, 877.22 mmol, 2.00 equiv) was added TFA (100 g, 877.01 mmol, 2.00 equiv) dropwise at 0° C. The reaction mixture was stirred at 0° C. for 1 h. Sodium bicarbonate/$H_2O$ was added and the mixture was extracted with dichloromethane thrice. The combined extracts were washed with brine and dried over $Na_2SO_4$, then concentrated and purified by chromatography on silica gel (10:1 PE/EA) to yield 4-(5-bromo-2-methoxybenzyl)-1,2-dihydrocyclobutabenzene as a colorless oil.

To a mixture of 4-(5-bromo-2-methoxybenzyl)-1,2-dihydrocyclobutabenzene (11 g, 36.28 mmol, 1.05 equiv) in THF (180 mL) was added n-BuLi (2.5M in hexane, 15.2 mL, 1.10 equiv) dropwise at −78° C., and the mixture was stirred at −78° C. for 30 min. (3R,4S,5R,6R)-3,4,5-Tris[(trimethylsilyl)oxy]-6-[[(trimethylsilyl)oxy]methyl]oxan-2-one (16.1 mg, 34.49 mmol, 1.00 equiv) in THF (20 mL) was then added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated to (3R,4S,5R,6R)-2-(3-((1,2-dihydrocyclobutabenzen-4-yl)methyl)-4-methoxyphenyl)-3,4,5-tris(trimethylsilyloxy)-6-((trimethylsilyloxy)methyl)-tetrahydro-2H-pyran-2-ol as a light yellow oil.

To a mixture of (3R,4S,5R,6R)-2-(3-((1,2-dihydrocyclobutabenzen-4-yl)methyl)-4-methoxyphenyl)-3,4,5-tris(trimethylsilyloxy)-6-((trimethylsilyloxy)methyl)-tetrahydro-2H-pyran-2-ol (26 g) in MeOH (300 mL) was added $CH_3SO_3H$ (3.61 g, 37.56 mmol, 1.00 equiv) at −78° C. The reaction mixture was stirred overnight at room temperature. Sodium bicarbonate/$H_2O$ was added and the mixture was extracted with EtOAc thrice. The combined extracts were washed with brine and dried over $Na_2SO_4$, then concentrated and purified by chromatography on silica gel (10:1 DCM/MeOH) to yield (3R,4S,5S,6R)-2-(3-((1,2-dihydrocyclobutabenzen-4-yl)methyl)-4-methoxyphenyl)-6-(hydroxymethyl)-2-methoxy-tetrahydro-2H-pyran-3,4,5-triol as a off-white solid. MS (ES) m/z: 415.1 [M−H]⁻.

To a mixture of (3R,4S,5S,6R)-2-(3-((1,2-dihydrocyclobutabenzen-4-yl)methyl)-4-methoxyphenyl)-6-(hydroxymethyl)-2-methoxy-tetrahydro-2H-pyran-3,4,5-triol (6 g, 14.41 mmol, 1.00 equiv) in dichloromethane (100 mL) with $Et_3SiH$ (3.35 g, 28.81 mmol, 2.00 equiv) was added $BF_3 \cdot Et_2O$ (3.07 g, 21.62 mmol, 1.50 equiv) dropwise at −40° C. The reaction mixture was stirred at −10° C. for 2 h. Sodium bicarbonate/$H_2O$ was added and the mixture was extracted with DCM thrice. The combined extracts were washed with brine and dried over $Na_2SO_4$, then concentrated and purified by chromatography on a C18 reversed phase column to yield the title compound as a white solid.

¹H NMR (300 MHz, $CD_3OD$) δ 7.27 (dd, J=8.3, 2.2 Hz, 1H), 7.19 (d, J=2.2 Hz, 1H), 7.01-7.09 (m, 1H), 6.84-6.99 (m, 3H), 4.06 (d, J=9.1 Hz, 1H), 3.78-4.00 (m, 6H), 3.69 (dd, J=12.0, 4.5 Hz, 1H), 3.37-3.51 (m, 4H), 3.11 (s, 4H); MS (ES) m/z: 385.1 [M−H]⁻.

Example 4: Compound #4

(2S,3R,4R,5S,6R)-2-(3-((1,2-dihydrocyclobutaben-zen-4-yl)methyl)-4-ethylphenyl)-6-(hydroxymethyl)-tetrahydro-2H-pyran-3,4,5-triol

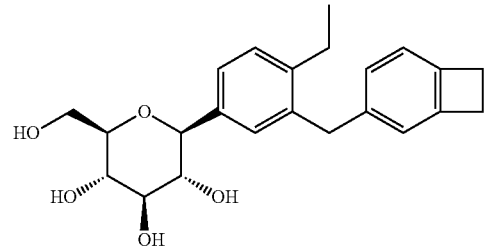 [SMILES: CCc1ccc([C@@H]2O[C@H](CO)[C@@H](O)[C@H](O)[C@H]2O)cc1Cc1ccc2c(c1)CC2]

To a mixture of 2-(bicyclo[4.2.0]octa-1(6),2,4-trien-3-ylmethyl)-4-((2S,3S,4R,5R,6R)-3,4,5-tris(benzyloxy)-6-((benzyloxy)methyl)tetrahydro-2H-pyran-2-yl)phenyl trifluoromethanesulfonate (200 mg, 0.23 mmol, 1.00 equiv) in tetrahydrofuran (15 mL) was added $Cs_2CO_3$ (226 mg, 0.69 mmol, 3.00 equiv), $Et_3B$ (0.7 mL, 3.00 equiv, 1N) Pd(dppf)$Cl_2$ (17 mg, 0.02 mmol, 0.10 equiv).

The reaction mixture was stirred for 1 h at 68° C. Water was added and the mixture was extracted with EtOAc thrice, then concentrated and purified by chromatography on silica gel (10:1 PE/EA) to yield (2R,3R,4R,5S,6S)-3,4,5-tris(benzyloxy)-2-(benzyloxymethyl)-6-(3-((1,2-dihydrocyclobutabenzen-4-yl)methyl)-4-ethylphenyl)-tetrahydro-2H-pyran as a colorless oil. 762.4 [M+$NH_4$].

To a mixture of (2R,3R,4R,5S,6S)-3,4,5-tris(benzyloxy)-2-(benzyloxymethyl)-6-(3-((1,2-dihydrocyclobutabenzen-4-yl)methyl)-4-ethylphenyl)-tetrahydro-2H-pyran (50 mg, 0.07 mmol, 1.00 equiv) in dichloromethane (10 mL) with 1,2,3,4,5-pentamethylbenzene (50 mg, 0.34 mmol, 5.03 equiv) was added $BCl_3$ (0.5 mL, 8.00 equiv, 1N) at −78° C. The reaction mixture was stirred for 1 h at −78° C. Methanol was added, and the resulting mixture concentrated and purified by chromatography on C18 (10%-50% $CH_3CN$/$H_2O$) to yield the title compound as a white solid.

1H-NMR: (300 MHz, CD₃OD) 1H NMR (300 MHz, Methanol-d4) δ 7.18-7.27 (m, 3H), 6.88-7.01 (m, 2H), 6.79 (s, 1H), 4.08 (d, J=9.1 Hz, 1H), 3.99 (d, J=1.8 Hz, 2H), 3.88 (dd, J=12.0, 1.5 Hz, 1H), 3.63-3.75 (m, 1H), 3.42 (qd, J=8.7, 5.9 Hz, 4H), 3.10 (s, 4H), 2.59 (q, J=7.5 Hz, 2H), 1.07 (t, J=7.5 Hz, 3H). MS (ES) m/z: 402.2 [M+NH₄]⁺

Example 5: Compound #5

(2S,3R,4R,5S,6R)-2-(4-cyclopropyl-3-((1,2-dihydrocyclobutabenzen-4-yl)methyl)phenyl)-6-(hydroxymethyl)-tetrahydro-2H-pyran-3,4,5-triol

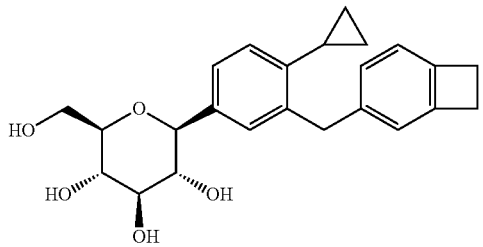 [SMILES: OC[C@H]1O[C@@H](c2ccc(C3CC3)c(Cc3ccc4c(c3)CC4)c2)[C@H](O)[C@@H](O)[C@@H]1O]

To a mixture of 5-bromo-2-hydroxybenzaldehyde (2 g, 9.95 mmol, 1.00 equiv) in N,N-dimethylformamide (20 mL) was added potassium carbonate (4.14 g, 29.95 mmol, 3.01 equiv), 3-bromoprop-1-ene (1.8 g, 14.88 mmol, 1.50 equiv). The reaction mixture was stirred overnight at room temperature. Water was added and the mixture was extracted with EtOAc thrice, then concentrated and purified by chromatography on silica gel (10:1 PE/EA) to yield 2-(allyloxy)-5-bromobenzaldehyde as a white solid. ¹H-NMR (300 MHz, CDCl₃) δ 10.44 (s, 1H), 7.93 (d, J=2.4 Hz, 1H), 7.61 (dd, J=2.7 Hz, 9.0 Hz, 1H), 6.89 (d, J=9.0 Hz, 1H), 6.00-6.12 (m, 1H), 5.33-5.48 (m, 2H), 4.64-4.67 (m, 2H).

To a mixture of 2-(allyloxy)-5-bromobenzaldehyde (1.0 g, 5.46 mmol, 1.10 equiv) in tetrahydrofuran (20 mL) was added n-BuLi (2.2 mL, 1.10 equiv, 2.5 N) at −78° C. The reaction mixture was stirred for 30 min at −78° C. To the resulting mixture was then added a solution of 5-bromo-2-(prop-2-en-1-yloxy)benzaldehyde (1.2 g, 4.98 mmol, 1.00 equiv) in tetrahydrofuran (5 mL) at −78° C. The reaction mixture was stirred for 1 h at −78° C. Water was added and the mixture was extracted with EtOAc thrice, then concentrated and purified by chromatography on silica gel (5:1 PE/EA) to yield (2-(allyloxy)-5-bromophenyl)(1,2-dihydrocyclobutabenzen-4-yl)methanol as a yellow oil. ¹H-NMR (300 MHz, CD₃OD) δ 7.53 (d, J=2.7 Hz, 1H), 7.31 (dd, J=8.7 Hz, 2.4 Hz, 1H), 7.21 (d, J=7.5 Hz, 1H), 7.08 (s, 1H), 6.99 (d, J=7.5 Hz, 1H), 6.70 (d, J=8.7 Hz, 1H), 6.02 (s, 1H), 5.88-6.00 (m, 1H), 5.24-5.34 (m, 2H), 4.47-4.49 (m, 2H), 3.14 (s, 4H).

To a mixture of (2-(allyloxy)-5-bromophenyl)(1,2-dihydrocyclobutabenzen-4-yl)methanol (1.3 g, 3.77 mmol, 1.00 equiv) in dichloromethane (20 mL) with Et₃SiH (880 mg, 7.57 mmol, 2.01 equiv) was added CF₃COOH (650 mg, 5.70 mmol, 1.51 equiv) at 0° C. The reaction mixture was stirred for 1 h at 0° C. Sodium bicarbonate was added and the mixture was extracted with DCM thrice, then concentrated and purified by chromatography on silica gel (5:1 PE/EA) to yield 14-(2-(allyloxy)-5-bromobenzyl)-1,2-dihydrocyclobutabenzene as a yellow oil. ¹H-NMR (300 MHz, CD₃OD) δ 7.24-7.31 (m, 2H), 7.11-7.13 (m, 1H), 7.98-7.03 (m, 2H), 6.74 (d, J=9.0 Hz, 1H), 6.01-6.14 (m, 1H), 5.30-5.47 (m, 2H), 4.54-4.57 (m, 2H), 3.98 (s, 2H), 3.19 (s, 4H).

To a mixture of 4-(2-(allyloxy)-5-bromobenzyl)-1,2-dihydrocyclobutabenzene (660 mg, 2.00 mmol, 1.08 equiv) in tetrahydrofuran (10 mL) was added n-BuLi (0.82 mL, 1.10 equiv) at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (1.0 g, 1.86 mmol, 1.00 equiv) in tetrahydrofuran (5 mL) dropwise with stirring at −78° C. The reaction mixture was stirred for 1 h at −78° C. Water was added and the mixture was extracted with EtOAc thrice, then concentrated and purified by chromatography on silica gel (5:1 PE/EA) to yield (3R,4S,5R,6R)-2-(4-(allyloxy)-3-((1,2-dihydrocyclobutabenzen-4-yl)methyl)phenyl)-3,4,5-tris(benzyloxy)-6-(benzyloxymethyl)-tetrahydro-2H-pyran-2-ol as a yellow oil. MS (ES) m/z: 771.3 [M−OH]⁺

To a mixture of (3R,4S,5R,6R)-2-(4-(allyloxy)-3-((1,2-dihydrocyclobutabenzen-4-yl)methyl)phenyl)-3,4,5-tris(benzyloxy)-6-(benzyloxymethyl)-tetrahydro-2H-pyran-2-ol (1.3 g, 1.65 mmol, 1.00 equiv) in dichloromethane (30 mL) with Et₃SiH (383 mg, 3.29 mmol, 2.00 equiv) was added BF₃.Et₂O (351 mg, 2.47 mmol, 1.50 equiv) at 0° C. The reaction mixture was stirred for 1 h at 0° C. Sodium bicarbonate was added and the mixture was extracted with DCM thrice, then concentrated and purified by chromatography on silica gel (5:1 PE/EA) to yield (2S,3S,4R,5R,6R)-2-(4-(allyloxy)-3-((1,2-dihydrocyclobutabenzen-4-yl)methyl)phenyl)-3,4,5-tris(benzyloxy)-6-(benzyloxymethyl)-tetrahydro-2H-pyran as a yellow oil. MS (ES) m/z: 790.6 [M+NH₄]⁺

To a mixture of (2S,3S,4R,5R,6R)-2-(4-(allyloxy)-3-((1,2-dihydrocyclobutabenzen-4-yl)methyl)phenyl)-3,4,5-tris(benzyloxy)-6-(benzyloxymethyl)-tetrahydro-2H-pyran (1.1 g, 1.42 mmol, 1.00 equiv) in tetrahydrofuran (20 mL) was added ZnCl₂ (388 mg, 2.85 mmol, 2.00 equiv), Pd(PPh₃)₄ (165 mg, 0.14 mmol, 0.10 equiv), PMHS (1.39 g, 4.26 mmol, 3.00 equiv). The reaction mixture was stirred for 5 h at room temperature. Water was added and the mixture was extracted with EtOAc thrice, then concentrated and purified by chromatography on silica gel (2:1 PE/EA) to yield 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenol as a yellow oil. MS (ES) m/z: 750.5 [M+NH₄]⁺

To a mixture of 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenol (950 mg, 1.30 mmol, 1.00 equiv) in dichloromethane (20 mL) with pyridine (308 mg, 3.89 mmol, 3.00 equiv) was added Tf₂O (732 mg, 2.59 mmol, 2.00 equiv). The resulting solution was stirred for 1 h at room temperature. Water was added and the mixture was extracted with EtOAc thrice, then concentrated and purified by chromatography on silica gel (5:1 PE/EA) to yield 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenyl trifluoromethanesulfonate as a colorless oil. MS (ES) m/z: 882.3 [M+NH₄]⁺

To a mixture of 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenyl trifluoromethanesulfonate (200 mg, 0.23 mmol, 1.00 equiv) in dioxane (10 mL) was added cyclopropylboronic acid (40 mg, 0.47 mmol, 2.01 equiv), potassium carbonate (96 mg, 0.69 mmol, 3.00 equiv), Pd(dppf)Cl₂ (17 mg, 0.02 mmol, 0.10 equiv). The reaction mixture was stirred overnight at 80° C. Water was added and the mixture was extracted with EtOAc thrice, then concentrated and purified by chromatography on silica gel (5:1 PE/EA) to yield (2R,3R,4R,5S,6S)-3,4,5-tris(benzyloxy)-2-(benzyloxymethyl)-6-(4-cyclopropyl-3-((1,2-dihydrocyclobutabenzen-4-yl)methyl)phenyl)-tetrahydro-2H-pyran as a yellow oil. MS (ES) m/z: 774.4 [M+NH$_4$]$^+$ To a mixture of (2R,3R,4R,5S,6S)-3,4,5-tris(benzyloxy)-2-(benzyloxymethyl)-6-(4-cyclopropyl-3-((1,2-dihydrocyclobutabenzen-4-yl)methyl)phenyl)-tetrahydro-2H-pyran (50 mg, 0.07 mmol, 1.00 equiv) in dichloromethane (5 mL) with 1,2,3,4,5-pentamethylbenzene (50 mg, 0.34 mmol, 5.11 equiv) was added BCl$_3$ (0.67 mg, 10.00 equiv, 1N) at −78° C. The reaction mixture was stirred for 1 h at −78° C. Methanol was added, and the resulting mixture concentrated and purified by chromatography on C18 reversed phase column (10%-50% CH$_3$CN/H$_2$O) to yield the title compound as a white solid.

$^1$H-NMR: (300 MHz, CD$_3$OD) δ 7.16-7.26 (m, 2H), 6.80-7.07 (m, 4H), 4.03-4.23 (m, 3H), 3.88 (dd, J=12.0, 1.5 Hz, 1H), 3.62-3.75 (m, 1H), 3.31-3.53 (m, 4H), 3.10 (s, 4H), 1.76-1.92 (m, 1H), 0.76-0.91 (m, 2H), 0.50-0.62 (m, 2H). MS (ES) m/z: 414.1 [M+NH$_4$]$^+$

Example 6: Compound #6

(2S,3R,4R,5S,6R)-2-(5-((1,2-dihydrocyclobutabenzen-4-yl)methyl)-2-hydroxy-4-methylphenyl)-6-(hydroxymethyl)-tetrahydro-2H-pyran-3,4,5-triol

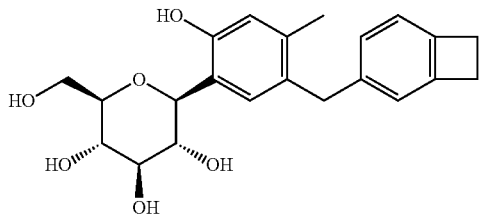 [SMILES: Cc1cc(O)c([C@@H]2O[C@H](CO)[C@@H](O)[C@H](O)[C@H]2O)cc1Cc1ccc2c(c1)CC2]

To a mixture of 2-(4-(benzyloxy)-5-bromo-2-methylphenyl)-1,3-dioxolane (4.2 g, 12.03 mmol, 1.00 equiv) in THF (40 mL) was added n-BuLi (2.5M in hexane, 5.06 mL, 1.05 equiv) dropwise at −78° C., and the reaction mixture was stirred at −78° C. for 30 min. (3R,4S,5R,6R)-3,4,5-Tris(benzyloxy)-6-[(benzyloxy)methyl]oxan-2-one (6.18 g, 11.47 mmol, 0.95 equiv) in THF (10 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated to yield (3R,4S,5R,6R)-3,4,5-tris(benzyloxy)-2-(2-(benzyloxy)-5-(1,3-dioxolan-2-yl)-4-methylphenyl)-6-(benzyloxymethyl)-tetrahydro-2H-pyran-2-ol as a light yellow oil.

To a mixture of (3R,4S,5R,6R)-3,4,5-tris(benzyloxy)-2-(2-(benzyloxy)-5-(1,3-dioxolan-2-yl)-4-methylphenyl)-6-(benzyloxymethyl)-tetrahydro-2H-pyran-2-ol (9 g) in THF (100 mL) was added hydrogen chloride (2M, 20 mL), the mixture was stirred for 30 min at room temperature. The mixture was extracted with EtOAc thrice. The combined extracts were washed with brine and dried over Na$_2$SO$_4$, then concentrated and purified by chromatography on silica gel (2:1 PE/EA) to yield 4-(benzyloxy)-2-methyl-5-((3R,4S,5R,6R)-3,4,5-tris(benzyloxy)-6-(benzyloxymethyl)-2-hydroxy-tetrahydro-2H-pyran-2-yl)benzaldehyde as a light yellow oil.

To a mixture of 4-(benzyloxy)-2-methyl-5-((3R,4S,5R,6R)-3,4,5-tris(benzyloxy)-6-(benzyloxymethyl)-2-hydroxy-tetrahydro-2H-pyran-2-yl)benzaldehyde (214 mg, 1.17 mmol, 2.98 equiv) in THF (5 mL) was added n-BuLi (2.5M in hexane, 0.48 mL, 3.00 equiv) dropwise at −78° C., and the reaction mixture was stirred at −78° C. for 30 min. 4-(Benzyloxy)-2-methyl-5-[(3R,4S,5R,6R)-3,4,5-tris(benzyloxy)-6-[(benzyloxy)methyl]-2-hydroxyoxan-2-yl]benzaldehyde (300 mg, 0.39 mmol, 1.00 equiv) in THF (1 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-2-(2-(benzyloxy)-5-((1,2-dihydrocyclobutabenzen-4-yl)(hydroxy)methyl)-4-methylphenyl)-6-(benzyloxymethyl)-tetrahydro-2H-pyran-2-ol as a light yellow oil.

To a mixture of (3R,4S,5R,6R)-3,4,5-tris(benzyloxy)-2-(2-(benzyloxy)-5-((1,2-dihydrocyclobutabenzen-4-yl)(hydroxy)methyl)-4-methylphenyl)-6-(benzyloxymethyl)-tetrahydro-2H-pyran-2-ol (310 mg, 0.36 mmol, 1.00 equiv) in DCM (10 mL) with Et$_3$SiH (208 mg, 1.79 mmol, 5.01 equiv) was added BF$_3$.Et$_2$O (203 mg, 1.43 mmol, 4.01 equiv) at 0° C. The reaction mixture was stirred at 0° C. for 2 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (5:1 PE/EA) to yield (2S,3S,4R,5R,6R)-3,4,5-tris(benzyloxy)-2-(2-(benzyloxy)-5-((1,2-dihydrocyclobutabenzen-4-yl)methyl)-4-methylphenyl)-6-(benzyloxymethyl)-tetrahydro-2H-pyran as a light yellow oil. MS (ES) m/z: 859.6 [M+Na]$^+$ To a mixture of (2S,3S,4R,5R,6R)-3,4,5-tris(benzyloxy)-2-(2-(benzyloxy)-5-((1,2-dihydrocyclobutabenzen-4-yl)methyl)-4-methylphenyl)-6-(benzyloxymethyl)-tetrahydro-2H-pyran (135 mg, 0.16 mmol, 1.00 equiv) in dichloromethane (5 mL) with 1,2,3,4,5-pentamethylbenzene (200 mg, 1.35 mmol, 8.37 equiv) was added BCl$_3$ (1 M in DCM, 2.5 mL) dropwise at −78° C. The reaction mixture was stirred at −78° C. for 1 h. 5 mL of methanol was added, and the resulting mixture was then concentrated and purified by chromatography on a C18 reversed phase column to yield the title compound as a white solid.

$^1$H NMR (300 MHz, CD$_3$OD) δ7.12 (s, 1H), 6.95 (dd, J=7.7, 1.5 Hz, 1H), 6.88 (dd, J=7.4, 0.9 Hz, 1H), 6.78 (s, 1H), 6.64 (s, 1H), 4.52 (d, J=9.4 Hz, 1H), 3.83-3.91 (m, 3H), 3.67-3.74 (m, 1H), 3.53-3.64 (m, 1H), 3.40-3.52 (m, 3H), 3.10 (s, 4H), 2.10 (s, 3H); MS (ES) m/z: 385.1 [M−H]$^−$.

Example 7: Compound #7

(2S,3R,4R,5S,6R)-2-(5-((1,2-dihydrocyclobutabenzen-4-yl)methyl)-2-methoxy-4-methylphenyl)-6-(hydroxymethyl)-tetrahydro-2H-pyran-3,4,5-triol

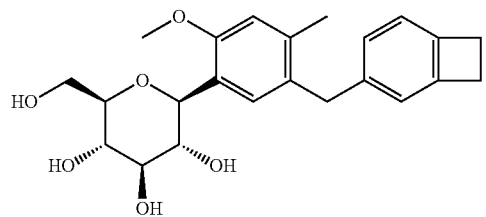 [SMILES: COc1cc(C)c(Cc2ccc3c(c2)CC3)cc1[C@@H]1O[C@H](CO)[C@@H](O)[C@H](O)[C@H]1O]

To a mixture of (2S,3R,4R,5S,6R)-2-(5-((1,2-dihydrocyclobutabenzen-4-yl)methyl)-2-hydroxy-4-methylphenyl)-6-(hydroxymethyl)-tetrahydro-2H-pyran-3,4,5-triol (Compound #6) (34 mg, 0.09 mmol, 1.00 equiv) in N,N-dimethylformamide (2 mL) with potassium carbonate (36 mg, 0.26 mmol, 2.96 equiv) was added CH$_3$I (62.5 mg, 0.44 mmol, 5.00 equiv) at room temperature.

The reaction mixture was stirred for 2 h at room temperature, then purified by chromatography on a C18 reversed phase column to yield the title compound as a white solid.

$^1$H NMR (300 MHz, CD$_3$OD) δ 7.21 (s, 1H), 6.96 (d, J=7.5 Hz, 1H), 6.88 (d, J=7.5 Hz, 1H), 6.79 (s, 2H), 4.65 (d, J=9.3 Hz, 1H), 3.80-3.93 (m, 6H), 3.66 (dd, J=12.5, 5.0 Hz, 1H), 3.56 (t, J=9.0 Hz, 1H), 3.44-3.51 (m, 1H), 3.39 (d, J=5.2 Hz, 2H), 3.10 (s, 4H), 2.18 (s, 3H); MS (ES) m/z: 399.1 [M−H]$^-$.

Example 8: Compound #8

(2S,3R,4R,5S,6R)-2-(5-(bicyclo[4.2.0]octa-1(6),2,4-trien-3-ylmethyl)-4-chloro-2-hydroxyphenyl)-6-(hydroxymethyl)oxane-3,4,5-triol

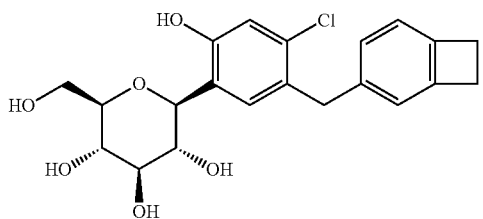 [SMILES: OC[C@H]1O[C@@H](c2cc(Cc3ccc4c(c3)CC4)c(Cl)cc2O)[C@H](O)[C@@H](O)[C@@H]1O]

To a mixture of 3-bromobicyclo[4.2.0]octa-1,3,5-triene (9.5 g, 51.90 mmol, 1.20 equiv) in tetrahydrofuran (250 mL) was added n-BuLi (2.5M in hexane, 19 mL, 1.10 equiv) dropwise with stirring at −78° C., and the mixture was stirred for 30 mins at −78° C. 4-(Benzyloxy)-5-bromo-2-chlorobenzaldehyde (14 g, 43.00 mmol, 1.00 equiv) in tetrahydrofuran (50 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (18% EA/PE) to yield [4-(benzyloxy)-5-bromo-2-chlorophenyl](bicyclo[4.2.0]octa-1(6),2,4-trien-3-yl)methanol as a light yellow oil. MS (ES) m/z: 413.0 [M−OH]$^+$ To a mixture of [4-(benzyloxy)-5-bromo-2-chlorophenyl](bicyclo[4.2.0]octa-1(6),2,4-trien-3-yl)methanol (14.6 g, 33.97 mmol, 1.00 equiv) in dichloromethane (100 mL) with Et$_3$SiH (7.8 g, 69.00 mmol, 2.00 equiv) was added CF$_3$COOH (6.0 g, 51.60 mmol, 1.50 equiv) dropwise at 0° C. The reaction mixture was stirred for 1 h at 0° C. Sodium bicarbonate/H$_2$O was added and the mixture was extracted with DCM thrice. The combined extracts were washed with brine and dried over Na$_2$SO$_4$, then concentrated and purified by chromatography on silica gel (12% EA/PE) to yield 3-{[4-(benzyloxy)-5-bromo-2-chlorophenyl]methyl}bicyclo[4.2.0]octa-1(6),2,4-triene as a yellow oil.

$^1$H NMR (300 MHz, Chloroform-d) δ 7.29-7.53 (m, 6H), 6.91-7.11 (m, 3H), 6.89 (s, 1H), 5.13 (s, 2H), 4.00 (d, J=10.3 Hz, 2H), 3.15 (d, J=3.3 Hz, 4H).

To a mixture of 3-{[4-(benzyloxy)-5-bromo-2-chlorophenyl]methyl}bicyclo[4.2.0]octa-1(6),2,4-triene (12.6 g, 30.45 mmol, 1.45 equiv) in tetrahydrofuran/toluene (50/100 mL) was added n-BuLi (2.5M in hexane, 9.6 mL, 1.15 equiv) dropwise at −78° C., and the mixture was stirred at −78° C. for 30 min. (3R,4S,5R,6R)-3,4,5-Tris(benzyloxy)-6-[(benzyloxy)methyl]oxan-2-one (11.3 g, 20.98 mmol, 1.00 equiv) in tetrahydrofuran (20 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (25% EA/PE) to yield (3R,4S,5R,6R)-3,4,5-tris(benzyloxy)-2-[2-(benzyloxy)-5-{bicyclo[4.2.0]octa-1(6),2,4-trien-3-ylmethyl}-4-chlorophenyl]-6-[(benzyloxy)methyl]oxan-2-ol as a yellow oil. MS (ES) m/z: 855.5 [M−OH]$^+$ To a mixture of (3R,4S,5R,6R)-3,4,5-tris(benzyloxy)-2-[2-(benzyloxy)-5-{bicyclo[4.2.0]octa-1(6),2,4-trien-3-ylmethyl}-4-chlorophenyl]-6-[(benzyloxy)methyl]oxan-2-ol (18.6 g, 21.29 mmol, 1.00 equiv) in DCM (200 mL) with Et$_3$SiH (4.86 g, 41.80 mmol, 2.00 equiv) was added BF$_3$.Et$_2$O (4.55 g, 32.04 mmol, 1.50 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (20% EA/PE) to yield (2S,3S,4R,5R,6R)-3,4,5-tris(benzyloxy)-2-[2-(benzyloxy)-5-{bicyclo[4.2.0]octa-1(6),2,4-trien-3-ylmethyl}-4-chlorophenyl]-6-[(benzyloxy)methyl]oxane as a light yellow oil. MS (ES) m/z: 879.6 [M+Na]$^+$ To a mixture of (2S,3S,4R,5R,6R)-3,4,5-tris(benzyloxy)-2-[2-(benzyloxy)-5-{bicyclo[4.2.0]octa-1(6),2,4-trien-3-ylmethyl}-4-chlorophenyl]-6-[(benzyloxy)methyl]oxane (8.5 g, 9.91 mmol, 1.00 equiv) in dichloromethane (300 mL) with 1,2,3,4,5-pentamethylbenzene (17 g, 114.68 mmol, 11.57 equiv) was added BCl$_3$ (1M in DCM, 170 ml, 17.0 equiv) dropwise at −78° C. The reaction mixture was stirred at −78° C. for 1 h. Methanol (100 mL) was added, and the resulting mixture was then concentrated and purified by chromatography on a C18 reversed phase column (42% CH$_3$CN/H$_2$O) to yield the title compound as a white solid.

$^1$H-NMR (MeOD, 300 MHz) δ 7.25 (s, 1H), 7.01 (d, J=8.7 Hz, 1H), 6.90 (d, J=6.9 Hz, 1H), 6.84 (s, 2H), 4.53 (d, J=9.3 Hz, 1H), 3.96 (d, J=3.9 Hz, 2H), 3.85-3.91 (m, 1H), 3.67-3.75 (m, 1H), 3.47-3.54 (m, 2H), 3.39-3.44 (m, 2H), 3.11 (s, 4H). MS (ES) m/z: 405.2 [M−H]$^-$.

Example 9: Compound #9

2S,3R,4R,5S,6R)-2-(4-chloro-5-((1,2-dihydrocyclobutabenzen-4-yl)methyl)-2-methoxyphenyl)-8-(hydroxymethyl)-tetrahydro-2H-pyran-3,4,5-triol

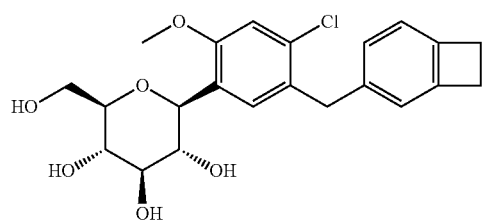 [SMILES: COc1cc(Cl)c(Cc2ccc3c(c2)CC3)cc1[C@@H]1O[C@H](CO)[C@@H](O)[C@H](O)[C@H]1O]

To a mixture of (2S,3R,4R,5S,6R)-2-(5-{bicyclo[4.2.0]octa-1(6),2,4-trien-3-ylmethyl}-4-chloro-2-hydroxyphenyl)-6-(hydroxymethyl)oxane-3,4,5-triol (Compound #8) (30 mg, 0.07 mmol, 1.00 equiv) in N,N-dimethylformamide (2 mL) with potassium carbonate (20.4 mg, 0.15 mmol, 2.1 equiv) was added CH₃I (52.6 mg, 0.37 mmol, 5.30 equiv) at room temperature. The reaction mixture was stirred for 2 h at room temperature. The resulting mixture was purified by chromatography on a C18 reversed phase column to yield the title compound as a white solid.

$^1$H NMR (300 MHz, CD₃OD) δ 7.34 (s, 1H), 7.02 (d, J=8.7 Hz, 2H), 6.85-6.95 (m, 2H), 4.62 (d, J=9.3 Hz, 1H), 4.00 (d, J=3.3 Hz, 2H), 3.82 (s, 4H), 3.63-3.68 (m, 1H), 3.36-3.47 (m, 4H), 3.11 (s, 4H). MS (ES) m/z: 419.1 [M−H]⁻

Example 10: Compound #10

(2S,3R,4R,5S,6R)-2-(5-((1,2-dihydrocyclobutabenzen-4-yl)methyl)-2-hydroxy-4-methoxyphenyl)-6-(hydroxymethyl)-tetrahydro-2H-pyran-3,4,5-triol

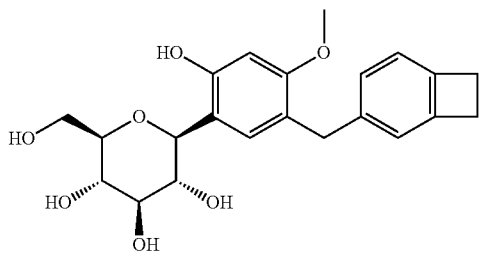

To a mixture of 3-bromobicyclo[4.2.0]octa-1,3,5-triene (569 mg, 3.11 mmol, 1.00 equiv) in THF (12 mL) was added n-BuLi (2.5M in hexane, 1.30 mL, 1.05 equiv) dropwise at −78° C., and the mixture was stirred at −78° C. for 30 min. 4-(Benzyloxy)-5-bromo-2-methoxybenzaldehyde (1 g, 3.11 mmol, 1.00 equiv) in THF (3 mL) was then added to the solution. The reaction mixture was stirred at −78° C. for 2 h. NH₄Cl/H₂O was added and the mixture was extracted with EtOAc thrice. The combined extracts were washed with brine and dried over Na₂SO₄, then concentrated and purified by chromatography on silica gel (5:1 PE/EA) to yield 1-(4-(benzyloxy)-5-bromo-2-methoxyphenyl)(1,2-dihydrocyclobutabenzen-4-yl)methanol as a light yellow oil. MS (ES) m/z: 409.0 [M−OH]⁺

To a mixture of (4-(benzyloxy)-5-bromo-2-methoxyphenyl)(1,2-dihydrocyclobutabenzen-4-yl)methanol (1.09 g, 2.56 mmol, 1.00 equiv) in DCM (20 mL) with Et₃SiH (895 mg, 7.70 mmol, 3.00 equiv) was added BF₃.Et₂O (730 mg, 5.14 mmol, 2.01 equiv) at 0° C. The reaction mixture was stirred at 0° C. for 2 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield 4-(4-(benzyloxy)-5-bromo-2-methoxybenzyl)-1,2-dihydrocyclobutabenzene as a white solid.

To a mixture of 4-(4-(benzyloxy)-5-bromo-2-methoxybenzyl)-1,2-dihydrocyclobutabenzene (510 mg, 1.25 mmol, 1.05 equiv) in THF (12 mL) was added n-BuLi (2.5M in hexane, 0.52 mL, 1.10 equiv) dropwise at −78° C., and the mixture was stirred at −78° C. for 30 min. (3R,4S,5R,6R)-3,4,5-Tris(benzyloxy)-6-[(benzyloxy)methyl]oxan-2-one (640 mg, 1.19 mmol, 1.00 equiv) in THF (3 mL) was then added to the solution. The reaction mixture was stirred at −78° C. for 2 h. NH₄Cl/H₂O was added and the mixture was extracted with EtOAc thrice. The combined extracts were washed with brine and dried over Na₂SO₄, then concentrated and purified by chromatography on silica gel (3:1 PE/EA) to yield (3R,4S,5R,6R)-3,4,5-tris(benzyloxy)-2-(2-(benzyloxy)-5-((1,2-dihydrocyclobutabenzen-4-yl)methyl)-4-methoxyphenyl)-6-(benzyloxymethyl)-tetrahydro-2H-pyran-2-ol as a light yellow oil. MS (ES) m/z: 851.6 [M−OH]⁺

To a mixture of (3R,4S,5R,6R)-3,4,5-tris(benzyloxy)-2-(2-(benzyloxy)-5-((1,2-dihydrocyclobutabenzen-4-yl)methyl)-4-methoxyphenyl)-6-(benzyloxymethyl)-tetrahydro-2H-pyran-2-ol (810 mg, 0.93 mmol, 1.00 equiv) in DCM (15 mL) with Et₃SiH (325 mg, 2.79 mmol, 3.00 equiv) was added BF₃.Et₂O (265 mg, 1.87 mmol, 2.00 equiv) at 0° C. The reaction mixture was stirred at 0° C. for 2 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield (2S,3S,4R,5R,6R)-3,4,5-tris(benzyloxy)-2-(2-(benzyloxy)-5-((1,2-dihydrocyclobutabenzen-4-yl)methyl)-4-methoxyphenyl)-6-(benzyloxymethyl)-tetrahydro-2H-pyran as a light yellow oil. MS (ES) m/z: 853.5 [M+H]⁺

To a mixture of BCl₃ (1 M in DCM, 6.0 mL) in dichloromethane (8 mL) was added (2S,3S,4R,5R,6R)-3,4,5-tris(benzyloxy)-2-(2-(benzyloxy)-5-((1,2-dihydrocyclobutabenzen-4-yl)methyl)-4-methoxyphenyl)-6-(benzyloxymethyl)-tetrahydro-2H-pyran (350 mg, 0.41 mmol, 1.00 equiv) and 1,2,3,4,5-pentamethylbenzene (600 mg, 4.05 mmol, 9.86 equiv) in DCM (2 mL) dropwise at −78° C. The reaction mixture was stirred at −78° C. for 1 h. Methanol was added, and the resulting mixture was then concentrated and purified by chromatography on a C18 reversed phase column to yield the title compound as a white solid.

$^1$H NMR (300 MHz, CD₃OD) δ 7.05 (s, 1H), 7.00 (d, J=7.9 Hz, 1H), 6.85 (d, J=7.4 Hz, 2H), 6.44 (s, 1H), 4.47 (d, J=9.3 Hz, 1H), 3.64-3.90 (m, 7H), 3.54 (t, J=8.9 Hz, 1H), 3.42-3.50 (m, 1H), 3.40 (d, J=6.4 Hz, 2H), 3.09 (s, 4H); MS (ES) m/z: 401.1 [M−H]⁻

Example 11: Compound #11

(2S,3R,4R,5S,6R)-2-(5-((1,2-dihydrocyclobutabenzen-4-yl)methyl)-2,4-dimethoxyphenyl)-6-(hydroxymethyl)-tetrahydro-2H-pyran-3,4,5-triol

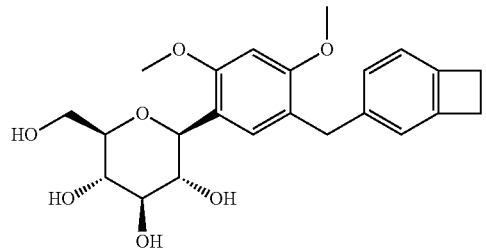 [SMILES: COc1cc(OC)c([C@@H]2O[C@H](CO)[C@@H](O)[C@H](O)[C@H]2O)cc1Cc1ccc2c(c1)CC2]

To a mixture of (2S,3R,4R,5S,6R)-2-(5-((1,2-dihydrocyclobutabenzen-4-yl)methyl)-2-hydroxy-4-methoxyphenyl)-6-(hydroxymethyl)-tetrahydro-2H-pyran-3,4,5-triol (Compound #10) (27 mg, 0.07 mmol, 1.00 equiv) in N,N-dimethylformamide (1.5 mL) with potassium carbonate (28 mg, 0.20 mmol, 3.02 equiv) was added CH$_3$I (48 mg, 0.34 mmol, 5.04 equiv) at room temperature. The reaction mixture was stirred for 2 h at room temperature. The resulting mixture was purified by chromatography on a C18 reversed phase column to yield the title compound as a white solid.

$^1$H NMR (300 MHz, CD$_3$OD) δ 7.17 (s, 1H), 7.03 (d, J=7.8 Hz, 1H), 6.84-6.91 (m, 2H), 6.61 (s, 1H), 4.61 (d, J=9.1 Hz, 1H), 3.82-3.89 (m, 9H), 3.65 (dd, J=12.3, 4.7 Hz, 1H), 3.50 (dt, J=20.5, 8.7 Hz, 2H), 3.38 (dd, J=5.3, 1.9 Hz, 2H), 3.10 (s, 4H); MS (ES) m/z: 415.1 [M–H]$^-$

Example 12: Compound #12

(2S,3R,4R,5S,6R)-2-(5-{bicyclo[4.2.0]octa-1(6),2,4-trien-3-ylmethyl}-4-ethyl-2-hydroxyphenyl)-6-(hydroxymethyl)oxane-3,4,6-triol

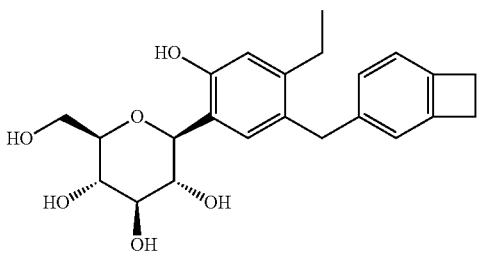 [SMILES: CCc1cc(O)c([C@@H]2O[C@H](CO)[C@@H](O)[C@H](O)[C@H]2O)cc1Cc1ccc2c(c1)CC2]

To a mixture of 3-bromobicyclo[4.2.0]octa-1,3,5-triene (2 g, 10.93 mmol, 1.00 equiv) in tetrahydrofuran (15 mL) was added n-BuLi (2.5M in hexane, 4.9 mL, 1.10 equiv) dropwise at −78° C., and the reaction was stirred for 30 min at −78° C. 4-(Benzyloxy)-5-bromo-2-ethylbenzaldehyde (3.85 g, 12.06 mmol, 1.10 equiv) in THF (15 mL) was then added to the solution. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (3:1 PE/EA) to yield [4-(benzyloxy)-5-bromo-2-ethylphenyl](bicyclo[4.2.0]octa-1(6),2,4-trien-3-yl)methanol as a light yellow oil. MS (ES) m/z: 405.0, 407.0 [M–OH]$^+$ To a mixture of [4-(benzyloxy)-5-bromo-2-ethylphenyl](bicyclo[4.2.0]octa-1(6),2,4-trien-3-yl)methanol (4.2 g, 9.92 mmol, 1.00 equiv) in DCM (20 mL) with Et$_3$SiH (3.48 g, 29.93 mmol, 3.00 equiv) was added TFA (2.84 g, 19.95 mmol, 2.00 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (5:1 PE/EA) to yield 3-{[4-(benzyloxy)-5-bromo-2-ethylphenyl]methyl}bicyclo[4.2.0]octa-1(6),2,4-triene as a yellow oil.

To a mixture of 3-{[4-(benzyloxy)-5-bromo-2-ethylphenyl]methyl}bicyclo[4.2.0]octa-1(6),2,4-triene ((2.5 g, 6.14 mmol, 1.00 equiv) in tetrahydrofuran (20 mL) was added n-BuLi (2.5M in hexane, 2.7 mL, 1.10 equiv) dropwise at −78° C., and the reaction mixture was stirred for 30 min at −78° C. (3R,4S,5R,6R)-3,4,5-Tris(benzyloxy)-6-[(benzyloxy)methyl]oxan-2-one (3.65 g, 6.78 mmol, 1.10 equiv) in THF (15 mL) was then added to the solution. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-2-[2-(benzyloxy)-5-{bicyclo[4.2.0]octa-1(6),2,4-trien-3-ylmethyl}-4-ethylphenyl]-6-[(benzyloxy)methyl]oxan-2-ol as a light yellow oil. MS (ES) m/z: 849.5 [M–OH]$^+$ To a mixture of (3R,4S,5R,6R)-3,4,5-tris(benzyloxy)-2-[2-(benzyloxy)-5-{bicyclo[4.2.0]octa-1(6),2,4-trien-3-ylmethyl}-4-ethylphenyl]-6-[(benzyloxy)methyl]oxan-2-ol (1.8 g, 2.08 mmol, 1.00 equiv) in DCM (15 mL) with Et$_3$SiH (724 mg, 6.23 mmol, 3.00 equiv) was added BF$_3$.Et$_2$O (591 mg, 4.15 mmol, 2.00 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (3:1 PE/EA) to yield (2S,3S,4R,5R,6R)-3,4,5-tris(benzyloxy)-2-[2-(benzyloxy)-5-{bicyclo[4.2.0]octa-1(6),2,4-trien-3-ylmethyl}-4-ethylphenyl]-6-[(benzyloxy)methyl]oxane as a yellow oil. MS (ES) m/z: 873.5 [M+Na]$^+$ To a mixture of (2S,3S,4R,5R,6R)-3,4,5-tris(benzyloxy)-2-[2-(benzyloxy)-5-{bicyclo[4.2.0]octa-1(6),2,4-trien-3-ylmethyl}-4-ethylphenyl]-6-[(benzyloxy)methyl]oxane (500 mg, 0.59 mmol, 1.00 equiv) in dichloromethane (20 mL) with 1,2,3,4,5-pentamethylbenzene (1 g, 6.75 mmol, 11.4 equiv) was added BCl$_3$ (1M in DCM, 10 mL, 16.95 equiv) dropwise at −78° C. The reaction mixture was stirred at −78° C. for 1 h. 5 mL of methanol was added, and the resulting mixture was then concentrated and purified by chromatography on a C18 reversed phase column to yield the title compound as a white solid.

1H-NMR (400 MHz, CD3OD) δ 7.13 (s, 1H), 6.96 (d, J=7.4 Hz, 1H), 6.89 (d, J=7.6 Hz, 1H), 6.79 (s, 1H), 6.69 (s, 1H), 4.53 (d, J=9.6 Hz, 1H), 3.85-3.94 (m, 3H), 3.72 (dd, J=12.0, 4.7 Hz, 1H), 3.60 (t, J=9.0 Hz, 1H), 3.40-3.55 (m, 3H), 3.11 (s, 4H), 2.50 (q, J=7.5 Hz, 2H), 1.06 (t, J=7.5 Hz, 3H); MS (ES) m/z: 399.1 [M–H]$^-$

Example 13: Compound #13

(2S,3R,4R,5S,6R)-2-(5-((1,2-dihydrocyclobutabenzen-4-yl)methyl)-4-ethyl-2-methoxyphenyl)-6-(hydroxymethyl)-tetrahydro-2H-pyran-3,4,5-triol

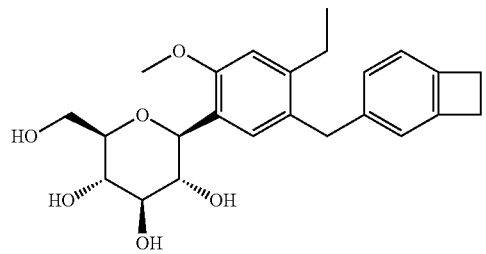 [SMILES: CCc1cc(OC)c([C@@H]2O[C@H](CO)[C@@H](O)[C@H](O)[C@H]2O)cc1Cc1ccc2c(c1)CC2]

To a mixture of (2S,3R,4R,5S,6R)-2-(5-((1,2-dihydrocyclobutabenzen-4-yl)methyl)-4-ethyl-2-hydroxyphenyl)-6-(hydroxymethyl)-tetrahydro-2H-pyran-3,4,5-triol (Compound #12) (15 mg, 0.04 mmol, 1.00 equiv) in DMF (1 ml) with K$_2$CO$_3$ (16 mg, 0.12 mmol, 3.00 equiv) was added MeI (27 mg, 0.19 mmol, 5.00 equiv). The reaction mixture was stirred at room temperature for 2 h, then concentrated and purified by chromatography on a C18 reversed phase column to yield the title compound as a white solid.

H-NMR (400 MHz, CD$_3$OD) δ 7.22 (s, 1H), 6.97 (d, J=7.5 Hz, 1H), 6.89 (d, J=7.5 Hz, 1H), 6.81 (d, J=10.6 Hz, 2H), 4.66 (d, J=9.5 Hz, 1H), 3.95 (s, 2H), 3.84-3.89 (m, 4H), 3.67 (dd, J=12.2, 4.1 Hz, 1H), 3.53 (dt, J=32.4, 8.9 Hz, 2H), 3.36-3.45 (m, 2H), 3.11 (s, 4H), 2.59 (q, J=7.6 Hz, 2H), 1.09 (t, J=7.5 Hz, 3H). MS (ES) m/z: 413.1 [M–H]$^-$

Example 14: Compound #14

(2S,3R,4R,5S,6R)-2-(5-(bicyclo[4.2.0]octa-1(6),2,4-trien-3-ylmethyl)-4-cyclopropyl-2-hydroxyphenyl)-6-(hydroxymethyl)oxane-3,4,5-triol

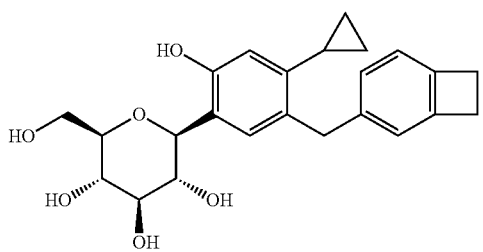 [SMILES: OC[C@H]1O[C@@H](c2cc(Cc3ccc4c(c3)CC4)c(C3CC3)cc2O)[C@H](O)[C@@H](O)[C@@H]1O]

To a mixture of 3-bromobicyclo[4.2.0]octa-1,3,5-triene (500 mg, 2.73 mmol, 1.20 equiv) in tetrahydrofuran (10 mL) was added n-BuLi (2.5M in hexane, 1 mL, 1.10 equiv) dropwise with stirring at −78° C., and the mixture was stirred for 20 min at −78° C. 3-Bromobicyclo[4.2.0]octa-1,3,5-triene (755 mg, 2.28 mmol, 1.00 equiv) in tetrahydrofuran (5 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (12% EA/PE) to yield [4-(benzyloxy)-5-bromo-2-cyclopropylphenyl](bicyclo[4.2.0]octa-1(6),2,4-trien-3-yl)methanol as a yellow oil. MS (ES) m/z: 417.1 [M–OH]$^+$ To a mixture of [4-(benzyloxy)-5-bromo-2-cyclopropylphenyl](bicyclo[4.2.0]octa-1(6),2,4-trien-3-yl)methanol (1.0 g, 2.30 mmol, 1.00 equiv) in dichloromethane (15 mL) with Et$_3$SiH (535 mg, 4.60 mmol, 2.00 equiv) was added CF$_3$COOH (394 mg, 3.46 mmol, 1.50 equiv) dropwise at 0° C. The reaction mixture was stirred for 1 h at 0° C. in a water/ice bath. Sodium bicarbonate/H$_2$O was added and the mixture was extracted with DCM thrice. The combined extracts were washed with brine and dried over Na$_2$SO$_4$, then concentrated and purified by chromatography on silica gel (5% EA/PE) to yield 3-{[4-(benzyloxy)-5-bromo-2-cyclopropylphenyl]methyl}bicyclo[4.2.0]octa-1(6),2,4-triene as an off-white solid. $^1$H NMR (300 MHz, Chloroform-d) 67.40-7.54 (m, 3H), 7.27-7.40 (m, 3H), 6.92-7.04 (m, 2H), 6.84 (s, 1H), 6.61 (s, 1H), 5.12 (s, 2H), 4.06 (s, 2H), 3.14 (s, 4H), 1.80 (tt, J=8.4, 5.4 Hz, 1H), 0.82-0.95 (m, 2H), 0.50-0.65 (m, 2H).

To a mixture of 3-{[4-(benzyloxy)-5-bromo-2-cyclopropylphenyl]methyl}bicyclo[4.2.0]octa-1(6),2,4-triene (400 mg, 0.95 mmol, 1.20 equiv) in tetrahydrofuran/toluene (3/6 mL) was added n-BuLi (2.5 M in hexane, 0.38 mL, 1.20 equiv) dropwise at −78° C., and the mixture was stirred at −78° C. for 20 min. (3R,4S,5R,6R)-3,4,5-Tris(benzyloxy)-6-[(benzyloxy)methyl]oxan-2-one (419 mg, 0.78 mmol, 1.00 equiv) in tetrahydrofuran (2 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (12% EA/PE) to yield (3R,4S,5R,6R)-3,4,5-tris(benzyloxy)-2-[2-(benzyloxy)-5-{bicyclo[4.2.0]octa-1(6),2,4-trien-3-ylmethyl}-4-cyclopropylphenyl]-6-[(benzyloxy)methyl]oxan-2-ol as a light yellow oil. MS (ES) m/z: 861.6 [M–OH]$^+$ To a mixture of (3R,4S,5R,6R)-3,4,5-tris(benzyloxy)-2-[2-(benzyloxy)-5-{bicyclo[4.2.0]octa-1(6),2,4-trien-3-ylmethyl}-4-cyclopropylphenyl]-6-[(benzyloxy)methyl]oxan-2-ol (500 mg, 0.57 mmol, 1.00 equiv) in DCM (8 mL) with Et$_3$SiH (132 mg, 1.14 mmol, 2.00 equiv) was added BF$_3$.Et$_2$O (122 mg, 0.86 mmol, 1.50 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (6% EA/PE) to yield (2S,3S,4R,5R,6R)-3,4,5-tris(benzyloxy)-2-[2-(benzyloxy)-5-{bicyclo[4.2.0]octa-1(6),2,4-trien-3-ylmethyl}-4-cyclopropylphenyl]-6-[(benzyloxy)methyl]oxane as a yellow oil. MS (ES) m/z: 885.4 [M+Na]$^+$ To a mixture of (2S,3S,4R,5R,6R)-3,4,5-tris(benzyloxy)-2-[2-(benzyloxy)-5-{bicyclo[4.2.0]octa-1(6),2,4-trien-3-ylmethyl}-4-cyclopropylphenyl]-6-[(benzyloxy)methyl]oxane (150 mg, 0.17 mmol, 1.00 equiv) in dichloromethane (5 mL) with 1,2,3,4,5-pentamethylbenzene (300 mg, 2.02 mmol, 12.00 equiv) was added BCl$_3$ (1M in DCM, 3 mL, 17.20 equiv) dropwise at −78° C. The reaction mixture was stirred at −78° C. for 1 h. Methanol was added, and the resulting mixture was then concentrated and purified by chromatography on a C18 reversed phase column (43% CH$_3$CN/H$_2$O (0.5% NH$_4$HCO$_3$)) to yield the title compound as a white solid.

$^1$H-NMR (MeOD, 300 MHz) δ 7.11 (s, 1H), 6.99 (d, J=7.2 Hz, 1H), 6.88 (d, J=7.8 Hz, 1H), 6.82 (s, 1H), 6.45 (s, 1H), 4.74 (d, J=9.3 Hz, 1H), 4.05 (t, J=15.9 Hz, 2H), 3.87 (d, J=11.1 Hz, 1H), 3.68-3.74 (m, 1H), 3.51-3.60 (m, 1H), 3.40-3.48 (m, 3H), 3.10 (s, 4H), 1.73-1.82 (m, 1H), 0.74-0.78 (m, 2H), 0.48-0.52 (m, 2H); MS (ES) m/z: 411.1 [M–H]$^-$.

Example 15: Compound #15

(2S,3R,4R,5S,6R)-2-(5-(bicyclo[4.2.0]octa-1(6),2,4-trien-3-ylmethyl)-4-cyclopropyl-2-methoxyphenyl)-6-(hydroxymethyl)oxane-3,4,5-triol

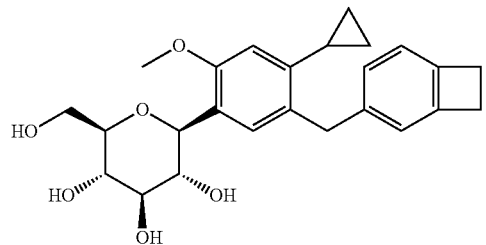 [SMILES: COc1cc(C2CC2)c(Cc2ccc3c(c2)CC3)cc1[C@@H]1O[C@H](CO)[C@@H](O)[C@H](O)[C@H]1O]

To a mixture of (2S,3R,4R,5S,6R)-2-(5-{bicyclo[4.2.0]octa-1(6),2,4-trien-3-ylmethyl}-4-cyclopropyl-2-hydroxyphenyl)-6-(hydroxymethyl)oxane-3,4,5-triol (Compound #14) (34.6 mg, 0.084 mmol, 1.00 equiv) in N,N-dimethylformamide (2 mL), with potassium carbonate (23.4 mg, 0.17 mmol, 2.00 equiv) was added CH₃I (60.3 mg, 0.42 mmol, 5.00 equiv) dropwise at room temperature. The reaction mixture was stirred for 1 h at room temperature. The solids were filtered out and chromatograph on a C18 reversed phase column (42% CH₃CN/H₂O) to yield the title compound as a white solid.

¹H NMR (MeOD, 300 MHz) δ 7.21 (s, 1H), 6.99 (d, J=7.5 Hz, 1H), 6.88 (d, J=7.5 Hz, 1H), 6.82 (s, 1H), 6.59 (s, 1H), 4.63 (d, J=9.3 Hz, 1H), 4.09 (s, 2H), 3.79-3.83 (m, 4H), 3.63-3.69 (m, 1H), 3.37-3.58 (m, 4H), 3.10 (s, 4H), 1.79-1.88 (m, 1H), 0.85 (d, J=8.4 Hz, 2H), 0.59 (d, J=7.6 Hz, 2H); MS (ES) m/z: 425.1 [M–H]⁻.

Example 16: Compound #16

2-((1,2-dihydrocyclobutabenzen-4-yl)methyl)-4-((2S,3R,4R,5S,6R)-3,4,5-trihydroxy-6-(hydroxymethyl)-tetrahydro-2H-pyran-2-yl)benzonitrile

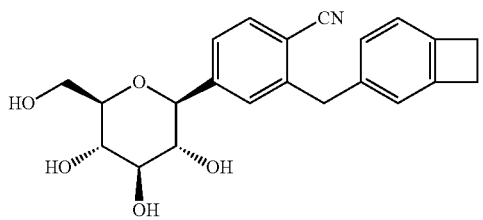

To a mixture of 2-(bicyclo[4.2.0]octa-1(6),2,4-trien-3-ylmethyl)-4-((2S,3S,4R,5R,6R)-3,4,5-tris(benzyloxy)-6-((benzyloxy)methyl)tetrahydro-2H-pyran-2-yl)phenyl trifluoromethanesulfonate (100 mg, 0.12 mmol, 1.00 equiv) in N,N-dimethylformamide (5 mL) was added Zn(CN)₂ (120 mg, 1.15 mmol, 9.98 equiv), Pd(PPh₃)₄ (15 mg, 0.01 mmol, 0.083 equiv). The reaction mixture was stirred for 2 h at 80° C. Water was added and the mixture was extracted with EtOAc thrice. The combined extracts were washed with brine and dried over Na₂SO₄, then concentrated and purified by chromatography on silica gel (3:1 PE/EA) to yield 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)benzonitrile as a yellow oil. MS (ES) m/z: 759.4 [M+NH₄]⁺

To a mixture of 2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)benzonitrile (50 mg, 0.07 mmol, 1.00 equiv) in dichloromethane (5 mL) with 1,2,3,4,5-pentamethylbenzene (50 mg, 0.34 mmol, 5.00 equiv) was added BCl₃ (0.5 mL, 7.60 equiv) at −78° C. The reaction mixture was stirred for 1 h at −78° C. Methanol was added, and the resulting mixture was then concentrated and purified by chromatography on C18 (10%-50% CH₃CN/H₂O) to yield the title compound as a white solid.

¹H-NMR: (300 MHz, CD₃OD) δ 7.66 (d, J=8.0 Hz, 1H), 7.41-7.54 (m, 2H), 7.08 (dd, J=7.2, 1.5 Hz, 1H), 6.69-6.89 (m, 2H), 4.06-4.24 (m, 3H), 3.89 (dd, J=12.0, 1.6 Hz, 1H), 3.72 (dd, J=12.0, 5.1 Hz, 1H), 3.36-3.54 (m, 3H), 3.18-3.31 (m, 1H), 3.12 (s, 4H). MS (ES) m/z: 380.1 [M–H]⁻

Example 17: Compound #17

2-((1,2-dihydrocyclobutabenzen-4-yl)methyl)-5-hydroxy-4-((2S,3R,4R,5S,6R)-3,4,5-trihydroxy-6-(hydroxymethyl)-tetrahydro-2H-pyran-2-yl)benzonitrile

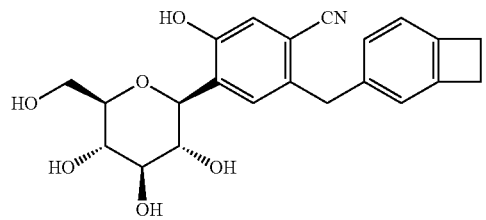

To a mixture of 4-(benzyloxy)-5-bromo-2-hydroxybenzaldehyde (4.2 g, 13.67 mmol, 1.00 equiv) in DMF (40 mL) with K₂CO₃ (5.6 g, 40.52 mmol, 2.96 equiv) was added 3-bromoprop-1-ene (3.3 g, 27.28 mmol, 1.99 equiv), and the reaction mixture was stirred at room temperature for 3 h. Water was added and the mixture was extracted with EtOAc thrice. The combined extracts were washed with brine and dried over Na₂SO₄, then concentrated and purified by chromatography on silica gel (4:1 PE/EA) to yield 42-(allyloxy)-4-(benzyloxy)-5-bromobenzaldehyde as a colorless oil.

To a mixture of 3-bromobicyclo[4.2.0]octa-1,3,5-triene (1.44 g, 7.87 mmol, 1.00 equiv) in THF (20 mL) was added n-BuLi (2.5 M in hexane, 3.2 mL, 1.00 equiv) dropwise with stirring at −78° C. The reaction mixture was stirred for min at −78° C. To the resulting mixture was then added a solution of 2-(allyloxy)-4-(benzyloxy)-5-bromobenzaldehyde (2.5 g, 7.20 mmol, 0.92 equiv) in THF (3 mL) dropwise at −78° C. The reaction mixture was stirred for 2 h at −78° C. NH₄Cl/H₂O was added and the mixture was extracted with EtOAc thrice, then concentrated and purified by chromatography on silica gel (2:1 PE/EA) to yield (2-(allyloxy)-4-(benzyloxy)-5-bromophenyl)(1,2-dihydrocyclobutabenzen-4-yl)methanol as a colorless oil.

To a mixture of (2-(allyloxy)-4-(benzyloxy)-5-bromophenyl)(1,2-dihydrocyclobutabenzen-4-yl)methanol (3.29 g, 7.29 mmol, 1.00 equiv) in DCM (30 mL) with Et₃SiH (1.67 g, 14.36 mmol, 1.97 equiv) was added trifluoroacetic acid (1.23 g, 10.88 mmol, 1.49 equiv) at 0° C. The reaction mixture was stirred at 0° C. for 1 h. Sodium bicarbonate/H₂O was added and the mixture was extracted with dichloromethane thrice. The combined extracts were washed with brine and dried over Na₂SO₄, then concentrated and purified by chromatography on silica gel (3:1 PE/EA) to yield 4-(2-(allyloxy)-4-(benzyloxy)-5-bromobenzyl)-1,2-dihydrocyclobutabenzene as a light yellow oil.

To a mixture of 4-(2-(allyloxy)-4-(benzyloxy)-5-bromobenzyl)-1,2-dihydrocyclobutabenzene (1.8 g, 4.13 mmol, 1.00 equiv) in tetrahydrofuran (20 mL) was added n-BuLi (2.5 M in hexane, 1.66 mL, 4.13 mmol, 1.0 equiv) dropwise with stirring at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (2.02 g, 3.75 mmol, 0.91 equiv) in tetrahydrofuran (2 mL) dropwise with stirring at −78° C. The reaction mixture was stirred for 2 h at −78° C. NH₄Cl/H₂O was added and the mixture was extracted with EtOAc thrice. Washed with brine, the resulting mixture was then concentrated and purified by chromatography on silica gel (3:1 PE/EA) to yield (3R,4S,5R,6R)-2-(4-(allyloxy)-2-(benzyloxy)-5-((1,2-dihydrocyclobutabenzen-4-yl)methyl)phenyl)-3,4,5-tris(benzyloxy)-6-(benzyloxymethyl)-tetrahydro-2H-pyran-2-ol as a colorless oil. MS (ES) m/z: 912 [M+NH$_4$]$^+$.

To a mixture of (3R,4S,5R,6R)-2-(4-(allyloxy)-2-(benzyloxy)-5-((1,2-dihydrocyclobutabenzen-4-yl)methyl)phenyl)-3,4,5-tris(benzyloxy)-6-(benzyloxymethyl)-tetrahydro-2H-pyran-2-ol (3.37 g, 3.76 mmol, 1.00 equiv) in dichloromethane (30 mL) with Et$_3$SiH (874 mg, 7.52 mmol, 2.00 equiv) was added BF$_3$.Et$_2$O (803 mg, 5.65 mmol, 1.50 equiv) dropwise at 0° C. The reaction mixture was stirred for 1.0 h at 0° C. Sodium bicarbonate was added and the mixture was extracted with DCM thrice, then concentrated and purified by chromatography on silica gel (3:1 PE/EA) to yield (2S,3S,4R,5R,6R)-2-(4-(allyloxy)-2-(benzyloxy)-5-((1,2-dihydrocyclobutabenzen-4-yl)methyl)phenyl)-3,4,5-tris(benzyloxy)-6-(benzyloxymethyl)-tetrahydro-2H-pyran as a colorless oil. MS (ES) m/z: 896 [M+NH$_4$].

To a mixture of (2S,3S,4R,5R,6R)-2-(4-(allyloxy)-2-(benzyloxy)-5-((1,2-dihydrocyclobutabenzen-4-yl)methyl)phenyl)-3,4,5-tris(benzyloxy)-6-(benzyloxymethyl)-tetrahydro-2H-pyran (1 g, 1.14 mmol, 1.00 equiv) in THF (10 mL) with ZnCl$_2$ (155 mg, 1.14 mmol, 1.00 equiv) and Pd(PPh$_3$)$_4$ (131 mg, 0.11 mmol, 0.10 equiv) was added PMHS (1.11 g, 3.40 mmol, 2.99 equiv), and the reaction mixture was stirred at room temperature for 16 h. Water was added and the mixture was extracted with EtOAc thrice. The combined extracts were washed with brine and dried over Na$_2$SO$_4$, then concentrated and purified by chromatography on silica gel (3:1 PE/EA) to yield 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenol as a colorless oil. MS (ES) m/z: 856.4 [M+NH$_4$]$^+$.

To a mixture of 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenol (600 mg, 0.72 mmol, 1.00 equiv) in DCM (8 mL) with pyridine (113 mg, 1.43 mmol, 2.00 equiv) was added Tf$_2$O (302 mg, 1.07 mmol, 1.50 equiv) dropwise at 0° C., and the reaction mixture was stirred at room temperature for 4 h. Water was added and the mixture was extracted with DCM thrice. The combined extracts were washed with brine and dried over Na$_2$SO$_4$, then concentrated and purified by chromatography on silica gel (4:1 PE/EA) to yield 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenyl trifluoromethanesulfonate as a colorless oil. MS (ES) m/z: 888 [M+NH$_4$]$^+$.

To a mixture of 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)phenyl trifluoromethanesulfonate (50 mg, 0.05 mmol, 1.00 equiv) in DMF (3 mL) with Zn(CN)$_2$ (12 mg, 0.10 mmol, 2.00 equiv) was added Pd(PPh$_3$)$_4$ (6 mg, 0.01 mmol, 0.20 equiv), and the reaction mixture was stirred at 85° C. for 16 h. Water was added and the mixture was extracted with EtOAc thrice. The combined extracts were washed with brine and dried over Na$_2$SO$_4$, then concentrated and purified by chromatography on silica gel (4:1 PE/EA) to yield 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)benzonitrile as a colorless oil. MS (ES) m/z: 865.3 [M+NH$_4$]$^+$.

To a mixture of 5-(benzyloxy)-2-((1,2-dihydrocyclobutabenzen-4-yl)methyl)-4-((2S,3S,4R,5R,6R)-3,4,5-tris(benzyloxy)-6-(benzyloxymethyl)-tetrahydro-2H-pyran-2-yl)benzonitrile (200 mg, 0.24 mmol, 1.00 equiv) in dichloromethane (5 mL) with 1,2,3,4,5-pentamethylbenzene (349 mg, 2.35 mmol, 9.98 equiv) was added BCl$_3$ (1 M in DCM, 1.8 mL) dropwise at −78° C. The reaction mixture was stirred at −78° C. for 1 h. Methanol was added, and the resulting mixture was then concentrated and purified by chromatography on a C18 reversed phase column to yield the title compound as a white solid.

$^1$H NMR (300 MHz, Methanol-d$_4$) δ 7.43 (s, 1H), 7.05-7.11 (m, 2H), 6.90-6.93 (m, 2H), 4.62 (d, J=9.3 Hz, 1H), 4.05 (s, 2H), 3.85-3.89 (m, 1H), 3.68-3.74 (m, 1H), 3.40-3.54 (m, 4H), 3.11 (s, 4H). MS (ES) m/z: 396.1 [M−H]$^-$.

Example 18: Compound #18

2-((1,2-dihydrocyclobutabenzen-4-yl)methyl)-5-methoxy-4-((2S,3R,4R,5S,6R)-3,4,8-trihydroxy-6-(hydroxymethyl)-tetrahydro-2H-pyran-2-yl)benzonitrile

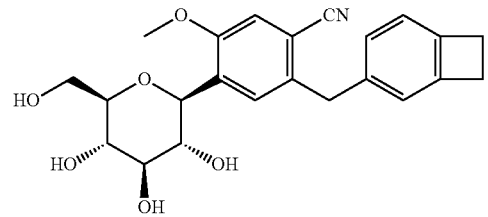 [SMILES: COc1cc(C#N)c(Cc2ccc3c(c2)CC3)cc1[C@@H]1O[C@H](CO)[C@@H](O)[C@H](O)[C@H]1O]

To a mixture of 2-((1,2-dihydrocyclobutabenzen-4-yl)methyl)-5-hydroxy-4-((2S,3R,4R,5S,6R)-3,4,5-trihydroxy-6-(hydroxymethyl)-tetrahydro-2H-pyran-2-yl)benzonitrile (Compound #17) (20 mg, 0.05 mmol, 1.00 equiv) in DMF (2 mL) with K$_2$CO$_3$ (69 mg, 0.50 mmol, 9.92 equiv) was added CH$_3$I (71 mg, 0.50 mmol, 9.92 equiv). The reaction mixture was stirred for 3 h at room temperature. Chromatograph on a C18 reversed phase column to yield the title compound as a white solid.

$^1$H NMR (300 MHz, CD$_3$OD) δ 7.51 (s, 1H), 7.26 (s, 1H), 7.06-7.12 (m, 1H), 7.91-7.94 (m, 2H), 4.70 (d, J=9.3 Hz, 1H), 4.14 (s, 2H), 3.84-3.87 (m, 4H), 3.64-3.70 (m, 1H), 3.39-3.48 (m, 4H), 3.12 (s, 4H). MS (ES) m/z: 438 [M+NH$_4$]$^+$.

Example 19: Compound #19

(2S,3R,4R,5S,6R)-2-(5-(bicyclo[4.2.0]octa-1(6),2,4-trien-3-ylmethyl)-4-fluoro-2-hydroxyphenyl)-6-(hydroxymethyl)tetrahydro-2H-pyran-3,4,5-triol

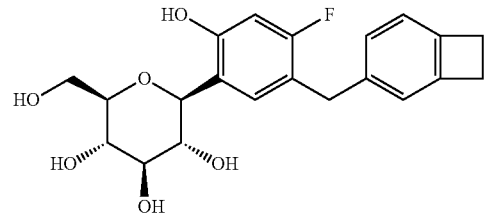 [SMILES: OC[C@H]1O[C@@H](c2cc(Cc3ccc4c(c3)CC4)c(F)cc2O)[C@H](O)[C@@H](O)[C@@H]1O]

To a mixture of 3-bromobicyclo[4.2.0]octa-1,3,5-triene (1 g, 5.46 mmol, 1.00 equiv) in THF (10 mL) was added n-BuLi (2.5 M in hexane, 2.2 mL, 1.00 equiv) dropwise at −78° C. The reaction mixture was stirred for 30 min at −78° C. To the resulting mixture was then added a solution of 4-(benzyloxy)-5-bromo-2-fluorobenzaldehyde (1.53 g, 4.95 mmol, 0.90 equiv) in tetrahydrofuran (4 mL) dropwise at −78° C. The reaction mixture was stirred for 1 h at −78° C. $NH_4Cl/H_2O$ was added and the mixture was extracted with EtOAc thrice. The combined extracts were washed with brine and dried over $Na_2SO_4$, then concentrated and purified by chromatography on silica gel (3:1 PE/EA) to yield (4-(benzyloxy)-5-bromo-2-fluorophenyl)(1,2-dihydrocyclobutabenzen-4-yl)methanol as a yellow solid.

To a mixture of (4-(benzyloxy)-5-bromo-2-fluorophenyl)(1,2-dihydrocyclobutabenzen-4-yl)methanol (2.3 g, 5.57 mmol, 1.00 equiv) in dichloromethane (10 mL) with $Et_3SiH$ (1.3 g, 11.18 mmol, 2.00 equiv) was added $CF_3COOH$ (960 mg, 8.49 mmol, 1.50 equiv) at 0° C. The reaction mixture was stirred for 1 h at 0° C. Sodium bicarbonate was added and the mixture was extracted with DCM thrice. The combined extracts were washed with brine and dried over $Na_2SO_4$, then concentrated and purified by chromatography on silica gel (5:1 PE/EA) to yield 4-(4-(benzyloxy)-5-bromo-2-fluorobenzyl)-1,2-dihydrocyclobutabenzene as a yellow solid.

To a mixture of 4-(4-(benzyloxy)-5-bromo-2-fluorobenzyl)-1,2-dihydrocyclobutabenzene (500 mg, 1.26 mmol, 1.00 equiv) in tetrahydrofuran (10 mL) was added n-BuLi (2.5 M in hexane, 0.51 mL, 1.27 mmol, 1.00 equiv) dropwise at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (680 mg, 1.26 mmol, 1.00 equiv) in tetrahydrofuran (3 mL) dropwise at −78° C. The reaction mixture was stirred for 2 h at −78° C. $NH_4Cl/H_2O$ was added and the mixture was extracted with EtOAc thrice. The combined extracts were washed with brine and dried over $Na_2SO_4$, then concentrated and purified by chromatography on silica gel (2:1 PE/EA) to yield (3R,4S,5R,6R)-3,4,5-tris(benzyloxy)-2-(2-(benzyloxy)-5-((1,2-dihydrocyclobutabenzen-4-yl)methyl)-4-fluorophenyl)-6-(benzyloxymethyl)-tetrahydro-2H-pyran-2-ol as colorless oil. MS (ES) m/z: 839.3 [M−OH]⁺.

To a mixture of (3R,4S,5R,6R)-3,4,5-tris(benzyloxy)-2-(2-(benzyloxy)-5-((1,2-dihydrocyclobutabenzen-4-yl)methyl)-4-fluorophenyl)-6-(benzyloxymethyl)-tetrahydro-2H-pyran-2-ol (660 mg, 0.77 mmol, 1.00 equiv) in dichloromethane (10 mL) with $Et_3SiH$ (179 mg, 1.54 mmol, 2.00 equiv) was added $BF_3 \cdot Et_2O$ (165 mg, 1.16 mmol, 1.50 equiv) dropwise at 0° C. The reaction mixture was stirred for 1 h at 0° C. Sodium bicarbonate was added and the mixture was extracted with DCM thrice. The combined extracts were washed with brine and dried over $Na_2SO_4$, then concentrated and purified by chromatography on silica gel (3:1 PE/EA) to yield (2S,3S,4R,5R,6R)-3,4,5-tris(benzyloxy)-2-(2-(benzyloxy)-5-((1,2-dihydrocyclobutabenzen-4-yl)methyl)-4-fluorophenyl)-6-(benzyloxymethyl)-tetrahydro-2H-pyran as a colorless solid. MS (ES) m/z: 863.4 [M+Na]⁺.

To a mixture of (2S,3S,4R,5R,6R)-3,4,5-tris(benzyloxy)-2-(2-(benzyloxy)-5-((1,2-dihydrocyclobutabenzen-4-yl)methyl)-4-fluorophenyl)-6-(benzyloxymethyl)-tetrahydro-2H-pyran (200 mg, 0.24 mmol, 1.00 equiv) in dichloromethane (5 mL) with 1,2,3,4,5-pentamethylbenzene (400 mg, 2.70 mmol, 11.25 equiv) was added $BCl_3$ (4 mL, 4 mmol, 16.67 equiv) dropwise at −78° C. The reaction mixture was stirred for 1 h at −78° C. Methanol was added, and the resulting mixture was then concentrated and purified by chromatography on C18 (10%-50% $CH_3CN/H_2O$) to yield the title compound as a white solid.

¹H NMR (400 MHz, Methanol-d₄) δ 7.21 (d, J=8.8 Hz, 1H), 7.03 (dd, J=7.4, 1.5 Hz, 1H), 6.85-7.00 (m, 2H), 6.53 (d, J=11.6 Hz, 1H), 4.54 (d J=9.2 Hz, 1H), 3.78-3.92 (m, 3H), 3.66-3.77 (m, 1H), 3.35-3.57 (m, 4H), 3.11 (s, 4H). MS (ES) m/z: 389.1 [M−H]⁻.

Example 20: Compound #20

(2S,3R,4R,5S,6R)-2-(5-((1,2-dihydrocyclobutabenzen-4-yl)methyl)-4-fluoro-2-methoxyphenyl)-6-(hydroxymethyl)-tetrahydro-2H-pyran-3,4,5-triol

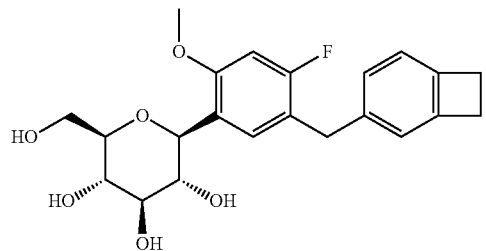 [SMILES: COc1cc(F)c(Cc2ccc3c(c2)CC3)cc1[C@@H]1O[C@H](CO)[C@@H](O)[C@H](O)[C@H]1O]

To a mixture of (2S,3R,4R,5S,6R)-2-(5-((1,2-dihydrocyclobutabenzen-4-yl)methyl)-4-fluoro-2-methoxyphenyl)-6-(hydroxymethyl)-tetrahydro-2H-pyran-3,4,5-triol (Compound #19) (25 mg, 0.06 mmol, 1.00 equiv) in N,N-dimethylformamide (1 mL) with potassium carbonate (27 mg, 0.20 mmol, 3.00 equiv) was added $CH_3I$ (46 mg, 5.00 equiv) at room temperature. The reaction mixture was stirred for 1 h at room temperature. The resulting mixture was purified by chromatography on a C18 reversed phase column to yield the title compound as a white solid.

1H NMR (400 MHz, $CD_3OD$) δ 7.30 (d, J=8.8 Hz, 1H), 7.01-7.08 (m, 1H), 6.86-6.94 (m, 2H), 6.75 (d, J=12.0 Hz, 1H), 4.50 (d, J=9.6 Hz, 1H), 3.79-3.92 (m, 6H), 3.62-3.71 (m, 1H), 3.43-3.54 (m, 2H), 3.34-3.44 (m, 2H), 3.11 (s, 4H). MS (ES) m/z: 403.1 [M−H]⁻

Example 21: Compound #21

(2S,3R,4R,5S,6R)-2-(3-(bicyclo[4.2.0]octa-1(6),2,4-trien-3-ylmethyl)-4-(dimethylamino)phenyl)-6-(hydroxymethyl)oxane-3,4,8-triol

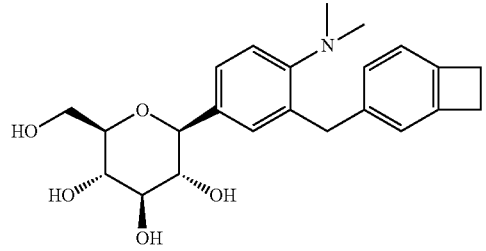 [SMILES: CN(C)c1ccc([C@@H]2O[C@H](CO)[C@@H](O)[C@H](O)[C@H]2O)cc1Cc1ccc2c(c1)CC2]

To a mixture of 3-bromobicyclo[4.2.0]octa-1,3,5-triene (385 mg, 2.10 mmol, 1.20 equiv) in tetrahydrofuran (7 mL) was added n-BuLi (2.5M in hexane, 0.77 mL, 1.10 equiv) dropwise at −78° C., and the reaction mixture was stirred for 30 min at −78° C. 5-Bromo-2-(dimethylamino)benzaldehyde (400 mg, 1.75 mmol, 1.00 equiv) in tetrahydrofuran (3 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (20% EA/PE) to yield bicyclo[4.2.0]octa-1(6),2,4-trien-3-yl[5-bromo-2-(dimethylamino)phenyl]methanol as a light yellow oil. MS (ES) m/z: 332.0 [M+H]$^+$ To a mixture of bicyclo[4.2.0]octa-1(6),2,4-trien-3-yl[5-bromo-2-(dimethylamino)phenyl]methanol (730 mg, 2.20 mmol, 1.00 equiv) in DCM (10 mL) with Et$_3$SiH (510 mg, 4.39 mmol, 2.00 equiv) was added BF$_3$.Et$_2$O (468 mg, 3.30 mmol, 1.50 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (9% EA/PE) to yield 2-{bicyclo[4.2.0]octa-1(6),2,4-trien-3-ylmethyl}-4-bromo-N,N-dimethylaniline as a yellow oil. $^1$H NMR (300 MHz, Chloroform-d) δ 7.32 (s, 1H), 7.17 (s, 1H), 7.06-6.97 (m, 3H), 6.90 (s, 1H), 4.06 (s, 2H), 3.17 (s, 4H), 2.70 (s, 6H).

To a mixture of 2-{bicyclo[4.2.0]octa-1(6),2,4-trien-3-ylmethyl}-4-bromo-N,N-dimethylaniline (141 mg, 0.45 mmol, 1.20 equiv) in tetrahydrofuran/toluene (4/8 mL) was added n-BuLi (2.5M in hexane, 0.18 mL, 1.20 equiv) dropwise at −78° C., and the reaction mixture was stirred at −78° C. for 30 min. (3R,4S,5R,6R)-3,4,5-Tris(benzyloxy)-6-[(benzyloxy)methyl]oxan-2-one (200 mg, 0.37 mmol, 1.00 equiv) in tetrahydrofuran (1.5 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (15% EA/PE) to yield (3R,4S,5R,6R)-3,4,5-tris(benzyloxy)-6-[(benzyloxy)methyl]-2-(3-{bicyclo[4.2.0]octa-1(6),2,4-trien-3-ylmethyl}-4-(dimethylamino)phenyl)oxan-2-ol as a yellow oil.

To a mixture of (3R,4S,5R,6R)-3,4,5-tris(benzyloxy)-6-[(benzyloxy)methyl]-2-(3-{bicyclo[4.2.0]octa-1(6),2,4-trien-3-ylmethyl}-4-(dimethylamino)phenyl)oxan-2-ol (250 mg, 0.32 mmol, 1.00 equiv) in DCM (8 mL) with Et$_3$SiH (149 mg, 1.28 mmol, 4.00 equiv) was added BF$_3$.Et$_2$O (183 mg, 1.29 mmol, 4.00 equiv) at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (9% EA/PE) to yield 2-{bicyclo[4.2.0]octa-1(6),2,4-trien-3-ylmethyl}-N,N-dimethyl-4-[(2S,3S,4R,5R,6R)-3,4,5-tris(benzyloxy)-6-[(benzyloxy)methyl]oxan-2-yl]aniline as a yellow oil. MS (ES) m/z: 760.2 [M+H]$^+$ To a mixture of 2-{bicyclo[4.2.0]octa-1(6),2,4-trien-3-ylmethyl}-N,N-dimethyl-4-[(2S,3S,4R,5R,6R)-3,4,5-tris(benzyloxy)-6-[(benzyloxy)methyl]oxan-2-yl]aniline (190 mg, 0.25 mmol, 1.00 equiv) in dichloromethane (5 mL) with 1,2,3,4,5-pentamethylbenzene (380 mg, 2.56 mmol, 10.00 equiv) was added BCl$_3$ (1 M in DCM, 3.8 mL, 15.00 equiv) dropwise at −78° C. The reaction mixture was stirred at −78° C. for 1 h. Methanol was added, and the resulting mixture was then concentrated and purified by chromatography on a C18 reversed phase column (41% CH$_3$CN/H$_2$O) to the title compound as a white solid.

$^1$H NMR (400 MHz, CD$_3$OD) δ 7.25 (d, J=8.4 Hz, 1H), 7.17 (d, J=8.4 Hz, 1H), 7.11 (d, J=2.1 Hz, 1H), 7.01 (d, J=7.5 Hz, 1H), 6.84-6.99 (m, 2H), 4.09 (d, J=12.3 Hz, 1H), 3.95-4.04 (m, 2H), 3.82-3.88 (m, 1H), 3.62-3.68 (m, 1H), 3.32-3.39 (m, 4H), 3.11 (s, 4H), 2.64 (s, 6H). MS (ES) m/z: 400.1 [M+H]$^+$

Example 22: Compound #22

(2S,3R,4R,5S,6R)-2-(5-((1,2-dihydrocyclobutabenzen-4-yl)methyl)-4-(dimethylamino)-2-hydroxyphenyl)-6-(hydroxymethyl)-tetrahydro-2H-pyran-3,4,5-triol

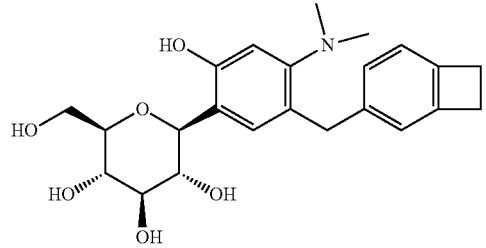 [SMILES: CN(C)c1cc(O)c([C@@H]2O[C@H](CO)[C@@H](O)[C@H](O)[C@H]2O)cc1Cc1ccc2c(c1)CC2]

To a mixture of 4-bromo-3-nitrophenol (5 g, 22.94 mmol, 1.00 equiv) in DMF (80 mL) with K$_2$CO$_3$ (15.8 g, 114.32 mmol, 4.98 equiv) was added BnBr (5.8 g, 33.91 mmol, 1.48 equiv), and the reaction mixture was stirred at room temperature for 3 h. Water was added and the mixture was extracted with EtOAc thrice. The combined extracts were washed with brine and dried over Na$_2$SO$_4$, then concentrated and purified by chromatography on silica gel (4:1 PE/EA) to yield 4-(benzyloxy)-1-bromo-2-nitrobenzene as a light yellow solid.

To a mixture of 4-(benzyloxy)-1-bromo-2-nitrobenzene (5.8 g, 18.82 mmol, 1.00 equiv) in ethanol (25 mL) with AcOH (25 g, 416.32 mmol, 22.12 equiv) was added Fe (3.2 g, 57.14 mmol, 3.00 equiv). The reaction mixture was stirred for 3 h at 80° C. EtOAc was added and the mixture was filtered out. The combined solution were washed with saturated brine, dried over anhydrous Na$_2$SO$_4$ and filtered, then concentrated and purified by chromatography on silica gel (2:1 PE/EA) to 5-(benzyloxy)-2-bromobenzenamine as a colorless oil.

To a mixture of 5-(benzyloxy)-2-bromobenzenamine (5 g, 17.98 mmol, 1.00 equiv) in acetonitrile (60 mL) with K$_2$CO$_3$ (19.9 g, 143.98 mmol, 8.01 equiv) was added MeI (15 g, 105.6 mmol, 5.87 equiv), and the reaction mixture was stirred at 80° C. for 48 h. Water was added and the mixture was extracted with EtOAc thrice. The combined extracts were washed with brine and dried over Na$_2$SO$_4$, then concentrated and purified by chromatography on silica gel (3:1 PE/EA) to yield 5-(benzyloxy)-2-bromo-N,N-dimethylbenzenamine as a colorless oil.

To a mixture of 5-(benzyloxy)-2-bromo-N,N-dimethylbenzenamine (4.6 g, 15.02 mmol, 1.00 equiv) in tetrahydrofuran (50 mL) was added n-BuLi (2.5 M in hexane, 7.2 mL, 18 mmol, 1.2 equiv) dropwise at −78° C. The reaction mixture was stirred for 30 min at −78° C. To the resulting mixture was then added DMF (3.3 g, 45.15 mmol, 3.01 equiv) in tetrahydrofuran (5 mL) dropwise at −78° C. The reaction mixture was stirred for 3 h at −78° C. NH$_4$Cl/H$_2$O was added and the mixture was extracted with EtOAc thrice. The combined extracts were washed with brine and dried over Na₂SO₄, then concentrated and purified by chromatography on silica gel (3:1 PE/EA) to yield 4-(benzyloxy)-2-(dimethylamino)benzaldehyde as a colorless oil.

To a mixture of 4-(benzyloxy)-2-(dimethylamino)benzaldehyde (3.4 g, 13.32 mmol, 1.00 equiv) in methanol (40 mL) was added pyridine hydrobromide perbromide (4.47 g, 13.98 mmol, 1.05 equiv) at −40° C., and the reaction mixture was stirred at −40° C. for 3 h. Water was added and the mixture was extracted with EtOAc thrice. The combined extracts were washed with brine and dried over Na₂SO₄, then concentrated and purified by chromatography on silica gel (3:1 PE/EA) to yield 4-(benzyloxy)-5-bromo-2-(dimethylamino)benzaldehyde as a white solid.

To a mixture of 3-bromobicyclo[4.2.0]octa-1(6),2,4-triene (300 mg, 1.64 mmol, 1.10 equiv) in THF (4 mL) was added n-BuLi (2.5 M in hexane, 0.66 mL, 1.64 mmol, 1.00 equiv) dropwise at −78° C. The reaction mixture was stirred for min at −78° C. To the resulting mixture was then added a solution of 4-(benzyloxy)-5-bromo-2-(dimethylamino)benzaldehyde (500 mg, 1.50 mmol, 1.00 equiv) in THF (1 mL) dropwise at −78° C. The reaction mixture was stirred for 3 h at −78° C. NH₄Cl/H₂O was added and the mixture was extracted with EtOAc thrice. The combined extracts were washed with brine and dried over Na₂SO₄, then concentrated and purified by chromatography on silica gel (3:1 PE/EA) to yield (4-(benzyloxy)-5-bromo-2-(dimethylamino)phenyl)(1,2-dihydrocyclobutabenzen-4-yl)methanol as a colorless oil.

To a mixture of (4-(benzyloxy)-5-bromo-2-(dimethylamino)phenyl)(1,2-dihydrocyclobutabenzen-4-yl)methanol (500 mg, 1.14 mmol, 1.00 equiv) in dichloromethane (15 mL) with Et₃SiH (530 mg, 4.56 mmol, 4.00 equiv) was added BF₃.Et₂O (812 mg, 5.72 mmol, 5.01 equiv) dropwise at 0° C. The reaction mixture was stirred for 16 h at room temperature. Sodium bicarbonate was added and the mixture was extracted with DCM thrice. The combined extracts were washed with brine and dried over Na₂SO₄, then concentrated and purified by chromatography on silica gel (3:1 PE/EA) to yield 5-(benzyloxy)-4-bromo-2-((1,2-dihydrocyclobutabenzen-4-yl)methyl)-N,N-dimethylbenzenamine as a white solid. ¹H NMR (400 MHz, CDCl₃): δ 7.49-7.56 (m, 2H), 7.40-7.46 (m, 2H), 7.32-7.39 (m, 1H), 7.21 (s, 1H), 6.96-7.08 (m, 2H), 6.89 (s, 1H), 6.74 (s, 1H), 5.17 (s, 2H), 3.98 (s, 2H), 3.17 (s, 4H), 2.66 (s, 6H).

To a mixture of 5-(benzyloxy)-4-bromo-2-((1,2-dihydrocyclobutabenzen-4-yl)methyl)-N,N-dimethylbenzenamine (370 mg, 0.88 mmol, 1.00 equiv) in tetrahydrofuran (5 mL) was added n-BuLi (2.5 M in hexane, 0.387 mL, 0.97 mmol, 1.1 equiv) dropwise at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (472 mg, 0.88 mmol, 1.00 equiv) in tetrahydrofuran (1 mL) dropwise at −78° C. The reaction mixture was stirred for 2 h at −78° C. NH₄Cl/H₂O was added and the mixture was extracted with EtOAc thrice. The combined extracts were washed with brine and dried over Na₂SO₄, then concentrated and purified by chromatography on silica gel (3:1 PE/EA) to yield (3R,4S,5R,6R)-3,4,5-tris(benzyloxy)-2-(2-(benzyloxy)-5-((1,2-dihydrocyclobutabenzen-4-yl)methyl)-4-(dimethylamino)phenyl)-6-(benzyloxymethyl)-tetrahydro-2H-pyran-2-ol as a colorless oil. MS (ES) m/z: 899 [M+NH₄].

To a mixture of (3R,4S,5R,6R)-3,4,5-tris(benzyloxy)-2-(2-(benzyloxy)-5-((1,2-dihydrocyclobutabenzen-4-yl)methyl)-4-(dimethylamino)phenyl)-6-(benzyloxymethyl)-tetrahydro-2H-pyran-2-ol (777 mg, 0.88 mmol, 1.00 equiv) in dichloromethane (15 mL) with Et₃SiH (305 mg, 2.62 mmol, 3.00 equiv) was added BF₃.Et₂O (374 mg, 2.62 mmol, 3.00 equiv) dropwise at 0° C. The reaction mixture was stirred for 16 h at room temperature. Sodium bicarbonate was added and the mixture was extracted with DCM thrice. The combined extracts were washed with brine and dried over Na₂SO₄, then concentrated and purified by chromatography on silica gel (3:1 PE/EA) to yield 5-(benzyloxy)-2-((1,2-dihydrocyclobutabenzen-4-yl)methyl)-N,N-dimethyl-4-((2S,3S,4R,5R,6R)-3,4,5-tris(benzyloxy)-6-(benzyloxymethyl)-tetrahydro-2H-pyran-2-yl)benzenamine as a colorless oil. MS (ES) m/z: 883 [M+NH₄].

To a mixture of 5-(benzyloxy)-2-((1,2-dihydrocyclobutabenzen-4-yl)methyl)-N,N-dimethyl-4-((2S,3S,4R,5R,6R)-3,4,5-tris(benzyloxy)-6-(benzyloxymethyl)-tetrahydro-2H-pyran-2-yl)benzenamine (220 mg, 0.25 mmol, 1.00 equiv) in dichloromethane (5 mL) with 1,2,3,4,5-pentamethylbenzene (200 mg, 1.35 mmol, 5.31 equiv) was added BCl₃ (1 M in DCM, 3 mL) dropwise at −78° C. The reaction mixture was stirred at −78° C. for 1 h. Methanol was added, and the resulting mixture was then concentrated and purified by chromatography on a C18 reversed phase column to yield the title compound as a white solid.

¹H NMR (300 MHz, Methanol-d₄) δ 7.00 (d, J=6.1 Hz, 2H), 6.81-6.92 (m, 2H), 6.65 (s, 1H), 4.43 (d, J=9.4 Hz, 1H), 3.79-4.05 (m, 3H), 3.60-3.72 (m, 1H), 3.35-3.58 (m, 4H), 3.10 (s, 4H), 2.60 (s, 6H). MS (ES) m/z: 416 [M+H]⁺.

Example 23: Compound #23

(2S,3R,4R,5S,6R)-2-(5-((1,2-dihydrocyclobutabenzen-4-yl)methyl)-4-(dimethylamino)-2-methoxyphenyl)-6-(hydroxymethyl)-tetrahydro-2H-pyran-3,4,5-triol

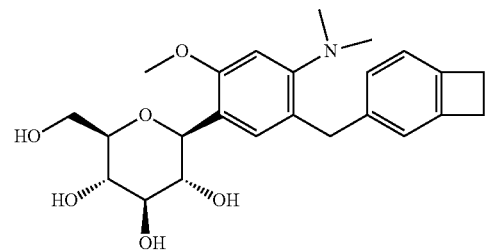 [SMILES: COc1cc(N(C)C)c(Cc2ccc3c(c2)CC3)cc1[C@@H]1O[C@H](CO)[C@@H](O)[C@H](O)[C@H]1O]

To a mixture of (2S,3R,4R,5S,6R)-2-(5-(bicyclo[4.2.0]octa-1(6),2,4-trien-3-ylmethyl)-4-(dimethylamino)-2-hydroxyphenyl)-6-(hydroxymethyl)tetrahydro-2H-pyran-3,4,5-triol (Compound #22) (15 mg, 0.04 mmol, 1.00 equiv) in acetonitrile (2 ml) with potassium carbonate (50 mg, 0.36 mmol, 10.02 equiv) was added MeI (51 mg, 0.36 mmol). The reaction mixture was stirred at room temperature for 5 h, then purified by chromatography on a C18 reversed phase column with MeCN/H₂O (30%-35%) to yield the title compound as a white solid.

¹H NMR (400 MHz, CD₃OD) δ 7.12 (s, 1H), 7.01 (d, J=7.7 Hz, 1H), 6.83-6.92 (m, 2H), 6.78 (s, 1H), 4.57 (d, J=9.0 Hz, 1H), 3.88-4.08 (m, 2H), 3.83 (s, 4H), 3.62 (dd, J=11.9, 5.4 Hz, 1H), 3.47 (dt, J=18.3, 8.8 Hz, 2H), 3.33-3.35 (m, 2H), 3.10 (s, 4H), 2.65 (s, 6H); MS (ES) m/z: 430.1 [M+H]⁺.

Example 24: Compound #24

(2S,3R,4R,5S,6R)-2-(3-((1,2-dihydrocyclobutabenzen-4-yl)methyl)phenyl)-6-(hydroxymethyl)-tetrahydro-2H-pyran-3,4,5-triol

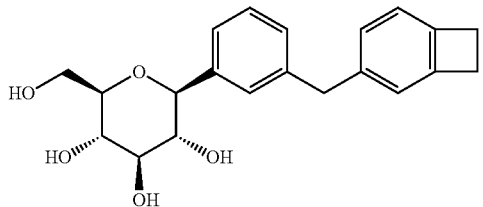 [SMILES: OC[C@H]1O[C@@H](c2cccc(Cc3ccc4c(c3)CC4)c2)[C@H](O)[C@@H](O)[C@@H]1O]

To a mixture of 3-bromobicyclo[4.2.0]octa-1,3,5-triene (1 g, 5.46 mmol, 1.00 equiv) in THF (10 mL) was added n-BuLi (2.5 M in hexane, 2.2 mL, 1.00 equiv) dropwise at −78° C. The reaction mixture was stirred for 30 min at −78° C. To the resulting mixture was then added a solution of 3-bromobenzaldehyde (910 mg, 4.92 mmol, 0.90 equiv) in THF (3 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (3:1 PE/EA) to yield (3-bromophenyl)(1,2-dihydrocyclobutabenzen-4-yl)methanol as a colorless oil. MS (ES) m/z: 271, 273 [M−OH]$^+$.

To a mixture of (3-bromophenyl)(1,2-dihydrocyclobutabenzen-4-yl)methanol (1.5 g, 5.19 mmol, 1.00 equiv) in dichloromethane (10 mL) with Et$_3$SiH (1.21 g, 10.41 mmol, 2.00 equiv) was added CF$_3$COOH (890 mg, 7.87 mmol, 1.50 equiv) at 0° C. The reaction mixture was stirred for 1 h at 0° C. Sodium bicarbonate was added and the mixture was extracted with DCM thrice. The combined extracts were washed with brine and dried over Na$_2$SO$_4$, then concentrated and purified by chromatography on silica gel (5:1 PE/EA) to yield 4-(3-bromobenzyl)-1,2-dihydrocyclobutabenzene as a yellow oil.

To a mixture of 4-(3-bromobenzyl)-1,2-dihydrocyclobutabenzene (800 mg, 2.93 mmol, 1.00 equiv) in tetrahydrofuran (15 mL) was added n-BuLi (2.5 M in hexane, 1.17 mL, 2.93 mmol, 1.00 equiv) dropwise at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (1.58 g, 2.93 mmol, 1.00 equiv) in tetrahydrofuran (15 mL) dropwise at −78° C. The reaction mixture was stirred for 2 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-6-(benzyloxymethyl)-2-(3-((1,2-dihydrocyclobutabenzen-4-yl)methyl)phenyl)-tetrahydro-2H-pyran-2-ol as a colorless oil. MS (ES) m/z: 715.3 [M−OH]$^+$.

To a mixture of (3R,4S,5R,6R)-3,4,5-tris(benzyloxy)-6-(benzyloxymethyl)-2-(3-((1,2-dihydrocyclobutabenzen-4-yl)methyl)phenyl)-tetrahydro-2H-pyran-2-ol (1.13 g, 1.54 mmol, 1.00 equiv) in dichloromethane (10 mL) with Et$_3$SiH (359 mg, 3.09 mmol, 2.00 equiv) was added BF$_3$·Et$_2$O (329 mg, 1.50 equiv) dropwise at 0° C. The reaction mixture was stirred for 1 h at 0° C. Sodium bicarbonate was added and the mixture was extracted with DCM thrice. The combined extracts were washed with brine and dried over Na$_2$SO$_4$, then concentrated and purified by chromatography on silica gel (3:1 PE/EA) to yield (2R,3R,4R,5S,6S)-3,4,5-tris(benzyloxy)-2-(benzyloxymethyl)-6-(3-((1,2-dihydrocyclobutabenzen-4-yl)methyl)phenyl)-tetrahydro-2H-pyran as a colorless oil. MS (ES) m/z: 739.4 [M+Na]$^+$.

To a mixture of (2R,3R,4R,5S,6S)-3,4,5-tris(benzyloxy)-2-(benzyloxymethyl)-6-(3-((1,2-dihydrocyclobutabenzen-4-yl)methyl)phenyl)-tetrahydro-2H-pyran (100 mg, 0.14 mmol, 1.00 equiv) in dichloromethane (3 mL) with 1,2,3,4,5-pentamethylbenzene (200 mg, 1.35 mmol, 9.60 equiv) was added BCl$_3$ (2.0 mL, 2 mmol, 14.30 equiv) dropwise at −78° C. The reaction mixture was stirred for 1 h at −78° C. Methanol was added, and the resulting mixture was then concentrated and purified by chromatography on C18 to yield the title compound as a white solid.

$^1$H NMR (400 MHz, Methanol-d$_4$) δ 7.20-7.32 (m, 3H), 7.12 (td, J=4.6, 1.7 Hz, 1H), 7.04 (dd, J=7.4, 1.4 Hz, 1H), 6.86-6.96 (m, 2H), 4.11 (d, J=9.3 Hz, 1H), 3.85-3.96 (m, 3H), 3.70 (dd, J=12.0, 5.4 Hz, 1H), 3.34-3.51 (m, 4H), 3.12 (s, 4H); MS (ES) m/z: 355.1 [M−H]$^-$.

Example 25: Compound #25

(2S,3R,4R,5S,6R)-2-(5-{bicyclo[4.2.0]octa-1(6),2,4-trien-3-ylmethyl}-2-hydroxyphenyl)-6-(hydroxymethyl)oxane-3,4,5-triol

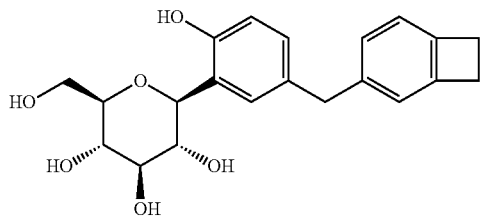 [SMILES: OC[C@H]1O[C@@H](c2cc(Cc3ccc4c(c3)CC4)ccc2O)[C@H](O)[C@@H](O)[C@@H]1O]

To a mixture of compound 3-bromo-4-hydroxybenzaldehyde (1.0 g, 4.97 mmol, 1.00 equiv) in CH$_3$CN (20 mL) with potassium carbonate (1.4 g, 10.13 mmol, 2.00 equiv) was added BnBr (1.3 g, 7.60 mmol, 1.50 equiv) dropwise at room temperature. The reaction mixture was heated to reflux for 2 h in an oil bath. H$_2$O was added and the mixture was extracted with EtOAc thrice. The combined extracts were washed with brine and dried over Na$_2$SO$_4$, then concentrated and purified by chromatography on silica gel (10% EA/PE) to yield 4-(benzyloxy)-3-bromobenzaldehyde as an off-white solid.

To a mixture of 4-(benzyloxy)-3-bromobenzaldehyde (377 mg, 2.06 mmol, 1.20 equiv) in tetrahydrofuran (8 mL) was added n-BuLi (2.5M in hexane, 0.76 mL, 1.10 equiv) dropwise with stirring at −78° C., the mixture was stirred for 30 min at −78° C. 4-(Benzyloxy)-3-bromobenzaldehyde (500 mg, 1.72 mmol, 1.00 equiv) in tetrahydrofuran (2 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (17% EA/PE) to yield [4-(benzyloxy)-3-bromophenyl](bicyclo[4.2.0]octa-1(6),2,4-trien-3-yl)methanol as a yellow oil.

To a mixture of [4-(benzyloxy)-3-bromophenyl](bicyclo[4.2.0]octa-1(6),2,4-trien-3-yl)methanol (700 mg, 1.77 mmol, 1.00 equiv) in dichloromethane (10 mL) with Et₃SiH (411 mg, 3.53 mmol, 2.00 equiv) was added CF₃COOH (303 mg, 2.68 mmol, 1.50 equiv) dropwise at 0° C. The reaction mixture was stirred for 1 h at 0° C. in a water/ice bath. Sodium bicarbonate/H₂O was added and the mixture was extracted with DCM thrice. The combined extracts were washed with brine and dried over Na₂SO₄, then concentrated and purified by chromatography on silica gel (6% EA/PE) to yield 3-{[4-(benzyloxy)-3-bromophenyl]methyl}bicyclo[4.2.0]octa-1(6),2,4-triene as a yellow oil. ¹H NMR (300 MHz, Chloroform-d) δ 7.32-7.52 (m, 6H), 6.95-7.18 (m, 3H), 6.82-6.92 (m, 2H), 5.15 (s, 2H), 3.88 (s, 2H), 3.16 (s, 4H).

To a mixture of 3-{[4-(benzyloxy)-3-bromophenyl]methyl}bicyclo[4.2.0]octa-1(6),2,4-triene (169 mg, 0.45 mmol, 1.20 equiv) in tetrahydrofuran/toluene (4/8 mL) was added n-BuLi (2.5M in hexane, 0.18 mL, 1.20 equiv) dropwise at −78° C., and the reaction mixture was stirred at −78° C. for 30 min. (3R,4S,5R,6R)-3,4,5-Tris(benzyloxy)-6-[(benzyloxy)methyl]oxan-2-one (200 mg, 0.37 mmol, 1.00 equiv) in tetrahydrofuran (1.5 mL) was then added to the solution. The reaction mixture was stirred at −78° C. for 2 h. NH₄Cl/H₂O was added and the mixture was extracted with EtOAc thrice. The combined extracts were washed with brine and dried over Na₂SO₄, then concentrated and purified by chromatography on silica gel (20% EA/PE) to yield (3R,4S,5R,6R)-3,4,5-tris(benzyloxy)-2-[2-(benzyloxy)-5-{bicyclo[4.2.0]octa-1(6),2,4-trien-3-ylmethyl}phenyl]-6-[(benzyloxy)methyl]oxan-2-ol as a yellow oil. MS (ES) m/z: 821.6 [M–OH]⁺

To a mixture of (3R,4S,5R,6R)-3,4,5-tris(benzyloxy)-2-[2-(benzyloxy)-5-{bicyclo[4.2.0]octa-1(6),2,4-trien-3-ylmethyl}phenyl]-6-[(benzyloxy)methyl]oxan-2-ol (275 mg, 0.33 mmol, 1.00 equiv) in DCM (8 mL) with Et₃SiH (76 mg, 0.65 mmol, 2.00 equiv) was added BF₃.Et₂O (70 mg, 0.49 mmol, 1.50 equiv) at 0° C. The reaction mixture was stirred at 0° C. for 1 h. Sodium bicarbonate/H₂O was added and the mixture was extracted with dichloromethane thrice. The combined extracts were washed with brine and dried over Na₂SO₄, then concentrated and purified by chromatography on silica gel (8% EA/PE) to yield (2S,3S,4R,5R,6R)-3,4,5-tris(benzyloxy)-2-[2-(benzyloxy)-5-{bicyclo[4.2.0]octa-1(6),2,4-trien-3-ylmethyl}phenyl]-6-[(benzyloxy)methyl]oxane as a yellow oil. MS (ES) m/z: 845.5 [M+Na]⁺

To a mixture of (2S,3S,4R,5R,6R)-3,4,5-tris(benzyloxy)-2-[2-(benzyloxy)-5-{bicyclo[4.2.0]octa-1(6),2,4-trien-3-ylmethyl}phenyl]-6-[(benzyloxy)methyl]oxane (130 mg, 0.16 mmol, 1.00 equiv) in dichloromethane (5 mL) with 1,2,3,4,5-pentamethylbenzene (260 mg, 1.75 mmol, 11.10 equiv) was added BCl₃ (1 M in DCM, 2.6 mL, 16.25 equiv) dropwise at −78° C. The reaction mixture was stirred at −78° C. for 1 h. 5 mL of methanol was added, and the resulting mixture was then concentrated and purified by chromatography on a C18 reversed phase column (33% CH₃CN/H₂O) to yield the title compound as white solid.

¹H-NMR (MeOD, 300 MHz) δ 7.19 (d, J=2.4 Hz, 1H), 7.01 (d, J=8.7 Hz, 1H), 6.86-6.95 (m, 3H), 6.72 (d, J=8.4 Hz, 1H), 4.55 (d, J=9.0 Hz, 1H), 3.83-3.89 (m, 3H), 3.67-3.74 (m, 1H), 3.46-3.55 (m, 2H), 3.42 (d, J=6.6 Hz, 2H), 3.10 (s, 4H). MS (ES) m/z: 371.1 [M–H]⁻

Example 26: Compound #26

(2S,3R,4R,5S,6R)-2-(5-(bicyclo[4.2.0]octa-1(6),2,4-trien-3-ylmethyl)-2-methoxyphenyl)-6-(hydroxymethyl)oxane-3,4,5-triol

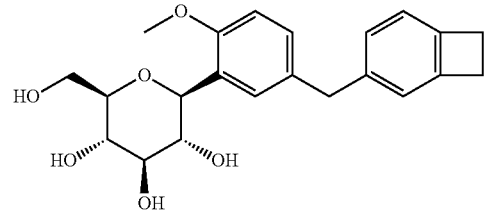 [SMILES: COc1ccc(Cc2ccc3c(c2)CC3)cc1[C@@H]1O[C@H](CO)[C@@H](O)[C@H](O)[C@H]1O]

To a mixture of (2S,3R,4R,5S,6R)-2-(5-((1,2-dihydrocyclobutabenzen-4-yl)methyl)-2-hydroxyphenyl)-6-(hydroxymethyl)-tetrahydro-2H-pyran-3,4,5-triol (Compound #25) (23 mg, 0.06 mmol, 1.00 equiv) in N,N-dimethylformamide (2 mL), with potassium carbonate (17.1 mg, 0.12 mmol, 2.00 equiv) was added CH₃I (44 mg, 0.31 mmol, 5.00 equiv) at room temperature. The reaction mixture was stirred for 1 h at room temperature. The solids were filtered out and chromatograph on a C18 reversed phase column (42% CH₃CN/H₂O) to yield the title compound as a white solid.

¹H-NMR (MeOD, 300 MHz) δ 7.28 (d, J=2.1 Hz, 1H), 7.01-7.09 (m, 2H), 6.87-6.92 (m, 3H), 4.67 (d, J=9.0 Hz, 1H), 3.79-3.86 (m, 6H), 3.63-3.67 (m, 1H), 3.43-3.56 (m, 2H), 3.37-3.39 (m, 2H), 3.11 (s, 4H). MS (ES) m/z: 385.1 [M–H]⁻

Example 27: Compound #27

(2S,3R,4R,5S,6R)-2-(5-((1,2-dihydrocyclobutabenzen-4-yl)methyl)-2-hydroxy-3-methylphenyl)-6-(hydroxymethyl)-tetrahydro-2H-pyran-3,4,5-triol

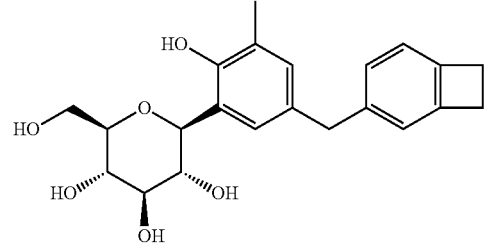 [SMILES: Cc1cc(Cc2ccc3c(c2)CC3)cc([C@@H]2O[C@H](CO)[C@@H](O)[C@H](O)[C@H]2O)c1O]

To a mixture of 4-hydroxy-3-methylbenzaldehyde (500 mg, 3.67 mmol) in DMF (5 ml) with K₂CO₃ (1014 mg, 7.34 mmol) was added BnBr (692 mg, 4.05 mmol) at room temperature. The reaction mixture was stirred at room temperature for 2 h. Water was added and the mixture was extracted with EA thrice. The combined extracts were washed with water, saturated brine and dried over anhydrous Na₂SO₄, then concentrated and purified by chromatography on silica gel (1:30 EA/PE) to yield 4-(benzyloxy)-3-methylbenzaldehyde as a yellow oil.

To a solution of 4-(benzyloxy)-3-methylbenzaldehyde (830 mg, 3.67 mmol) in MeOH (8 ml) was added pyridium tribromide (1.75 g, 5.47 mmol) at room temperature. The reaction mixture was stirred at room temperature for 2 h.

Water was added and the mixture was extracted with EA thrice. The combined extracts were washed with water, saturated brine and dried over anhydrous $Na_2SO_4$, then concentrated and purified by chromatography on silica gel (1:30 EA/PE) to yield 4-(benzyloxy)-3-bromo-5-methylbenzaldehyde as a yellow solid. MS (ES) m/z: 348.0 $[M+MeCN+H]^+$ To a solution of 3-bromobicyclo[4.2.0]octa-1,3,5-triene (132 mg, 0.72 mmol) in THF (1.5 ml) was added dropwise n-BuLi (2.5 M in n-hexane) (0.29 ml, 0.72 mmol) at −78° C. under $N_2$. The reaction mixture was stirred at −78° C. for 30 min. 4-(Benzyloxy)-3-bromo-5-methylbenzaldehyde (200 mg, 0.66 mmol) in THF (0.5 ml) was added dropwise at −78° C. The reaction mixture was stirred at −78° C. for 1 h. Saturated $NH_4Cl$ (aq) was added and the mixture was extracted with EA thrice. The combined extracts were washed with water, saturated brine and dried over anhydrous $Na_2SO_4$, then concentrated and purified by chromatography on silica gel (1:3 EA/PE) to yield (4-(benzyloxy)-3-bromo-5-methylphenyl)(1,2-dihydrocyclobutabenzen-4-yl)methanol as a yellow oil.

To a solution of (4-(benzyloxy)-3-bromo-5-methylphenyl)(1,2-dihydrocyclobutabenzen-4-yl)methanol (120 mg, 0.29 mmol) in DCM (1 ml) with $Et_3SiH$ (68 mg, 0.58 mmol) was added $BF_3\cdot Et_2O$ (83 mg, 0.58 mmol) at 0° C. The reaction mixture was stirred at 0° C. for 1 h. Saturated $NaHCO_3$ (aq) was added and the mixture was extracted with DCM thrice. The combined extracts were washed with water, saturated brine and dried over anhydrous $Na_2SO_4$, then concentrated and purified by chromatography on silica gel (1:30 EA/PE) to yield 4-(4-(benzyloxy)-3-bromo-5-methylbenzyl)-1,2-dihydrocyclobutabenzene as a yellow oil.

To a solution of 4-(4-(benzyloxy)-3-bromo-5-methylbenzyl)-1,2-dihydrocyclobutabenzene (100 mg, 0.25 mmol) in THF (1 ml) was added dropwise n-BuLi (2.5 M in n-hexane) (0.1 ml, 0.25 mmol) at −78° C. under $N_2$. The reaction mixture was stirred at −78° C. for 30 min. (3R,4S,5R,6R)-3,4,5-tris(benzyloxy)-6-[(benzyloxy)-methyl]oxan-2-one (120 mg, 0.22 mmol) in THF (0.2 ml) was added dropwise at −78° C. The reaction mixture was stirred at −78° C. for 1 h. Saturated $NH_4Cl$ (aq) was added and the mixture was extracted with EA thrice. The combined extracts were washed with water, saturated brine and dried over anhydrous $Na_2SO_4$, then concentrated and purified by chromatography on silica gel (1:3 EA/PE) to yield (3R,4S,5R,6R)-3,4,5-tris(benzyloxy)-2-(2-(benzyloxy)-5-((1,2-dihydrocyclobutabenzen-4-yl)methyl)-3-methylphenyl)-6-(benzyloxymethyl)-tetrahydro-2H-pyran-2-ol as a yellow oil.

To a solution of (3R,4S,5R,6R)-3,4,5-tris(benzyloxy)-2-(2-(benzyloxy)-5-((1,2-dihydrocyclobutabenzen-4-yl)methyl)-3-methylphenyl)-6-(benzyloxymethyl)-tetrahydro-2H-pyran-2-ol (100 mg, 0.12 mmol) in DCM (1 ml) with $Et_3SiH$ (27 mg, 0.23 mmol) was added $BF_3\cdot Et_2O$ (33 mg, 0.23 mmol) at 0° C. The reaction mixture was stirred at 0° C. for 1 h. Saturated $NaHCO_3$ (aq) was added and the mixture was extracted with DCM thrice. The combined extracts were washed with water, saturated brine and dried over anhydrous $Na_2SO_4$, then concentrated and purified by chromatography on silica gel (1:30 EA/PE) to yield (2S,3S,4R,5R,6R)-3,4,5-tris(benzyloxy)-2-(2-(benzyloxy)-5-((1,2-dihydrocyclobutabenzen-4-yl)methyl)-3-methylphenyl)-6-(benzyloxymethyl)-tetrahydro-2H-pyran as a yellow oil.

To a solution of (2S,3S,4R,5R,6R)-3,4,5-tris(benzyloxy)-2-(2-(benzyloxy)-5-((1,2-dihydrocyclobutabenzen-4-yl)methyl)-3-methylphenyl)-6-(benzyloxymethyl)-tetrahydro-2H-pyran (90 mg, 0.11 mmol) in DCM (1 ml) with 1,2,3,4,5-pentamethylbenzene (180 mg, 1.21 mmol) was added $BCl_3$ (1 M in DCM) (1.8 mL, 1.8 mmol) dropwise at −78° C. The reaction mixture was stirred at −78° C. for 1 h. Methanol was added, and the resulting mixture was then concentrated and purified by chromatography on C18 reverse phase column (25-70% $MeCN/H_2O$) to yield the title compound as a white solid.

$^1H$ NMR (300 MHz, $CD_3OD$) δ 7.10-7.04 (m, 2H), 6.99-6.94 (m, 1H), 6.92 (s, 2H), 4.56-4.46 (m, 1H), 4.01-3.93 (m, 1H), 3.87 (s, 2H), 3.86-3.79 (m, 1H), 3.59-3.48 (m, 4H), 3.18 (s, 4H), 2.23 (s, 3H); MS (ES) m/z: 385.1 $[M-H]^-$.

Example 28: Compound #28

(2S,3R,4R,5S,6R)-2-(3-((1,2-dihydrocyclobutabenzen-4-yl)methyl)-6-hydroxy-2-methylphenyl)-6-(hydroxymethyl)-tetrahydro-2H-pyran-3,4,5-triol

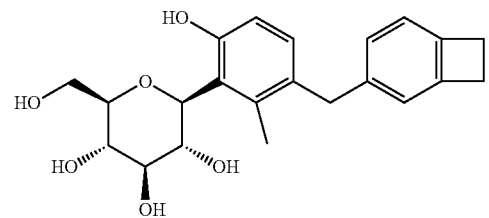 [SMILES: Cc1c(Cc2ccc3c(c2)CC3)ccc(O)c1[C@@H]1O[C@H](CO)[C@@H](O)[C@H](O)[C@H]1O]

To a mixture of 3-methyl-2-nitrophenol (20 g, 130.60 mmol) in DMF (200 ml) with $K_2CO_3$ (36 g, 260.47 mmol) was added BnBr (25 g, 146.17 mmol) at room temperature. The reaction mixture was stirred at room temperature overnight. Water was added and the mixture was extracted with EA thrice. The combined extracts were washed with water, saturated brine and dried over anhydrous $Na_2SO_4$, then concentrated and purified by chromatography on silica gel (1:100 EA/PE) to yield 1-(benzyloxy)-3-methyl-2-nitrobenzene as a yellow oil.

To a mixture of 1-(benzyloxy)-3-methyl-2-nitrobenzene (31 g, 127.44 mmol) in $MeOH/H_2O$ (300 ml/100 ml) with $NH_4Cl$ (34 g, 635.63 mmol) was added Fe (21 g, 375.00 mmol). The reaction mixture was stirred at 95° C. for 1 h. The reaction mixture was cooled and the solids were filtered out. The filtrate was evaporated to remove excess methanol. Water was added and the mixture was extracted with EA thrice. The resulting mixture was then concentrated to yield 2-(benzyloxy)-6-methylbenzenamine as a brown oil. MS (ES) m/z: 214.1 $[M+H]^+$.

To a mixture of 2-(benzyloxy)-6-methylbenzenamine (10 g, 46.89 mmol) in DMF (100 ml) with HCl (12 M, 30 ml) was added a solution of $NaNO_2$ (3.6 g, 52.17 mmol) in water (30 mL) dropwise at 0° C. The reaction mixture was stirred at 0° C. for 30 min. This resulting solution was added to a solution of KI (39 g, 234.94 mmol) in water (400 mL) dropwise with stirring at 40° C. The reaction mixture was stirred at 40° C. for 1 h. Water was added and the mixture was extracted with EA thrice. The combined extracts were washed with saturated $NaHSO_3$ (aq), brine and dried over anhydrous $Na_2SO_4$, then concentrated and purified by chromatography on silica gel (1:100 EA/PE) to yield 1-(benzyloxy)-2-iodo-3-methylbenzene as a light yellow oil. $^1H$ NMR (400 MHz, $CDCl_3$-d) δ 7.55-7.49 (m, 2H), 7.47 (d, J=8.7 Hz, 1H), 7.45-7.38 (m, 2H), 7.26-7.29 (m, 2H), 6.59 (d, J=8.8 Hz, 1H), 5.16 (s, 2H), 2.73 (s, 3H).

To a mixture of 1-(benzyloxy)-2-iodo-3-methylbenzene (10 g, 30.85 mmol) in MeOH (100 ml) was added pyridium tribromide (13 g, 40.65 mmol) at room temperature. The reaction mixture was stirred at room temperature for 1 h. Water was added and the precipitation was filtered. The solids were dried to 1-(benzyloxy)-4-bromo-2-iodo-3-methylbenzene as an off-white solid. $^1$H NMR (400 MHz, DMSO-$d_6$) δ 7.81 (d, J=7.8 Hz, 1H), 7.30-7.48 (m, 3H), 7.17 (t, J=7.8 Hz, 1H), 6.97 (d, J=7.5 Hz, 1H), 6.85-6.92 (m, 1H), 4.95 (s, 2H), 2.64 (s, 3H).

To a mixture of 1-(benzyloxy)-4-bromo-2-iodo-3-methylbenzene (3 g, 7.44 mmol) in THF (30 ml) was added n-BuLi (2.5 M in n-hexane) (3 mL, 7.44 mmol) dropwise at −78° C. under $N_2$. The reaction mixture was stirred at −78° C. for 30 min. (3R,4S,5R,6R)-3,4,5-tris(benzyloxy)-6-[(benzyloxy)methyl]oxan 2-one (3.6 g, 6.68 mmol) in THF (15 ml) was added dropwise at −78° C. The reaction mixture was stirred at −78° C. for 1 h. Water was added and the mixture was extracted with EA thrice. The combined extracts were washed with water, saturated brine and dried over anhydrous $Na_2SO_4$, then concentrated and purified by chromatography on silica gel (1:3 EA/PE) to yield (3R,4S,5R,6R)-3,4,5-tris(benzyloxy)-2-(6-(benzyloxy)-3-bromo-2-methylphenyl)-6-(benzyloxymethyl)-tetrahydro-2H-pyran-2-ol as a yellow oil. MS (ES) m/z: 818.3 [M+H]$^+$.

To a mixture of (3R,4S,5R,6R)-3,4,5-tris(benzyloxy)-2-(6-(benzyloxy)-3-bromo-2-methylphenyl)-6-(benzyloxymethyl)-tetrahydro-2H-pyran-2-ol (500 mg, 0.61 mmol) in DCM (5 ml) with $Et_3SiH$ (210 mg, 1.81 mmol) was added $CF_3COOH$ (210 mg, 1.84 mmol) at 0° C. The reaction mixture was stirred at 0° C. for 4 h. Saturated $NaHCO_3$ (aq) was added and the mixture was extracted with EA thrice. The combined extracts were washed with water, saturated brine and dried over anhydrous $Na_2SO_4$, then concentrated and purified by chromatography on silica gel (1:30 EA/PE) to yield (2S,3S,4R,5R,6R)-3,4,5-tris(benzyloxy)-2-(6-(benzyloxy)-3-bromo-2-methylphenyl)-6-(benzyloxymethyl)-tetrahydro-2H-pyran as a yellow oil. MS (ES) m/z: 840.5 [M+MeCN+H]$^+$.

To a mixture of (2S,3S,4R,5R,6R)-3,4,5-tris(benzyloxy)-2-(6-(benzyloxy)-3-bromo-2-methylphenyl)-6-(benzyloxymethyl)-tetrahydro-2H-pyran (700 mg, 0.88 mmol) in THF (7 ml) was added n-BuLi (2.5 M in n-hexane) (0.39 mL, 0.98 mmol) dropwise at −78° C. under $N_2$. The reaction mixture was stirred at −78° C. for 30 min. DMF (130 mg, 1.78 mmol) in THF was added dropwise at −78° C. The reaction mixture was stirred at −78° C. for 1 h. Saturated $NH_4Cl$ (aq) was added and the mixture was extracted with EA thrice. The combined extracts were washed with water, saturated brine and dried over anhydrous $Na_2SO_4$, then concentrated and purified by chromatography on silica gel (1:5 EA/PE) to yield 4-(benzyloxy)-2-methyl-3-((2S,3S,4R,5R,6R)-3,4,5-tris(benzyloxy)-6-(benzyloxymethyl)-tetrahydro-2H-pyran-2-yl)benzaldehyde as a yellow oil. MS (ES) m/z: 818.3 [M+NH$_4$]$^+$.

To a mixture of 3-bromobicyclo[4.2.0]octa-1,3,5-triene (117 mg, 0.64 mmol) in THF (2 ml) was added dropwise n-BuLi (2.5 M in n-hexane) (0.25 ml, 0.64 mmol) at −78° C. under $N_2$. The reaction mixture was stirred at −78° C. for min. 4-(benzyloxy)-2-methyl-3-((2S,3S,4R,5R,6R)-3,4,5-tris(benzyloxy)-6-(benzyloxymethyl)-tetrahydro-2H-pyran-2-yl)benzaldehyde ((240 mg, 0.32 mmol) in THF (1 ml) was added dropwise at −78° C. The reaction mixture was stirred at −78° C. for 1 h. Saturated $NH_4Cl$ (aq) was added and the mixture was extracted with EA thrice. The combined extracts were washed with water, saturated brine and dried over anhydrous $Na_2SO_4$, then concentrated and purified by chromatography on silica gel (1:3 EA/PE) to (4-(benzyloxy)-2-methyl-3-((2S,3S,4R,5R,6R)-3,4,5-tris(benzyloxy)-6-(benzyloxymethyl)-tetrahydro-2H-pyran-2-yl)phenyl)(1,2-dihydrocyclo-butabenzen-4-yl)methanol as a yellow oil. MS (ES) m/z: 875.5 [M+Na]$^+$.

To a mixture of (4-(benzyloxy)-2-methyl-3-((2S,3S,4R,5R,6R)-3,4,5-tris(benzyloxy)-6-(benzyloxymethyl)-tetrahydro-2H-pyran-2-yl)phenyl)(1,2-dihydrocyclo-butabenzen-4-yl)methanol (200 mg, 0.23 mmol) in DCM (2 ml) with $Et_3SiH$ (54 mg, 0.46 mmol) was added $CF_3COOH$ (54 mg, 0.47 mmol) at 0° C. The reaction mixture was stirred at 0° C. for 1 h. Saturated $NaHCO_3$ (aq) was added and the mixture was extracted with DCM thrice. The combined extracts were washed with water, saturated brine and dried over anhydrous $Na_2SO_4$, then concentrated and purified by chromatography on silica gel (1:30 EA/PE) to yield (2S,3S,4R,5R,6R)-3,4,5-tris(benzyloxy)-2-(6-(benzyloxy)-3-((1,2-dihydrocyclobutabenzen-4-yl)methyl)-2-methylphenyl)-6-(benzyloxymethyl)-tetrahydro-2H-pyran as a yellow oil.

To a mixture of (2S,3S,4R,5R,6R)-3,4,5-tris(benzyloxy)-2-(6-(benzyloxy)-3-((1,2-dihydrocyclobutabenzen-4-yl)methyl)-2-methylphenyl)-6-(benzyloxymethyl)-tetrahydro-2H-pyran (160 mg, 0.19 mmol) with 1,2,3,4,5-pentamethylbenzene (320 mg, 2.16 mmol) in DCM (2 ml) was added dropwise $BCl_3$ (1 M in DCM) (3.2 mL, 3.2 mmol) at −78° C. The reaction mixture was stirred at −78° C. for 1 h. MeOH was added, and the resulting mixture was then concentrated and purified by chromatography on C18 reverse column (36-40% MeCN/$H_2O$) to yield the title compound as a white solid.

$^1$H NMR (400 MHz, $CD_3OD$) δ 7.04-6.86 (m, 3H), 6.76 (s, 1H), 6.65 (d, J=8.2 Hz, 1H), 4.81 (brs, 1H), 3.83-3.94 (m, 4H), 3.78 (m, 1H), 3.47 (m, 3H), 3.11 (s, 4H), 2.22 (s, 3H); MS (ES) m/z: 385.1 [M−H]$^−$.

Example 29: Compound #29

(2S,3R,4R,5S,6R)-2-(5-[bicyclo[4.2.0]octa-1,3,5-trien-3-ylmethyl]-2-fluoro-4-methylphenyl)-6-(hydroxymethyl)oxane-3,4,5-triol

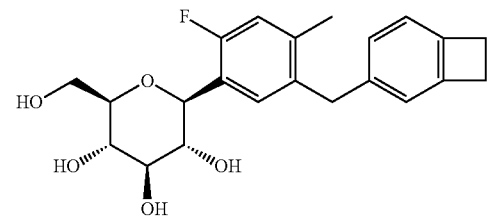 [SMILES: Cc1cc(F)c([C@@H]2O[C@H](CO)[C@@H](O)[C@H](O)[C@H]2O)cc1Cc1ccc2c(c1)CC2]

To a mixture of 5-bromo-4-fluoro-2-methylbenzoic acid (10 g, 42.91 mmol, 1.00 equiv) in DMF (200 mL) with HATU (21.3 g, 56.02 mmol, 1.30 equiv) was added DIEA (16.7 g, 129.22 mmol, 3.00 equiv) dropwise at 0° C., and the reaction mixture was stirred for 5 min at 0° C. Methoxy (methyl)amine Hydrochloride (6.2 g, 63.56 mmol, 1.50 equiv) was then added, in portions at 0° C. The reaction mixture was stirred for an overnight at room temperature. Brine was added and the mixture was extracted with EtOAc thrice, then concentrated and purified by chromatography on silica gel (4:1 PE/EA) to 5-bromo-4-fluoro-N-methoxy-N,2-dimethylbenzamide as a yellow oil.

To a mixture of Mg (2.43 g, 99.96 mmol, 4.00 equiv) in THF (20 mL) with 1,2-dibromoethane (238 mg, 1.27 mmol, 0.05 equiv) was added 3-bromobicyclo[4.2.0]octa-1(6),2,4-triene (14 g, 76.48 mmol, 3.00 equiv) in tetrahydrofuran (150 ml) dropwise with stirring at 70° C., and the reaction mixture was stirred for 1 h at 70° C. The reaction mixture was cooled down and the supernatant liquor was added to 5-bromo-4-fluoro-N-methoxy-N,2-dimethylbenzamide (7 g, 25.35 mmol, 1.00 equiv) in tetrahydrofuran (70 mL) dropwise at 0° C. The reaction mixture was stirred for an overnight at room temperature. Water/ice (150 mL) was added and the mixture was extracted with EtOAc thrice, then concentrated and purified by chromatography on silica gel (9:1 PE/EA) to yield (5-bromo-4-fluoro-2-methylphenyl)(1,2-dihydrocyclobutabenzen-4-yl)methanone as a yellow oil.

To a mixture of (5-bromo-4-fluoro-2-methylphenyl)(1,2-dihydrocyclobutabenzen-4-yl)methanone (1 g, 3.13 mmol, 1.00 equiv) in dichloromethane (7 mL) and CH₃CN (15 mL) with Et₃SiH (2.18 g, 18.75 mmol, 6.00 equiv) was added BF₃.Et₂O (2.23 g, 15.71 mmol, 5.00 equiv) dropwise at room temperature. The reaction mixture was stirred for 3 h at 50° C. NaHCO₃/H₂O was added and the mixture was extracted with DCM thrice, then concentrated and purified by chromatography on silica gel (11:1 PE/EA) to yield 4-(5-bromo-4-fluoro-2-methylbenzyl)-1,2-dihydrocyclobutabenzene as a yellow oil. $^1$H-NMR (400 MHz, CDCl₃) δ 7.23 (d, J=7.2 Hz, 0.5H), 7.00-7.04 (m, 0.5H), 6.89-6.97 (m, 3H), 6.77 (d, J=7.2 Hz, 1H), 3.98 (s, 0.5H), 3.87 (s, 1.5H), 3.13 (s, 4H), 2.35 (s, 1H), 2.20 (s, 2H).

To a mixture of 4-(5-bromo-4-fluoro-2-methylbenzyl)-1,2-dihydrocyclobutabenzene in tetrahydrofuran (8 mL) and toluene (16 mL) was added n-BuLi (2.5M in hexane, 1.18 mL, 1.00 equiv) dropwise at −78° C., and the reaction mixture was stirred for 20 min at −78° C. (3R,4S,5R,6R)-3,4,5-Tris(benzyloxy)-6-[(benzyloxy)methyl]oxan-2-one (1.51 g, 2.80 mmol, 0.95 equiv) in tetrahydrofuran (8 mL) was then added to the solution. The reaction mixture was stirred at −78° C. for 1 h. NH₄Cl/H₂O was added and the mixture was extracted with EtOAc thrice. The combined extracts were washed with brine and dried over Na₂SO₄, then concentrated to yield (3R,4S,5R,6R)-3,4,5-tris(benzyloxy)-6-(benzyloxymethyl)-2-(5-((1,2-dihydrocyclobutabenzen-4-yl)methyl)-2-fluoro-4-methylphenyl)-tetrahydro-2H-pyran-2-ol as a yellow oil. MS (ES) m/z: 787.5 [M+Na]⁺.

To a mixture of (3R,4S,5R,6R)-3,4,5-tris(benzyloxy)-6-(benzyloxymethyl)-2-(5-((1,2-dihydrocyclobutabenzen-4-yl)methyl)-2-fluoro-4-methylphenyl)-tetrahydro-2H-pyran-2-ol in dichloromethane (20 mL) with Et₃SiH (1 g, 8.60 mmol, 3.00 equiv) was added TFA (980 mg, 8.67 mmol, 3.00 equiv) dropwise at 0° C. The reaction mixture was stirred at 0° C. for 1 h. NaHCO₃/H₂O was added and the mixture was extracted with DCM thrice, then concentrated and purified by chromatography on silica gel (9:1 PE/EA) to yield (2R,3R,4R,5S,6S)-3,4,5-tris(benzyloxy)-2-(benzyloxymethyl)-6-(5-((1,2-dihydrocyclobutabenzen-4-yl)methyl)-2-fluoro-4-methylphenyl)-tetrahydro-2H-pyran as a yellow oil. MS (ES) m/z: 766.4 [M+NH₄]⁺.

To a mixture of (2R,3R,4R,5S,6S)-3,4,5-tris(benzyloxy)-2-(benzyloxymethyl)-6-(5-((1,2-dihydrocyclobutabenzen-4-yl)methyl)-2-fluoro-4-methylphenyl)-tetrahydro-2H-pyran in dichloromethane (10 mL) with 1,2,3,4,5-pentamethylbenzene (988 mg, 6.66 mmol, 10.00 equiv) was added BCl₃ (1M in DCM, 10 mL, 15.00 equiv) dropwise with stirring at −78° C. The reaction mixture was stirred for 1 h at −78° C. Methanol (5 mL) was added, and the resulting mixture was then concentrated and purified by chromatography on a C18 reversed phase column to yield the title compound as a white solid.

$^1$H-NMR (400 MHz, CD₃OD) δ7.30 (d, J=7.2 Hz, 1H), 6.87-7.00 (m, 3H), 6.80 (s, 1H), 4.48 (d, J=9.2 Hz, 1H), 3.95 (s, 2H), 3.89 (d, J=11.6 Hz, 1H), 3.67-3.71 (m, 1H), 3.49-3.55 (m, 2H), 3.38-3.44 (m, 2H), 3.12 (s, 4H), 2.19 (s, 3H); MS (ES) m/z: 387.1 [M−H]⁺.

Example 30: Compound #30

(2S,3R,4R,5S,6R)-2-(4-chloro-5-((1,2-dihydrocyclobutabenzen-4-yl)methyl)-2-fluorophenyl)-6-(hydroxymethyl)-tetrahydro-2H-pyran-3,4,5-triol

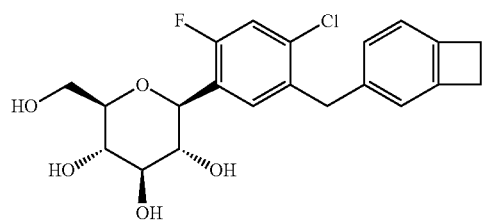

To a mixture of bicyclo[4.2.0]octa-1(6),2,4-trien-3-yl(5-bromo-2-chloro-4-fluorophenyl)methanone (500 mg, 1.47 mmol, 1.00 equiv) in CH₃CN/DCM (8 mL/4 mL) with Et₃SiH (341 mg, 2.94 mmol, 2.00 equiv) was added BF₃.Et₂O (313 mg, 2.20 mmol, 1.50 equiv). The reaction mixture was stirred for 1 h at 50° C. Sodium bicarbonate (a.q) was added and the mixture was extracted with DCM thrice, then concentrated and purified by chromatography on silica gel (100:1 PE/EA) to yield 4-(5-bromo-2-chloro-4-fluorobenzyl)-1,2-dihydrocyclobutabenzene as a yellow oil.

To a mixture of 4-(5-bromo-2-chloro-4-fluorobenzyl)-1,2-dihydrocyclobutabenzene (242 mg, 0.74 mmol, 1.10 equiv) in tetrahydrofuran (10 ml) was added n-BuLi (2.5M, 0.33 mL, 1.21 equiv) dropwise with stirring at −78° C. The reaction mixture was stirred for 30 min at −78° C. To the resulting mixture was then added a solution of (3R,4S,5R,6R)-3,4,5-tris(benzyloxy)-6-[(benzyloxy)methyl]oxan-2-one (365 mg, 0.68 mmol, 1.00 equiv) in tetrahydrofuran (2 ml) dropwise with stirring at −78° C. The reaction mixture was stirred for 1 h at −78° C. Water was added and the mixture was extracted with EtOAc thrice, then concentrated to yield (3R,4S,5R,6R)-3,4,5-tris(benzyloxy)-6-(benzyloxymethyl)-2-(4-chloro-5-((1,2-dihydrocyclobutabenzen-4-yl)methyl)-2-fluorophenyl)-tetrahydro-2H-pyran-2-ol as a yellow oil. MS (ES) m/z: 767.2 [M−OH]⁺

To a mixture of (3R,4S,5R,6R)-3,4,5-tris(benzyloxy)-6-(benzyloxymethyl)-2-(4-chloro-5-((1,2-dihydrocyclobutabenzen-4-yl)methyl)-2-fluorophenyl)-tetrahydro-2H-pyran-2-ol (500 mg, 0.64 mmol, 1.00 equiv) in dichloromethane (20 mL) with Et₃SiH (148 mg, 1.28 mmol, 2.00 equiv) was added BF₃.Et₂O (181 mg, 1.27 mmol, 2.00 equiv) at 0° C. The reaction mixture was stirred for 1 h at 0° C. Sodium bicarbonate was added and the mixture was extracted with DCM thrice, then concentrated and purified by chromatography on silica gel (10:1 PE/EA) to yield (2R,3R,4R,5S,6S)-3,4,5-tris(benzyloxy)-2-(benzyloxymethyl)-6-(4-chloro-5-((1,2-dihydrocyclobutabenzen-4-yl)methyl)-2-fluorophenyl)-tetrahydro-2H-pyran as a yellow oil. MS (ES) m/z: 769.5 [M+H]⁻

To a mixture of (2R,3R,4R,5S,6S)-3,4,5-tris(benzyloxy)-2-(benzyloxymethyl)-6-(4-chloro-5-((1,2-dihydrocyclobutabenzen-4-yl)methyl)-2-fluorophenyl)-tetrahydro-2H-pyran (250 mg, 0.32 mmol, 1.00 equiv) in dichloromethane (10 mL) with 1,2,3,4,5-pentamethylbenzene (500 mg, 3.37 mmol, 10.38 equiv) was added BCl₃ (5 mL, 5 mmol 15.6 equiv, 1 N) at −78° C. The reaction mixture was stirred for 1 h at −78° C. Methanol was added, and the resulting mixture was then concentrated and purified by chromatography on C18 reverse phase column (10%-50% CH₃CN/H₂O) to yield the title compound as a white solid.

¹H NMR (300 MHz, CD₃OD) δ 7.44 (d, J=7.4 Hz, 1H), 7.17 (d, J=9.7 Hz, 1H), 7.02 (d, J=7.7 Hz, 1H), 6.69-6.83 (m, 2H), 4.45 (d, J=9.0 Hz, 1H), 3.95-4.13 (m, 2H), 3.87 (d, J=11.9 Hz, 1H), 3.62-3.74 (m, 1H), 3.35-3.54 (m, 4H), 3.11 (s, 4H); MS (ES) m/z: 407.1 [M−H]⁻

Example 31: Compound #31

(2S,3R,4R,5S,6R)-2-(5-((1,2-dihydrocyclobutaben-zen-4-yl)methyl)-2-fluoro-4-methoxyphenyl)-6-(hy-droxymethyl)-tetrahydro-2H-pyran-3,4,5-triol

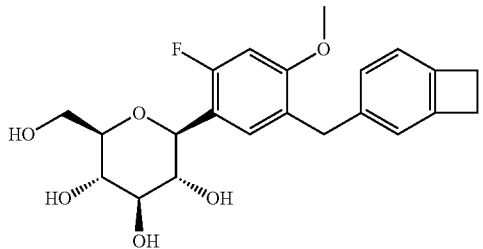 [SMILES: COc1cc(F)c([C@@H]2O[C@H](CO)[C@@H](O)[C@H](O)[C@H]2O)cc1Cc1ccc2c(c1)CC2]

To a mixture of 4-fluoro-2-methoxybenzaldehyde (12 g, 77.85 mmol, 1.00 equiv) in DMF (200 mL) was added NBS (69.4 g, 389.93 mmol, 5.01 equiv). The reaction mixture was stirred for 3 h at 60° C. Water was added and the mixture was extracted with EtOAc thrice. The combined extracts were washed with brine and dried over Na₂SO₄, then concentrated and purified by chromatography on silica gel (5:1 PE/EA) to 5-bromo-4-fluoro-2-methoxybenzaldehyde as a colorless oil.

To a mixture of 5-bromo-4-fluoro-2-methoxybenzalde-hyde (7 g, 30.04 mmol, 1.00 equiv) in THF (100 mL) was added bicyclo[4.2.0]octa-1,3,5-trien-3-yl(bromo)magne-sium (1 M in THF, 100 mL, 3.33 equiv) dropwise at 0° C. The reaction mixture was stirred overnight at room temperature. NH₄Cl/H₂O was added and the mixture was extracted with EtOAc thrice. The combined extracts were washed with brine and dried over Na₂SO₄, then concentrated and purified by chromatography on silica gel (5:1 PE/EA) to yield (5-bromo-4-fluoro-2-methoxyphenyl)(1,2-dihydrocyclobutabenzen-4-yl)methanol as a yellow oil. MS (ES) m/z: 319.1, 321.1 [M−OH]⁺.

To a mixture of (5-bromo-4-fluoro-2-methoxyphenyl)(1,2-dihydrocyclobutabenzen-4-yl)methanol (300 mg, 0.89 mmol, 1.00 equiv) in DCM (10 mL) with Et₃SiH (300 mg, 2.58 mmol, 2.90 equiv) was added trifluoroacetic acid (200 mg, 1.75 mmol, 1.97 equiv) at 0° C. The reaction mixture was stirred for 2 h at room temperature. NaHCO₃/H₂O was added and the mixture was extracted with DCM thrice. The combined extracts were washed with brine and dried over Na₂SO₄, then concentrated and purified by chromatography on silica gel (20:1 PE/EA) to yield 4-(5-bromo-4-fluoro-2-methoxybenzyl)-1,2-dihydrocyclobutabenzene as a colorless oil. MS (ES) m/z: 321.2, 323.2 [M+H]⁺.

To a mixture of 4-(5-bromo-4-fluoro-2-methoxybenzyl)-1,2-dihydrocyclobutabenzene (200 mg, 0.62 mol, 1.00 equiv) in tetrahydrofuran (15 mL) was added n-BuLi (2.5 M in hexane, 0.25 mL, 0.62 mol, 1.00 equiv) dropwise at −78° C. The reaction mixture was stirred for 20 min at −78° C. To the resulting mixture was then added a solution of (3R,4S,5R,6R)-3,4,5-tris(benzyloxy)-6-[(benzyloxy)methyl]oxan-2-one (336 mg, 0.62 mmol, 1.00 equiv) in tetrahydrofuran (2 mL) dropwise at −78° C. The reaction mixture was stirred for 1 h at −78° C. NH₄Cl/H₂O was added and the mixture was extracted with EtOAc thrice. The combined extracts were washed with brine and dried over Na₂SO₄, then concentrated and purified by chromatography on silica gel (5:1 PE/EA) to (3R,4S,5R,6R)-3,4,5-tris(benzyloxy)-6-(benzyloxymethyl)-2-(5-((1,2-dihydrocyclobutabenzen-4-yl)methyl)-2-fluoro-4-methoxyphenyl)-tetrahydro-2H-pyran-2-ol as a yellow oil.

To a mixture of (3R,4S,5R,6R)-3,4,5-tris(benzyloxy)-6-(benzyloxymethyl)-2-(5-((1,2-dihydrocyclobutabenzen-4-yl)methyl)-2-fluoro-4-methoxyphenyl)-tetrahydro-2H-pyran-2-ol (210 mg, 0.27 mmol, 1.00 equiv) in dichloromethane (20 mL) with Et₃SiH (180 mg, 1.55 mmol, 5.76 equiv) was added BF₃.Et₂O (200 mg, 1.41 mmol, 5.24 equiv) dropwise at 0° C. The reaction mixture was stirred for 2 h at 0° C. Sodium bicarbonate was added and the mixture was extracted with DCM thrice. The combined extracts were washed with brine and dried over Na₂SO₄, then concentrated and purified by chromatography on silica gel (10:1 PE/EA) to yield (2R,3R,4R,5S,6S)-3,4,5-tris(benzyloxy)-2-(benzyloxymethyl)-6-(5-((1,2-dihydrocyclobutabenzen-4-yl)methyl)-2-fluoro-4-methoxyphenyl)-tetrahydro-2H-pyran as a colorless oil. MS (ES) m/z: 787.3 [M+Na]⁺.

To a mixture of (2R,3R,4R,5S,6S)-3,4,5-tris(benzyloxy)-2-(benzyloxymethyl)-6-(5-((1,2-dihydrocyclobutabenzen-4-yl)methyl)-2-fluoro-4-methoxyphenyl)-tetrahydro-2H-pyran (120 mg, 0.16 mmol, 1.00 equiv) in dichloromethane (5 mL) with 1,2,3,4,5-pentamethylbenzene (100 mg, 0.67 mmol, 4.30 equiv) was added BCl₃ (10 mL, 10 mmol, 62.50 equiv) dropwise at −78° C. The reaction mixture was stirred for 1 h at −78° C. Methanol was added, and the resulting mixture was then concentrated and purified by chromatography on C18 (10%-50% CH₃CN/H₂O) to yield the title compound as a white solid.

¹H NMR (400 MHz, Methanol-d₄) δ 7.24 (d, J=8.1 Hz, 1H), 7.03 (dd, J=7.4, 1.5 Hz, 1H), 6.81-6.94 (m, 2H), 6.71 (d, J=12.1 Hz, 1H), 4.34-4.51 (m, 1H), 3.83-3.99 (m, 3H), 3.80 (d, J=1.5 Hz, 3H), 3.59-3.73 (m, 1H), 3.42-3.56 (m, 2H), 3.36-3.42 (m, 2H), 3.10 (s, 4H). MS (ES) m/z: 403.1 [M−H]⁻

Example 32: Compound #32

(2S,3R,4R,5S,6R)-2-(5-((1,2-dihydrocyclobutaben-zen-4-yl)methyl)-4-ethyl-2-fluorophenyl)-6-(hy-droxymethyl)-tetrahydro-2H-pyran-3,4,5-triol

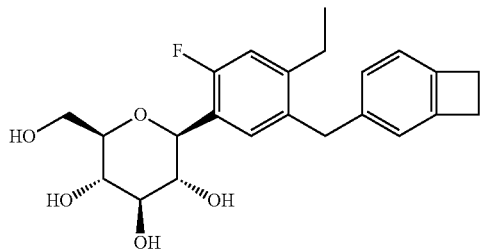 [SMILES: CCc1cc(F)c([C@@H]2O[C@H](CO)[C@@H](O)[C@H](O)[C@H]2O)cc1Cc1ccc2c(c1)CC2]

To a mixture of 3-bromobicyclo[4.2.0]octa-1,3,5-triene (238 mg, 1.30 mmol, 3.00 equiv) in THF (10 ml) was added n-BuLi (0.52 mL, 1.30 mmol, 3.00 equiv) dropwise at −78° C. The reaction mixture was stirred for 20 min at −78° C. To the resulting mixture was then added a solution of 2-ethyl-4-fluoro-5-((3R,4S,5R,6R)-3,4,5-tris(benzyloxy)-6-((benzyloxy)methyl)-2-hydroxytetrahydro-2H-pyran-2-yl)benzaldehyde (300 mg, 0.43 mmol, 1.00 equiv) in THF (5 ml) dropwise at −78° C. The reaction mixture was stirred for 1 h at −78° C. Water was added and the mixture was extracted with EtOAc thrice, then concentrated to yield (3R,4S,5R,6R)-3,4,5-tris(benzyloxy)-6-(benzyloxymethyl)-2-(5-((1,2-dihydrocyclobutabenzen-4-yl)(hydroxy)methyl)-4-ethyl-2-fluorophenyl)-tetrahydro-2H-pyran-2-ol as a yellow oil. MS (ES) m/z: 777.4 [M−OH]$^+$ To a mixture of (3R,4S,5R,6R)-3,4,5-tris(benzyloxy)-6-(benzyloxymethyl)-2-(5-((1,2-dihydrocyclobutabenzen-4-yl)(hydroxy)methyl)-4-ethyl-2-fluorophenyl)-tetrahydro-2H-pyran-2-ol (500 mg, 0.63 mmol, 1.00 equiv) in dichloromethane (15 mL) with Et$_3$SiH (292 mg, 2.51 mmol, 4.00 equiv) was added BF$_3$.Et$_2$O (357 mg, 2.51 mmol, 4.00 equiv) at 0° C. The reaction mixture was stirred for 1 h at 0° C. Sodium bicarbonate was added and the mixture was extracted with DCM thrice, then concentrated and purified by chromatography on silica gel (20:1 PE/EA) to yield (2R,3R,4R,5S,6S)-3,4,5-tris(benzyloxy)-2-(benzyloxymethyl)-6-(5-((1,2-dihydrocyclobutabenzen-4-yl)methyl)-4-ethyl-2-fluorophenyl)-tetrahydro-2H-pyran as a yellow oil. MS (ES) m/z: 785.4 [M+Na]$^+$ To a mixture of (2R,3R,4R,5S,6S)-3,4,5-tris(benzyloxy)-2-(benzyloxymethyl)-6-(5-((1,2-dihydrocyclobutabenzen-4-yl)methyl)-4-ethyl-2-fluorophenyl)-tetrahydro-2H-pyran (100 mg, 0.13 mmol, 1.00 equiv) in dichloromethane (10 mL) with 1,2,3,4,5-pentamethylbenzene (200 mg, 1.35 mmol, 10.00 equiv) was added BCl$_3$ (2 mL, 2.00 mmol, 15.00 equiv) at −78° C. The reaction mixture was stirred for 1 h at −78° C. Methanol was added, and the resulting mixture was then concentrated and purified by chromatography on C18 reverse phase column (10%-50% CH$_3$CN/H$_2$O) to yield the title compound as a white solid.

$^1$H NMR (400 MHz, CD$_3$OD) δ7.30 (d, J=7.2 Hz, 1H), 6.87-7.00 (m, 3H), 6.80 (s, 1H), 4.48 (d, J=8.8 Hz, 1H), 3.98 (s, 2H), 3.89 (dd, J=12.0, 1.5 Hz, 1H), 3.64-3.74 (m, 1H), 3.35-3.58 (m, 4H), 3.12 (s, 4H), 2.58 (d, J=7.5 Hz, 2H), 1.09 (t, J=7.5 Hz, 3H); MS (ES) m/z: 401.1 [M−H]$^−$

Example 33: Compound #33

(2S,3R,4R,5S,6R)-2-(5-((1,2-dihydrocyclobutaben-zen-4-yl)methyl)-4-methyl-2-(trifluoromethoxy)phenyl)-6-(hydroxymethyl)-tetrahydro-2H-pyran-3,4,5-triol

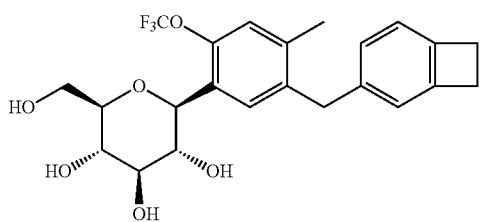 [SMILES: Cc1cc(OC(F)(F)F)c([C@@H]2O[C@H](CO)[C@@H](O)[C@H](O)[C@H]2O)cc1Cc1ccc2c(c1)CC2]

To a mixture of 2-methyl-4-(trifluoromethoxy)benzaldehyde (0.1 g, 0.49 mmol, 1.00 equiv) in trifluoroacetic acid (1 mL) and sulfuric acid (0.5 mL) was added NBS (174 mg, 0.98 mmol, 2.00 equiv). The reaction mixture was stirred for 16 h at 25° C. NaHCO$_3$ (aq.) was added and the mixture was extracted with EtOAc thrice, then concentrated and purified by chromatography on silica gel (10:1 PE/EA) to yield 5-bromo-2-methyl-4-(trifluoromethoxy)benzaldehyde as a yellow oil.

To a mixture of 5-bromo-2-methyl-4-(trifluoromethoxy)benzaldehyde (1.1 g, 3.89 mmol, 1.00 equiv) in tetrahydrofuran (10 mL) was added bicyclo[4.2.0]octa-1,3,5-trien-3-yl(bromo)magnesium (15.5 mL, 15.5 mmol, 3.98 equiv) dropwise at 0° C. The reaction mixture was stirred for 2 h at 0° C. Water was added and the mixture was extracted with EtOAc thrice, then concentrated and purified by chromatography on silica gel (10:1 PE/EA) to yield 1(5-bromo-2-methyl-4-(trifluoromethoxy)phenyl)(1,2-dihydrocyclobutabenzen-4-yl)methanol as a yellow oil.

To a mixture of (5-bromo-2-methyl-4-(trifluoromethoxy)phenyl)(1,2-dihydrocyclobutabenzen-4-yl)methanol (1.2 g, 3.10 mmol, 1.00 equiv) in dichloromethane (10 mL) with Et$_3$SiH (700 mg, 6.02 mmol, 1.94 equiv) was added TFA (700 mg, 6.19 mmol, 2.00 equiv) dropwise at 25° C. The reaction mixture was stirred for 2 h at 25° C. NaHCO$_3$ (aq.) was added and the mixture was extracted with EtOAc thrice, then concentrated and purified by chromatography on silica gel (10:1 PE/EA) to yield 4-(5-bromo-2-methyl-4-(trifluoromethoxy)benzyl)-1,2-dihydrocyclobutabenzene as a yellow oil.

To a mixture of 4-(5-bromo-2-methyl-4-(trifluoromethoxy)benzyl)-1,2-dihydrocyclobutabenzene (450 mg, 1.21 mmol, 1.00 equiv) in tetrahydrofuran (5 mL) was added n-BuLi (2.5M in hexane, 2.7 mL, 1.2 equiv) dropwise with stirring at −78° C., and the mixture was stirred for 20 min at −78° C. (3R,4S,5R,6R)-3,4,5-Tris(benzyloxy)-6-(benzyloxymethyl)-tetrahydropyran-2-one (600 mg, 1.11 mmol, 0.92 equiv) in THF (1 mL) was then added to the solution. The reaction mixture was stirred at −78° C. for 1 h. NH$_4$Cl (aq.) was added and the mixture was extracted with EtOAc thrice, then concentrated and purified by chromatography on silica gel (3:1 PE/EA) to yield (3R,4S,5R,6R)-3,4,5-tris(benzyloxy)-6-(benzyloxymethyl)-2-(5-((1,2-dihydrocyclobutabenzen-4-yl)methyl)-4-methyl-2-(trifluoromethoxy)phenyl)-tetrahydro-2H-pyran-2-ol as a yellow oil. MS (ES) m/z: 813.3 [M−OH]$^+$ To a mixture of (3R,4S,5R,6R)-3,4,5-tris(benzyloxy)-6-(benzyloxymethyl)-2-(5-((1,2-dihydrocyclobutabenzen-4-yl)methyl)-4-methyl-2-(trifluoromethoxy)phenyl)-tetrahydro-2H-pyran-2-ol (500 mg, 0.60 mmol, 1.00 equiv) in dichloromethane (10 mL) with Et$_3$SiH (140 mg, 1.20 mmol, 2.00 equiv) was added BF$_3$.Et$_2$O (170 mg, 1.20 mmol, 1.99 equiv) dropwise at 0° C. The reaction mixture was stirred for 1 h at 0° C. NaHCO$_3$ (aq.) was added and the mixture was extracted with EtOAc thrice, then concentrated and purified by chromatography on silica gel (5:1 PE/EA) to yield (2R,3R,4R,5S,6S)-3,4,5-tris(benzyloxy)-2-(benzyloxymethyl)-6-(5-((1,2-dihydrocyclobutabenzen-4-yl)methyl)-4-methyl-2-(trifluoromethoxy)phenyl)-tetrahydro-2H-pyran as a white solid.

To a mixture of (2R,3R,4R,5S,6S)-3,4,5-tris(benzyloxy)-2-(benzyloxymethyl)-6-(5-((1,2-dihydrocyclobutabenzen-4-yl)methyl)-4-methyl-2-(trifluoromethoxy)phenyl)-tetrahydro-2H-pyran (150 mg, 0.18 mmol, 1.00 equiv) in dichloromethane (5 mL) with 1,2,3,4,5-pentamethylbenzene (300 mg, 2.02 mmol, 10.99 equiv) was added BCl$_3$ (1M in DCM, 3 mL, 3 mmol, 16.67 equiv) dropwise at −78° C. The reaction mixture was stirred at −78° C. for 1 h. Methanol was added, and the resulting mixture was then concentrated and purified by chromatography on a C18 reversed phase column to yield the title compound as a white solid.

$^1$H-NMR (300 MHz, CD$_3$OD) δ 7.40 (s, 1H), 7.07 (d, J=2.1 Hz, 1H), 6.87-7.02 (m, 2H), 6.80 (s, 1H), 4.50 (d, J=8.9 Hz, 1H), 3.98 (s, 2H), 3.86 (dd, J=12.1, 1.7 Hz, 1H), 3.68 (dd, J=12.0, 4.9 Hz, 1H), 3.36-3.56 (m, 4H), 3.11 (s, 4H), 2.21 (s, 3H); MS (ES) m/z: 472.1 [M+NH$_4$]$^+$.

Example 34: Compound #34

(2S,3R,4R,5S,6R)-2-(5-((1,2-dihydrocyclobutaben-zen-4-yl)methyl)-4-methoxy-2-(trifluoromethoxy)phenyl)-6-(hydroxymethyl)-tetrahydro-2H-pyran-3,4,5-triol

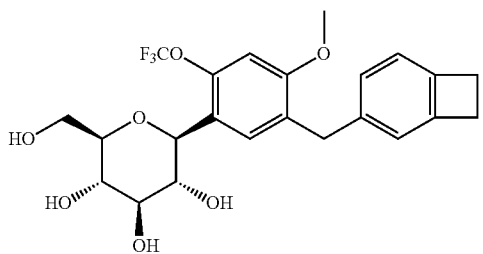

To a mixture of 2-methoxy-4-(trifluoromethoxy)benzaldehyde (1 g, 4.54 mmol, 1.00 equiv) in methanol (10 mL) was added pyridinium bromide perbromide (2.5 g, 7.84 mmol, 1.73 equiv). The reaction mixture was stirred for 16 h at 40° C. Water was added and the mixture was extracted with EtOAc thrice, then concentrated and purified by chromatography on a C18 reversed phase column to yield 5-bromo-2-methoxy-4-(trifluoromethoxy)benzaldehyde as a yellow solid.

To a mixture of 5-bromo-2-methoxy-4-(trifluoromethoxy)benzaldehyde (900 mg, 3.01 mmol, 1.00 equiv) in tetrahydrofuran (10 mL) was added bicyclo[4.2.0]octa-1,3,5-trien-3-yl(bromo)magnesium (0.5 M, in tetrahydrofuran, 15 mL, 7.5 mmol, 2.49 equiv) dropwise at 0° C. The reaction mixture was stirred for 3 h at 25° C. Water was added and the mixture was extracted with EtOAc thrice, then concentrated and purified by chromatography on silica gel (10:1 PE/EA) to yield (5-bromo-2-methoxy-4-(trifluoromethoxy)phenyl)(1,2-dihydrocyclobutabenzen-4-yl)methanol as a yellow oil.

To a mixture of (5-bromo-2-methoxy-4-(trifluoromethoxy)phenyl)(1,2-dihydrocyclobutabenzen-4-yl)methanol (450 mg, 1.12 mmol, 1.00 equiv) in dichloromethane (5 mL) with Et$_3$SiH (400 mg, 3.44 mmol, 3.08 equiv) was added trifluoroacetic acid (400 mg, 3.54 mmol, 3.17 equiv) dropwise at 25° C. The reaction mixture was stirred for 1 h at 25° C. NaHCO$_3$ (aq.) was added and the mixture was extracted with EtOAc thrice, then concentrated and purified by chromatography on silica gel (10:1 PE/EA) to yield 4-(5-bromo-2-methoxy-4-(trifluoromethoxy)benzyl)-1,2-dihydrocyclobutabenzene as a yellow oil. $^1$H-NMR (400 MHz, CDCl$_3$): δ 7.27 (t, J=0.7 Hz, 1H), 6.96-7.09 (m, 2H), 6.91 (s, 1H), 6.81 (d, J=1.2 Hz, 1H), 3.90 (s, 2H), 3.85 (s, 3H), 3.17 (s, 4H).

To a mixture of 4-(5-bromo-2-methoxy-4-(trifluoromethoxy)benzyl)-1,2-dihydrocyclobutabenzene (300 mg, 0.77 mmol, 1.00 equiv) in tetrahydrofuran (5 mL) was added n-BuLi (2.5 M in hexane, 0.3 mL, 0.97 equiv) dropwise with stirring at −78° C., the mixture was stirred for 15 mins at −78° C. (3R,4S,5R,6R)-3,4,5-tris(benzyloxy)-6-(benzyloxymethyl)-tetrahydropyran-2-one (380 mg, 0.71 mmol, 0.91 equiv) in THF (1 mL) was then added to the solution. The reaction mixture was stirred at −78° C. for 2 h. NH$_4$Cl (aq.) was added and the mixture was extracted with EtOAc thrice, then concentrated and purified by chromatography on silica gel (5:1 PE/EA) to yield (3R,4S,5R,6R)-3,4,5-tris(benzyloxy)-6-(benzyloxymethyl)-2-(5-((1,2-dihydrocyclobutabenzen-4-yl)methyl)-4-methoxy-2-(trifluoromethoxy)phenyl)-tetrahydro-2H-pyran-2-ol as a yellow oil.

To a mixture of (3R,4S,5R,6R)-3,4,5-tris(benzyloxy)-6-(benzyloxymethyl)-2-(5-((1,2-dihydrocyclobutabenzen-4-yl)methyl)-4-methoxy-2-(trifluoromethoxy)phenyl)-tetrahydro-2H-pyran-2-ol (400 mg, 0.47 mmol, 1.00 equiv) in dichloromethane (5 mL) was followed by the addition of Et$_3$SiH (109 mg, 0.94 mmol, 1.98 equiv) and BF$_3$.Et$_2$O (134 mg, 0.94 mmol, 2.00 equiv) dropwise with stirring at 0° C. The reaction mixture was stirred for 2 h at 0° C. NaHCO$_3$ (aq.) was added and the mixture was extracted with EtOAc thrice, then concentrated and purified by chromatography on silica gel (10:1 PE/EA) to yield (2R,3R,4R,5S,6S)-3,4,5-tris(benzyloxy)-2-(benzyloxymethyl)-6-(5-((1,2-dihydrocyclobutabenzen-4-yl)methyl)-4-methoxy-2-(trifluoromethoxy)phenyl)-tetrahydro-2H-pyran as a yellow oil.

To a mixture of (2R,3R,4R,5S,6S)-3,4,5-tris(benzyloxy)-2-(benzyloxymethyl)-6-(5-((1,2-dihydrocyclobutabenzen-4-yl)methyl)-4-methoxy-2-(trifluoromethoxy)phenyl)-tetrahydro-2H-pyran (150 mg, 0.18 mmol, 1.00 equiv) in dichloromethane (5 mL) with 1,2,3,4,5-pentamethylbenzene (300 mg, 2.02 mmol, 11.21 equiv) was added BCl$_3$ (1 M in DCM, 3 mL, 3 mmol, 16.66 equiv) dropwise at −78° C. The reaction mixture was stirred at −78° C. for 1 h. Methanol was added, and the resulting mixture was then concentrated and purified by chromatography on a C18 reversed phase column to yield the title compound as a white solid.

$^1$H-NMR (400 MHz, CD$_3$OD): δ 7.36 (s, 1H), 7.08-7.01 (m, 1H), 6.90 (d, J=8.4 Hz, 2H), 6.83 (d, J=1.6 Hz, 1H), 4.40-4.51 (m, 1H), 3.80-3.98 (m, 6H), 3.67 (dd, J=12.0, 5.2 Hz, 1H), 3.33-3.54 (m, 4H), 3.11 (s, 4H); MS (ES) m/z: 488.1 [M+NH$_4$]$^+$

Example 35: Compound #35

(2S,3R,4R,5S,6R)-2-(5-((1,2-dihydrocyclobutabenzen-4-yl)methyl)-4-ethyl-2-(trifluoromethoxy)phenyl)-6-(hydroxymethyl)-tetrahydro-2H-pyran-3,4,5-triol

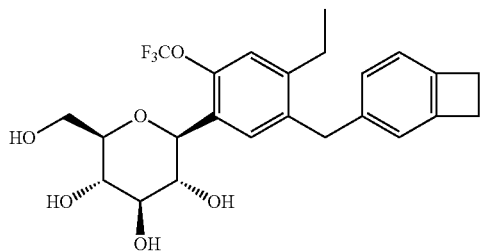 [SMILES: CCc1cc(OC(F)(F)F)c([C@@H]2O[C@H](CO)[C@@H](O)[C@H](O)[C@H]2O)cc1Cc1ccc2c(c1)CC2]

To a mixture of 2-bromo-4-(trifluoromethoxy)benzaldehyde (900 mg, 3.35 mmol, 1.00 equiv), Cs$_2$CO$_3$ (2.3 g, 7.04 mmol, 2.10 equiv) and Pd(dppf)Cl$_2$ (270 mg, 0.37 mmol, 0.11 equiv) in tetrahydrofuran (10 mL) was added Et$_3$B (1 M, in hexane, 10 mL, 10 mmol, 2.98 equiv). The reaction mixture was stirred at 75° C. for 3 h. Water was added and the mixture was extracted with EtOAc thrice, then concentrated and purified by chromatography on silica gel (10:1 PE/EA) to yield 2-ethyl-4-(trifluoromethoxy)benzaldehyde as a yellow oil.

To a mixture of 2-ethyl-4-(trifluoromethoxy)benzaldehyde (400 mg, 1.83 mmol, 1.00 equiv) in dichloromethane (2 mL) was added trifluoroacetic acid (2 mL), H$_2$SO$_4$ (con, 1 mL) and NBS (490 mg, 2.75 mmol, 1.50 equiv). The reaction mixture was stirred for 16 h at 25° C. Ice and NaHCO$_3$ (aq.) was added and the mixture was extracted with EtOAc thrice, then concentrated and purified by chromatography on silica gel (30:1 PE/EA) to yield 5-bromo-2-ethyl-4-(trifluoromethoxy)benzaldehyde as a yellow oil. $^1$H-NMR (400 MHz, CDCl$_3$): δ 10.26 (s, 1H), 8.10 (s, 1H), 7.25 (s, 1H), 3.08 (q, J=7.5 Hz, 2H), 1.30 (t, J=7.5 Hz, 3H).

To a mixture of 5-bromo-2-ethyl-4-(trifluoromethoxy)benzaldehyde (400 mg, 1.35 mmol, 1.00 equiv) in tetrahydrofuran (15 mL) was added of bicyclo[4.2.0]octa-1,3,5-trien-3-yl(bromo)magnesium (1 M in tetrahydrofuran, 4 mL, 4 mmol, 2.96 equiv) dropwise at 0° C. The reaction mixture was stirred at 0° C. for 1 h. Water was added and the mixture was extracted with EtOAc thrice, then concentrated and purified by chromatography on silica gel (5:1 PE/EA) to yield (5-bromo-2-ethyl-4-(trifluoromethoxy)phenyl)(1,2-dihydrocyclobutabenzen-4-yl)methanol as a yellow oil.

To a mixture of (5-bromo-2-ethyl-4-(trifluoromethoxy)phenyl)(1,2-dihydrocyclobutabenzen-4-yl)methanol (370 mg, 0.92 mmol, 1.00 equiv) in dichloromethane (6 mL) with Et$_3$SiH (210 mg, 1.81 mmol, 1.96 equiv) was added trifluoroacetic acid (210 mg, 1.86 mmol, 2.01 equiv) dropwise at 25° C. The reaction mixture was stirred for 1 h at 25° C. NaHCO$_3$ (aq.) was added and the mixture was extracted with EtOAc thrice, then concentrated and purified by chromatography on silica gel (10:1 PE/EA) to yield 4-(5-bromo-2-ethyl-4-(trifluoromethoxy)benzyl)-1,2-dihydrocyclobutabenzene as a yellow oil. $^1$H-NMR (400 MHz, CDCl$_3$): δ 7.33 (s, 1H), 7.28 (s, 1H), 6.98 (q, J=7.5 Hz, 2H), 6.81 (s, 1H), 3.95 (s, 2H), 3.16 (s, 4H), 2.61 (q, J=7.5 Hz, 2H), 1.16 (t, J=7.5 Hz, 3H).

To a mixture of 4-(5-bromo-2-ethyl-4-(trifluoromethoxy)benzyl)-1,2-dihydrocyclobutabenzene (270 mg, 0.70 mmol, 1.00 equiv) in tetrahydrofuran (5 mL) was added n-BuLi (2.5M in hexane, 0.3 mL, 1.07 equiv) dropwise at −78° C., the mixture was stirred for 15 mins at −78° C. (3R,4S,5R,6R)-3,4,5-Tris(benzyloxy)-6-(benzyloxymethyl)-tetrahydropyran-2-one (380 mg, 0.71 mmol, 1.01 equiv) in THF (1 mL) was then added to the solution. The reaction mixture was stirred at −78° C. for 1 h. NH$_4$Cl (aq.) was added and the mixture was extracted with EtOAc thrice, then concentrated and purified by chromatography on silica gel (5:1 PE/EA) to yield (3R,4S,5R,6R)-3,4,5-tris(benzyloxy)-6-(benzyloxymethyl)-2-(5-((1,2-dihydrocyclobutabenzen-4-yl)methyl)-4-ethyl-2-(trifluoromethoxy)phenyl)-tetrahydro-2H-pyran-2-ol as a yellow oil.

To a mixture of (3R,4S,5R,6R)-3,4,5-tris(benzyloxy)-6-(benzyloxymethyl)-2-(5-((1,2-dihydrocyclobutabenzen-4-yl)methyl)-4-ethyl-2-(trifluoromethoxy)phenyl)-tetrahydro-2H-pyran-2-ol (400 mg, 0.47 mmol, 1.00 equiv) in dichloromethane (10 mL) with Et$_3$SiH (100 mg, 0.86 mmol, 1.82 equiv) was added BF$_3$.Et$_2$O (100 mg, 0.70 mmol, 1.49 equiv) dropwise at 0° C. The reaction mixture was stirred for 1 h at 0° C. NaHCO$_3$ (aq.) was added and the mixture was extracted with EtOAc thrice, then concentrated and purified by chromatography on silica gel (3:1 PE/EA) to yield 0 (2R,3R,4R,5S,6S)-3,4,5-tris(benzyloxy)-2-(benzyloxymethyl)-6-(5-((1,2-dihydrocyclobutabenzen-4-yl)methyl)-4-ethyl-2-(trifluoromethoxy)phenyl)-tetrahydro-2H-pyran as a yellow oil.

To a mixture of (2R,3R,4R,5S,6S)-3,4,5-tris(benzyloxy)-2-(benzyloxymethyl)-6-(5-((1,2-dihydrocyclobutabenzen-4-yl)methyl)-4-ethyl-2-(trifluoromethoxy)phenyl)-tetrahydro-2H-pyran (150 mg, 0.18 mmol, 1.00 equiv) in dichloromethane (5 mL) with 1,2,3,4,5-pentamethylbenzene (300 mg, 2.02 mmol, 11.18 equiv) was added BCl$_3$ (1M in DCM, 3 mL) dropwise at −78° C. The reaction mixture was stirred at −78° C. for 1 h. Methanol was added, and the resulting mixture was then concentrated and purified by chromatography on a C18 reversed phase column to yield the title compound as a white solid.

$^1$H-NMR (300 MHz, CD$_3$OD): δ7.40 (s, 1H), 7.09 (d, J=1.8 Hz, 1H), 6.86-7.02 (m, 2H), 6.80 (s, 1H), 4.50 (d, J=9.0 Hz, 1H), 4.01 (s, 2H), 3.80-3.92 (m, 1H), 3.68 (dd, J=12.1, 5.0 Hz, 1H), 3.36-3.59 (m, 4H), 3.11 (s, 4H), 2.61 (q, J=7.5 Hz, 2H), 1.08 (t, J=7.5 Hz, 3H); MS (ES) m/z: 486.1 [M−H]$^-$.

Example 36: Compound #36

2S,3R,4R,5S,6R)-2-(5-([bicyclo[4.2.0]octa-1(6),2,4-trien-3-ylmethyl]-2-(difluoromethoxy)-4-methylphenyl)-6-(hydroxymethyl)oxane-3,4,5-triol

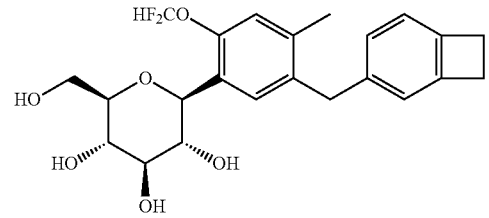

To a mixture of (2S,3R,4R,5S,6R)-2-(5-(bicyclo[4.2.0]octa-1(6),2,4-trien-3-ylmethyl)-2-hydroxy-4-methylphenyl)-6-(hydroxymethyl)tetrahydro-2H-pyran-3,4,5-triol (Compound #6) (100 mg, 0.26 mmol, 1.00 equiv) in N,N-dimethylformamide (10 mL) with K$_2$CO$_3$ (180 mg, 1.30 mmol, 5.00 equiv) was stirred at room temperature for 30 min. Ethyl 2-chloro-2,2-difluoroacetate (250 mg, 1.58 mmol, 6.00 equiv) was then added. The reaction mixture was stirred at 70° C. for overnight. Brine was added and the mixture was extracted with EtOAc thrice, then concentrated and purified by chromatography on a C18 reversed phase column to yield the title compound as a yellow solid.

$^1$H-NMR (300 MHz, CD$_3$OD) δ 7.31 (s, 1H), 6.91-7.07 (m, 3H), 6.79 (s, 1H), 6.68 (d, J=75 Hz, 1H), 4.47 (d, J=9.6 Hz, 1H), 3.96 (s, 2H), 3.88 (dd, J=12.0, 1.7 Hz, 1H), 3.57-3.70 (m, 2H), 3.44-3.52 (m, 1H), 3.35-3.42 (m, 2H), 3.10 (s, 4H), 2.20 (s, 3H); MS (ES) m/z: 435.1 [M−H]$^+$.

Example 37: Compound #37

(2S,3R,4R,5S,6R)-2-(4-chloro-2-(difluoromethoxy)-5-((1,2-dihydrocyclobutabenzen-4-yl)methyl)phenyl)-6-(hydroxymethyl)-tetrahydro-2H-pyran-3,4,5-triol

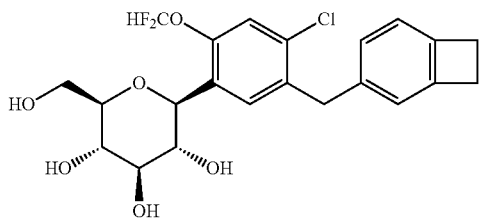

To a mixture of (2S,3R,4R,5S,6R)-2-(5-(bicyclo[4.2.0]octa-1(6),2,4-trien-3-ylmethyl)-4-chloro-2-hydroxyphenyl)-6-(hydroxymethyl)tetrahydro-2H-pyran-3,4,5-triol (Compound #8) (260 mg, 0.64 mmol) in N,N-dimethylformamide (3.0 mL) with $Cs_2CO_3$ (416 mg, 1.28 mmol) was added ethyl 2-chloro-2,2-difluoroacetate (151 mg, 0.95 mmol). The reaction mixture was stirred at room temperature for overnight, then purified by chromatography on a C18 reversed phase column to yield the title compound as a white solid.

$^1$H NMR (400 MHz, $CD_3OD$) δ 7.47 (s, 1H), 7.23 (s, 1H), 7.04 (d, J=7.6 Hz, 1H), 6.93 (d, J=7.6 Hz, 1H), 6.88 (s, 1H), 6.75 (t, J=72.4 Hz, 1H), 4.48 (d, J=9.6 Hz, 1H), 4.03-4.12 (m, 2H), 3.88 (d, J=12.0 Hz, 1H), 3.64-3.68 (m, 1H), 3.45-3.56 (m, 2H), 3.35-3.42 (m, 2H), 3.13 (s, 4H); MS (ES) m/z: 474.1 $[M+NH_4]^+$.

Example 38: Compound #38

(2S,3R,4R,5S,6R)-2-(2-(difluoromethoxy)-5-((1,2-dihydrocyclobutabenzen-4-yl)methyl)-4-methoxyphenyl)-6-(hydroxymethyl)-tetrahydro-2H-pyran-3,4,5-triol

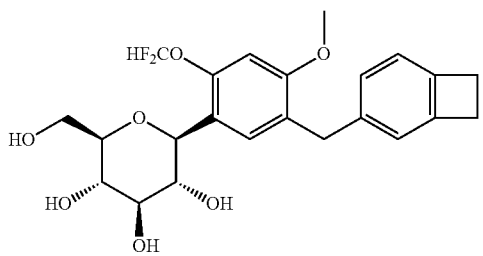

To a mixture of (2S,3R,4R,5S,6R)-2-(5-((1,2-dihydrocyclobutabenzen-4-yl)methyl)-2-hydroxy-4-m ethoxyphenyl)-6-(hydroxymethyl)-tetrahydro-2H-pyran-3,4,5-triol (Compound #9) (200 mg, 0.50 mmol, 1.00 equiv) in N,N-dimethylformamide (5.0 mL) with $Cs_2CO_3$ (325 mg, 1.00 mmol, 2.00 equiv) was added ethyl 2-chloro-2,2-difluoroacetate (119 mg, 0.75 mmol, 1.50 equiv). The reaction mixture was stirred at room temperature for overnight, then purified by chromatography on a C18 reversed phase column to yield the title compound as a white solid.

$^1$H NMR (400 MHz, $CD_3OD$) δ 7.27 (s, 1H), 7.03 (d, J=7.2 Hz, 1H), 6.89 (dd, J=11.3, 3.6 Hz, 2H), 6.74 (s, 1H), 6.72 (t, J=75.6 Hz, 1H), 4.43 (d, J=9.6 Hz, 1H), 3.85-3.96 (m, 3H), 3.82 (s, 3H), 3.55-3.69 (m, 2H), 3.46 (t, J=8.6 Hz, 1H), 3.33-3.43 (m,

Example 39: Compound #39

(2S,3R,4R,5S,6R)-2-(5-[bicyclo[4.2.0]octa-1(6),2,4-trien-3-ylmethyl]-2-(fluoromethoxy)-4-methylphenyl)-6-(hydroxymethyl)oxane-3,4,8-triol

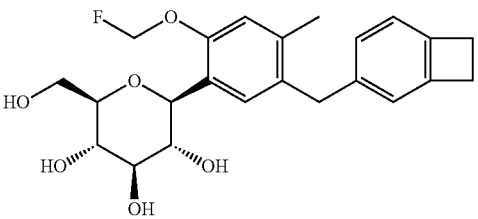 [SMILES: Cc1cc(OCF)c([C@@H]2O[C@H](CO)[C@@H](O)[C@H](O)[C@H]2O)cc1Cc1ccc2c(c1)CC2]

To a mixture of (2S,3R,4R,5S,6R)-2-(5-(bicyclo[4.2.0]octa-1(6),2,4-trien-3-ylmethyl)-2-hydroxy-4-m ethylphenyl)-6-(hydroxymethyl)tetrahydro-2H-pyran-3,4,5-triol (Compound #6) (100 mg, 0.26 mmol, 1.00 equiv) in N,N-dimethylformamide (3 mL) with potassium carbonate (107 mg, 0.77 mmol, 3.00 equiv) was added bromo(fluoro)methane (585 mg, 5.18 mmol, 20.00 equiv). The reaction mixture was stirred at room temperature for 5 h. The solids were filtered, and the filtrate applied onto a C18 reversed phase column to yield the title compound as a white solid.

$^1$H-NMR (300 MHz, $CD_3OD$) δ 7.24 (s, 1H), 6.89-6.96 (m, 2H), 6.83-6.89 (m, 1H), 6.75 (s, 1H), 5.74 (s, 1H), 5.54 (s, 1H), 4.56 (d, J=9.0 Hz, 1H), 3.90 (s, 2H), 3.83 (d, J=12.0 Hz, 1H), 3.58-3.67 (m, 1H), 3.38-3.55 (m, 2H), 3.32-3.38 (m, 2H), 3.06 (s, 4H), 2.15 (s, 3H); MS (ES) m/z: 417.1 $[M-H]^+$.

Example 40: Compound #40

(2S,3R,4R,5S,6R)-2-(4-chloro-5-((1,2-dihydrocyclobutabenzen-4-yl)methyl)-2-(fluoromethoxy)phenyl)-6-(hydroxymethyl)-tetrahydro-2H-pyran-3,4,5-triol

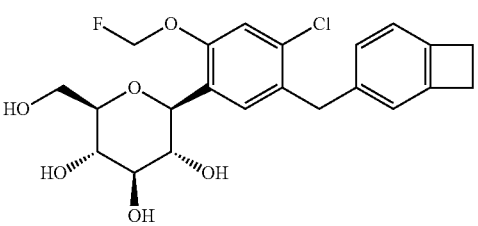 [SMILES: OC[C@H]1O[C@@H](c2cc(Cc3ccc4c(c3)CC4)c(Cl)cc2OCF)[C@H](O)[C@@H](O)[C@@H]1O]

To a mixture of (2S,3R,4R,5S,6R)-2-(4-chloro-5-((1,2-dihydrocyclobutabenzen-4-yl)methyl)-2-hydroxyphenyl)-6-(hydroxymethyl)-tetrahydro-2H-pyran-3,4,5-triol (Compound #8) (200 mg, 0.49 mmol) in N,N-dimethylformamide (2.0 mL) with $K_2CO_3$ (400 mg, 2.87 mmol) was added bromo(fluoro)methane (280 mg, 2.48 mmol). The reaction mixture was stirred at room temperature for 4 h, then purified by chromatography on a C18 reversed phase column to yield the title compound as a white solid.

¹H NMR (400 MHz, CD₃OD) δ 7.40 (s, 1H), 7.18 (s, 1H), 7.01 (d, J=7.6 Hz, 1H), 6.90 (d, J=7.6 Hz, 1H), 6.85 (s, 1H), 5.69 (d, J=57.2 Hz, 2H), 4.56 (d, J=8.8 Hz, 1H), 3.98-4.07 (m, 2H), 3.65 (d, J=8.0 Hz, 1H), 3.65 (d, J=8.0 Hz, 1H), 3.36-3.46 (m, 4H), 3.10 (s, 4H); MS (ES) m/z: 456.1 [M+NH₄]⁺.

Example 41: Compound #41

(2S,3R,4R,5S,6R)-2-(5-((1,2-dihydrocyclobutaben-zen-4-yl)methyl)-2-(fluoromethoxy)-4-methoxyphenyl)-6-(hydroxymethyl)-tetrahydro-2H-pyran-3,4,5-triol

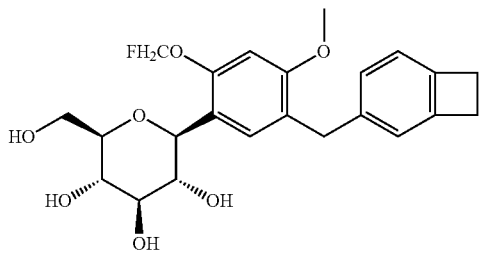

To a mixture of (2S,3R,4R,5S,6R)-2-(5-(bicyclo[4.2.0]octa-1(6),2,4-trien-3-ylmethyl)-2-hydroxy-4-m ethoxyphenyl)-6-(hydroxymethyl)tetrahydro-2H-pyran-3,4,5-triol (Compound #9) (150 mg, 0.37 mmol, 1.00 equiv) in N,N-dimethylformamide (4.0 mL) with potassium carbonate (154 mg, 1.11 mmol, 2.99 equiv) was added bromo(fluoro)methane (211 mg, 1.87 mmol, 5.01 equiv) at room temperature. The reaction mixture was stirred for 3 h at room temperature, then purified by chromatography on a C18 reversed phase column to yield the title compound as an off-white solid.

¹H NMR (300 MHz, CD₃OD) δ 7.23 (s, 1H), 7.02 (d, J=7.8 Hz, 1H), 6.87 (d, J=7.3 Hz, 2H), 6.77 (s, 1H), 5.80 (s, 1H), 5.61 (s, 1H), 4.54 (d, J=9.0 Hz, 1H), 3.76-3.92 (m, 6H), 3.58-3.71 (m, 1H), 3.41-3.56 (m, 2H), 3.34-3.41 (m, 2H), 3.09 (s, 4H); MS (ES) m/z: 433.1 [M–H].

Example 42: Compound #42

(2S,3R,4R,5S,6R)-2-(5-((1,2-dihydrocyclobutaben-zen-4-yl)methyl)-4-ethyl-2-(fluoromethoxy)phenyl)-6-(hydroxymethyl)-tetrahydro-2H-pyran-3,4,5-triol

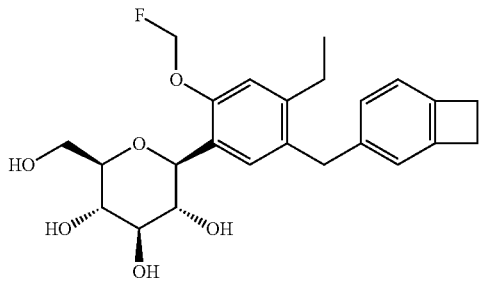 [SMILES: CCc1cc(OCF)c([C@@H]2O[C@H](CO)[C@@H](O)[C@H](O)[C@H]2O)cc1Cc1ccc2c(c1)CC2]

To a mixture of (2S,3R,4R,5S,6R)-2-(5-(bicyclo[4.2.0]octa-1(6),2,4-trien-3-ylmethyl)-4-ethyl-2-hydroxyphenyl)-6-(hydroxymethyl)tetrahydro-2H-pyran-3,4,5-triol (Compound #12) (200 mg, 0.50 mmol) in DMF (2 ml) with potassium carbonate (688 mg, 4.98 mmol) was added CH₂BrF (282 mg, 2.50 mmol). The reaction mixture was stirred at room temperature for 2 h, brine was added and the mixture was extracted with EtOAc thrice. The combined extracts were washed with saturated brine, dried over anhydrous Na₂SO₄ and filtered, then concentrated and purified by chromatography on a C18 reversed phase column with MeCN/H₂O (30%-35%) to yield the title compound as a white solid ¹H NMR (400 MHz, CD₃OD) δ 7.29 (s, 1H), 6.87-7.05 (m, 3H), 6.80 (s, 1H), 5.78 (d, J=1.5 Hz, 1H), 5.64 (q, J=3.1 Hz, 1H), 4.60 (d, J=9.4 Hz, 1H), 3.98 (s, 2H), 3.88 (d, J=12.0 Hz, 1H), 3.63-3.72 (m, 1H), 3.34-3.60 (m, 4H), 3.11 (s, 4H), 2.59 (q, J=7.5 Hz, 2H), 1.09 (t, J=7.6 Hz, 3H); MS (ES) m/z: 431.1 [M–H]⁻.

Example 43: Compound #51

(2S,3R,4R,5S,6R)-2-(3-(dideuterium(1,2-dihydrocyclobutabenzen-4-yl)methyl)-4-methylphenyl)-6-(hydroxymethyl)-tetrahydro-2H-pyran-3,4,6-triol

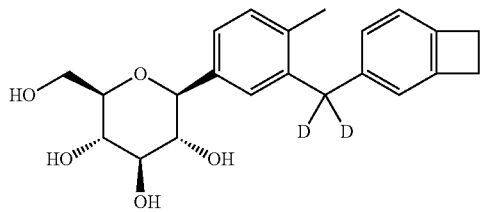 [SMILES: [2H]C([2H])(c1ccc2c(c1)CC2)c1cc([C@@H]2O[C@H](CO)[C@@H](O)[C@H](O)[C@H]2O)ccc1C]

To a mixture of 3-bromobicyclo[4.2.0]octa-1,3,5-triene (3.03 g, 16.55 mmol, 1.10 equiv) in THF (30 ml) was added dropwise n-BuLi (2.5 M in n-hexane, 6.6 ml, 1.10 equiv) at −78° C. under N₂. The reaction mixture was stirred at −78° C. for 30 min. 5-bromo-2-methylbenzaldehyde (3 g, 15.07 mmol, 1.00 equiv) in THF (30 ml) was added dropwise at −78° C. The reaction mixture was stirred at −78° C. for 1 h. Saturated NH₄Cl (aq) was added and the mixture was extracted with EA thrice. The combined extracts were washed with water, saturated brine and dried over anhydrous Na₂SO₄, then concentrated and purified by chromatography on silica gel (1:3 EA/PE) to yield (5-bromo-2-methylphenyl)(1,2-dihydrocyclobutabenzen-4-yl)methanol as a yellow oil. MS (ES) m/z: 286.9 [M–OH]⁺.

To a mixture of (5-bromo-2-methylphenyl)(1,2-dihydrocyclobutabenzen-4-yl)methanol (1 g, 3.30 mmol, 1.00 equiv) in DCM (1 ml) was added Dess-Martin Reagent (2 g, 4.71 mmol, 1.42 equiv) at 20° C. The reaction mixture was stirred at 20° C. for 1 h. The solids were filtered out. Concentration to yield (5-bromo-2-methylphenyl)(1,2-dihydrocyclobutabenzen-4-yl)methanone as a light yellow oil.

¹H NMR (400 MHz, CDCl₃) δ 2.23 (s, 3H), 3.18-3.29 (m, 4H), 7.14 (dd, J=8.0, 4.0 Hz, 2H), 7.40 (d, J=2.2 Hz, 1H), 7.45-7.52 (m, 2H), 7.66 (m, 1H); MS (ES) m/z: 301.0 [M+H]⁺.

To a mixture of (5-bromo-2-methylphenyl)(1,2-dihydrocyclobutabenzen-4-yl)methanone (500 mg, 1.66 mmol, 1.00 equiv) in THF (10 ml) with AlCl₃ (2.2 g, 16.54 mmol, 10.00 equiv) was added portionwise NaBD₄ (349 mg, 8.31 mmol, 5.00 equiv) at 20° C. under N₂. The reaction mixture was stirred at 80° C. for 2 h. Water was added and the mixture was extracted with EA thrice. The combined extracts were washed with water, saturated brine and dried over anhydrous Na$_2$SO$_4$, then concentrated and purified by chromatography on silica gel (1:1000 EA/PE) to yield 4-((5-bromo-2-methylphenyl)dideuteriummethyl)-1,2-dihydrocyclobutabenzene as a yellow oil. $^1$H NMR (CDCl$_3$, 300 MHz): δ 2.20 (s, 3H), 3.13 (s, 4H), 6.80 (s, 1H), 6.99 (d, J=21.4 Hz, 3H), 7.23-7.26 (t, J=2.5 Hz, 2H).

To a mixture of 4-((5-bromo-2-methylphenyl)dideuteriummethyl)-1,2-dihydrocyclobutabenzene (200 mg, 0.69 mmol, 1.10 equiv) in THF (2 ml) was added dropwise n-BuLi (2.5 M in n-hexane) (0.28 ml, 0.69 mmol, 1.10 equiv) at −78° C. under N$_2$. The reaction mixture was stirred at −78° C. for 30 min. (3R,4S,5R,6R)-3,4,5-tris(benzyloxy)-6-[(benzyloxy)methyl]oxan-2-one (340 mg, 0.63 mmol, 1.00 equiv) in THF (3 ml) was added dropwise at −78° C. The reaction mixture was stirred at −78° C. for 1 h. Saturated NH$_4$Cl (aq) was added and the mixture was extracted with EA thrice. The combined extracts were washed with water, saturated brine and dried over anhydrous Na$_2$SO$_4$, then concentrated and purified by chromatography on silica gel (1:3 EA/PE) to yield (3R,4S,5R,6R)-3,4,5-tris(benzyloxy)-6-(benzyloxymethyl)-2-(3-(dideuterium(1,2-dihydrocyclobutabenzen-4-yl)methyl)-4-methylphenyl)-tetrahydro-2H-pyran-2-ol as a yellow oil.

To a mixture of (3R,4S,5R,6R)-3,4,5-tris(benzyloxy)-6-(benzyloxymethyl)-2-(3-(dideuterium (1,2-dihydrocyclobutabenzen-4-yl)methyl)-4-methylphenyl)-tetrahydro-2H-pyran-2-ol (400 mg, 0.53 mmol, 1.00 equiv) in DCM (4 ml) with Et$_3$SiH (124 mg, 1.07 mmol, 2.00 equiv) was added trifluoroacetic acid (122 mg, 1.08 mmol, 2.00 equiv) at 0° C. The reaction mixture was stirred at 0° C. for 1 h. Saturated NaHCO$_3$ (aq) was added and the mixture was extracted with DCM thrice. The combined extracts were washed with water, saturated brine and dried over anhydrous Na$_2$SO$_4$, then concentrated and purified by chromatography on silica gel (1:30 EA/PE) to yield (2R,3R,4R,5S,6S)-3,4,5-tris(benzyloxy)-2-(benzyloxymethyl)-6-(3-(dideuterium(1,2-dihydrocyclobutabenzen-4-yl)methyl)-4-methylphenyl)-tetrahydro-2H-pyranas a colorless oil. MS (ES) m/z: 755.3 [M+Na]$^+$.

To a mixture of (2R,3R,4R,5S,6S)-3,4,5-tris(benzyloxy)-2-(benzyloxymethyl)-6-(3-(dideuterium(1,2-dihydrocyclobutabenzen-4-yl)methyl)-4-methylphenyl)-tetrahydro-2H-pyran (200 mg, 0.27 mmol, 1.00 equiv) in DCM (2 ml) with 1,2,3,4,5-pentamethylbenzene (400 mg, 2.70 mmol, 10.00 equiv) was added dropwise BCl$_3$ (1 M in DCM) (4 mL, 4 mmol, 14.81 equiv) at −78° C. The reaction mixture was stirred at −78° C. for 1 h. MeOH was added, and the resulting mixture was then concentrated and purified by chromatography on C18 reverse column (30-40% MeCN/H$_2$O) to yield the title compound as a white solid.

$^1$H NMR (400 MHz, CD$_3$OD,): δ 7.17-7.25 (m, 2H), 7.14 (d, J=7.6 Hz, 1H), 6.98 (d, J=7.2 Hz, 1H), 6.90 (d, J=7.6 Hz, 1H), 6.81 (s, 1H), 4.10 (d, J=9.3 Hz, 1H), 3.86-3.98 (m, 1H), 3.66-3.75 (m, 1H), 3.35-3.51 (m, 4H), 3.11 (s, 4H), 2.20 (s, 3H); MS (ES) m/z: 371.1 [M−H]$^−$.

Example 44: Compound #52

(2S,3R,4R,5S,6R)-2-(5-[bicyclo[4.2.0]octa-1(6),2,4-trien-3-yl(dideuterium)methyl]-2-hydroxy-4-methylphenyl)-6-(hydroxymethyl)oxane-3,4,5-triol

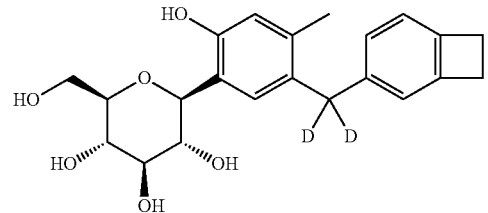 [SMILES: [2H]C([2H])(c1ccc2c(c1)CC2)c1cc([C@@H]2O[C@H](CO)[C@@H](O)[C@H](O)[C@H]2O)c(O)cc1C]

To a mixture of (4-(benzyloxy)-5-bromo-2-methylphenyl)(bicyclo[4.2.0]octa-1(6),2,4-trien-3-yl)methanone (1150 mg, 2.82 mmol, 1.00 equiv) in THF (20 mL) with NaBD$_4$ (1.42 g, 33.88 mmol, 12.00 equiv) was added AlCl$_3$ (4.52 g, 33.88 mmol, 12.00 equiv) in portions at 0° C. The reaction mixture was stirred for an overnight at 65° C. Ice/water was added and the mixture was extracted with EtOAc thrice. The combined extracts were washed with water, saturated brine and dried over anhydrous Na$_2$SO$_4$, then concentrated and purified by chromatography on silica gel (49:1 PE/EA) to yield 3-[[4-(benzyloxy)-5-bromo-2-methylphenyl](dideuterium)methyl]bicyclo[4.2.0]octa-1(6),2,4-triene as a white solid. $^1$H-NMR (300 MHz, CDCl$_3$) δ 7.41-7.50 (m, 2H), 7.27-7.43 (m, 4H), 6.95 (d, J=1.3 Hz, 2H), 6.72-6.82 (m, 2H), 5.12 (s, 2H), 3.13 (s, 4H), 2.18 (s, 3H).

To a mixture of 3-[[4-(benzyloxy)-5-bromo-2-methylphenyl](dideuterium)methyl]bicyclo[4.2.0]octa-1(6),2,4-triene (820 mg, 2.07 mmol, 1.00 equiv) in tetrahydrofuran (15 mL) was added n-BuLi (2.5M in hexane, 0.83 mL, 1.00 equiv) dropwise with stirring at −78° C., and the mixture was stirred for 20 mins at −78° C. (3R,4S,5R,6R)-3,4,5-Tris(benzyloxy)-6-[(benzyloxy)methyl]oxan-2-one (1.23 g, 2.28 mmol, 1.10 equiv) in tetrahydrofuran (3 mL) was then added to the solution. The reaction mixture was stirred at −78° C. for 1 h. NH$_4$Cl/H$_2$O was added and the mixture was extracted with EtOAc thrice. The combined extracts were dried over Na$_2$SO$_4$, then concentrated and purified by chromatography on silica gel (4:1 PE/EA) to yield (3R,4S,5R,6R)-3,4,5-tris(benzyloxy)-2-[2-(benzyloxy)-5-[bicyclo[4.2.0]octa-1(6),2,4-trien-3-yl(dideuterium)methyl]-4-methylphenyl]-6-[(benzyloxy)methyl]oxan-2-ol as a yellow oil.

To a mixture of (3R,4S,5R,6R)-3,4,5-tris(benzyloxy)-2-[2-(benzyloxy)-5-[bicyclo[4.2.0]octa-1(6),2,4-trien-3-yl(dideuterium)methyl]-4-methylphenyl]-6-[(benzyloxy)methyl]oxan-2-ol (900 mg, 1.05 mmol, 1.00 equiv) in dichloromethane (20 mL) with Et$_3$SiH (367 mg, 3.16 mmol, 3.00 equiv) was added TFA (360 mg, 3.18 mmol, 3.00 equiv) dropwise at 0° C. The reaction mixture was stirred at 0° C. for 1 h. NaHCO$_3$/H$_2$O was added and the mixture was extracted with DCM thrice. The combined extracts were washed with water, saturated brine and dried over anhydrous Na$_2$SO$_4$, then concentrated and purified by chromatography on silica gel (22:3 PE/EA) to yield (2S,3S,4R,5R,6R)-3,4,5-tris(benzyloxy)-2-[2-(benzyloxy)-5-[bicyclo[4.2.0]octa-1(6),2,4-trien-3-yl(dideuterium)methyl]-4-methylphenyl]-6-[(benzyloxy)methyl]oxane as a yellow oil.

To a mixture of (2S,3S,4R,5R,6R)-3,4,5-tris(benzyloxy)-2-[2-(benzyloxy)-5-[bicyclo[4.2.0]octa-1(6),2,4-trien-3-yl (dideuterium)methyl]-4-methylphenyl]-6-[(benzyloxy) methyl]oxane (670 mg, 0.80 mmol, 1.00 equiv) in dichloromethane (15 mL) with 1,2,3,4,5-pentamethylbenzene (1.18 g, 7.96 mmol, 10.00 equiv) was added BCl₃ (12 mL, 15.00 equiv, 1 M in DCM) dropwise at −78° C. The reaction mixture was stirred for 1 h at −78° C. Methanol (5 mL) was added, and the resulting mixture was then concentrated and purified by chromatography on a C18 reversed phase column to yield the title compound as a white solid.

¹H NMR (400 MHz, CD₃OD): δ 7.13 (s, 1H), 6.96 (m, 1H), 6.89 (d, J=7.6 Hz, 1H), 6.79 (s, 1H), 6.65 (s, 1H), 4.53 (d, J=9.6 Hz, 1H), 3.89 (m, 1H), 3.73 (m, 1H), 3.59 (t, J=9.1 Hz, 1H), 3.46-3.54 (m, 1H), 3.43 (m, 2H), 3.11 (s, 4H), 2.11 (s, 3H); MS (ES) m/z: 387.2 [M−H]⁻.

Example 45: Compound #63

(2S,3R,4R,5S,6R)-2-(5-(dideuterium(1,2-dihydrocyclobutabenzen-4-yl)methyl)-2-methoxy-4-methylphenyl)-6-(hydroxymethyl)-tetrahydro-2H-pyran-3,4,6-triol

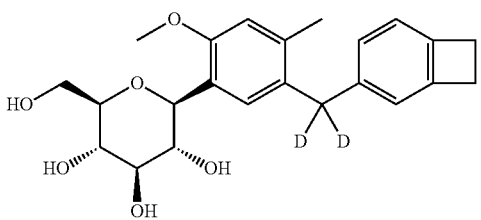 [SMILES: [2H]C([2H])(c1ccc2c(c1)CC2)c1cc([C@@H]2O[C@H](CO)[C@@H](O)[C@H](O)[C@H]2O)c(OC)cc1C]

To a solution of 4-methoxy-2-methylbenzaldehyde (1 g, 6.659 mmol, 1.00 equiv) in MeOH (50 ml) was added pyridium tribromide (2.343 g, 7.325 mmol, 1.10 equiv) at −20° C. The reaction mixture was stirred at 20° C. overnight. Water was added and the precipitation was filtered to yield 5-bromo-4-methoxy-2-methylbenzaldehyde as an off-white solid. MS (ES) m/z: 230.9 [M+H]⁺.

To a solution of 4-bromo-3,2-dihydrocyclobutabenzene (1.143 g, 6.243 mmol, 1.10 equiv) in THF (10 ml) was added n-BuLi (2.5 M in n-hexane, 2.497 ml, 6.243 mmol, 1.10 equiv) dropwise at −78° C. under N₂. The reaction mixture was stirred at −78° C. for 30 min. 5-Bromo-4-methoxy-2-methylbenzaldehyde (1.3 g, 5.675 mmol, 1.00 equiv) in THF (10 ml) was added dropwise at −78° C. The reaction mixture was stirred at −78° C. for 1 h. Saturated NH₄Cl (aq) was added and the mixture was extracted with EA thrice. The combined extracts were washed with water, saturated brine and dried over anhydrous Na₂SO₄, then concentrated and purified by chromatography on silica gel (1:3 EA/PE) to yield (5-bromo-4-methoxy-2-methylphenyl)(1,2-dihydrocyclobutabenzen-4-yl)methanol as a yellow oil. MS (ES) m/z: 317.0 [M−OH]⁺.

To a solution of (5-bromo-4-methoxy-2-methylphenyl)(1,2-dihydrocyclobutabenzen-4-yl)methanol (1.5 g, 4.502 mmol, 1.00 equiv) in DCM (20 ml) was added Dess-Martin Reagent (2.864 g, 6.753 mmol, 1.50 equiv) at 20° C. The reaction mixture was stirred at 20° C. for 1 h. The solids were filtered out, then concentrated and purified by chromatography on silica gel (1:10 EA/PE) to yield (5-bromo-4-methoxy-2-methylphenyl)(1,2-dihydrocyclobutabenzen-4-yl)methanone as a yellow oil. MS (ES) m/z: 333.0 [M+H]⁺

To a mixture of (5-bromo-4-methoxy-2-methylphenyl)(1,2-dihydrocyclobutabenzen-4-yl)methanone (1.5 g, 4.529 mmol, 1.00 equiv) in THF (20 ml) with AlCl₃ (6.039 g, 45.29 mmol, 10.00 equiv) was added portionwise NaBD₄ (0.948 g, 22.645 mmol, 5.00 equiv) at 20° C. under N₂. The reaction mixture was stirred at 80° C. for 2 h. Water was added and the mixture was extracted with EA thrice. The combined extracts were washed with water, saturated brine and dried over anhydrous Na₂SO₄, then concentrated and purified by chromatography on silica gel (1:10 EA/PE) to yield 14-((5-bromo-4-methoxy-2-methylphenyl)dideuteriummethyl)-1,2-dihydrocyclobutabenzene as a colorless oil.

¹H NMR (400 MHz, Chloroform-d) δ: 7.26 (s, 1H), 6.95 (d, J=1.2 Hz, 2H), 6.79 (d, J=1.4 Hz, 1H), 6.71 (s, 1H), 3.87 (s, 3H), 3.13 (s, 4H), 2.22 (s, 3H).

To a solution of 4-((5-bromo-4-methoxy-2-methylphenyl)dideuteriummethyl)-1,2-dihydrocyclobutabenzene (1.25 g, 3.916 mmol, 1.10 equiv) in THF (10 ml) was added dropwise n-BuLi (2.5 M in n-hexane, 1.566 ml, 3.916 mmol, 1.10 equiv) at −78° C. under N₂. The reaction mixture was stirred at −78° C. for 30 min. (3R,4S,5R,6R)-3,4,5-tris(benzyloxy)-6-[(benzyloxy)methyl]oxan-2-one (1.918 g, 3.56 mmol, 1.00 equiv) in THF (20 ml) was added dropwise at −78° C. The reaction mixture was stirred at −78° C. for 1 h. Saturated NH₄Cl (aq) was added and the mixture was extracted with EA thrice. The combined extracts were washed with water, saturated brine and dried over anhydrous Na₂SO₄, then concentrated and purified by chromatography on silica gel (1:3 EA/PE) to yield (3R,4S,5R,6R)-3,4,5-tris(benzyloxy)-6-(benzyloxymethyl)-2-(5-(dideuterium(1,2-dihydrocyclobutabenzen-4-yl)methyl)-2-methoxy-4-methylphenyl)-tetrahydro-2H-pyran-2-ol as a yellow oil. MS (ES) m/z: 761.4 [M−OH]⁺

To a mixture of (3R,4S,5R,6R)-3,4,5-tris(benzyloxy)-6-(benzyloxymethyl)-2-(5-(dideuterium(1,2-dihydrocyclobutabenzen-4-yl)methyl)-2-methoxy-4-methylphenyl)-tetrahydro-2H-pyran-2-ol (2.18 g, 2.799 mmol, 1.00 equiv) in DCM (20 ml) with Et₃SiH (0.904 ml, 5.598 mmol, 2.00 equiv) was added BF₃.Et₂O (0.709 ml, 5.598 mmol, 2.00 equiv) at 0° C. The reaction mixture was stirred at 0° C. for 1 h. Saturated NaHCO₃ (aq) was added and the mixture was extracted with DCM thrice. The combined extracts were washed with water, saturated brine and dried over anhydrous Na₂SO₄, then concentrated and purified by chromatography on silica gel (1:10 EA/PE) to yield (2R,3R,4R,5S,6S)-3,4,5-tris(benzyloxy)-2-(benzyloxymethyl)-6-(5-(dideuterium(1,2-dihydrocyclobutabenzen-4-yl)methyl)-2-methoxy-4-methylphenyl)-tetrahydro-2H-pyran as a colorless oil. MS (ES) m/z: 785.6 [M+Na]⁺.

To a mixture of (2R,3R,4R,5S,6S)-3,4,5-tris(benzyloxy)-2-(benzyloxymethyl)-6-(5-(dideuterium(1,2-dihydrocyclobutabenzen-4-yl)methyl)-2-methoxy-4-methylphenyl)-tetrahydro-2H-pyran (600 mg, 0.786 mmol, 1.00 equiv) in DCM (6 ml) with 1,2,3,4,5-pentamethylbenzene (1.049 g, 7.074 mmol, 9.8 equiv) was added dropwise BCl₃ (1 M in DCM) (4.716 ml, 4.716 mmol, 6.0 equiv) at −78° C. The reaction mixture was stirred at −78° C. for 1 h, then concentrated and purified by chromatography on C18 reverse column (40% MeCN/H₂O) to yield the title compound as a white solid.

¹H NMR (400 MHz, CD₃OD): δ7.20 (s, 1H), 6.95 (dd, J=7.4, 1.4 Hz, 1H), 6.87 (d, J=7.5 Hz, 1H), 6.77 (d, J=1.8 Hz, 2H), 4.63 (d, J=9.5 Hz, 1H), 3.82-3.88 (m, 1H), 3.80 (s, 3H), 3.61-3.70 (m, 1H), 3.55 (t, J=9.2 Hz, 1H), 3.44-3.50 (m, 1H), 3.35-3.42 (m, 2H), 3.09 (s, 4H), 2.18 (s, 3H); MS (ES) m/z: 401.1 [M−H]⁻.

Example 46: Compound #54

(2S,3R,4R,5S,6R)-2-(3-[bicyclo[4.2.0]octa-1(6),2,4-trien-3-yl(dedeuterium)methyl]-4-chlorophenyl)-6-(hydroxymethyl)oxane-3,4,5-triol

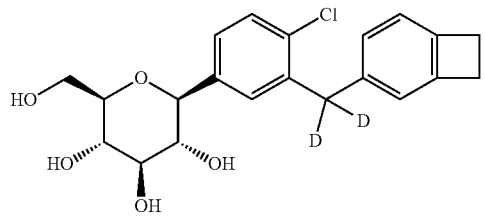 [SMILES: [2H]C([2H])(c1ccc2c(c1)CC2)c1cc([C@@H]2O[C@H](CO)[C@@H](O)[C@H](O)[C@H]2O)ccc1Cl]

To a mixture of bicyclo[4.2.0]octa-1(6),2,4-trien-3-yl(5-bromo-2-chlorophenyl)methanol (3.24 g, 10.01 mmol, 1.00 equiv) in dichloromethane (35 mL) was added Dess-Martin Reagent (6.36 g, 15.00 mmol, 1.50 equiv). The reaction mixture was stirred for 1 h at room temperature. The solids were filtered out. The filtrate was, then concentrated and purified by chromatography on silica gel (3:1 PE/EA) to yield [bicyclo[4.2.0]octa-1(6),2,4-trien-3-yl](5-bromo-2-chlorophenyl)methanone as a light yellow oil. $^1$H NMR (400 MHz, Chloroform-d) δ 7.68 (d, J=7.6 Hz, 1H), 7.47-7.58 (m, 3H), 7.33 (d, J=7.8 Hz, 1H), 7.16 (d, J=7.6 Hz, 1H), 3.25 (s, 4H).

To a mixture of [bicyclo[4.2.0]octa-1(6),2,4-trien-3-yl](5-bromo-2-chlorophenyl)methanone (1.0 g, 3.11 mmol, 1.00 equiv) and NaBD$_4$ (1.57 g, 37.51 mmol, 12.06 equiv) in THF (20 mL) was added AlCl$_3$ (4.96 g, 37.20 mmol, 11.96 equiv) in portions at 0° C. The reaction mixture was stirred for overnight at 80° C. Ice/water was added and the mixture was extracted with EtOAc twice. The combined extracts were washed with brine and dried over Na$_2$SO$_4$, then concentrated and purified by chromatography on a C18 (0%-100% CH$_3$CN/H$_2$O) reversed phase column to yield 3-[(5-bromo-2-chlorophenyl)(dideuterium)methyl]bicyclo[4.2.0]octa-1(6),2,4-triene as a yellow oil. $^1$H NMR (400 MHz, Chloroform-d) δ 7.23-7.30 (m, 3H), 6.99-7.05 (m, 2H), 6.90 (s, 1H), 3.16 (s, 4H).

To a mixture of 3-[(5-bromo-2-chlorophenyl)(dideuterium)methyl]bicyclo[4.2.0]octa-1(6),2,4-triene (450 mg, 1.45 mmol, 1.05 equiv) in tetrahydrofuran (10 mL) was added n-BuLi (2.5 M in hexane, 0.61 mL, 1.52 mmol, 1.10 equiv) dropwise at −78° C., and the mixture was stirred at −78° C. for 1 h. (3R,4S,5R,6R)-3,4,5-Tris(benzyloxy)-6-[(benzyloxy)methyl]oxan-2-one (745 mg, 1.38 mmol, 1.00 equiv) in tetrahydrofuran (5 mL) was then added dropwise at −78° C. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-6-[(benzyloxy)methyl]-2-(3-[bicyclo[4.2.0]octa-1(6),2,4-trien-3-yl(dideuterium)methyl]-4-chlorophenyl)oxan-2-ol as a yellow oil. MS (ES) m/z: 751.3 [M−OH$^-$]$^+$.

To a mixture of (3R,4S,5R,6R)-3,4,5-tris(benzyloxy)-6-[(benzyloxy)methyl]-2-(3-[bicyclo[4.2.0]octa-1(6),2,4-trien-3-yl(dideuterium)methyl]-4-chlorophenyl)oxan-2-ol (680 mg, 0.88 mmol, 1.00 equiv) in dichloromethane (10 mL) with Et$_3$SiH (205 mg, 1.76 mmol, 1.99 equiv) was added BF$_3$.Et$_2$O (251 mg, 1.77 mmol, 2.00 equiv) dropwise at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (3:1 PE/EA) to yield (2R,3R,4R,5S,6S)-3,4,5-tris(benzyloxy)-2-[(benzyloxy)methyl]-6-(3-[bicyclo[4.2.0]octa-1(6),2,4-trien-3-yl(dideuterium)methyl]-4-chlorophenyl)oxane as a colorless oil. MS (ES) m/z: 775.3 [M+Na]$^+$.

To a mixture of (2R,3R,4R,5S,6S)-3,4,5-tris(benzyloxy)-2-[(benzyloxy)methyl]-6-(3-[bicyclo[4.2.0]octa-1(6),2,4-trien-3-yl(dideuterium)methyl]-4-chlorophenyl)oxane (470 mg, 0.62 mmol, 1.00 equiv) in dichloromethane (25 mL) with 1,2,3,4,5-pentamethylbenzene (940 mg, 6.34 mmol, 10.16 equiv) was added BCl$_3$ (1M in DCM, 9.4 mL, 9.4 mmol, 15.00 equiv) dropwise at −78° C. The reaction mixture was stirred at −78° C. for 1 h. 10 mL of methanol was added, and the resulting mixture was then concentrated and purified by chromatography on a C18 (0%-50% CH$_3$CN/H$_2$O) reversed phase column to yield the title compound as a gray solid.

$^1$H-NMR (400 MHz, CD$_3$OD) δ 7.33-7.36 (m, 2H), 7.28 (d, J=8.2 Hz, 1H), 7.04 (d, J=7.6 Hz, 1H), 6.92 (d, J=7.6 Hz, 1H), 6.88 (s, 1H), 4.09 (d, J=9.6 Hz, 1H), 3.89 (d, J=12.4 Hz, 1H), 3.66-3.72 (m, 1H), 3.39-3.49 (m, 3H), 3.28-3.37 (m, 1H), 3.12 (s, 4H); MS (ES) m/z: 410.2 [M+NH$_4$].

Example 47: Compound #55

(2S,3R,4R,S,6R)-2-(5-[bicyclo[4.2.0]octa-1(6),2,4-trien-3-yl(dideuterium)methyl]-4-chloro-2-hydroxyphenyl)-6-(hydroxymethyl)oxane-3,4,5-triol

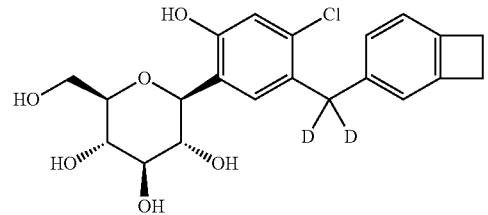 [SMILES: [2H]C([2H])(c1ccc2c(c1)CC2)c1cc([C@@H]2O[C@H](CO)[C@@H](O)[C@H](O)[C@H]2O)c(O)cc1Cl]

To a mixture of 3-bromobicyclo[4.2.0]octa-1,3,5-triene (70 g, 382.42 mmol, 2.50 equiv) and 1,2-dibromoethane (2.9 g) in THF (150 mL) was added Mg (9.5 g, 395.83 mmol, 2.60 equiv). The solution was heated to reflux for 30 min and then added to a mixture of 4-(benzyloxy)-5-bromo-2-chlorobenzaldehyde (50 g, 153.57 mmol, 1.00 equiv) in THF (500 mL) dropwise at 0° C. under nitrogen. The reaction mixture was stirred for 1 h at 0° C. Ice water was added and the mixture was extracted with EtOAc twice. The combined extracts were washed with brine and dried over Na$_2$SO$_4$, then concentrated and purified by chromatography on silica gel (10:1 PE/EA) to yield [4-(benzyloxy)-5-bromo-2-chlorophenyl](bicyclo[4.2.0]octa-1,3,5-trien-3-yl)methanol as a yellow oil. MS (ES) m/z: 412.9 [M−OH]$^+$.

To a mixture of [4-(benzyloxy)-5-bromo-2-chlorophenyl](bicyclo[4.2.0]octa-1,3,5-trien-3-yl)methanol (6 g, 13.96 mmol, 1.00 equiv) in dichloromethane (100 mL) was added Dess-Martin Reagent (7.11 g, 16.77 mmol, 1.20 equiv). The reaction mixture was stirred for 2 h at room temperature, then concentrated and purified by chromatography on silica gel (10:1 PE/EA) to yield [4-(benzyloxy)-5-bromo-2-chlorophenyl]([bicyclo[4.2.0]octa-1,3,5-trien-3-yl])methanone as a colorless oil.

To a mixture of [4-(benzyloxy)-5-bromo-2-chlorophenyl]([bicyclo[4.2.0]octa-1,3,5-trien-3-yl])methanone (1.0 g, 2.34 mmol, 1.00 equiv) and NaBD₄ (1.47 g, 35.00 mmol, 15.00 equiv) in THF (30 mL) was added AlCl₃ (4.66 g, 35.04 mmol, 15.00 equiv) in portions at 0° C. The solution was heated to reflux for 16 h. Ice/water was added and the mixture was extracted with EtOAc twice. The combined extracts were washed with brine and dried over Na₂SO₄, then concentrated and purified by chromatography on silica gel (1:0 PE/EA) to yield 3-[[4-(benzyloxy)-5-bromo-2-chlorophenyl](dideuterium)methyl]bicyclo[4.2.0]octa-1,3,5-triene as a white solid. ¹H NMR (400 MHz, Chloroform-d) δ 7.33-7.46 (m, 6H), 6.95-7.02 (m, 3H), 6.87 (s, 1H), 5.11 (s, 2H), 3.13 (s, 4H).

To a mixture of 3-[[4-(benzyloxy)-5-bromo-2-chlorophenyl](dideuterium)methyl]bicyclo[4.2.0]octa-1,3,5-triene (436 mg, 1.05 mmol, 1.05 equiv) in tetrahydrofuran (8 mL) was added n-BuLi (2.5 M in hexane, 0.44 mL, 1.10 mmol, 1.10 equiv) dropwise at −78° C., and the mixture was stirred at −78° C. for 1 h. (3R,4S,5R,6R)-3,4,5-Tris(benzyloxy)-6-[(benzyloxy)methyl]oxan-2-one (540 mg, 1.00 mmol, 1.00 equiv) in tetrahydrofuran (2 mL) was then added dropwise at −78° C. The reaction mixture was stirred at −78° C. for 1 h. NH₄Cl/H₂O was added and the mixture was extracted with EtOAc thrice. The combined extracts were washed with brine and dried over Na₂SO₄, then concentrated and purified by chromatography on silica gel (3:1 PE/EA) to yield (3R,4S,5R,6R)-3,4,5-tris(benzyloxy)-2-[2-(benzyloxy)-5-[bicyclo[4.2.0]octa-1(6),2,4-trien-3-yl(dideuterium)methyl]-4-chlorophenyl]-6-[(benzyloxy)methyl]oxan-2-ol as a white solid. MS (ES) m/z: 897.4 [M+Na]⁺.

To a mixture of (3R,4S,5R,6R)-3,4,5-tris(benzyloxy)-2-[2-(benzyloxy)-5-[bicyclo[4.2.0]octa-1(6),2,4-trien-3-yl(dideuterium)methyl]-4-chlorophenyl]-6-[(benzyloxy)methyl]oxan-2-ol (400 mg, 0.46 mmol, 1.00 equiv) in dichloromethane (8 mL) with Et₃SiH (106 mg, 0.91 mmol, 2.00 equiv) was added BF₃.Et₂O (130 mg, 0.92 mmol, 2.00 equiv) dropwise at 0° C. The reaction mixture was stirred at 0° C. for 1 h. Sodium bicarbonate/H₂O was added and the mixture was extracted with dichloromethane thrice. The combined extracts were washed with brine and dried over Na₂SO₄, then concentrated and purified by chromatography on silica gel (3:1 PE/EA) to yield (2S,3S,4R,5R,6R)-3,4,5-tris(benzyloxy)-2-[2-(benzyloxy)-5-[bicyclo[4.2.0]octa-1(6),2,4-trien-3-yl(diderterium)methyl]-4-chlorophenyl]-6-[(benzyloxy)methyl]oxane as a white solid.

To a mixture of (2S,3S,4R,5R,6R)-3,4,5-tris(benzyloxy)-2-[2-(benzyloxy)-5-[bicyclo[4.2.0]octa-1(6),2,4-trien-3-yl(diderterium)methyl]-4-chlorophenyl]-6-[(benzyloxy)methyl]oxane (250 mg, 0.29 mmol, 1.00 equiv) in dichloromethane (12.5 mL) with 1,2,3,4,5-pentamethylbenzene (500 mg, 3.37 mmol, 11.60 equiv) was added BCl₃ (1 M in DCM, 5 mL, 5 mmol, 17.2 equiv) dropwise at −78° C. The reaction mixture was stirred at −78° C. for 0.5 h. Methanol (5 mL) was added, and the resulting mixture was then concentrated and purified by chromatography on a C18 (0%-50% CH₃CN/H₂O) reversed phase column to yield the title compound as a white solid.

¹H NMR (400 MHz, CD₃OD): δ 7.26 (s, 1H), 7.02 (dd, J=7.6, 1.4 Hz, 1H), 6.90 (d, J=7.5 Hz, 1H), 6.86 (d, J=1.9 Hz, 2H), 4.54 (d, J=9.0 Hz, 1H), 3.87 (dd, J=12.2, 1.6 Hz, 1H), 3.71 (dd, J=11.9, 4.7 Hz, 1H), 3.39-3.54 (m, 4H), 3.11 (s, 4H); MS (ES) m/z: 406.9 [M−H]⁺.

Example 48: Compound #56

(2S,3R,4R,5S,6R)-2-(5-[bicyclo[4.2.0]octa-(6),2,4-trien-3-yl(dideuterium)methyl]-4-chloro-2-methoxyphenyl)-6-(hydroxymethyl)oxane-3,4,5-triol

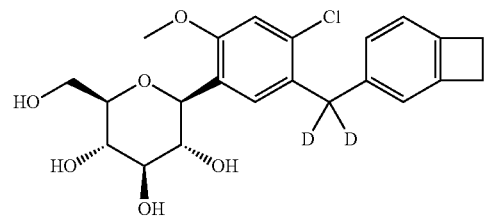 [SMILES: [2H]C([2H])(c1ccc2c(c1)CC2)c1cc([C@@H]2O[C@H](CO)[C@@H](O)[C@H](O)[C@H]2O)c(OC)cc1Cl]

To a mixture of (2S,3R,4R,5S,6R)-2-(5-(bicyclo[4.2.0]octa-1(6),2,4-trien-3-ylmethyl-d2)-4-chloro-2-hydroxyphenyl)-6-(hydroxymethyl)tetrahydro-2H-pyran-3,4,5-triol (Compound #55) (50 mg, 0.12 mmol, 1.00 equiv) and K₂CO₃ (165 mg, 1.19 mmol, 9.76 equiv) in DMF (2 mL) was added iodomethane (170 mg, 1.20 mmol, 9.79 equiv). The reaction mixture was stirred for 2 h at room temperature. The solids were filtered out. The filtrate was concentration and purified by Prep-HPLC (0%-55% MeCN/H₂O) to yield the title compound as a white solid.

¹H NMR (300 MHz, CD₃OD): δ 7.33 (s, 1H), 7.00-7.03 (m, 2H), 6.85-6.91 (m, 2H), 4.61 (d, J=9.3 Hz, 1H), 3.81-3.82 (m, 4H), 3.62-3.68 (m, 1H), 3.40-3.48 (m, 4H), 3.10 (s, 4H); MS (ES) m/z: 440.0 [M+NH₄].

Example 49: Compound #57

(2S,3R,4R,5S,6R)-2-(3-{bicyclo[4.2.0]octa-1(6),2,4-trien-3-yl(dideuterium)methyl}-4-methoxyphenyl)-6-(hydroxymethyl)oxane-3,4,5-triol

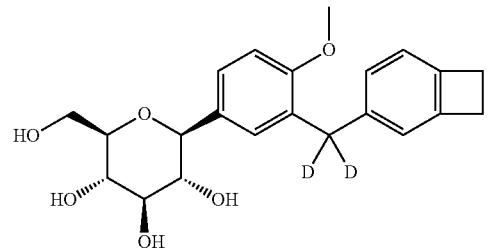 [SMILES: [2H]C([2H])(c1ccc2c(c1)CC2)c1cc([C@@H]2O[C@H](CO)[C@@H](O)[C@H](O)[C@H]2O)ccc1OC]

To a mixture of 3-bromobicyclo[4.2.0]octa-1,3,5-triene (1.5 g, 8.19 mmol, 1.00 equiv) in THF (20 ml) was added dropwise n-BuLi (2.5 M in n-hexane, 3.28 mL, 1.00 equiv) at −78° C. under N₂. The reaction mixture was stirred at −78° C. for 30 min. 5-Bromo-2-methoxybenzaldehyde (1.76 g, 8.18 mmol, 1.00 equiv) in THF (5 ml) was added dropwise at −78° C. The reaction mixture was stirred at −78° C. for 1 h. Saturated NH₄Cl (aq) was added and the mixture was extracted with EA thrice. The combined extracts were washed with water, saturated brine and dried over anhydrous Na₂SO₄, then concentrated to yield (5-bromo-2-methoxyphenyl)(1,2-dihydrocyclobutabenzen-4-yl)methanol as a yellow oil.

To a mixture of (5-bromo-2-methoxyphenyl)(1,2-dihydrocyclobutabenzen-4-yl)methanol (2.7 g, 8.46 mmol, 1.00 equiv) in DCM (50 ml) was added Dess-Martin Reagent (7.2 g, 16.98 mmol, 2.00 equiv) at 20° C. The reaction mixture was stirred at 20° C. for 1 h. The solids were filtered out, then concentrated and purified by chromatography on silica gel (5:1 PE/EA) to yield 5-bromo-2-methoxyphenyl)(1,2-dihydrocyclobutabenzen-4-yl)methanone as a white solid.

To a mixture of 5-bromo-2-methoxyphenyl)(1,2-dihydrocyclobutabenzen-4-yl)methanone (1.2 g, 3.78 mmol, 1.00 equiv) in THF (40 ml) with AlCl$_3$ (5 g, 37.50 mmol, 10.00 equiv) was added portionwise NaBD$_4$ (1.6 g, 38.22 mmol, 10.00 equiv) at 20° C. under N$_2$. The reaction mixture was stirred at 80° C. for 2 h. Water was added and the mixture was extracted with EA thrice. The combined extracts were washed with water, saturated brine and dried over anhydrous Na$_2$SO$_4$, then concentrated and purified by chromatography on silica gel (1:50 EA/PE) to yield 3-[((5-bromo-2-methoxyphenyl)(dideuteriumm)methyl)bicyclo[4.2.0]octa-1(6),2,4-triene as a white solid.

To a mixture of 3-[((5-bromo-2-methoxyphenyl)(dideuteriumm)methyl)bicyclo[4.2.0]octa-1(6),2,4-triene (1.1 g, 3.60 mmol, 1.00 equiv) in THF (15 ml) was added dropwise n-BuLi (2.5 M in n-hexane) (0.28 ml, 1.45 mL, 1.00 equiv) at −78° C. under N$_2$. The reaction mixture was stirred at −78° C. for 20 min. (3R,4S,5R,6R)-3,4,5-tris(benzyloxy)-6-[(benzyloxy)methyl]oxan-2-one (1.72 g, 3.68 mmol, 1.02 equiv) in THF (6 ml) was added dropwise at −78° C. The reaction mixture was stirred at −78° C. for 1 h. Saturated NH$_4$Cl (aq) was added and the mixture was extracted with EA thrice. The combined extracts were washed with water, saturated brine and dried over anhydrous Na$_2$SO$_4$, then concentrated to yield (3R,4S,5R,6R)-3,4,5-tri(benzyloxy)-6-[(benzyoxyl)methyl]-2-(3-{bicyclo[4.2.0]octa-1(6),2,4-trien-3-yl(dideuterium)methyl}-4-methoxyphenyl)oxan-2-ol as a yellow oil.

To a mixture of (3R,4S,5R,6R)-3,4,5-tri(benzyloxy)-6-[(benzyoxyl)methyl]-2-(3-{bicyclo[4.2.0]octa-1(6),2,4-trien-3-yl(dideuterium)methyl}-4-methoxyphenyl)oxan-2-ol (2.6 g, 3.75 mmol, 1.00 equiv) in methanol (40 mL) was added a solution of methanesulfonic acid (720 mg, 7.49 mmol, 2.00 equiv) in methanol (4 mL) dropwise at −78° C. The reaction mixture was stirred for 16 h at 25° C. NaHCO$_3$/H$_2$O was added and the mixture was extracted with EtOAc twice. The combined extracts were washed with brine and dried over Na$_2$SO$_4$, then concentrated and purified by chromatography on silica gel (93:7 dichloromethane/methanol) to yield (2R,3R,4R,5S,6S)-3,4,5-tris(benzyloxy)-2-[(benzyloxy)methyl]-6-(3-{bicyclo[4.2.0]octa-1(6),2,4-trien-3-yl(dideuterium)methyl}-4-methoxyphenyl)oxane as an yellow solid.

To a mixture of (2R,3R,4R,5S,6S)-3,4,5-tris(benzyloxy)-2-[(benzyloxy)methyl]-6-(3-{bicyclo[4.2.0]octa-1(6),2,4-trien-3-yl(dideuterium)methyl}-4-methoxyphenyl)oxane (128.9 mg, 0.31 mmol, 1.00 equiv) in dichloromethane (10 mL) with Et$_3$SiH (71.7 mg, 0.62 mmol, 2.00 equiv) was added BF$_3$.Et$_2$O (87.8 mg, 0.62 mmol, 2.00 equiv) dropwise at −10° C. The reaction was stirred for 1.5 h at −10° C. NaHCO$_3$/H$_2$O was added and the mixture was extracted with EtOAc twice. The combined extracts were washed with brine and dried over Na$_2$SO$_4$, then concentrated and purified by chromatography on C18 reverse phase column (41% CH$_3$CN/H$_2$O) to yield the title compound as a white solid.

$^1$H NMR (300 MHz, CD$_3$OD): δ 7.21 (dd, J=8.4, 2.3 Hz, 1H), 7.13 (d, J=2.2 Hz, 1H), 6.99 (dd, J=7.7, 1.3 Hz, 1H), 6.88 (d, J=8.4 Hz, 1H), 6.80-6.85 (m, 2H), 4.00 (d, J=9.1 Hz, 1H), 3.83 (dd, J=11.7, 1.6 Hz, 1H), 3.77 (s, 3H), 3.58-3.69 (m, 1H), 3.30-3.46 (m, 4H), 3.05 (s, 4H); MS (ES) m/z: 387.1 [M−H]$^-$.

Example 50: Compound #58

(2S,3R,4R,5S,6R)-2-(3-[bicyclo[4.2.0]octa-(6),2,4-trien-3-yl(dideuterium)methyl]-4-ethylphenyl)-6-(hydroxymethyl)oxane-3,4,5-triol

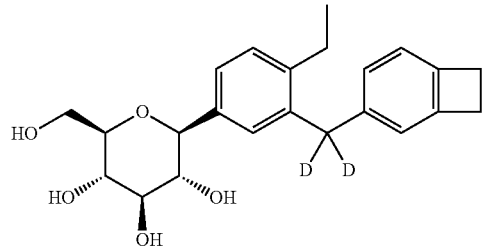 [SMILES: [2H]C([2H])(c1ccc2c(c1)CC2)c1cc([C@@H]2O[C@H](CO)[C@@H](O)[C@H](O)[C@H]2O)ccc1CC]

To a mixture of AcOH (100 mL) and acetic anhydride (50 mL) was added NaIO$_4$ (12.26 g, 57.29 mmol, 0.53 equiv), I$_2$ (9.6 g, 37.80 mmol, 0.35 equiv) and sulfuric acid (20 mL). The reaction mixture was stirred for 10 min at room temperature. Then, 1-bromo-4-ethylbenzene (20 g, 108.07 mmol, 1.00 equiv) was added. The reaction mixture was stirred for 2 h at 25° C. Ice/water was added and the mixture was extracted with ethyl acetate three times. The combined extracts were washed with brine and dried over Na$_2$SO$_4$, then concentrated and purified by chromatography on C18 reverse phase column (88%, MeCN/H$_2$O) to yield 4-bromo-1-ethyl-2-iodobenzene as a colorless oil. $^1$H NMR (400 MHz, Chloroform-d) δ 7.97 (d, J=2.0 Hz, 1H), 7.43 (dd, J=8.2, 2.0 Hz, 1H), 7.11 (d, J=8.2 Hz, 1H), 2.71 (q, J=7.5 Hz, 2H), 1.21 (t, J=7.5 Hz, 3H).

To a mixture of 4-bromo-1-ethyl-2-iodobenzene (6.1 g, 19.62 mmol, 1.00 equiv) in tetrahydrofuran (65 mL) was added i-PrMgCl.LiCl (16.6 mL, 1.10 equiv) dropwise at −78° C. The mixture was stirred for 40 min at the temperature. Then a solution of DMF (4.0 g, 50.63 mmol, 2.58 equiv) in tetrahydrofuran (5 mL) was added dropwise. The reaction mixture was stirred for 30 min at −78° C. and stirred for 1.5 h at 25° C. NH$_4$Cl/H$_2$O was added and the mixture was extracted with ethyl acetate three times. The combined extracts were washed with brine and dried over Na$_2$SO$_4$, then concentrated and purified by chromatography on silica gel (1:50 ethyl acetate/petroleum ether) to yield 5-bromo-2-ethylbenzaldehyde as a light yellow oil. $^1$H NMR (400 MHz, Chloroform-d) δ 10.26 (s, 1H), 7.97 (d, J=2.2 Hz, 1H), 7.65 (dd, J=8.2, 2.2 Hz, 1H), 7.21 (d, J=8.2 Hz, 1H), 3.04 (q, J=7.6 Hz, 2H), 1.29 (t, J=7.5 Hz, 3H).

To a mixture of 3-bromobicyclo[4.2.0]octa-1,3,5-triene (309.3 mg, 1.69 mmol, 1.20 equiv) in tetrahydrofuran (12 mL) was added n-BuLi (0.68 mL, 1.20 equiv, 2.5 M in hexane) dropwise at −78° C. The solution was stirred for 30 min at −78° C. To the resulting mixture was then added a solution of 5-bromo-2-ethylbenzaldehyde (300 mg, 1.41 mmol, 1.00 equiv) in tetrahydrofuran (3 mL) dropwise at −78° C. The reaction mixture was stirred for 2 h at −78° C. NH$_4$Cl/H$_2$O was added and the mixture was extracted with ethyl acetate three times. The combined extracts were washed with brine and dried over Na$_2$SO$_4$, then concentrated and purified by chromatography on silica gel (1:5 EA/PE) to yield bicyclo[4.2.0]octa-1(6),2,4-trien-3-yl(5-bromo-2-ethylphenyl)methanol as a yellow oil. MS (ES) m/z: 299.0, 301.0[M−OH]$^+$.

To a mixture of bicyclo[4.2.0]octa-1(6),2,4-trien-3-yl(5-bromo-2-ethylphenyl)methanol (358 mg, 1.13 mmol, 1.00 equiv) in dichloromethane (10 mL) was added Dess-Martin Reagent (961 mg, 2.27 mmol, 2.00 equiv). The reaction mixture was stirred for 16 h at 25° C. The solids were filtered out, then concentrated and purified by chromatography on silica gel (1:10, ethyl acetate/petroleum ether) to yield [bicyclo[4.2.0]octa-1(6),2,4-trien-3-yl](5-bromo-2-ethylphenyl)methanone as a light yellow oil. MS (ES) m/z: 315.0[M+H]$^+$.

To a mixture of [bicyclo[4.2.0]octa-1(6),2,4-trien-3-yl](5-bromo-2-ethylphenyl)methanone (295 mg, 0.94 mmol, 1.00 equiv) in tetrahydrofuran (10 mL) with NaBD$_4$ (472 mg, 11.24 mmol, 12.00 equiv) was added AlCl$_3$ (1.5 g, 11.28 mmol, 12.00 equiv) in portions at 0° C. The reaction mixture was stirred for 6 h at 70° C. Ice/water was added and the mixture was extracted with EtOAc twice. The combined extracts were washed with brine and dried over Na$_2$SO$_4$, then concentrated and purified by chromatography on silica gel (1:20 ethyl acetate/petroleum ether) to yield 3-[(5-bromo-2-ethylphenyl)(dideuterium)methyl]bicyclo[4.2.0]octa-1(6),2,4-triene as a light yellow oil. $^1$H NMR (400 MHz, Chloroform-d) δ 7.32 (dd, J=8.2, 2.2 Hz, 1H), 7.23 (d, J=2.2 Hz, 1H), 7.08 (d, J=8.1 Hz, 1H), 6.97 (t, J=1.3 Hz, 2H), 6.81 (d, J=1.5 Hz, 1H), 3.15 (s, 4H), 2.59 (q, J=7.5 Hz, 2H), 1.16 (t, J=7.6 Hz, 3H).

To a mixture of 3-[(5-bromo-2-ethylphenyl)(dideuterium)methyl]bicyclo[4.2.0]octa-1(6),2,4-triene (237 mg, 0.78 mmol, 1.10 equiv) in tetrahydrofuran/toluene (2/4 mL) was added n-BuLi (0.31 mL, 1.10 equiv, 2.5M in hexane) dropwise with stirring at −78° C. The solution was stirred for 30 min at −78° C. To the resulting mixture was then added a solution of (3R,4S,5R,6R)-3,4,5-tris[(trimethylsilyl)oxy]-6-[[(trimethylsilyl)oxy]methyl]oxan-2-one (332 mg, 0.71 mmol, 1.00 equiv) in tetrahydrofuran/toluene (0.5/1 mL). The reaction was stirred for 2 h at −78° C. NH$_4$Cl/H$_2$O was added and the mixture was extracted with EtOAc twice. The combined extracts were washed with brine and dried over Na$_2$SO$_4$, then concentrated to yield (3R,4S,5R,6R)-2-(3-[bicyclo[4.2.0]octa-1(6),2,4-trien-3-yl(dideuterium)methyl]-4-ethylphenyl)-3,4,5-tris-[(trimethylsilyl)oxy]-6-[[(trimethylsilyl)oxy]methyl]oxan-2-ol as a light brown oil.

To a mixture of (3R,4S,5R,6R)-2-(3-[bicyclo[4.2.0]octa-1(6),2,4-trien-3-yl(dideuterium)methyl]-4-ethylphenyl)-3,4,5-tris-[(trimethylsilyl)oxy]-6-[[(trimethylsilyl)oxy]methyl]oxan-2-ol (539.6 mg, 0.78 mmol, 1.00 equiv) in methanol (7 mL) was added a solution of methanesulfonic acid (149.2 mg, 1.55 mmol, 2.00 equiv) in methanol (1 mL) dropwise at −78° C. The reaction mixture was stirred for 16 h at 25° C. NaHCO$_3$/H$_2$O was added and the mixture was extracted with EtOAc twice. The combined extracts were washed with brine and dried over Na$_2$SO$_4$, then concentrated and purified by chromatography on silica gel (93:7 dichloromethane/methanol) to yield (2S,3R,4S,5S,6R)-2-(3-[bicyclo[4.2.0]octa-1(6),2,4-trien-3-yl(dideuterium)methyl]-4-ethylphenyl)-6-(hydroxymethyl)-2-methoxyoxane-3,4,5-triol as an off-white solid. MS (ES) m/z: 385.2[M−OCH$_3$]$^+$.

To a mixture of (2S,3R,4S,5S,6R)-2-(3-[bicyclo[4.2.0]octa-1(6),2,4-trien-3-yl(dideuterium)methyl]-4-ethylphenyl)-6-(hydroxymethyl)-2-methoxyoxane-3,4,5-triol (128.9 mg, 0.31 mmol, 1.00 equiv) in dichloromethane (10 mL) with Et$_3$SiH (71.7 mg, 0.62 mmol, 2.00 equiv) was added BF$_3$.Et$_2$O (87.8 mg, 0.62 mmol, 2.00 equiv) dropwise at −10° C. The reaction was stirred for 1.5 h at −10° C. NaHCO$_3$/H$_2$O was added and the mixture was extracted with EtOAc twice. The combined extracts were washed with brine and dried over Na$_2$SO$_4$, then concentrated and purified by chromatography on C18 reverse column (41% CH$_3$CN/H$_2$O) to yield the title compound as a white solid.

$^1$H NMR (400 MHz, CD$_3$OD): δ 7.26 (dd, J=7.8, 1.9 Hz, 1H), 7.12-7.24 (m, 2H), 6.98 (d, J=7.4 Hz, 1H), 6.90 (d, J=7.6 Hz, 1H), 6.81 (s, 1H), 4.10 (d, J=9.3 Hz, 1H), 3.89 (d, J=11.8 Hz, 1H), 3.70 (dd, J=12.0, 4.6 Hz, 1H), 3.36-3.52 (m, 4H), 3.11 (s, 4H), 2.61 (q, J=7.6 Hz, 2H), 1.09 (t, J=7.5 Hz, 3H); MS (ES) m/z: 385.2 [M−H]$^-$.

Example 51: Compound #59

(2S,3R,4R,5S,6R)-2-(5-(bicyclo[4.2.0]octa-1(6),2,4-trien-3-yl(dideuterium)methyl)-2,4-dimethoxyphenyl)-6-(hydroxymethyl)oxane-3,4,5-triol

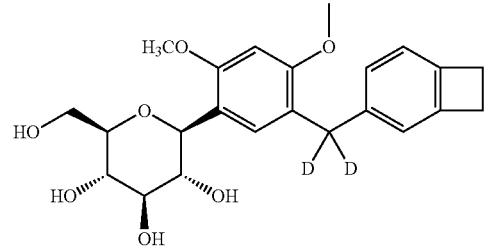 [SMILES: [2H]C([2H])(c1ccc2c(c1)CC2)c1cc([C@@H]2O[C@H](CO)[C@@H](O)[C@H](O)[C@H]2O)c(OC)cc1OC]

To a mixture of 3-bromobicyclo[4.2.0]octa-1,3,5-triene (1 g, 5.46 mmol, 1.00 equiv) in THF (20 ml) was added dropwise n-BuLi (2.5 M in n-hexane, 2.18 mL, 1.00 equiv) at −78° C. under N$_2$. The reaction mixture was stirred at −78° C. for 20 min. 4-(benzyloxy)-5-bromo-2-methoxybenzaldehyde (1.75 g, 5.45 mmol, 1.00 equiv) in THF (10 ml) was added dropwise at −78° C. The reaction mixture was stirred at −78° C. for 1 h. Saturated NH$_4$Cl (aq) was added and the mixture was extracted with EA thrice. The combined extracts were washed with water, saturated brine and dried over anhydrous Na$_2$SO$_4$, then concentrated and purified by chromatography on silica gel (1:4 EA/PE) to yield (4-(benzyloxy)-5-bromo-2-methoxyphenyl)(1,2-dihydrocyclobutabenzen-4-yl)methanol as a yellow oil. MS (ES) m/z: 407 [M−OH]$^+$.

To a mixture of (4-(benzyloxy)-5-bromo-2-methoxyphenyl)(1,2-dihydrocyclobutabenzen-4-yl)methanol (2 g, 4.70 mmol, 1.00 equiv) in DCM (30 ml) was added Dess-Martin Reagent (3.99 g, 9.41 mmol, 2.00 equiv) at room temperature. The reaction mixture was stirred at room temperature for 3 h, then concentrated and purified by chromatography on silica gel (1:4 EA/PE) to yield (4-(benzyloxy)-5-bromo-2-methoxyphenyl)(1,2-dihydrocyclobutabenzen-4-yl)methanone as a light yellow oil.

To a mixture of (4-(benzyloxy)-5-bromo-2-methoxyphenyl)(1,2-dihydrocyclobutabenzen-4-yl)methanone (1.7 g, 4.02 mmol, 1.00 equiv) in THF (30 ml) with AlCl$_3$ (6.38 g, 47.97 mmol, 12.00 equiv) was added portionwise NaBD$_4$ (2 g, 47.62 mmol, 12.00 equiv) at 20° C. under N$_2$. The reaction mixture was stirred at 80° C. for 2 h. Water was added and the mixture was extracted with EA thrice. The combined extracts were washed with water, saturated brine and dried over anhydrous Na$_2$SO$_4$, then concentrated and purified by chromatography on silica gel (1:4 EA/PE) to yield 3-{[4-(benzyloxy)-5-bromo-2-methoxyphenyl](dideuterium)methyl}bicyclo[4.2.0]octa-1(6),2,4-triene as a colorless oil.

To a mixture of 3-{[4-(benzyloxy)-5-bromo-2-methoxyphenyl](dideuterium)methyl}bicyclo[4.2.0]octa-1(6),2,4-triene (1.5 g, 3.65 mmol, 1.00 equiv) in THF (30 ml) was added dropwise n-BuLi (2.5 M in n-hexane) (1.46 mL, 1.00 equiv) at −78° C. under $N_2$. The reaction mixture was stirred at −78° C. for 30 min. (3R,4S,5R,6R)-3,4,5-tris(benzyloxy)-6-[(benzyloxy)methyl]oxan-2-one (1.97 g, 3.66 mmol, 1.00 equiv) in THF (10 ml) was added dropwise at −78° C. The reaction mixture was stirred at −78° C. for 1 h. Saturated $NH_4Cl$ (aq) was added and the mixture was extracted with EA thrice. The combined extracts were washed with water, saturated brine and dried over anhydrous $Na_2SO_4$, then concentrated and purified by chromatography on silica gel (1:3 EA/PE) to yield (3R,4S,5R,6R)-3,4,5-tris(benzyloxy)-2-[2-(benzyloxy)-5-{bicyclo[4.2.0]octa-1(6),2,4-trien-3-yl(dideuterium)methyl}-4-methoxyphenyl]-6-[(benzyloxy)methyl]oxan-2-ol as a yellow oil. MS (ES) m/z: 853 [M−OH]$^+$.

To a mixture of (3R,4S,5R,6R)-3,4,5-tris(benzyloxy)-2-[2-(benzyloxy)-5-{bicyclo[4.2.0]octa-1(6),2,4-trien-3-yl(dideuterium)methyl}-4-methoxyphenyl]-6-[(benzyloxy)methyl]oxan-2-ol (1.3 g, 1.49 mmol, 1.00 equiv) in DCM (25 ml) with $Et_3SiH$ (350 mg, 3.01 mmol, 2.00 equiv) was added $BF_3.Et_2O$ (0.42 g, 2.00 equiv) at 0° C. The reaction mixture was stirred at 0° C. for 1 h. Saturated $NaHCO_3$ (aq) was added and the mixture was extracted with DCM thrice. The combined extracts were washed with water, saturated brine and dried over anhydrous $Na_2SO_4$, then concentrated and purified by chromatography on silica gel (1:30 EA/PE) to yield (2S,3S,4R,5R,6R)-3,4,5-tris(benzyloxy)-2-[2-(benzyloxy)-5-{bicyclo[4.2.0]octa-1(6),2,4-trien-3-yl(dideuterium)methyl}-4-methoxyphenyl]-6-[(benzyloxy)methyl]oxane as a yellow oil. MS (ES) m/z: 872 [M+NH$_4$]$^+$.

To a mixture of (2S,3S,4R,5R,6R)-3,4,5-tris(benzyloxy)-2-[2-(benzyloxy)-5-{bicyclo[4.2.0]octa-1(6),2,4-trien-3-yl(dideuterium)methyl}-4-methoxyphenyl]-6-[(benzyloxy)methyl]oxane (400 mg, 0.47 mmol, 1.00 equiv) in DCM (10 ml) with 1,2,3,4,5-pentamethylbenzene (417.4 mg, 2.82 mmol, 6.00 equiv) was added dropwise $BCl_3$ (1 M in DCM) (4.7 mL, 10.00 equiv) at −78° C. The reaction mixture was stirred at −78° C. for 1 h. MeOH was added, and the resulting mixture was then concentrated and purified by chromatography on C18 reverse column (30-40% MeCN/$H_2O$) to yield (2S,3R,4R,5S,6R)-2-(5-{bicyclo[4.2.0]octa-1(6),2,4-trien-3-yl(dideuterium)methyl}-2-hydroxy-4-methoxyphenyl)-6-(hydroxymethyl)oxane-3,4,5-triol as a white solid.

To a mixture of (2S,3R,4R,5S,6R)-2-(5-{bicyclo[4.2.0]octa-1(6),2,4-trien-3-yl(dideuterium)methyl}-2-hydroxy-4-methoxyphenyl)-6-(hydroxymethyl)oxane-3,4,5-triol (50 mg, 0.12 mmol, 1.00 equiv) in N,N-dimethylformamide (2 mL) with potassium carbonate (34 mg, 0.25 mmol, 2.1 equiv) was added $CH_3I$ (88 mg, 0.62 mmol, 5.00 equiv) at room temperature. The reaction mixture was stirred for 2 h at room temperature. The resulting mixture was purified by chromatography on a C18 reversed phase column to yield to yield the title compound as a white solid.

$^1$H NMR (300 MHz, CD$_3$OD): δ 7.15 (s, 1H), 7.02 (d, J=8.4 Hz, 1H), 6.85-6.87 (m, 2H), 6.60 (s, 1H), 4.59 (d, J=9.2 Hz, 1H), 3.86 (s, 1H), 3.84 (s, 3H), 3.83 (s, 3H), 3.32-3.67 (m, 5H), 3.09 (s, 4H); MS (ES) m/z: 417 [M−H]$^-$.

Example 52: Compound #60

(2S,3R,4R,5S,6R)-2-(5-(dideuterium(1,2-dihydrocyclobutabenzen-4-yl)methyl)-4-ethyl-2-methoxyphenyl)-6-(hydroxymethyl)-tetrahydro-2H-pyran-3,4,5-triol

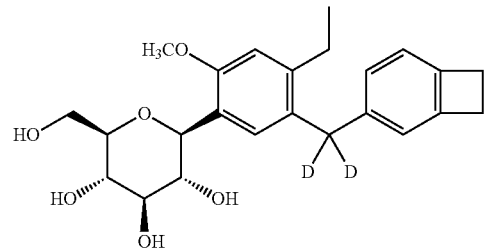 [SMILES: [2H]C([2H])(c1ccc2c(c1)CC2)c1cc([C@@H]2O[C@H](CO)[C@@H](O)[C@H](O)[C@H]2O)c(OC)cc1CC]

To a mixture of 4-bromo-1,2-dihydrocyclobutabenzene (700 mg, 3.82 mmol, 1.10 equiv) in THF (12 mL) was added n-BuLi (2.5M in hexane, 1.53 mL, 3.82 mmol, 1.10 equiv) dropwise at −78° C., the mixture was stirred at −78° C. for 30 min. After that, 4-(benzyloxy)-5-bromo-2-ethylbenzaldehyde (1.11 g, 3.48 mmol, 1.00 equiv) in THF (3 mL) was added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated and purified by chromatography on silica gel (5:1 PE/EA) to yield (4-(benzyloxy)-5-bromo-2-ethylphenyl)(1,2-dihydrocyclobutabenzen-4-yl)methanol as a light yellow oil. MS (ES) m/z: 407.0 [M−OH]$^+$.

To a mixture of (4-(benzyloxy)-5-bromo-2-ethylphenyl)(1,2-dihydrocyclobutabenzen-4-yl)methanol (1.3 g, 3.07 mmol, 1.00 equiv) in DCM (30 mL) was added Dess-Martin Reagent (3.26 g, 7.69 mmol, 2.50 equiv) in portions at 0° C. The reaction mixture was stirred at room temperature for 2 h, then concentrated and purified by chromatography on silica gel (5:1 PE/EA) to yield (4-(benzyloxy)-5-bromo-2-ethylphenyl)(1,2-dihydrocyclobutabenzen-4-yl)methanone as a colorless oil. MS (ES) m/z: 421.0 [M−OH]$^+$.

To a mixture of (4-(benzyloxy)-5-bromo-2-ethylphenyl)(1,2-dihydrocyclobutabenzen-4-yl)methanone (1.16 g, 2.75 mmol, 1.00 equiv) in THF (30 mL) with $NaBD_4$ (1.39 g, 33.10 mmol, 12.02 equiv) was added $AlCl_3$ (4.41 g, 33.16 mmol, 12.04 equiv) in portions at 0° C. The reaction mixture was stirred overnight at 65° C. Ice/water was added and the mixture was extracted with EtOAc thrice. The combined extracts were washed with brine and dried over $Na_2SO_4$, then concentrated and purified by chromatography on silica gel (10:1 PE/EA) to yield 4-((4-(benzyloxy)-5-bromo-2-ethylphenyl)dideuteriummethyl)-1,2-dihydrocyclobutabenzene as a white solid.

To a mixture of 4-((4-(benzyloxy)-5-bromo-2-ethylphenyl)dideuteriummethyl)-1,2-dihydrocyclobutabenzene (1 g, 2.44 mmol, 1.10 equiv) in THF (15 mL) was added n-BuLi (2.5M in hexane, 0.98 mL, 1.10 equiv) dropwise at −78° C., and the mixture was stirred at −78° C. for 30 min. (3R,4S,5R,6R)-3,4,5-Tris(benzyloxy)-6-[(benzyloxy)methyl]oxan-2-one (1.2 g, 2.23 mmol, 1.00 equiv) in THF (5 mL) was then added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated to yield (3R,4S,5R,6R)-3,4,5-tris(benzyloxy)-

2-(2-(benzyloxy)-5-(dideuterium(1,2-dihydrocyclobutabenzen-4-yl)methyl)-4-ethylphenyl)-6-(benzyloxymethyl)-tetrahydro-2H-pyran-2-ol as a light yellow oil.

To a mixture of (3R,4S,5R,6R)-3,4,5-tris(benzyloxy)-2-(2-(benzyloxy)-5-(dideuterium(1,2-dihydrocyclobutabenzen-4-yl)methyl)-4-ethylphenyl)-6-(benzyloxymethyl)-tetrahydro-2H-pyran-2-ol (2.12 g, 2.44 mmol, 1.00 equiv) in DCM (30 mL) with Et$_3$SiH (567 mg, 4.88 mmol, 2.00 equiv) was added BF$_3$.Et$_2$O (520 mg, 3.66 mmol, 1.50 equiv) at 0° C. The reaction mixture was stirred at 0° C. for 2 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (5:1 PE/EA) to yield (2S,3S,4R,5R,6R)-3,4,5-tris(benzyloxy)-2-(2-(benzyloxy)-5-(dideuterium (1,2-dihydrocyclobutabenzen-4-yl)methyl)-4-ethylphenyl)-6-(benzyloxymethyl)-tetrahydro-2H-pyran as a light yellow oil. MS (ES) m/z: 870.4 [M+NH$_4$]$^+$ To a mixture of (2S,3S,4R,5R,6R)-3,4,5-tris(benzyloxy)-2-(2-(benzyloxy)-5-(dideuterium(1,2-dihydrocyclobutabenzen-4-yl)methyl)-4-ethylphenyl)-6-(benzyloxymethyl)-tetrahydro-2H-pyran (470 mg, 0.55 mmol, 1.00 equiv) in dichloromethane (15 mL) with 1,2,3,4,5-pentamethylbenzene (850 mg, 5.73 mmol, 10.41 equiv) was added BCl$_3$ (1M in DCM, 10 mL) dropwise at −78° C. The reaction mixture was stirred at −78° C. for 1 h. 15 mL of methanol was added, and the resulting mixture was then concentrated and purified by chromatography on a C18 reversed phase column to yield (2S,3R,4R,5S,6R)-2-(5-(dideuterium (1,2-dihydrocyclobutabenzen-4-yl)methyl)-4-ethyl-2-hydroxyphenyl)-6-(hydroxymethyl)-tetrahydro-2H-pyran-3,4,5-triol as a white solid.

To a mixture of (2S,3R,4R,5S,6R)-2-(5-(dideuterium(1,2-dihydrocyclobutabenzen-4-yl)methyl)-4-ethyl-2-hydroxyphenyl)-6-(hydroxymethyl)-tetrahydro-2H-pyran-3,4,5-triol (30 mg, 0.07 mmol, 1.00 equiv) in N,N-dimethylformamide (3 mL) with potassium carbonate (31 mg, 0.22 mmol, 3.01 equiv) was added CH$_3$I (53 mg, 0.37 mmol, 5.01 equiv) at room temperature. The reaction mixture was stirred for 2 h at room temperature, then purified by chromatography on a C18 reversed phase column to yield the title compound as an off-white solid.

$^1$H NMR (300 MHz, CD$_3$OD): δ 7.23 (s, 1H), 6.95-7.05 (m, 1H), 6.87-6.95 (m, 1H), 6.75-6.87 (m, 2H), 4.67 (d, J=9.6 Hz, 1H), 3.82-3.97 (m, 4H), 3.47-3.72 (m, 3H), 3.38-3.47 (m, 2H), 3.12 (s, 4H), 2.51-2.69 (q, J=7.5 Hz, 2H), 1.10 (t, J=7.5 Hz, 3H); MS (ES) m/z: 415.2 [M−H]$^-$.

Example 53: Compound #61

(2S,3R,4R,5S,6R)-2-(5-((2,2-dideuterium-1,2-dihydrocyclobutabenzen-4-yl)methyl)-2-hydroxy-4-methylphenyl)-6-(hydroxymethyl)-tetrahydro-2H-pyran-3,4,5-triol

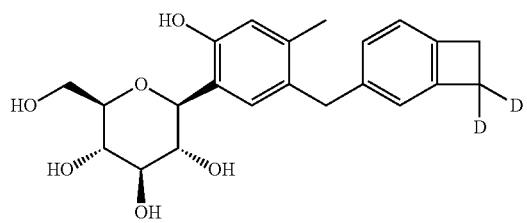 [SMILES: [2H]C1([2H])Cc2ccc(Cc3cc([C@@H]4O[C@H](CO)[C@@H](O)[C@H](O)[C@H]4O)c(O)cc3C)cc21]

To a mixture of 4-bromospiro[bicyclo[4.2.0]octane-7,2'-[1,3]dioxolane]-1,3,5-triene (2 g, 8.30 mmol, 1.10 equiv) in THF (25 mL) was added n-BuLi (2.5M in hexane, 3.32 mL, 1.10 equiv) dropwise at −78° C., the mixture was stirred at −78° C. for 30 min. 4-(Benzyloxy)-5-bromo-2-methylbenzaldehyde (2.3 g, 7.54 mmol, 1.00 equiv) in THF (5 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated and purified by chromatography on silica gel (1:1 PE/EA) to yield [4-(benzyloxy)-5-bromo-2-methylphenyl](spiro[bicyclo[4.2.0]octane-7,2_1,3]dioxolane]-1,3,5-trien-4-yl)methanol as a white solid. MS (ES) m/z: 449.0 [M−OH]$^+$.

To a mixture of [4-(benzyloxy)-5-bromo-2-methylphenyl](spiro[bicyclo[4.2.0]octane-7,2_1,3]dioxolane]-1,3,5-trien-4-yl)methanol (3 g, 6.42 mmol, 1.00 equiv) in DCM (50 mL) with Et$_3$SiH (2.23 g, 19.18 mmol, 2.99 equiv) was added BF$_3$.Et$_2$O (2.73 g, 19.23 mmol, 3.00 equiv) at 0° C. The reaction mixture was stirred at 0° C. for 2 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (5:1 PE/EA) to yield 5-(4-(benzyloxy)-5-bromo-2-methylbenzyl)cyclobutabenzen-1(2H)-one as a light yellow oil.

To a mixture of HgCl$_2$ (107 mg, 0.39 mmol, 0.20 equiv) and Zn (1.28 g, 19.69 mmol, 10.03 equiv) in D$_2$O (4 mL) was added conc. DCl (0.1 mL). The mixture was stirred for 15 min at room temperature. The water was poured out. Then to the solid was added a solution of 5-(4-(benzyloxy)-5-bromo-2-methylbenzyl)cyclobutabenzen-1(2H)-one (800 mg, 1.96 mmol, 1.00 equiv) in CH$_3$CH$_2$OD (7 mL) and toluene (7 mL), conc. DCl (11 mL). The reaction mixture was stirred overnight at 110° C. H$_2$O was added and the mixture was extracted with EtOAc thrice. The combined extracts were washed with brine and dried over Na$_2$SO$_4$, then concentrated and purified by chromatography on silica gel (5:1 PE/EA) to yield 5-(4-(benzyloxy)-5-bromo-2-methylbenzyl)-1,1-dideuterium-1,2-dihydrocyclobutabenzene as a light yellow oil. H NMR (400 MHz, CD$_3$OD): δ 7.46-7.52 (m, 2H), 7.38-7.46 (m, 2H), 7.30-7.38 (m, 1H), 7.29 (s, 1H), 7.05 (s, 1H), 6.92-7.02 (m, 2H), 6.79-6.88 (m, 1H), 5.17 (s, 2H), 3.84 (s, 2H), 3.07 (s, 2H), 2.29 (s, 3H).

To a mixture of 5-(4-(benzyloxy)-5-bromo-2-methylbenzyl)-1,1-dideuterium-1,2-dihydrocyclobutabenzene (630 mg, 1.59 mmol, 1.10 equiv) in THF (12 mL) was added n-BuLi (2.5M in hexane, 0.64 mL, 1.10 equiv) dropwise at −78° C., the mixture was stirred at −78° C. for 30 min. (3R,4S,5R,6R)-3,4,5-Tris(benzyloxy)-6-[(benzyloxy)methyl]oxan-2-one (780 mg, 1.45 mmol, 1.00 equiv) in THF (3 mL) was then added to the solution. The reaction mixture was stirred at −78° C. for 2 h. NH$_4$Cl/H$_2$O was added and the mixture was extracted with EtOAc thrice. The combined extracts were washed with brine and dried over Na$_2$SO$_4$, then concentrated to yield (3R,4S,5R,6R)-3,4,5-tris(benzyloxy)-2-(2-(benzyloxy)-5-((2,2-dideuterium-1,2-dihydrocyclobutabenzen-4-yl)methyl)-4-methylphenyl)-6-(benzyloxymethyl)-tetrahydro-2H-pyran-2-ol as a light yellow oil.

To a mixture of (3R,4S,5R,6R)-3,4,5-tris(benzyloxy)-2-(2-(benzyloxy)-5-((2,2-dideuterium-1,2-dihydrocyclobutabenzen-4-yl)methyl)-4-methylphenyl)-6-(benzyloxymethyl)-tetrahydro-2H-pyran-2-ol (1.4 g, 1.64 mmol, 1.00 equiv) in DCM (20 mL) with Et$_3$SiH (380 mg, 3.27 mmol, 2.00 equiv) was added BF$_3$.Et$_2$O (349 mg, 2.46 mmol, 1.50 equiv) at 0° C. The reaction mixture was stirred at 0° C. for 2 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield (2S,3S,4R,5R,6R)-3,4,5-tris(benzyloxy)-2-(2-(benzyloxy)-5-((2,2-dideuterium-1,2-dihydrocyclobutabenzen-4-yl)methyl)-4-methylphenyl)-6-(benzyloxymethyl)-tetrahydro-2H-pyran as a light yellow oil. MS (ES) m/z: 856.4 [M+NH₄]⁺.

To a mixture of (2S,3S,4R,5R,6R)-3,4,5-tris(benzyloxy)-2-(2-(benzyloxy)-5-((2,2-dideuterium-1,2-dihydrocyclobutabenzen-4-yl)methyl)-4-methylphenyl)-6-(benzyloxymethyl)-tetrahydro-2H-pyran (450 mg, 0.54 mmol, 1.00 equiv) in dichloromethane (15 mL) with 1,2,3,4,5-pentamethylbenzene (800 mg, 5.40 mmol, 10.06 equiv) was added BCl₃ (1M in DCM, 10 mL) dropwise at −78° C. The reaction mixture was stirred at −78° C. for 1 h. 15 mL of methanol was added, and the resulting mixture was then concentrated and purified by chromatography on a C18 reversed phase column to yield the title compound as a white solid.

¹H NMR (300 MHz, CD₃OD) δ 7.12 (s, 1H), 6.86-7.00 (m, 2H), 6.78 (s, 1H), 6.63 (s, 1H), 4.52 (d, J=9.5 Hz, 1H), 3.82-3.93 (m, 3H), 3.71 (dd, J=12.0, 5.0 Hz, 1H), 3.54-3.63 (m, 1H), 3.37-3.53 (m, 3H), 3.09 (s, 2H), 2.10 (s, 3H); MS (ES) m/z: 387.1 [M−H]⁻.

Example 54: Compound #62

(2S,3R,4R,5S,6R)-2-[3-[(8,8-dideuterium)bicyclo[4.2.0]octa-1(6),2,4-trien-3-ylmethyl]-4-chlorophenyl]-6-(hydroxymethyl)oxane-3,4,5-triol

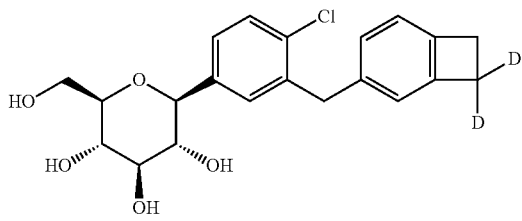 [SMILES: [2H]C1([2H])Cc2ccc(Cc3cc([C@@H]4O[C@H](CO)[C@@H](O)[C@H](O)[C@H]4O)ccc3Cl)cc21]

To a mixture of 4-bromospiro[bicyclo[4.2.0]octane-7,2′-[1,3]dioxolane]-1,3,5-triene (4 g, 16.59 mmol, 1.10 equiv) in THF (40 mL) was added n-BuLi (2.5 M in hexane, 6.9 mL, 17.4 mmol, 1.15 equiv) dropwise at −78° C. The reaction mixture was stirred for 1 h at −78° C. To the resulting mixture was then added a solution of 5-bromo-2-chlorobenzaldehyde (3.3 g, 15.04 mmol, 1.00 equiv) in THF (20 mL) dropwise at −78° C. The reaction mixture was stirred for 1 h at −78° C. NH₄Cl/H₂O was added and the mixture was extracted with EtOAc thrice. The combined extracts were washed with brine and dried over Na₂SO₄, then concentrated and purified by chromatography on silica gel (3:1, PE/EA) to yield (5-bromo-2-chlorophenyl)(spiro[bicyclo[4.2.0]octane-7,2_1,3]dioxolane]-1,3,5-trien-4-yl)methanol as a colorless oil. MS (ES) m/z: 364.9 [M−OH]⁺.

To a mixture of (5-bromo-2-chlorophenyl)(spiro[bicyclo[4.2.0]octane-7,2_1,3]dioxolane]-1,3,5-trien-4-yl)methanol (4.5 g, 11.79 mmol, 1.00 equiv) and NaI (7.1 g, 47.33 mmol, 4.01 equiv) in acetonitrile (40 mL) was added TMSCl (5.1 g, 46.94 mmol, 3.98 equiv). The reaction mixture was stirred for 1 h at 50° C. Ice/water was added and the mixture was extracted with EA twice. The combined extracts were washed with brine and dried over Na₂SO₄, then concentrated and purified by chromatography on silica gel (5:1 PE/EA) to yield 4-[(5-bromo-2-chlorophenyl)methyl]bicyclo[4.2.0]octa-1(6),2,4-trien-7-one as a light yellow solid. ¹H NMR (300 MHz, Chloroform-d) δ 7.48 (d, J=7.8 Hz, 1H), 7.15-7.39 (m, 5H), 4.09 (s, 2H), 3.95 (s, 2H).

To a mixture of HgCl₂ (500 mg, 1.84 mmol, 0.20 equiv) and Zn (powder) (6.1 g, 93.26 mmol, 10.00 equiv) in D₂O (15 mL) was added 2 drops of conc. DCl. The reaction mixture was stirred for 15 min at room temperature. D₂O was poured out and CH₃CH₂OD (18 mL), toluene (18 mL), conc. DCl (30 mL), and 4-[(5-bromo-2-chlorophenyl)methyl]bicyclo[4.2.0]octa-1(6),2,4-trien-7-one (3 g, 9.33 mmol, 1.00 equiv) was added. The reaction mixture was stirred overnight at 110° C. The reaction mixture was cooled to room temperature and extracted with EA twice. The combined extracts were washed with brine and dried over Na₂SO₄, then concentrated and purified by chromatography on silica gel (10:1 PE/EA) to yield 3-[(5-bromo-2-chlorophenyl)methyl](8,8-dideuterium)bicyclo[4.2.0]octa-1(6),2,4-triene as a colorless oil. ¹H NMR (400 MHz, Chloroform-d) δ 0.719-7.31 (m, 3H), 7.01-7.06 (m, 2H), 6.91 (s, 1H), 4.05 (s, 2H), 3.16 (s, 2H).

To a mixture of 3-[(5-bromo-2-chlorophenyl)methyl](8,8-dideuterium)bicyclo[4.2.0]octa-1(6),2,4-triene (1.5 g, 4.84 mmol, 1.05 equiv) in tetrahydrofuran (30 mL) was added n-BuLi (2.5M in hexane, 2.03 mL, 5.07 mmol, 1.10 equiv) dropwise at −78° C., the mixture was stirred at −78° C. for 1 h. (3R,4S,5R,6R)-3,4,5-Tris(benzyloxy)-6-[(benzyloxy)methyl]oxan-2-one (2.49 g, 4.62 mmol, 1.00 equiv) in tetrahydrofuran (10 mL) was then added dropwise at −78° C. The reaction mixture was stirred at −78° C. for 1 h. NH₄Cl/H₂O was added and the mixture was extracted with EtOAc thrice. The combined extracts were washed with brine and dried over Na₂SO₄, then concentrated and purified by chromatography on silica gel (5:1 PE/EA) to yield (3R,4S,5R,6R)-3,4,5-tris(benzyloxy)-6-[(benzyloxy)methyl]-2-[3-[(8,8-dideuterium)bicyclo[4.2.0]octa-1(6),2,4-trien-3-ylmethyl]-4-chlorophenyl]oxan-2-ol as a white solid. MS (ES) m/z: 751.5 [M−OH]⁺.

To a mixture of (3R,4S,5R,6R)-3,4,5-tris(benzyloxy)-6-[(benzyloxy)methyl]-2-[3-[(8,8-dideuterium)bicyclo[4.2.0]octa-1(6),2,4-trien-3-ylmethyl]-4-chlorophenyl]oxan-2-ol (3.0 g, 3.90 mmol, 1.00 equiv) in dichloromethane (30 mL) with Et₃SiH (910 mg, 7.83 mmol, 2.01 equiv) was added BF₃.Et₂O (1.10 g, 7.75 mmol, 1.99 equiv) dropwise at 0° C. The reaction mixture was stirred at 0° C. for 1 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-chlorophenyl]oxane as a colorless oil. MS (ES) m/z: 775.2 [M+Na]⁺.

To a mixture of (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-chlorophenyl]oxane (1 g, 1.33 mmol, 1.00 equiv) in dichloromethane (50 mL) with 1,2,3,4,5-pentamethylbenzene (2 g, 13.49 mmol, 10.16 equiv) was added BCl₃ (1M in DCM, 20 mL, 20 mmol, 15.00 equiv) dropwise at −78° C. The reaction mixture was stirred at −78° C. for 1 h. 20 mL of methanol was added, and the resulting mixture was then concentrated and purified by chromatography on Prep-HPLC (0%-45% CH₃CN/H₂O) to yield the title compound as an off-white solid.

¹H NMR (300 MHz, CD₃OD): δ 7.26-7.36 (m, 3H), 7.30 (d, J=7.5 Hz, 1H), 6.87-6.93 (m, 2H), 4.00-4.12 (m, 3H), 3.88 (d, J=12 Hz, 1H), 3.66-3.72 (m, 1H), 3.26-3.48 (m, 4H), 3.10 (s, 2H); MS (ES) m/z: 410.1 [M+NH₄]⁺.

Example 55: Compound #63

(2S,3R,4R,5S,6R)-2-(5-((2,2-dideuterium-1,2-dihydrocyclobutabenzen-4-yl)methyl)-2-methoxy-4-methylphenyl)-6-(hydroxymethyl)-tetrahydro-2H-pyran-3,4,5-triol

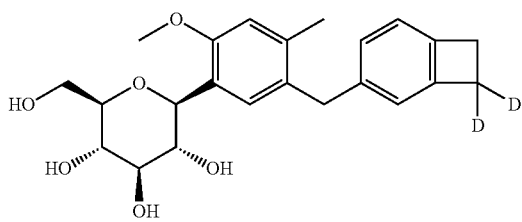 [SMILES: [2H]C1([2H])Cc2ccc(Cc3cc([C@@H]4O[C@H](CO)[C@@H](O)[C@H](O)[C@H]4O)c(OC)cc3C)cc21]

To a mixture of (2S,3R,4R,5S,6R)-2-(5-((2,2-dideuterium-1,2-dihydrocyclobutabenzen-4-yl)methyl)-2-hydroxy-4-methylphenyl)-6-(hydroxymethyl)-tetrahydro-2H-pyran-3,4,5-triol (Compound #61) (27 mg, 0.07 mmol, 1.00 equiv) in N,N-dimethylformamide (3 mL) with potassium carbonate (32 mg, 0.23 mmol, 3.00 equiv) was added CH₃I (55 mg, 0.39 mmol, 5.02 equiv) at room temperature. The reaction mixture was stirred for 2 h at room temperature, then purified by chromatography on a C18 reversed phase column to yield the title compound as a white solid.

¹H NMR (400 MHz, CD₃OD): δ 7.10 (s, 1H), 6.85 (d, J=7.6 Hz, 1H), 6.77 (d, J=7.6 Hz, 1H), 6.68 (s, 2H), 4.54 (d, J=9.5 Hz, 1H), 3.80 (s, 2H), 3.75 (dd, J=12.1, 1.5 Hz, 1H), 3.70 (s, 3H), 3.53-3.59 (m, 1H), 3.45 (t, J=9.1 Hz, 1H), 3.34-3.41 (m, 1H), 3.28 (dd, J=5.4, 1.7 Hz, 2H), 2.98 (s, 2H), 2.08 (s, 3H); MS (ES) m/z: 401.1 [M-H]⁻.

Example 56: Compound #64

(2S,3R,4R,5S,6R)-2-[3-[(8,8-dideuterium)bicyclo[4.2.0]octa-1(6),2,4-trien-3-ylmethyl]-4-methoxyphenyl]-6-(hydroxymethyl)oxane-3,4,5-triol

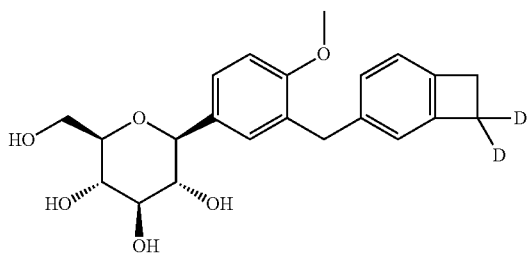 [SMILES: [2H]C1([2H])Cc2ccc(Cc3cc([C@@H]4O[C@H](CO)[C@@H](O)[C@H](O)[C@H]4O)ccc3OC)cc21]

To a mixture of 4-bromospiro[bicyclo[4.2.0]octane-7,2'-[1,3]dioxolane]-1,3,5-triene (400 mg, 1.66 mmol, 1.10 equiv) in THF (4 mL) was added n-BuLi (2.5 M in hexane, 0.7 mL, 1.73 mmol, 1.15 equiv) dropwise at −78° C. The reaction mixture was stirred for 30 min at −78° C. To the resulting mixture was then added a solution of 5-bromo-2-methoxybenzaldehyde (323 mg, 1.50 mmol, 1.00 equiv) in THF (2 mL) dropwise at −78° C. The reaction mixture was stirred for 1 h at −78° C. NH₄Cl/H₂O was added and the mixture was extracted with EtOAc thrice. The combined extracts were washed with brine and dried over Na₂SO₄, then concentrated and purified by chromatography on silica gel (2:1, PE/EA) to yield (5-bromo-2-methoxyphenyl)(spiro[bicyclo[4.2.0]octane-7,2_1,3]dioxolane]-1(6),2,4-trien-4-yl)methanol as a colorless oil. MS (ES) m/z: 361.1 [M−OH]⁺.

To a mixture of (5-bromo-2-methoxyphenyl)(spiro[bicyclo[4.2.0]octane-7,2_1,3]dioxolane]-1(6),2,4-trien-4-yl) methanol (430 mg, 1.14 mmol, 1.00 equiv) and NaI (600 mg, 4.00 mmol, 4.02 equiv) in acetonitrile (8 mL) was added TMSCl (495 mg, 4.56 mmol, 4.00 equiv). The reaction mixture was stirred for 1 h at 50° C. Ice/water was added and the mixture was extracted with EA twice. The combined extracts were washed with brine and dried over Na₂SO₄, then concentrated and purified by chromatography on silica gel (5:1 PE/EA) to yield 4-[(5-bromo-2-methoxyphenyl)methyl]bicyclo[4.2.0]octa-1(6),2,4-trien-7-one as a colorless oil. ¹H NMR (400 MHz, Chloroform-d) δ 7.44 (d, J=7.6 Hz, 1H), 7.38 (d, J=7.7 Hz, 1H), 7.31 (d, J=8.7 Hz, 1H), 7.16-7.17 (m, 2H), 6.73 (d, J=8.7 Hz, 1H), 3.94 (s, 2H), 3.92 (s, 2H), 3.78 (s, 3H).

To a mixture of HgCl₂ (51.4 mg, 0.19 mmol, 0.20 equiv) and Zn (powder) (615 mg, 9.40 mmol, 9.94 equiv) in D₂O (1.5 mL) was added 2 drops of concentrated DCl. The reaction mixture was stirred for 0.5 h at room temperature. D₂O was poured out and CH₃CH₂OD (1.5 mL), toluene (1.5 mL), concentrated DCl (2.5 mL), and 4-[(5-bromo-2-methoxyphenyl)methyl]bicyclo[4.2.0]octa-1(6),2,4-trien-7-one (300 mg, 0.95 mmol, 1.00 equiv) was added. The reaction mixture was stirred overnight at 110° C. The reaction mixture was cooled to room temperature and extracted with EA twice. The combined extracts were washed with brine and dried over Na₂SO₄, then concentrated and purified by chromatography on silica gel (10:1 PE/EA) to yield 3-[(5-bromo-2-methoxyphenyl)methyl](8,8-dideuterium)bicyclo[4.2.0]octa-1(6),2,4-triene as a light yellow oil. ¹H NMR (400 MHz, Chloroform-d) δ 7.31-7.27 (m, 1H), 7.18 (d, J=2.5 Hz, 1H), 7.04-7.08 (m, 1H), 6.97-6.99 (m, 1H), 6.92 (s, 1H), 6.75 (d, J=8.7 Hz, 1H), 3.91 (s, 2H), 3.83 (s, 3H), 3.14 (s, 2H).

To a mixture of 3-[(5-bromo-2-methoxyphenyl)methyl] (8,8-dideuterium)bicyclo[4.2.0]octa-1(6),2,4-triene (220 mg, 0.72 mmol, 1.05 equiv) in tetrahydrofuran (6 mL) was added n-BuLi (2.5M in hexane, 0.32 mL, 0.789 mmol, 1.15 equiv) dropwise at −78° C., the mixture was stirred at −78° C. for 30 mins. (3R,4S,5R,6R)-3,4,5-Tris(benzyloxy)-6-[(benzyloxy)methyl]oxan-2-one (370 mg, 0.69 mmol, 1.00 equiv) in tetrahydrofuran (2 mL) was then added dropwise at −78° C. The reaction mixture was stirred at −78° C. for 1 h. NH₄Cl/H₂O was added and the mixture was extracted with EtOAc thrice. The combined extracts were washed with brine and dried over Na₂SO₄, then concentrated and purified by chromatography on silica gel (2:1 PE/EA) to yield (3R,4S,5R,6R)-3,4,5-tris(benzyloxy)-6-[(benzyloxy) methyl]-2-[3-[(8,8-dideuterium)bicyclo[4.2.0]octa-1(6),2,4-trien-3-ylmethyl]-4-methoxyphenyl]oxan-2-ol as a colorless oil. MS (ES) m/z: 747.6 [M−OH]⁺.

To a mixture of (3R,4S,5R,6R)-3,4,5-tris(benzyloxy)-6-[(benzyloxy)methyl]-2-[3-[(8,8-dideuterium)bicyclo[4.2.0] octa-(6),2,4-trien-3-ylmethyl]-4-methoxyphenyl]oxan-2-ol (210 mg, 0.27 mmol, 1.00 equiv) in dichloromethane (6 mL) with Et₃SiH (66.7 mg, 0.57 mmol, 2.09 equiv) was added BF₃·Et₂O (81.7 mg, 0.58 mmol, 2.10 equiv) dropwise at 0° C. The reaction mixture was stirred at 0° C. for 1 h. Sodium bicarbonate/H₂O was added and the mixture was extracted with dichloromethane thrice. The combined extracts were washed with brine and dried over Na$_2$SO$_4$, then concentrated and purified by chromatography on silica gel (5:1 PE/EA) to yield (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-methoxyphenyl]oxane as a colorless oil.

To a mixture of (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-methoxyphenyl]oxane (160 mg, 0.21 mmol, 1.00 equiv) in dichloromethane (8 mL) with 1,2,3,4,5-pentamethylbenzene (320 mg, 2.16 mmol, 10.10 equiv) was added BCl$_3$ (1M in DCM, 3.2 mL, 3.2 mmol, 15.20 equiv) dropwise at −78° C. The reaction mixture was stirred at −78° C. for 1 h. 5 mL of methanol was added, and the resulting mixture was then concentrated and purified by chromatography on a C18 (0%-45% CH$_3$CN/H$_2$O) reversed phase column to yield the title compound as a white solid.

$^1$H NMR (300 MHz, CD$_3$OD) δ 7.21 (dd, J=8.4, 2.2 Hz, 1H), 7.13 (d, J=2.2 Hz, 1H), 6.99 (dd, J=7.7, 1.2 Hz, 1H), 6.99 (d, J=8.4 Hz, 1H), 6.82-6.89 (m, 1H), 4.00 (d, J=9.1 Hz, 1H), 3.74-3.93 (m, 6H), 3.63 (dd, J=12.0, 5.2 Hz, 1H), 3.45-3.29 (m, 4H), 3.04 (s, 2H); MS (ES) m/z: 406.1 [M+NH$_4$].

Example 57: Compound #65

(2S,3R,4R,5S,6R)-2-[3-[(8,8-dideuterium)bicyclo[4.2.0]octa-1(6),2,4-trien-3-ylmethyl]-4-methylphenyl]-6-(hydroxymethyl)oxane-3,4,5-triol

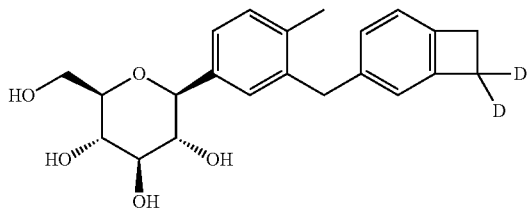 [SMILES: [2H]C1([2H])Cc2ccc(Cc3cc([C@@H]4O[C@H](CO)[C@@H](O)[C@H](O)[C@H]4O)ccc3C)cc21]

To a mixture of 4-bromospiro[bicyclo[4.2.0]octane-7,2'-[1,3]dioxolane]-1,3,5-triene (400 mg, 1.66 mmol, 1.10 equiv) in THF (4 mL) was added n-BuLi (2.5 M in hexane, 0.7 mL, 1.15 equiv) dropwise at −78° C. The reaction mixture was stirred for 30 min at −78° C. To the resulting mixture was then added a solution of 5-bromo-2-methylbenzaldehyde (300 mg, 1.51 mmol, 1.00 equiv) in THF (2 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (1:2 PE/EA) to yield (5-bromo-2-methylphenyl)(spiro[bicyclo[4.2.0]octane-7,2_1,3]dioxolane]-1(6),2,4-trien-4-yl)methanol as a colorless oil. MS (ES) m/z: 345.0 [M−OH]$^+$.

To a mixture of (5-bromo-2-methylphenyl)(spiro[bicyclo[4.2.0]octane-7,2_1,3]dioxolane]-1(6),2,4-trien-4-yl)methanol (360 mg, 1.00 mmol, 1.00 equiv) and NaI (600 mg, 4.00 mmol, 4.02 equiv) in acetonitrile (6 mL) was added TMSCl (434 mg, 3.99 mmol, 4.01 equiv). The reaction mixture was stirred for 3 h at 50° C. Ice water was added and the mixture was extracted with EA twice. The combined extracts were washed with brine and dried over Na$_2$SO$_4$, then concentrated and purified by chromatography on silica gel (5:1 PE/EA) to yield 4-[(5-bromo-2-methylphenyl)methyl]bicyclo[4.2.0]octa-1(6),2,4-trien-7-one as a colorless oil. $^1$H NMR (400 MHz, Chloroform-d) δ 7.38 (d, J=7.6 Hz, 1H), 7.19-7.24 (m, 2H), 7.13 (s, 1H), 6.96-6.99 (m, 2H), 3.90 (s, 2H), 3.87 (s, 2H), 2.09 (s, 3H).

To a mixture of HgCl$_2$ (51 mg, 0.19 mmol, 0.20 equiv) and Zn (powder) (604 mg, 9.23 mmol, 9.93 equiv) in D$_2$O (1.5 mL) was added 2 drops of conc. DCl. The reaction mixture was stirred for 0.5 h at room temperature. D$_2$O was poured out and CH$_3$CH$_2$OD (1.5 mL), toluene (1.5 mL), conc. DCl (2.5 mL), and 4-[(5-bromo-2-methylphenyl)methyl]bicyclo[4.2.0]octa-1(6),2,4-trien-7-one (280 mg, 0.93 mmol, 1.00 equiv) was added. The reaction mixture was stirred overnight at 110° C. The reaction mixture was cooled to room temperature and extracted with EA twice. The combined extracts were washed with brine and dried over Na$_2$SO$_4$, then concentrated and purified by chromatography on silica gel (10:1 PE/EA) to yield 3-[(5-bromo-2-methylphenyl)methyl](8,8-dideuterium)bicyclo[4.2.0]octa-1(6),2,4-triene as a light yellow oil. $^1$H NMR (400 MHz, Chloroform-d) δ 7.27-7.30 (m, 2H), 7.04 (d, J=8.0 Hz, 1H), 6.95-7.00 (m, 2H), 6.82 (s, 1H), 3.92 (s, 2H), 3.14 (s, 2H), 2.22 (s, 3H).

To a mixture of 3-[(5-bromo-2-methylphenyl)methyl](8,8-dideuterium)bicyclo[4.2.0]octa-1(6),2,4-triene (190 mg, 0.66 mmol, 1.05 equiv) in tetrahydrofuran (6 mL) was added n-BuLi (2.5M in hexane, 0.29 mL, 0.72 mmol, 1.15 equiv) dropwise at −78° C., the mixture was stirred at −78° C. for 30 mins. (3R,4S,5R,6R)-3,4,5-Tris(benzyloxy)-6-[(benzyloxy)methyl]oxan-2-one (337 mg, 0.63 mmol, 1.00 equiv) in tetrahydrofuran (2 mL) was then added dropwise at −78° C. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-6-[(benzyloxy)methyl]-2-[3-[(8,8-dideuterium)bicyclo[4.2.0]octa-1(6),2,4-trien-3-ylmethyl]-4-methylphenyl]oxan-2-ol as a light yellow oil. MS (ES) m/z: 731.5 [M−OH]$^+$.

To a mixture of (3R,4S,5R,6R)-3,4,5-tris(benzyloxy)-6-[(benzyloxy)methyl]-2-[3-[(8,8-dideuterium)bicyclo[4.2.0]octa-1(6),2,4-trien-3-ylmethyl]-4-methylphenyl]oxan-2-ol (170 mg, 0.23 mmol, 1.00 equiv) in dichloromethane (5 mL) with Et$_3$SiH (52.6 mg, 0.45 mmol, 1.99 equiv) was added BF$_3$.Et$_2$O (64.4 mg, 0.45 mmol, 2.00 equiv) dropwise at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (5:1 PE/EA) to yield (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-methylphenyl]oxane as a light yellow oil.

To a mixture of (2R,3R,4R,5S,6S)-3,4,5-tris(benzyloxy)-2-[(benzyloxy)methyl]-6-[3-[(8,8-dideuterium)bicyclo[4.2.0]octa-1(6),2,4-trien-3-ylmethyl]-4-methylphenyl]oxane (50 mg, 0.07 mmol, 1.00 equiv) in dichloromethane (2.5 mL) with 1,2,3,4,5-pentamethylbenzene (100 mg, 0.67 mmol, 9.89 equiv) was added BCl$_3$ (1 M in DCM, 1 mL, 1 mmol, 14.70 equiv) dropwise at −78° C. The reaction mixture was stirred at −78° C. for 1 h. 2 mL of methanol was added, and the resulting mixture was then concentrated and purified by chromatography on a C18 (0%-45% CH₃CN/H₂O) reversed phase column to yield the title compound as a white solid.

¹H NMR (300 MHz, CD₃OD): δ 7.15-7.17 (m, 2H), 7.08 (d, J=8.4 Hz, 1H), 6.92 (d, J=7.6 Hz, 1H), 6.85 (d, J=7.6 Hz, 1H), 6.75 (s, 1H), 4.05 (d, J=9.2 Hz, 1H), 3.92 (s, 2H), 3.85 (d, J=12.2, 1H), 3.60-3.70 (m, 1H), 3.30-3.48 (m, 4H), 3.05 (s, 2H), 2.15 (s, 3H); MS (ES) m/z: 390.1 [M+NH₄].

Example 58: Compound #66

(2S,3R,4R,5S,6R)-2-(3-((2,2-dideuterium-1,2-dihydrocyclobutabenzen-4-yl)methyl)-4-ethylphenyl)-6-(hydroxymethyl)-tetrahydro-2H-pyran-3,4,5-triol

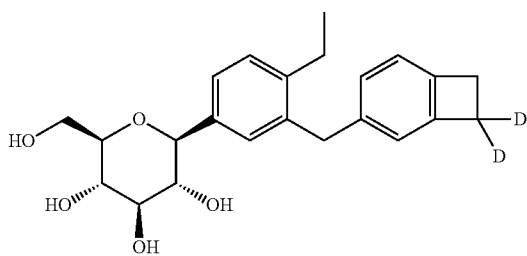 [SMILES: [2H]C1([2H])Cc2ccc(Cc3cc([C@@H]4O[C@H](CO)[C@@H](O)[C@H](O)[C@H]4O)ccc3CC)cc21]

To a mixture of 4-bromospiro[bicyclo[4.2.0]octane-7,2'-[1,3]dioxolane]-1,3,5-triene (300 mg, 1.24 mmol, 1.20 equiv) in tetrahydrofuran (4 mL) was added n-BuLi (0.5 mL, 1.20 equiv, 2.5M in hexane) dropwise at −78° C. The mixture was stirred for 30 min at −78° C. To the resulting mixture was then added a solution of 5-bromo-2-ethylbenzaldehyde (221 mg, 1.04 mmol, 1.00 equiv) in tetrahydrofuran (1 mL) dropwise at −78° C. The reaction mixture was stirred for 2 h at −78° C. NH₄Cl/H₂O was added and the mixture was extracted with EtOAc thrice. The combined extracts were washed with brine and dried over Na₂SO₄, then concentrated and purified by chromatography on silica gel (1:5 ethyl acetate/petroleum ether) to yield (5-bromo-2-ethylphenyl)-(spiro[bicyclo[4.2.0]octane-7,2'-[1,3]di-oxolane]-1,3,5-trien-4-yl)methanol as a light yellow oil. MS (ES) m/z: 356.9 [M−OH]⁺.

To a mixture of (5-bromo-2-ethylphenyl)-(spiro[bicyclo[4.2.0]octane-7,2'-[1,3]di-oxolane]-1,3,5-trien-4-yl)methanol (368 mg, 0.98 mmol, 1.00 equiv) in acetonitrile (10 mL) with NaI (588.8 mg, 3.93 mmol, 4.00 equiv) was added TMSCl (427.9 mg, 3.94 mmol, 4.00 equiv), and the reaction mixture was stirred for 1 h at 50° C. Ice water was added and the mixture was extracted with EtOAc thrice. The combined extracts were washed with Na₂SO₃/H₂O, brine and dried over Na₂SO₄, then concentrated and purified by chromatography on silica gel (1:10 ethyl acetate/petroleum ether) to yield 4-[(5-bromo-2-ethylphenyl)-methyl]bicyclo[4.2.0]octa-1,3,5-trien-7-one as a light yellow oil. ¹H NMR (300 MHz, Chloroform-d) δ 7.37-7.47 (m, 1H), 7.30 (ddd, J=9.2, 7.9, 1.8 Hz, 2H), 7.17 (d, J=2.2 Hz, 1H), 7.00-7.11 (m, 2H), 3.98 (s, 2H), 3.92 (s, 2H), 2.50 (q, J=7.5 Hz, 2H), 1.10 (t, J=7.5 Hz, 3H).

To a mixture of HgCl₂ (39.5 mg, 0.15 mmol, 0.20 equiv) in D₂O (1.5 mL), DCl (2 drops g, 35% in D₂O) was added Zn (472 mg, 7.26 mmol, 10.00 equiv). The mixture was stirred for 10 min. Then D₂O was poured out. To the resulting mixture was then added a solution of 4-[(5-bromo-2-ethylphenyl)-methyl]bicyclo[4.2.0]octa-1,3,5-trien-7-one (236 mg, 0.75 mmol, 1.00 equiv) in toluene/CH₃CH₂OD (2/2 mL), DCl (3.3 mL, 35% in D₂O). The reaction mixture was stirred for 16 h at 110° C. Ice water was added and the mixture was extracted with EtOAc thrice. The combined extracts were washed with brine and dried over Na₂SO₄, then concentrated and purified by chromatography on silica gel (1:20 ethyl acetate/petroleum ether) to yield 3-[(5-bromo-2-ethylphenyl)-methyl](8,8-dideuterium)bicyclo-[4.2.0]octa-1,3,5-triene as a light yellow oil. ¹H NMR (400 MHz, Chloroform-d) δ 7.32 (dd, J=8.1, 2.2 Hz, 1H), 7.24 (d, J=2.1 Hz, 1H), 7.09 (d, J=8.3 Hz, 1H), 6.98 (d, J=1.6 Hz, 2H), 6.82 (s, 1H), 3.96 (s, 2H), 3.15 (s, 2H), 2.60 (q, J=7.5 Hz, 2H), 1.17 (t, J=7.5 Hz, 3H).

To a mixture of 3-[(5-bromo-2-ethylphenyl)-methyl](8,8-dideuterium)bicyclo-[4.2.0]octa-1,3,5-triene (182.5 mg, 0.60 mmol, 1.15 equiv) in tetrahydrofuran/toluene (1.5/3 mL) was added n-BuLi (0.24 mL, 1.15 equiv, 2.5M in hexane) dropwise at −78° C. The mixture was stirred for 30 min at −78° C. To the resulting mixture was then added a solution of (3R,4S,5R,6R)-3,4,5-tris[(trimethylsilyl)oxy]-6-[[(trimethylsilyl)oxy]methyl]oxan-2-one (244.6 mg, 0.52 mmol, 1.00 equiv) in tetrahydrofuran/toluene (0.5/1 mL). The reaction mixture was stirred for 2 h at −78° C. NH₄Cl/H₂O was added and the mixture was extracted with EtOAc thrice. The combined extracts were washed with brine and dried over Na₂SO₄, then concentrated to yield (3R,4S,5R,6R)-2-[3-[(8,8-dideuterium)bicyclo-[4.2.0]octa-1,3,5-trien-3-ylmethyl]-4-ethylphenyl]-3,4,5-tris[(trimethylsilyl)oxy]-6-[[(trimethylsilyl)oxy]methyl]oxan-2-ol as a light brown oil.

To a mixture of (3R,4S,5R,6R)-2-[3-[(8,8-dideuterium)bicyclo-[4.2.0]octa-1,3,5-trien-3-ylmethyl]-4-ethylphenyl]-3,4,5-tris[(trimethylsilyl)oxy]-6-[[(trimethylsilyl)oxy]methyl]oxan-2-ol (385 mg, 0.56 mmol, 1.00 equiv) in methanol (5 mL) was added a solution of methanesulfonic acid (107 mg, 1.11 mmol, 2.00 equiv) in methanol (1 mL) dropwise at −78° C. The reaction mixture was stirred for 16 h at 25° C. NaHCO₃/H₂O was added and the mixture was extracted with EtOAc thrice. The combined extracts were washed with brine and dried over Na₂SO₄, then concentrated and purified by chromatography on silica gel (93:7 dichloromethane/methanol) to yield (2S,3R,4S,5S,6R)-2-[3-[(8,8-dideuterium)-bicyclo[4.2.0]octa-1,3,5-trien-3-ylmethyl]-4-ethylphenyl]-6-(hydroxymethyl)-2-methoxyoxane-3,4,5-triol as an off-white solid. MS (ES) m/z: 385.2 [M−OCH₃]⁺.

To a mixture of (2S,3R,4S,5S,6R)-2-[3-[(8,8-dideuterium)-bicyclo[4.2.0]octa-1,3,5-trien-3-ylmethyl]-4-ethylphenyl]-6-(hydroxymethyl)-2-methoxyoxane-3,4,5-triol (130 mg, 0.31 mmol, 1.00 equiv) in dichloromethane (5 mL) with Et₃SiH (72.3 mg, 0.62 mmol, 2.00 equiv) was added BF₃·Et₂O (88.5 mg, 0.62 mmol, 2.00 equiv) dropwise at −10° C. The reaction mixture was stirred for 1 h at −10° C. NaHCO₃/H₂O was added and the mixture was extracted with EtOAc thrice. The combined extracts were washed with brine and dried over Na₂SO₄, then concentrated and purified by chromatography on C18 reverse phase column (39.5% CH₃CN/H₂O) to yield the title compound as a white solid.

¹H NMR (400 MHz, CD₃OD) δ 7.24-7.31 (m, 1H), 7.16-7.22 (m, 2H), 6.98 (d, J=7.6 Hz, 1H), 6.90 (d, J=7.6 Hz, 1H), 6.80 (s, 1H), 4.10 (d, J=9.3 Hz, 1H), 4.00 (d, J=3.2 Hz, 2H), 3.89 (dd, J=12.0, 1.6 Hz, 1H), 3.70 (dd, J=12.1, 4.7 Hz, 1H), 3.38-3.52 (m, 4H), 3.10 (s, 2H), 2.60 (q, J=7.5 Hz, 2H), 1.09 (t, J=7.5 Hz, 3H); MS (ES) m/z: 385.2 [M−H]⁻.

Example 59: Compound #67

(2S,3R,4R,5S,6R)-2-(5-{[(8,8-dideuterium)bicyclo[4.2.0]octa-1(6),2,4-trien-3-yl]methyl}-4-chloro-2-methoxyphenyl)-6-(hydroxymethyl)oxane-3,4,5-triol

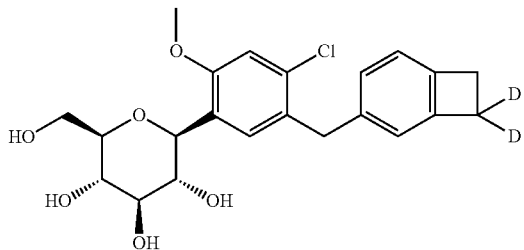 [SMILES: [2H]C1([2H])Cc2ccc(Cc3cc([C@@H]4O[C@H](CO)[C@@H](O)[C@H](O)[C@H]4O)c(OC)cc3Cl)cc21]

To a mixture of 2-chloro-4-hydroxybenzaldehyde (5 g, 31.94 mmol, 1.00 equiv) in N,N-dimethylformamide (80 mL) with potassium carbonate (9 g, 65.12 mmol, 2.04 equiv) was added $CH_3I$ (9 g, 63.41 mmol, 1.99 equiv). The reaction mixture was stirred for 16 h at 25° C. Water was added and the mixture was extracted with ethyl acetate thrice. The combined extracts were concentrated and chromatograph on silica gel (10:1 PE/EA) to yield 2-chloro-4-methoxybenzaldehyde as a light white solid.

To a mixture of 2-chloro-4-methoxybenzaldehyde (1 g, 5.86 mmol, 1.00 equiv) in methanol (10 mL) was added pyridinium bromide perbromide (3.7 g, 11.61 mmol, 1.98 equiv). The reaction mixture was stirred for 16 h at 25° C. Water was added and the mixture was extracted with ethyl acetate thrice. The combined extracts were washed with brine and dried over $Na_2SO_4$, then concentrated to yield 5-bromo-2-chloro-4-methoxybenzaldehyde as a white solid.

To a mixture of 4-bromospiro[bicyclo[4.2.0]octane-7,2'-1,3]dioxolane]-1,3,5-triene (412 mg, 1.71 mmol, 1.00 equiv) in THF (10 mL) was added n-BuLi (2.5 M in hexane, 0.7 mL, 1.75 mmol, 1.02 equiv) dropwise at −78° C. The reaction mixture was stirred for 30 min at −78° C. To the resulting mixture was then added a solution of 5-bromo-2-chloro-4-methoxybenzaldehyde (370 mg, 1.48 mmol, 0.87 equiv) in THF (1 mL) dropwise at −78° C. The reaction mixture was stirred for 2 h at −78° C. $NH_4Cl/H_2O$ was added and the mixture was extracted with EtOAc thrice. The combined extracts were washed with brine and dried over $Na_2SO_4$, then concentrated and purified by chromatography on silica gel (5:1 PE/EA) to yield (5-bromo-2-chloro-4-methoxyphenyl)({spiro[bicyclo[4.2.0]octane-7,2'-[1,3]dioxolane]-1(6),2,4-trien-4-yl})methanol as a yellow oil.

To a mixture of (5-bromo-2-chloro-4-methoxyphenyl)({spiro[bicyclo[4.2.0]octane-7,2'-[1,3]dioxolane]-1(6),2,4-trien-4-yl})methanol (350 mg, 0.85 mmol, 1.00 equiv) in dichloromethane (6 mL) with $Et_3SiH$ (400 mg, 3.44 mmol, 4.05 equiv) was added $CF_3COOH$ (400 mg, 3.54 mmol, 4.16 equiv). The reaction mixture was stirred for 3 h at 25° C. Sodium bicarbonate was added and the mixture was extracted with DCM thrice. The combined extracts were washed with brine and dried over $Na_2SO_4$, then concentrated and purified by chromatography on silica gel (10:1 PE/EA) to yield 4-[(5-bromo-2-chloro-4-methoxyphenyl)methyl]bicyclo[4.2.0]octa-1(6),2,4-trien-7-one as a white solid.

To a mixture of $HgCl_2$ (29 mg, 0.11 mmol, 0.20 equiv) in $D_2O$ (1 mL) with Zn (350 mg, 5.47 mmol, 10.12 equiv) was added DCl (0.05 mL). The reaction mixture was stirred for 115 min. The water was poured out. 4-[(5-bromo-2-chloro-4-methoxyphenyl)methyl]bicyclo[4.2.0]octa-1(6),2,4-trien-7-one, $CH_3CH_2OD$ (2 mL), toluene (2 mL) and conc. DCl (3 mL) was added to the solid. The reaction mixture was stirred for 16 h at 110° C. Water was added and the mixture was extracted with ethyl acetate thrice. The combined extracts were washed with $NaHCO_3$ (aq.) and dried over $Na_2SO_4$, then concentrated and purified by chromatography on silica gel (5:1 PE/EA) to yield 3-[(5-bromo-2-chloro-4-methoxyphenyl)methyl](8,8-dideuterium)bicyclo[4.2.0]octa-1(6),2,4-triene as a light yellow oil. $^1$H-NMR (400 MHz, $CDCl_3$): δ 7.34 (s, 1H), 6.96-7.09 (m, 2H), 6.91 (d, J=15.8 Hz, 2H), 4.00 (s, 2H), 3.89 (s, 3H), 3.15 (s, 2H).

To a mixture of 3-[(5-bromo-2-chloro-4-methoxyphenyl)methyl](8,8-dideuterium)bicyclo[4.2.0]octa-1(6),2,4-triene (90 mg, 0.26 mmol, 1.00 equiv) in THF (3 mL) was added n-BuLi (2.5 M in hexane, 0.12 mL, 0.3 mmol, 1.15 equiv) dropwise with stirring at −78° C. The reaction mixture was stirred for 10 min at −78° C. To the resulting mixture was then added a solution of (3R,4S,5R,6R)-3,4,5-tris(benzyloxy)-6-[(benzyloxy)methyl]oxan-2-one (160 mg, 0.297 mmol, 1.14 equiv) in THF (1 mL) dropwise at −78° C. The reaction mixture was stirred for 2 h at −78° C. $NH_4Cl/H_2O$ was added and the mixture was extracted with EtOAc thrice. The combined extracts were concentrated and chromatograph on silica gel (3:1 PE/EA) to yield (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl]methyl}-4-chloro-2-methoxyphenyl)oxan-2-ol as a yellow oil.

To a mixture of (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl]methyl}-4-chloro-2-methoxyphenyl)oxan-2-ol (140 mg, 0.18 mmol, 1.00 equiv) in dichloromethane (3 mL) with $Et_3SiH$ (40 mg, 0.34 mmol, 1.96 equiv) was added $BF_3.Et_2O$ (50 mg, 0.35 mmol, 2.01 equiv) dropwise at 0° C. The reaction mixture was stirred for 2 h at 0° C. Sodium bicarbonate was added and the mixture was extracted with DCM thrice. The combined extracts were concentrated and chromatograph on silica gel (5:1 PE/EA) to yield (2R,3R,4R,5S,6S)-3,4,5-tris(benzyloxy)-2-[(benzyloxy)methyl]-6-(5-{[(8,8-dideuterium)bicyclo[4.2.0]octa-1(6),2,4-trien-3-yl]methyl}-4-chloro-2-methoxyphenyl)oxane as a yellow oil. MS (ES) m/z: 800.3 $[M+NH_4]^+$.

To a mixture of (2R,3R,4R,5S,6S)-3,4,5-tris(benzyloxy)-2-[(benzyloxy)methyl]-6-(5-{[(8,8-dideuterium)bicyclo[4.2.0]octa-1(6),2,4-trien-3-yl]methyl}-4-chloro-2-methoxyphenyl)oxane (60 mg, 0.08 mmol, 1.00 equiv) in dichloromethane (5 mL) with 1,2,3,4,5-pentamethylbenzene (120 mg, 0.81 mmol, 10.57 equiv) was added $BCl_3$ (1 M, in DCM, 1.2 mL, 1.2 mmol, 15.66 equiv) dropwise at −78° C. The reaction mixture was stirred for 1 h at −78° C. Methanol was added, and the resulting mixture was then concentrated and purified by chromatography on C18 (10%-50% $CH_3CN/H_2O$) to yield the title compound as a white solid.
$^1$H NMR (300 MHz, Methanol-$d_4$) δ 7.33 (s, 1H), 6.97-7.07 (m, 2H), 6.82-6.94 (m, 2H), 4.62 (d, J=9.3 Hz, 1H), 3.91-4.09 (m, 2H), 3.82 (s, 4H), 3.60-3.72 (m, 1H), 3.33-3.51 (m, 4H), 3.09 (s, 2H). MS (ES) m/z: 440.1 $[M+NH_4]^+$.

Example 60: Compound #88

(2S,3R,4R,5S,6R)-2-[5-[(8,8-dideuterium)bicyclo[4.2.0]octa-1,3,5-trien-3-ylmethyl]-2,4-dimethoxyphenyl]-6-(hydroxymethyl)oxane-3,4,8-triol

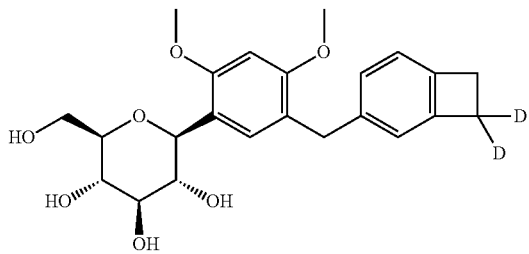 [SMILES: [2H]C1([2H])Cc2ccc(Cc3cc([C@@H]4O[C@H](CO)[C@@H](O)[C@H](O)[C@H]4O)c(OC)cc3OC)cc21]

To a mixture of 4-bromospiro[bicyclo[4.2.0]octane-7,2'-[1,3]dioxolane]-1,3,5-triene (500 mg, 2.07 mmol, 1.20 equiv) in tetrahydrofuran (10 mL) was added n-BuLi (0.83 mL, 1.20 equiv, 2.5M in hexane) dropwise at −78° C. The mixture was stirred for 30 min at −78° C. To the resulting mixture was then added a solution of 5-bromo-2,4-dimethoxybenzaldehyde (423.6 mg, 1.73 mmol, 1.00 equiv) in tetrahydrofuran (2 mL) dropwise at −78° C. The reaction mixture was stirred for 2 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel to yield (5-bromo-2,4-dimethoxyphenyl)-(spiro[bicyclo[4.2.0]octane-7,2'-[1,3]dioxolane]-1,3,5-trien-4-yl)methanol as a light yellow oil. MS (ES) m/z: 389.0 [M−OH]$^+$.

To a mixture of (5-bromo-2,4-dimethoxyphenyl)-(spiro[bicyclo[4.2.0]octane-7,2'-[1,3]dioxolane]-1,3,5-trien-4-yl)methanol (700 mg, 1.72 mmol, 1.00 equiv) and Et$_3$SiH (997.5 mg, 8.58 mmol, 5.00 equiv) in dichloromethane (30 mL) was added trifluoroacetic acid (975.8 mg, 8.63 mmol, 5.00 equiv) dropwise at 0° C. The mixture was stirred for 2 h at 0° C. Sodium bicarbonate/H$_2$O was added and the mixture was extracted with EtOAc thrice. The combined extracts were washed with brine and dried over Na$_2$SO$_4$, then concentrated and purified by chromatography on silica gel (1:8 ethyl acetate/petroleum ether) to yield 4-[(5-bromo-2,4-dimethoxyphenyl)-methyl]bicyclo[4.2.0]octa-1,3,5-trien-7-one as a light yellow oil. $^1$H NMR (400 MHz, Chloroform-d) δ: 7.36-7.48 (m, 2H), 7.24 (s, 1H), 7.17 (s, 1H), 6.49 (s, 1H), 3.89-3.96 (m, 7H), 3.84 (s, 3H).

To a mixture of HgCl$_2$ (60.4 mg, 0.22 mmol, 0.20 equiv) in D$_2$O (2 mL), DCl (3 drops, 35% in D$_2$O) was added Zn (722.2 mg, 11.11 mmol, 10.00 equiv) and the mixture was stirred for 10 min. The D$_2$O was then poured out. To the resulting mixture was then added a solution of 4-[(5-bromo-2,4-dimethoxyphenyl)-methyl]bicyclo[4.2.0]octa-1,3,5-trien-7-one (410 mg, 1.18 mmol, 1.00 equiv) in toluene/CH$_3$CH$_2$OD (3/3 mL), DCl (5 mL, 35% in D$_2$O). The reaction mixture was stirred for 16 h at 110° C. H$_2$O was added and the mixture was extracted with EtOAc thrice. The combined extracts were washed with brine and dried over Na$_2$SO$_4$, then concentrated and purified by chromatography on silica gel (1:15 ethyl acetate/petroleum ether) to yield 3-[(5-bromo-2,4-dimethoxyphenyl)methyl]-(8,8-dideuterium)bicyclo[4.2.0]octa-1,3,5-triene as a white solid. $^1$H NMR (400 MHz, Chloroform-d) δ 7.21 (s, 1H), 6.94-7.09 (m, 2H), 6.90 (s, 1H), 6.50 (s, 1H), 3.91 (s, 3H), 3.85 (s, 5H), 3.13 (s, 2H).

To a mixture of 3-[(5-bromo-2,4-dimethoxyphenyl)methyl]-(8,8-dideuterium)bicyclo[4.2.0]octa-1,3,5-triene (155 mg, 0.46 mmol, 1.15 equiv) in tetrahydrofuran (3.5 mL) was added n-BuLi (0.19 mL, 1.15 equiv, 2.5M in hexane) dropwise at −78° C. The mixture was stirred for 30 min at −78° C. To the resulting mixture was then added a solution of (3R,4S,5R,6R)-3,4,5-tris(benzyloxy)-6-[(benzyloxy)methyl]oxan-2-one (216.9 mg, 0.40 mmol, 1.00 equiv) in tetrahydrofuran (0.5 mL). The reaction mixture was stirred for 2 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel to yield (3R,4S,5R,6R)-3,4,5-tris(benzyloxy)-6-[(benzyl-oxy)methyl]-2-[5-[(8,8-dideuterium)bicyclo[4.2.0]octa-1,3,5-trien-3-ylmethyl]-2,4-dimethoxyphenyl]oxan-2-ol as a light brown oil. MS (ES) m/z: 777.3 [M−OH]$^+$.

To a mixture of (3R,4S,5R,6R)-3,4,5-tris(benzyloxy)-6-[(benzyl-oxy)methyl]-2-[5-[(8,8-dideuterium)bicyclo[4.2.0]octa-1,3,5-trien-3-ylmethyl]-2,4-dimethoxyphenyl]oxan-2-ol (360 mg, 0.45 mmol, 1.00 equiv) and Et$_3$SiH (105.1 mg, 0.90 mmol, 2.00 equiv) in dichloromethane (2 mL) was added BF$_3$.Et$_2$O (128.6 mg, 0.91 mmol, 2.00 equiv) dropwise at 0° C. The reaction mixture was stirred for 1.5 h at 0° C. Sodium bicarbonate/H$_2$O was added and the mixture was extracted with EtOAc thrice. The combined extracts were washed with brine and dried over Na$_2$SO$_4$, then concentrated and purified by chromatography on silica gel (1:5 EA/PE) to yield (2R,3R,4R,5S,6S)-3,4,5-tris(benzyloxy)-2-[(benzyloxy)methyl]-6-[5-[(8,8-dideuterium)bicyclo[4.2.0]octa-1,3,5-trien-3-ylmethyl]-2,4-dimethoxyphenyl]oxane as a light brown oil. MS (ES) m/z: 801.5 [M+Na]$^+$.

To a mixture of (2R,3R,4R,5S,6S)-3,4,5-tris(benzyloxy)-2-[(benzyloxy)methyl]-6-[5-[(8,8-dideuterium)bicyclo[4.2.0]octa-1,3,5-trien-3-ylmethyl]-2,4-dimethoxyphenyl]oxane (170 mg, 0.22 mmol, 1.00 equiv) and 1,2,3,4,5-pentamethylbenzene (340 mg, 2.29 mmol, 10.50 equiv) in dichloromethane (5 mL) was added BCl$_3$ (3.4 mL, 15.60 equiv) dropwise at −78° C. The reaction mixture was stirred for 1 h at −78° C. Methanol was added, and the resulting mixture was then concentrated and purified by chromatography on C18 reverse column (39.8% CH$_3$CN/H$_2$O) to yield the title compound as a white solid.

$^1$H NMR (400 MHz, CD$_3$OD): δ 7.16 (s, 1H), 7.03 (d, J=7.6 Hz, 1H), 6.84-6.92 (m, 2H), 6.61 (s, 1H), 4.60 (d, J=9.5 Hz, 1H), 3.82-3.87 (m, 9H), 3.66 (dt, J=11.8, 3.2 Hz, 1H), 3.44-3.57 (m, 2H), 3.35-3.40 (m, 2H), 3.08 (s, 2H); MS (ES) m/z: 417.1 [M−H]$^−$.

Example 61: Compound #69

(2S,3R,4R,5S,6R)-2-(5-[(8,8-H2)bicyclo[4.2.0]octa-1(6),2,4-trien-3-ylmethyl]-4-ethyl-2-methoxyphenyl)-6-(hydroxymethyl)oxane-3,4,5-triol

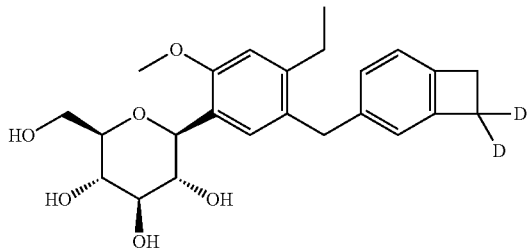 [SMILES: [2H]C1([2H])Cc2ccc(Cc3cc([C@@H]4O[C@H](CO)[C@@H](O)[C@H](O)[C@H]4O)c(OC)cc3CC)cc21]

To a mixture of 4-bromospiro[bicyclo[4.2.0]octane-7,2'-[1,3]dioxolane]-1,3,5-triene (608 mg, 2.52 mmol, 1.15 equiv) in tetrahydrofuran (15 mL) was added n-BuLi (0.96 mL, 1.10 equiv, 2.5M) dropwise at −78° C., the mixture was stirred for 30 min at −78° C. 4-(Benzyloxy)-5-bromo-2-ethylbenzaldehyde (700 mg, 2.19 mmol, 1.00 equiv) in tetrahydrofuran (5 mL) was then added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated and purified by chromatography on silica gel (16% EA/PE) to yield [4-(benzyloxy)-5-bromo-2-ethylphenyl]spiro[bicyclo[4.2.0]octane-7,2'-[1,3]dioxolane]-1(6),2,4-trien-4-yl)methanol yellow oil. MS (ES) m/z: 465.2 [M−OH]$^+$.

To a mixture of [4-(benzyloxy)-5-bromo-2-ethylphenyl]spiro[bicyclo[4.2.0]octane-7,2'-[1,3]dioxolane]-1(6),2,4-trien-4-yl)methanol (1 g, 2.08 mmol, 1.00 equiv) in dichloromethane (20 mL) with $Et_3SiH$ (1.23 g, 10.58 mmol, 5.00 equiv) was added $CF_3COOH$ (1.22 g, 10.79 mmol, 5.00 equiv) dropwise at 0° C. The reaction mixture was stirred for 1 h at 0° C. Sodium bicarbonate/$H_2O$ was added and the mixture was extracted with DCM thrice. The combined extracts were washed with brine and dried over $Na_2SO_4$, then concentrated and purified by chromatography on silica gel (10% EA/PE) to yield 4-{[4-(benzyloxy)-5-bromo-2-ethylphenyl]methyl}bicyclo[4.2.0]octa-1(6),2,4-trien-4-one as a yellow oil. 1H NMR (400 MHz, Chloroform-d) δ 7.48 (d, J=7.6 Hz, 2H), 7.39-7.45 (m, 3H), 7.28-7.37 (m, 2H), 7.25 (s, 1H), 7.05 (s, 1H), 6.79 (s, 1H), 5.17 (s, 2H), 3.96 (d, J=5.8 Hz, 4H), 2.52 (q, J=7.5 Hz, 2H), 1.11 (t, J=7.5 Hz, 3H).

To a mixture of $HgCl_2$ (29.6 mg, 0.11 mmol, 0.20 equiv) in $D_2O$ (3 mL) was added con. DCl (0.04 mL) and Zn (355 mg, 5.55 mmol, 10.00 equiv). After stirring vigorously for 10 min, the $D_2O$ was decanted. To the mixture was added a solution of 4-{[4-(benzyloxy)-5-bromo-2-ethylphenyl]methyl}bicyclo[4.2.0]oct-1(6),2,4-trien-4-one (230 mg, 0.55 mmol, 1.00 equiv) in $CH_3CH_2OD$/Toluene (1.5/1.5 mL). Then con.DCl (2 mL) was added. The reaction mixture was stirred overnight at 110° C. $H_2O$ was added and the mixture was extracted with EA thrice. The combined extracts were washed with brine and dried over $Na_2SO_4$, then concentrated and purified by chromatography on silica gel (1% EA/PE) to yield 3-{[4-(benzyloxy)-5-bromo-2-ethylphenyl]methyl}(8,8-dideuterium)bicyclo[4.2.0]octa-1(6),2,4-trien-4-one as a white solid. 1H NMR (400 MHz, Chloroform-d) δ 7.52 (d, J=7.2 Hz, 2H), 7.42 (t, J=7.5 Hz, 2H), 7.33-7.39 (m, 1H), 7.29 (s, 1H), 6.97 (s, 2H), 6.81 (d, J=2.0 Hz, 2H), 5.16 (s, 2H), 3.91 (s, 2H), 3.14 (s, 2H), 2.57 (q, J=7.5 Hz, 2H), 1.13 (t, J=7.5 Hz, 3H).

To a mixture of 3-{[4-(benzyloxy)-5-bromo-2-ethylphenyl]methyl}(8,8-dideuterium)bicyclo[4.2.0]oc-1(6),2,4-trien-4-one (160 mg, 0.39 mmol, 1.10 equiv) in tetrahydrofuran (3 mL) was added n-BuLi (0.16 mL, 1.10 equiv, 2.5M) dropwise at −78° C., the mixture was stirred at −78° C. for 30 min. (3R,4S,5R,6R)-3,4,5-Tris(benzyloxy)-6-[(benzyloxy)methyl]oxan-2-one (192 mg, 0.36 mmol, 1.00 equiv) in tetrahydrofuran (2 mL) was then added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated and purified by chromatography on silica gel (15% EA/PE) to yield (3R,4S,5R,6R)-3,4,5-tri(benzyloxy)-2-[2-(benzyloxy)-5-[(8,8-dideuterium)bicyclo[4.2.0]octa-1(6),2,4-trien-3-ylmethyl]-4-ethylphenyl]-6-[(benzyloxy)methyl]oxan-2-ol as a yellow oil. MS (ES) m/z: 851.6 [M−OH]$^+$.

To a mixture of (3R,4S,5R,6R)-3,4,5-tri(benzyloxy)-2-[2-(benzyloxy)-5-[(8,8-dideuterium)bicyclo[4.2.0]octa-1(6),2,4-trien-3-ylmethyl]-4-ethylphenyl]-6-[(benzyloxy)methyl]oxan-2-ol (160 mg, 0.18 mmol, 1.00 equiv) in dichloromethane (5 mL) with $Et_3SiH$ (43 mg, 0.37 mmol, 2.00 equiv) was added $BF_3.Et_2O$ (52.3 mg, 0.37 mmol, 2.00 equiv) at 0° C. The reaction mixture was stirred at 0° C. for 1 h. Sodium bicarbonate/$H_2O$ was added and the mixture was extracted with dichloromethane thrice. The combined extracts were washed with brine and dried over $Na_2SO_4$, then concentrated and purified by chromatography on silica gel (7% EA/PE) to yield (2S,3S,4R,5R,6R)-3,4,5-tri(benzyloxy)-2-[2-(benzyloxy)-5-[(8,8-dideuterium)bicyclo[4.2.0]octa-1(6),2,4-trien-3-ylmethyl]-4-ethylphenyl]-6-[(benzyloxy)methyl]oxane as a yellow oil. MS (ES) m/z: 875.6 [M+Na]$^+$.

To a mixture of (2S,3S,4R,5R,6R)-3,4,5-tri(benzyloxy)-2-[2-(benzyloxy)-5-[(8,8-dideuterium)bicyclo[4.2.0]octa-1(6),2,4-trien-3-ylmethyl]-4-ethylphenyl]-6-[(benzyloxy)methyl]oxane (100 mg, 0.12 mmol, 1.00 equiv) in dichloromethane (5 mL) with 1,2,3,4,5-pentamethylbenzene (200 mg, 1.35 mmol, 11.51 equiv) was added $BCl_3$ (1M in DCM, 2 mL, 16.6 equiv) dropwise at −78° C. The reaction mixture was stirred at −78° C. for 1 h. Methanol was added, and the resulting mixture concentrated and purified by chromatography on a C18 reversed phase column (38% $CH_3CN/H_2O$) to yield (2S,3S,4R,5S,6R)-2-{5-[(8,8-dideuterium)bicyclo[4.2.0]octa-1(6),2,4-trien-3-ylmethyl]-4-ethyl-2-hydroxyphenyl}-6-(hydroxymethyl)oxane-3,4,5-triol as a white solid. MS (ES) m/z: 401.1 [M−H]$^-$.

To a mixture of (2S,3S,4R,5S,6R)-2-{5-[(8,8-dideuterium)bicyclo[4.2.0]octa-1(6),2,4-trien-3-ylmethyl]-4-ethyl-2-hydroxyphenyl}-6-(hydroxymethyl)oxane-3,4,5-triol (20 mg, 0.05 mmol, 1.00 equiv) in N,N-dimethylformamide (2 mL) with potassium carbonate (14 mg, 0.10 mmol, 2.00 equiv) was added $CH_3I$ (35.3 mg, 0.25 mmol, 5.00 equiv) at room temperature. The reaction mixture was stirred for 2 h at room temperature. The solids were filtered out and chromatograph on a C18 reversed phase column (45% $CH_3CN/H_2O$) to yield the title compound as a white solid. 1H NMR (300 MHz, MeOD) δ 7.21 (s, 1H), 6.96 (d, J=6.3 Hz, 1H), 6.88 (d, J=7.5 Hz, 1H), 6.79 (d, J=7.5 Hz, 2H), 4.65 (d, J=9.6 Hz, 1H), 3.93 (s, 2H), 3.83 (s, 4H), 3.45-3.69 (m, 3H), 3.37-3.42 (m, 2H), 3.09 (s, 2H), 2.52-2.61 (m, 2H), 1.11 (t, J=9.0 Hz, 3H). MS (ES) m/z: 415.2 [M−H]$^-$.

Example 62: Compound #70

(2S,3R,4R,5S,6R)-2-(5-{[(8,8-dideuterium)bicyclo[4.2.0]octa-1(6),2,4-trien-3-yl]methyl}-2-fluoro-4-methylphenyl)-6-(hydroxymethyl)oxane-3,4,5-triol

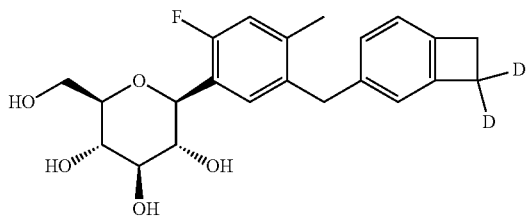 [SMILES: [2H]C1([2H])Cc2ccc(Cc3cc([C@@H]4O[C@H](CO)[C@@H](O)[C@H](O)[C@H]4O)c(F)cc3C)cc21]

To a mixture of 3-bromo(8,8-dideuterium)bicyclo[4.2.0]octa-1,3,5-triene (200 mg, 1.081 mmol, 3.00 equiv) in tetrahydrofuran (4 mL) was added n-BuLi (2.5M in hexane, 0.475 ml, 1.188 mmol, 3.30 equiv) dropwise at −78° C., the mixture was stirred at −78° C. for 30 min. 4-Fluoro-2-methyl-5-((3R,4S,5R,6R)-3,4,5-tris(benzyloxy)-6-((benzyloxy)methyl)-2-hydroxytetrahydro-2H-pyran-2-yl)benzaldehyde (243 mg, 0.359 mmol, 1.00 equiv) in tetrahydrofuran (5 mL) was then added dropwise at −78° C. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (1:1 PE/EA) to yield (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl](hydroxy)methyl}-2-fluoro-4-methylphenyl)oxan-2-ol as a colorless oil. MS (ES) m/z: 765.4 [M−OH]$^+$.

To a mixture of (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl](hydroxy)methyl}-2-fluoro-4-methylphenyl)oxan-2-ol (210 mg, 0.268 mmol, 1.00 equiv) in dichloromethane (4 mL) with Et$_3$SiH (93 mg, 0.800 mmol, 3.00 equiv) was added BF$_3$.Et$_2$O (114 mg, 0.803 mmol, 3.00 equiv) dropwise at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl]methyl}-2-fluoro-4-methylphenyl)oxan-2-ol as a colorless oil. MS (ES) m/z: 773.5 [M+Na]$^+$.

To a mixture of (3R,4S,5R,6R)-3,4,5-tris(benzyloxy)-6-[(benzyloxy)methyl]-2-(5-{[(8,8-dideuterium)bicyclo[4.2.0]octa-1(6),2,4-trien-3-yl]methyl}-2-fluoro-4-methylphenyl)oxan-2-ol (100 mg, 0.133 mmol, 1.00 equiv) in dichloromethane (5 mL) with 1,2,3,4,5-pentamethylbenzene (200 mg, 1.349 mmol, 10.1 mmol) was added BCl$_3$ (1M in DCM, 2 ml, 2.00 mmol, 15.0 equiv) dropwise at −78° C. The reaction mixture was stirred at −78° C. for 1 h. 2 mL of methanol was added, and the resulting mixture was then concentrated and purified by chromatography on a C18 (0%-45% CH$_3$CN/H$_2$O) reversed phase column to yield the title compound as a white solid.

$^1$H NMR (300 MHz, CD$_3$OD): δ 7.27 (d, J=7.2 Hz, 1H), 6.95 (d, J=7.6, 1H), 6.84-6.91 (m, 2H), 6.77 (s, 1H), 4.45 (d, J=9.0 Hz, 1H), 3.93 (s, 2H), 3.84-3.90 (m, 1H), 3.64-3.70 (m, 1H), 3.37-3.54 (m, 4H), 3.08 (s, 2H), 2.17 (s, 3H); MS (ES) m/z: 408.1 [M+NH$_4$].

Example 63: Compound #71

(2S,3R,4R,5S,6R)-2-{5-[(8,8-dideuterium)bicyclo[4.2.0]octa-1(6),2,4-trien-3-ylmethyl]-4-chloro-2-fluorophenyl}-6-(hydroxymethyl)oxane-3,4,5-triol

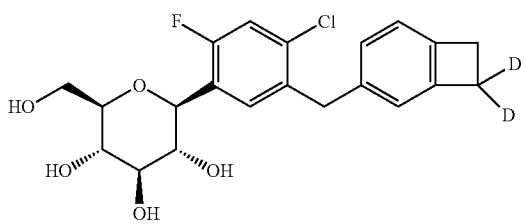 [SMILES: [2H]C1([2H])Cc2ccc(Cc3cc([C@@H]4O[C@H](CO)[C@@H](O)[C@H](O)[C@H]4O)c(F)cc3Cl)cc21]

To a mixture of 5-bromo-1,1-dideuterium-1,2-dihydrocyclobutabenzene (160 mg, 0.865 mmol, 3 eq) in THF (8 mL) was added n-BuLi (0.35 ml, 0.875 mmol, 3 eq) dropwise at −78° C. The reaction mixture was stirred for 20 min at −78° C. To the resulting mixture was then added a solution of 2-chloro-4-fluoro-5-((3R,4S,5R,6R)-3,4,5-tris(benzyloxy)-6-((benzyloxy)methyl)-2-hydroxytetrahydro-2H-pyran-2-yl)benzaldehyde (200 mg, 0.287 mmol, 1 eq) in THF (2 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (3:1 PE/EA) to yield (3R,4S,5R,6R)-3,4,5-tris(benzyloxy)-6-[(benzyloxy)methyl]-2-{5-[(8,8-dideuterium)bicyclo[4.2.0]octa-1(6),2,4-trien-3-yl(hydroxy)methyl]-4-chloro-2-fluorophenyl}oxan-2-ol as a colorless oil. MS (ES) m/z: 825.5 [M+Na]$^+$.

To a mixture of (3R,4S,5R,6R)-3,4,5-tris(benzyloxy)-6-[(benzyloxy)methyl]-2-{5-[(8,8-dideuterium)bicyclo[4.2.0]octa-1(6),2,4-trien-3-yl(hydroxy)methyl]-4-chloro-2-fluorophenyl}oxan-2-ol (100 mg, 0.112 mmol, 1 eq) in dichloromethane (5 mL) with Et$_3$SiH (65 mg, 0.559 mmol, 5 eq) was added BF$_3$.Et$_2$O (64 mg, 0.451 mmol, 4 eq) at 0° C. The reaction mixture was stirred for 1 h at 0° C. Sodium bicarbonate was added and the mixture was extracted with DCM thrice. The combined extracts were washed with brine and dried over Na$_2$SO$_4$, then concentrated and purified by chromatography on silica gel (5:1 PE/EA) to yield (2R,3R,4R,5S,6S)-3,4,5-tris(benzyloxy)-2-[(benzyloxy)methyl]-6-{5-[(8,8-dideuterium)bicyclo[4.2.0]octa-1(6),2,4-trien-3-yl-methyl]-4-chloro-2-fluorophenyl}oxane as a colorless oil. MS (ES) m/z: 793.3 [M+Na]$^+$.

To a mixture of (2R,3R,4R,5S,6S)-3,4,5-tris(benzyloxy)-2-[(benzyloxy)methyl]-6-{5-[(8,8-dideuterium)bicyclo[4.2.0]octa-1(6),2,4-trien-3-ylmethyl]-4-chloro-2-fluorophenyl}oxane (70 mg, 0.082 mmol, 1 eq) in dichloromethane (3 mL) with 1,2,3,4,5-pentamethylbenzene (70 mg, 0.472 mol, eq) was added BCl$_3$ (1.4 mL, 1.4 mmol, 17.1 equiv) dropwise at −78° C. The reaction mixture was stirred for 1 h at −78° C. Methanol was added, and the resulting mixture was then concentrated and purified by chromatography on C18 (10%-50% CH$_3$CN/H$_2$O) to yield the title compound as a white solid.

¹H NMR (400 MHz, CD₃OD): δ 7.46 (d, J=7.4 Hz, 1H), 7.18 (d, J=9.7 Hz, 1H), 7.03 (dd, J=7.5, 1.4 Hz, 1H), 6.93 (d, J=7.6 Hz, 1H), 6.87 (s, 1H), 4.46 (d, J=9.3 Hz, 1H), 3.98-4.15 (m, 2H), 3.87-3.90 (m, 1H), 3.64-3.75 (m, 1H), 3.36-3.57 (m, 4H), 3.11 (s, 2H); MS (ES) m/z: 409.0 [M−H]⁻.

Example 64: Compound #72

(2S,3R,4R,5S,6R)-2-{5-[(8,8-dideuterio)bicyclo[4.2.0]octa-1(6),2,4-trien-3-ylmethyl]-2-fluoro-4-methoxyphenyl}-6-(hydroxymethyl)oxane-3,4,5-triol

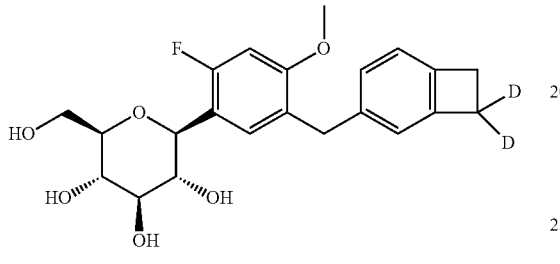

To a mixture of 3-(5-bromo-4-fluoro-2-methoxybenzyl)bicyclo[4.2.0]octa-1(6),2,4-triene-8,8-(dideuterium) (160 mg, 0.495 mmol, 1.00 equiv) in THF (15 mL) was added n-BuLi (0.237 mL, 0.593 mmol, 1.20 equiv, 2.5 M in hexane) dropwise with stirring at −78° C. The reaction mixture was stirred for 20 min at −78° C. To the resulting mixture was then added a solution of (3R,4S,5R,6R)-3,4,5-tris(benzyloxy)-6-(benzyloxymethyl)-tetrahydropyran-2-one (320 mg, 0.594 mmol, 1.20 equiv) in THF (2 mL) dropwise at −78° C. The reaction mixture was stirred for 1 h at −78° C. NH₄Cl/H₂O was added and the mixture was extracted with EtOAc thrice. The combined extracts were dried over Na₂SO₄, then concentrated to yield (2R,3S,4R,5R)-2,3,4-tris(benzyloxy)-5-[(benzyloxy)methyl]-1-{5-[(8,8-dideuterio)bicyclo[4.2.0]octa-1(6),2,4-trien-3-ylmethyl]-2-fluoro-4-methoxyphenyl}cyclohexan-1-ol as a yellow oil. MS (ES) m/z: 765.5 [M−OH]⁺.

To a mixture of (2R,3S,4R,5R)-2,3,4-tris(benzyloxy)-5-[(benzyloxy)methyl]-1-{5-[(8,8-dideuterio)bicyclo[4.2.0]octa-1(6),2,4-trien-3-ylmethyl]-2-fluoro-4-methoxyphenyl}cyclohexan-1-ol (480 mg, 0.615 mmol, 1.00 equiv) in DCM (20 mL) with Et₃SiH (357 mg, 3.070 mmol, 5.00 equiv) was added TFA (350 mg, 3.070 mmol, 5.00 equiv) dropwise at 0° C. The reaction mixture was stirred for 1 h at 0° C. NaHCO₃/water was added and the mixture was extracted with DCM thrice. The combined extracts were dried over Na₂SO₄, then concentrated and purified by chromatography on silica gel (97:13 PE/EA) to yield (2R,3R,4R,5S,6S)-3,4,5-tris(benzyloxy)-2-[(benzyloxy)methyl]-6-{5-[(8,8-dideuterio)bicyclo[4.2.0]octa-1(6),2,4-trien-3-ylmethyl]-2-fluoro-4-methoxyphenyl}oxane as a yellow oil. MS (ES) m/z: 784.4 [M+NH₄].

To a mixture of (2R,3R,4R,5S,6S)-3,4,5-tris(benzyloxy)-2-[(benzyloxy)methyl]-6-{5-[(8,8-dideuterio)bicyclo[4.2.0]octa-1(6),2,4-trien-3-ylmethyl]-2-fluoro-4-methoxyphenyl}oxane (160 mg, 0.209 mmol, 1.00 equiv) in dichloromethane (20 mL) with 1,2,3,4,5-pentamethylbenzene (309 mg, 2.084 mmol, 10.00 equiv) was added BCl₃ (4.17 mL, 4.17 mmol, 20.00 equiv, 1M in DCM) dropwise at −78° C. The reaction mixture was stirred for 1 h at −78° C. 5 mL of methanol was added, and the resulting mixture was then concentrated and purified by chromatography on a C18 reversed phase column to yield the title compound as a white solid.

¹H NMR (400 MHz, CD₃OD): δ 7.22 (d, J=8 Hz, 1H), 7.01 (d, J=8.8 Hz, 1H), 6.86 (d, J=11.2 Hz, 2H), 6.69 (d, J=12 Hz, 1H), 4.41 (d, J=4.8 Hz, 1H), 3.84-3.90 (m, 3H), 3.79-3.81 (m, 3H), 3.65 (q, J=6.4 Hz, 1H), 3.42-3.49 (m, 2H), 3.32-3.40 (m, 2H), 3.07 (s, 2H); MS (ES) m/z: 405.1 [M−H]⁻.

Example 65: Compound #73

(2S,3R,4R,5S,6R)-2-(5-((2,2-dideuterium-1,2-dihydrocyclobutabenzen-4-yl)methyl)-4-ethyl-2-fluorophenyl)-6-(hydroxymethyl)-tetrahydro-2H-pyran-3,4,5-triol

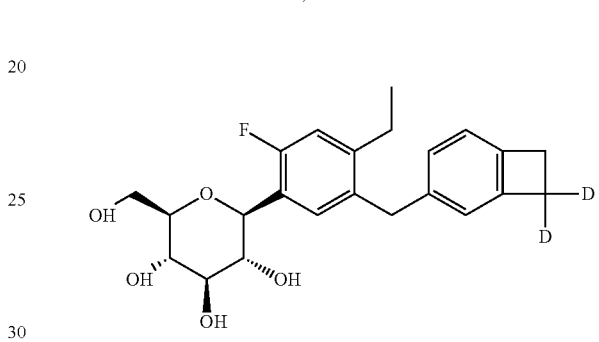

To a mixture of 2-bromo-4-fluorobenzoic acid (10 g, 59.47 mmol, 1.00 equiv) in MeOH (100 ml) was added SOCl₂ (10.9 g, 91.60 mmol, 1.50 equiv) dropwise at 20° C. The reaction mixture was stirred at 80° C. for 2 h, then concentrated to yield methyl 2-bromo-4-fluorobenzoate as a yellow oil.

To a mixture of methyl 2-bromo-4-fluorobenzoate (10.1 g, 43.34 mmol, 1.00 equiv) in THF (100 ml) with Cs₂CO₃ (42 g, 128.91 mmol, 3.00 equiv) and Pd(dppf)Cl₂ (3.5 g, 4.78 mmol, 0.11 equiv) was added Et₃B (1M in tetrahydrofuran) (65 mL, 65 mmol, 1.50 equiv). The reaction mixture was stirred overnight at 80° C. Water was added and the mixture was extracted with EA thrice. The combined extracts were washed with water, saturated brine and dried over anhydrous Na₂SO₄, then concentrated and purified by chromatography on silica gel (1:30 EA/PE) to yield methyl 2-ethyl-4-fluorobenzoate as a yellow oil.

To a mixture of methyl 2-ethyl-4-fluorobenzoate (7.88 g, 43.25 mmol, 1.00 equiv) in MeOH (100 ml) was added sodium hydroxide (2 M in water) (65 mL, 129.89 mmol, 3.00 equiv) at 20° C. The reaction mixture was stirred at 20° C. overnight. HCl (2 M) was added and the mixture was extracted with EA thrice. The combined extracts were washed with water, saturated brine and dried over anhydrous Na₂SO₄, then concentrated to yield 2-ethyl-4-fluorobenzoic acid as a yellow oil.

To a mixture of 2-ethyl-4-fluorobenzoic acid (6 g, 35.68 mmol, 1.00 equiv) in H₂SO₄ (60 ml) was added NBS (7 g, 39.33 mmol, 1.10 equiv). The reaction mixture was stirred at 65° C. for 2 h. Ice water was added and precipitation was collected to yield 5-bromo-2-ethyl-4-fluorobenzoic acid as an off-white solid. GCMS m/z: 246/248.

To a mixture of 5-bromo-2-ethyl-4-fluorobenzoic acid (7.5 g, 30.36 mmol, 1.00 equiv) in THF (50 ml) was added BH₃.THF (1 M) (151.82 mL, 151.82 mmol, 5.00 equiv). The reaction mixture was stirred overnight at 20° C. Water was added and the mixture was extracted with EA thrice. The combined extracts were washed with water, saturated brine and dried over anhydrous Na$_2$SO$_4$, then concentrated to yield (5-bromo-2-ethyl-4-fluorophenyl)methanol as a yellow oil. GCMS m/z: 232/234.

To a mixture of (5-bromo-2-ethyl-4-fluorophenyl)methanol (7 g, 30.03 mmol, 1.00 equiv) in DCM (100 ml) was added MnO$_2$ (26 g, 299.06 mmol, 10.00 equiv). The reaction mixture was stirred overnight at 20° C. The solids were filtered out, and the filtrate concentrated to yield 5-bromo-2-ethyl-4-fluorobenzaldehyde as a yellow oil.

To a mixture of 5-bromo-2-ethyl-4-fluorobenzaldehyde (2.6 g, 11.25 mmol, 1.00 equiv) with p-toluenesulfonic acid (p-TsOH) (200 mg, 1.16 mmol, 0.10 equiv) in benzene (30 ml) was added ethane-1,2-diol (7 g, 112.78 mmol, 10.00 equiv). The reaction mixture was stirred overnight at 110° C. Water was added and the mixture was extracted with EA thrice. The combined extracts were washed with water, saturated brine and dried over anhydrous Na$_2$SO$_4$, then concentrated to yield 2-(5-bromo-2-ethyl-4-fluorophenyl)-1,3-dioxolane as a yellow oil. MS (ES) m/z: 275.0 [M+H]$^+$.

To a mixture of 2-(5-bromo-2-ethyl-4-fluorophenyl)-1,3-dioxolane (2.8 g, 10.18 mmol, 1.10 equiv) in THF (30 ml) was added n-BuLi (2.5 M in n-hexane, 4.1 ml, 10.18 mmol, 1.10 equiv) dropwise at −78° C. under N$_2$. The reaction mixture was stirred at −78° C. for 30 min. (3R,4S,5R,6R)-13,4,5-tris(benzyloxy)-6-[(benzyloxy)methyl]oxan-2-one (5 g, 9.28 mmo, 1.00 equivl) in THF (20 ml) was added dropwise at −78° C. The reaction mixture was stirred at −78° C. for 1 h. Saturated NH$_4$Cl (aq) was added and the mixture was extracted with EA thrice. The combined extracts were washed with water, saturated brine and dried over anhydrous Na$_2$SO$_4$, then concentrated and purified by chromatography on silica gel (1:3 EA/PE) to yield (3R,4S,5R,6R)-2-(5-(1,3-dioxolan-2-yl)-4-ethyl-2-fluorophenyl)-3,4,5-tris(benzyloxy)-6-(benzyloxymethyl)-tetrahydro-2H-pyran-2-ol as a yellow oil. MS (ES) m/z: 757.5 [M+Na]$^+$.

To a mixture of (3R,4S,5R,6R)-2-(5-(1,3-dioxolan-2-yl)-4-ethyl-2-fluorophenyl)-3,4,5-tris(benzyloxy)-6-(benzyloxymethyl)-tetrahydro-2H-pyran-2-ol (5 g, 6.80 mmol, 1.00 equiv) in THF (50 ml) was added HCl (2 M) (50 mL, 100 mmol, 14.7 equiv). The reaction mixture was stirred at 20° C. for 1 h. The mixture was extracted with EA thrice. The combined extracts were washed with water, saturated brine and dried over anhydrous Na$_2$SO$_4$, then concentrated to yield 2-ethyl-4-fluoro-5-((3R,4S,5R,6R)-3,4,5-tris(benzyloxy)-6-(benzyloxymethyl)-2-hydroxy-tetrahydro-2H-pyran-2-yl)benzaldehyde as a yellow oil. MS (ES) m/z: 713.1 [M+Na]$^+$.

To a mixture of 5-bromo-1,1-dideuterium-1,2-dihydrocyclobutabenzene (188.8 mg, 0.870 mmol, 3.00 equiv) in THF (2 ml) was added dropwise n-BuLi (2.5 M in n-hexane, 0.348 ml, 0.870 mmol, 3.00 equiv) at −78° C. under N$_2$. The reaction mixture was stirred at −78° C. for 30 min. 2-ethyl-4-fluoro-5-((3R,4S,5R,6R)-3,4,5-tris(benzyloxy)-6-(benzyloxymethyl)-2-hydroxy-tetrahydro-2H-pyran-2-yl)benzaldehyde (200 mg, 0.290 mmol, 1.00 equiv) in THF (2 ml) was added dropwise at −78° C. The reaction mixture was stirred at −78° C. for 1 h. Saturated NH$_4$Cl (aq) was added and the mixture was extracted with EA thrice. The combined extracts were washed with water, saturated brine and dried over anhydrous Na$_2$SO$_4$, then concentrated and purified by chromatography on silica gel (1:3 EA/PE) to yield (3R,4S,5R,6R)-3,4,5-tris(benzyloxy)-6-(benzyloxymethyl)-2-(5-((2,2-dideuterium-1,2-dihydrocyclobutabenzen-4-yl)(hydroxy)methyl)-4-ethyl-2-fluorophenyl)-tetrahydro-2H-pyran-2-ol as a yellow oil. MS (ES) m/z: 819.4 [M−OH]$^+$ To a mixture of (3R,4S,5R,6R)-3,4,5-tris(benzyloxy)-6-(benzyloxymethyl)-2-(5-((2,2-dideuterium-1,2-dihydrocyclobutabenzen-4-yl)(hydroxy)methyl)-4-ethyl-2-fluorophenyl)-tetrahydro-2H-pyran-2-ol (230 mg, 0.289 mmol, 1.00 equiv) in DCM (3 ml) with Et$_3$SiH (0.187 ml, 1.156 mmol, 4.00 equiv) was added BF$_3$·Et$_2$O (0.146 ml, 1.156 mmol, 4.00 equiv) at 0° C. The reaction mixture was stirred at 0° C. for 1 h. Saturated NaHCO$_3$ (aq) was added and the mixture was extracted with DCM thrice. The combined extracts were washed with water, saturated brine and dried over anhydrous Na$_2$SO$_4$, then concentrated and purified by chromatography on silica gel (1:10 EA/PE) to yield (2R,3R,4R,5S,6S)-3,4,5-tris(benzyloxy)-2-(benzyloxymethyl)-6-(5-((2,2-dideuterium-1,2-dihydrocyclobutabenzen-4-yl)methyl)-4-ethyl-2-fluorophenyl)-tetrahydro-2H-pyran as a colorless oil. MS (ES) m/z: 787.6 [M+Na]$^+$.

To a mixture of (2R,3R,4R,5S,6S)-3,4,5-tris(benzyloxy)-2-(benzyloxymethyl)-6-(5-((2,2-dideuterium-1,2-dihydrocyclobutabenzen-4-yl)methyl)-4-ethyl-2-fluorophenyl)-tetrahydro-2H-pyran (150 mg, 0.196 mmol, 1.00 equiv) in DCM (1 ml) with 1,2,3,4,5-pentamethylbenzene (300 mg, 2.024 mmol, 10.00 equiv) was added dropwise BCl$_3$ (1 M in DCM) (3 ml, 3 mmol, 15.00 equiv) at −78° C. The reaction mixture was stirred at −78° C. for 1 h, then concentrated and purified by chromatography on C18 reverse column (40% MeCN/H$_2$O) to yield the title compound as a white solid.

$^1$H NMR (400 MHz, CD$_3$OD): δ 7.27 (d, J=7.2 Hz, 1H), 6.85-6.98 (m, 3H), 6.77 (s, 1H), 4.46 (d, J=8.9 Hz, 1H), 3.96 (s, 2H), 3.87 (dd, J=12.0, 1.6 Hz, 1H), 3.63-3.71 (m, 1H), 3.42-3.55 (m, 2H), 3.39 (m, 2H), 3.08 (s, 2H), 2.56 (q, J=7.6 Hz, 2H), 1.06 (t, J=7.5 Hz, 3H); MS (ES) m/z: 403.1 [M−H]$^−$.

Example 66: Compound #74

(2S,3R,4R,5S,6R)-2-(4-cyclopropyl-5-((2,2-dideuterium-1,2-dihydrocyclobutabenzen-4-yl)methyl)-2-fluorophenyl)-6-(hydroxymethyl)-tetrahydro-2H-pyran-3,4,5-triol

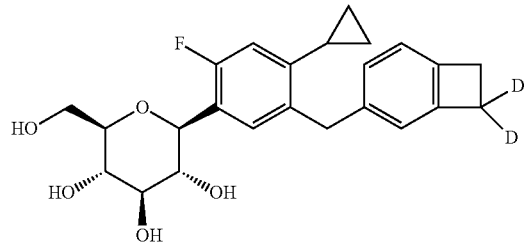 [SMILES: [2H]C1([2H])Cc2ccc(Cc3cc([C@@H]4O[C@H](CO)[C@@H](O)[C@H](O)[C@H]4O)c(F)cc3C3CC3)cc21]

To a mixture of 3-bromo(8,8-dideuterium)bicyclo[4.2.0]octa-1,3,5-triene (150 mg, 0.811 mmol, 3 eq) in THF (5 mL) was added n-BuLi (2.5 M in hexane, 0.32 mL, 3.00 equiv) dropwise at −78° C. The reaction mixture was stirred for 20 min at −78° C. To the resulting mixture was then added a solution of 2-cyclopropyl-4-fluoro-5-((3R,4S,5R,6R)-3,4,5-tris(benzyloxy)-6-((benzyloxy)methyl)-2-hydroxytetrahydro-2H-pyran-2-yl)benzaldehyde (200 mg, 0.256 mmol, 1 eq) in THF (2 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (2:1 PE/EA) to yield (3R,4S,5R,6R)-3,4,5-tris(benzyloxy)-6-(benzyloxymethyl)-2-(4-cyclopropyl-5-((2,2-dideuterium-1,2-dihydrocyclobutabenzen-4-yl)(hydroxy)methyl)-2-fluorophenyl)-tetrahydro-2H-pyran-2-ol as a colorless oil.

To a mixture of (3R,4S,5R,6R)-3,4,5-tris(benzyloxy)-6-(benzyloxymethyl)-2-(4-cyclopropyl-5-((2,2-dideuterium-1,2-dihydrocyclobutabenzen-4-yl)(hydroxy)methyl)-2-fluorophenyl)-tetrahydro-2H-pyran-2-ol (150 mg, 0.145 mmol, 1 eq) in dichloromethane (3 mL) with Et₃SiH (85 mg, 0.731 mmol, 5 eq) was added BF₃.Et₂O (83 mg, 0.585 mmol, 4 eq) at 0° C. The reaction mixture was stirred for 1 h at 0° C. Sodium bicarbonate was added and the mixture was extracted with DCM thrice. The combined extracts were washed with brine and dried over Na₂SO₄, then concentrated and purified by chromatography on silica gel (5:1 PE/EA) to yield (2R,3R,4R,5S,6S)-3,4,5-tris(benzyloxy)-2-(benzyloxymethyl)-6-(4-cyclopropyl-5-((2,2-dideuterium-1,2-dihydrocyclobutabenzen-4-yl)methyl)-2-fluorophenyl)-tetrahydro-2H-pyran as a light yellow oil. MS (ES) m/z: 799.1 [M+Na]⁺.

To a mixture of (2R,3R,4R,5S,6S)-3,4,5-tris(benzyloxy)-2-(benzyloxymethyl)-6-(4-cyclopropyl-5-((2,2-dideuterium-1,2-dihydrocyclobutabenzen-4-yl)methyl)-2-fluorophenyl)-tetrahydro-2H-pyran (100 mg, 0.129 mmol, 1 eq) in dichloromethane (5 mL) with 1,2,3,4,5-pentamethylbenzene (100 mg, 0.675 mmol, 5.23 eq) was added BCl₃ (2 mL, 2 mmol, 15.5 equiv) dropwise at −78° C. The reaction mixture was stirred for 1 h at −78° C. Methanol was added, and the resulting mixture was then concentrated and purified by chromatography on C18 (10%-50% CH₃CN/H₂O) to yield the title compound as a white solid.

¹H NMR (400 MHz, CD₃OD): δ 7.29 (d, J=7.3 Hz, 1H), 7.00 (d, J=7.6 Hz, 1H), 6.91 (d, J=7.6 Hz, 1H), 6.84 (s, 1H), 6.68 (d, J=11.6 Hz, 1H), 4.46 (d, J=8.7 Hz, 1H), 4.08-4.13 (m, 2H), 3.87-3.90 (m, 1H), 3.66-3.71 (m, 1H), 3.43-3.54 (m, 2H), 3.37-3.41 (m, 2H), 3.11 (s, 2H), 1.82-1.89 (m, 1H), 0.85-0.91 (m, 2H), 0.56-0.65 (m, 2H); MS (ES) m/z: 415.1 [M−H]⁻.

Example 67: Compound #81

(2S,3R,4R,5S,6R)-2-{3-[(7,7-dideuterio)bicyclo[4.2.0]octa-1(6),2,4-trien-3-ylmethyl]-4-chlorophenyl}-6-(hydroxymethyl)oxane-3,4,5-triol

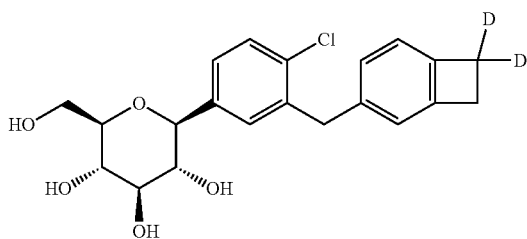 [SMILES: [2H]C1([2H])Cc2cc(Cc3cc([C@@H]4O[C@H](CO)[C@@H](O)[C@H](O)[C@H]4O)ccc3Cl)ccc21]

To a mixture of 3-bromospiro[bicyclo[4.2.0]octane-7,2'-[1,3]dioxolane]-1,3,5-triene (600 mg, 2.489 mmol, 1.00 equiv) in THF (20 mL) was added n-BuLi (1.2 mL, 3.00 mmol, 1.20 equiv, 2.5 M in hexane) dropwise with stirring at −78° C., the mixture was stirred for 20 mins at −78° C. 5-Bromo-2-chlorobenzaldehyde (655 mg, 2.985 mmol, 1.20 equiv) in tetrahydrofuran (4 mL) was then added to the solution. The reaction mixture was stirred at −78° C. for 1 h. NH₄Cl/H₂O was added and the mixture was extracted with EtOAc thrice. The combined extracts were dried over Na₂SO₄, then concentrated and purified by chromatography on silica gel (7:3 PE/EA) to yield (5-bromo-2-chlorophenyl)({spiro[bicyclo[4.2.0]octane-7,2'-[1,3]dioxolane]-1(6),2,4-trien-3-yl})methanol as a yellow oil. MS (ES) m/z: 382.9 [M+H]⁺.

To a mixture of (5-bromo-2-chlorophenyl)({spiro[bicyclo[4.2.0]octane-7,2'-[1,3]dioxolane]-1(6),2,4-trien-3-yl})methanol (490 mg, 1.284 mmol, 1.00 equiv) in CH₃CN (20 mL) with NaI (3.86 g, 25.752 mmol, 20.00 equiv) was added TMSCl (2.79 g, 25.681 mmol, 20.00 equiv) dropwise with stirring at room temperature. The reaction mixture was stirred for an overnight at 80° C. Ice/water was added and the mixture was extracted with EtOAc thrice. The combined extracts were dried over Na₂SO₄, then concentrated and purified by chromatography on silica gel (9:1 PE/EA) to yield 4-(5-bromo-2-chlorobenzyl)cyclobutabenzen-1(2H)-one as a yellow oil. MS (ES) m/z: 323.0 [M+H]⁺.

A mixture of HgCl₂ (27 mg, 0.099 mmol, 0.10 equiv), Zn (650 mg, 9.937 mmol, 10.00 equiv) and DCl (0.2 mL, 35%) in D₂O (3 mL) was stirred for 20 min at room temperature. D₂O was poured out, and to the residue was added 4-(5-bromo-2-chlorobenzyl)cyclobutabenzen-1 (2H)-one (320 mg, 0.995 mmol, 1.00 equiv), DCl (3 mL, 35%), CH₃CH₂OD (2 mL) and toluene (2 mL). The reaction mixture was stirred for an overnight at 110° C. Ice/water was added and the mixture was extracted with EtOAc thrice. The combined extracts were washed with brine, dried over Na₂SO₄, then concentrated and purified by chromatography on silica gel (49:1 PE/EA) to yield 3-[(5-bromo-2-chlorophenyl)methyl](7,7-dideuterio)bicyclo[4.2.0]octa-1(6),2,4-triene as a colorless oil. MS (ES) m/z: 310.1 [M].

To a mixture of 3-[(5-bromo-2-chlorophenyl)methyl](7,7-dideuterio)bicyclo[4.2.0]octa-1(6),2,4-triene (550 mg, 1.777 mmol, 1.00 equiv) in THF (15 mL) was added n-BuLi (0.78 mL, 1.950 mmol, 1.10 equiv, 2.5M in hexane) dropwise with stirring at −78° C., the mixture was stirred for 20 mins at −78° C. (3R,4S,5R,6R)-3,4,5-Tris(benzyloxy)-6-(benzyloxymethyl)-tetrahydropyran-2-one (1.052 g, 1.953 mmol, 1.10 equiv) in tetrahydrofuran (4 mL) was then added to the solution. The reaction mixture was stirred at −78° C. for 1 h. NH₄Cl/H₂O was added and the mixture was extracted with EtOAc thrice. The combined extracts were dried over Na₂SO₄, then concentrated and purified by chromatography on silica gel (3:1 PE/EA) to yield 1(2R,3R,4R,5S,6S)-3,4,5-tris(benzyloxy)-2-[(benzyloxy)methyl]-6-{3-[(7,7-dideuterio)bicyclo[4.2.0]octa-1(6),2,4-trien-3-ylmethyl]-4-chlorophenyl}oxane as a yellow oil. MS (ES) m/z: 751.4 [M−OH]⁺.

To a mixture of (2R,3R,4R,5S,6S)-3,4,5-tris(benzyloxy)-2-[(benzyloxy)methyl]-6-{3-[(7,7-dideuterio)bicyclo[4.2.0]octa-1(6),2,4-trien-3-ylmethyl]-4-chlorophenyl}oxane (1.14 g, 1.482 mmol, 1.00 equiv) in DCM (20 mL) with Et₃SiH (691 mg, 5.943 mmol, 4.00 equiv) was added TFA (677 mg, 5.937 mmol, 4.00 equiv) dropwise at 0° C. The reaction mixture was stirred for 1 h at 0° C. NaHCO₃/water was added and the mixture was extracted with DCM thrice. The combined extracts were dried over Na₂SO₄, then concentrated and purified by chromatography on silica gel (17:3 PE/EA) to yield (2R,3R,4R,5S,6S)-3,4,5-tris(benzyloxy)-2-[(benzyloxy)methyl]-6-{3-[(7,7-dideuterio)bicyclo[4.2.0]octa-1(6),2,4-trien-3-ylmethyl]-4-chlorophenyl}oxane as a yellow oil. MS (ES) m/z: 775.5 [M+Na]⁺.

To a mixture of (2R,3R,4R,5S,6S)-3,4,5-tris(benzyloxy)-2-[(benzyloxy)methyl]-6-{3-[(7,7-dideuterio)bicyclo[4.2.0]octa-1(6),2,4-trien-3-ylmethyl]-4-chlorophenyl}oxane (800 mg, 1.062 mmol, 1.00 equiv) in dichloromethane (20 mL) with 1,2,3,4,5-pentamethylbenzene (1.571 g, 10.597 mmol, 10.00 equiv) was added BCl₃ (21.0 mL, 21.000 mml, 20.00 equiv, 1M in DCM) dropwise at −78° C. The reaction mixture was stirred for 1 h at −78° C. 5 mL of methanol was added, and the resulting mixture was then concentrated and purified by chromatography on a C18 reversed phase column to yield the title compound as a white solid.

¹H NMR (300 MHz, CD₃OD): δ 7.31 (d, J=8.1 Hz, 1H), 7.25 (s, 1H), 7.24 (d, J=6.3 Hz, 1H), 6.99 (d, J=8.1 Hz, 1H), 6.87 (d, J=8.1 Hz, 1H), 6.83 (s, 1H), 3.96-4.08 (m, 3H), 3.84 (d, J=10.5 Hz, 1H), 3.65 (dd, J=12.0, 5.2 Hz, 1H), 3.31-3.49 (m, 3H), 3.22-3.25 (m, 1H), 3.06 (s, 2H); MS (ES) m/z: 410.1 [M+NH₄]⁺.

Example 688: Compound #82

(2S,3R,4R,5S,6R)-2-{3-[(7,7-dideuterium)bicyclo [4.2.0]octa-1(6),2,4-trien-3-ylmethyl]-4-methoxy-phenyl}-6-(hydroxymethyl)oxane-3,4,5-triol

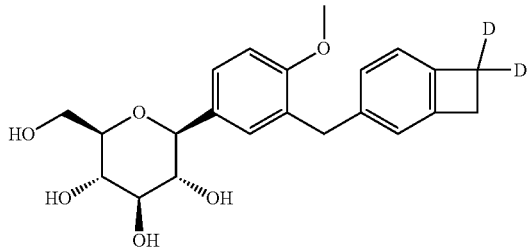 [SMILES: [2H]C1([2H])Cc2cc(Cc3cc([C@@H]4O[C@H](CO)[C@@H](O)[C@H](O)[C@H]4O)ccc3OC)ccc21]

To a mixture of 3-bromospiro[bicyclo[4.2.0]octane-7,2'-[1,3]dioxolane]-1,3,5-triene (600 mg, 2.489 mmol, 1.00 equiv) in THF (20 mL) was added n-BuLi (1.0 mL, 2.50 mmol, 1.00 equiv, 2.5 M in hexane) dropwise with stirring at −78° C., the mixture was stirred for 20 mins at −78° C. 5-Bromo-2-methoxybenzaldehyde (535 mg, 2.5 mmol, 1.00 equiv) in tetrahydrofuran (4 mL) was then added to the solution. The reaction mixture was stirred at −78° C. for 1 h. NH₄Cl/H₂O was added and the mixture was extracted with EtOAc thrice. The combined extracts were dried over Na₂SO₄, then concentrated to yield (5-bromo-2-methoxyphenyl)(spiro[bicyclo[4.2.0]octane-7,2'-[1,3]dioxolane]-1 (6),2,4-trien-3-yl)methanol as a yellow oil.

To a mixture of (5-bromo-2-methoxyphenyl)(spiro[bicyclo[4.2.0]octane-7,2'-[1,3]dioxolane]-1(6),2,4-trien-3-yl) methanol (800 mg, 2.121 mmol, 1.00 equiv) in CH₃CN (20 mL) with NaI (1.27 g, 8.484 mmol, 4.00 equiv) was added TMSCl (921.7 mg, 8.484 mmol, 4.00 equiv) dropwise at room temperature. The reaction mixture was stirred for an overnight at 80° C. Ice/water was added and the mixture was extracted with EtOAc thrice. The combined extracts were dried over Na₂SO₄, then concentrated and purified by chromatography on silica gel (10:1 PE/EA) to yield 4-(5-bromo-2-methoxybenzyl)cyclobutabenzen-1(2H)-one as a yellow oil.

To a mixture of HgCl₂ (115 mg, 0.424 mmol, 0.20 equiv), Zn (1.381 g, 21.12 mmol, 10.00 equiv) and DCl (0.3 mL, 35%) in D₂O (3 mL) was stirred for min at room temperature. D₂O was poured out, and to the residue was added to 4-(5-bromo-2-methoxybenzyl)cyclobutabenzen-1 (2H)-one (670 mg, 2.112 mmol, 1.00 equiv), DCl (8 mL, 35%), CH₃CH₂OD (7 mL) and toluene (7 mL). The reaction mixture was stirred for an overnight at 110° C. Ice/water was added and the mixture was extracted with EtOAc thrice. The combined extracts were washed with brine, dried over Na₂SO₄, then concentrated and purified by chromatography on silica gel (10:1 PE/EA) to yield 3-[(5-bromo-2-methoxyphenyl)methyl](7,7-dideuterium)bicyclo[4.2.0]octa-1(6),2,4-triene as a yellow oil. ¹H NMR (300 MHz, Chloroform-d): δ 7.23-7.33 (m, 1H), 7.16 (d, J=2.5 Hz, 1H), 6.87-7.09 (m, 3H), 6.73 (d, J=8.7 Hz, 1H), 3.90 (s, 2H), 3.82 (s, 3H), 3.13 (s, 2H).

To a mixture of 3-[(5-bromo-2-methoxyphenyl)methyl](7,7-dideuterium)bicyclo[4.2.0]octa-1(6),2,4-triene (360 mg, 1.180 mmol, 1.00 equiv) in THF (10 mL) was added n-BuLi (0.566 mL, 1.416 mmol, 1.20 equiv, 2.5M in hexane) dropwise with stirring at −78° C., the mixture was stirred for 20 mins at −78° C. (3R,4S,5R,6R)-3,4,5-Tris(benzyloxy)-6-(benzyloxymethyl)-tetrahydropyran-2-one (550.9 mg, 1.18 mmol, 1.00 equiv) in tetrahydrofuran (4 mL) was then added to the solution. The reaction mixture was stirred at −78° C. for 1 h. NH₄Cl/H₂O was added and the mixture was extracted with EtOAc thrice. The combined extracts were dried over Na₂SO₄, then concentrated to yield (3R,4S,5R,6R)-3,4,5-tris(benzyloxy)-6-[(benzyloxy)methyl]-2-{3-[(7,7-dideuterium)bicyclo[4.2.0]octa-1(6),2,4-trien-3-ylmethyl]-4-methoxyphenyl}oxan-2-ol as a yellow oil.

To a mixture of (3R,4S,5R,6R)-3,4,5-tris(benzyloxy)-6-[(benzyloxy)methyl]-2-{3-[(7,7-dideuterium)bicyclo[4.2.0]octa-1(6),2,4-trien-3-ylmethyl]-4-methoxyphenyl}oxan-2-ol (800 mg, 1.154 mmol, 1.00 equiv) in MeOH (10 mL) was added a solution of methanesulfonic acid (110.8 mg, 1.154 mmol, 1.00 equiv) in CH₃OH (1 mL) dropwise at −78° C. under N₂. The reaction mixture was stirred at room temperature for 16 h. Sodium bicarbonate/H₂O was added and the mixture was extracted with dichloromethane thrice. The combined extracts were washed with brine and dried over Na₂SO₄, then concentrated and purified by chromatography on silica gel (7% CH₃OH/DCM) to yield (2R,3R,4R,5S,6S)-3,4,5-tris(benzyloxy)-2-[(benzyloxy)methyl]-6-{3-[(7,7-dideuterium)bicyclo[4.2.0]octa-1(6),2,4-trien-3-ylmethyl]-4-methoxyphenyl}oxane as a yellow oil. MS (ES) m/z: 387.1 [M-OCH₃].

To a mixture of (2R,3R,4R,5S,6S)-3,4,5-tris(benzyloxy)-2-[(benzyloxy)methyl]-6-{3-[(7,7-dideuterium)bicyclo [4.2.0]octa-1(6),2,4-trien-3-ylmethyl]-4-methoxyphenyl}oxane (250 mg, 0.597 mmol, 1.00 equiv) in dichloromethane (8 mL) with Et₃SiH (208.3 mg, 1.791 mmol, 3.00 equiv) was added BF₃.Et₂O (169.5 mg, 1.194 mmol, 2.00 equiv) dropwise at 0° C. The reaction mixture was stirred for 1.5 h at 0° C. Sodium bicarbonate/H₂O was added and the mixture was extracted with dichloromethane thrice. The combined extracts were washed with brine and dried over Na₂SO₄, then concentrated and purified by chromatography on C18 reverse column (40% CH₃CN/H₂O) to yield the title compound as a white solid.

¹H NMR (400 MHz, CD₃OD): δ 7.25 (d, J=8.8 Hz, 1H), 7.18 (s, 1H), 7.04 (d, J=7.6 Hz, 1H), 6.93 (d, J=8.4 Hz, 1H), 6.87-6.89 (m, 1H), 4.05 (d, J=9.2 Hz, 1H), 3.79-3.98 (m, 6H), 3.68 (dd, J=11.9, 5.4 Hz, 1H), 3.33-3.51 (m, 4H), 3.29 (s, 1H), 3.09 (s, 2H); MS (ES) m/z: 387.1 [M−H]⁻.

Example 69: Compound #83

(2S,3R,4R,5S,6R)-2-(5-{[(7,7-dideuterium)bicyclo[4.2.0]octa-1(6),2,4-trien-3-yl]methyl}-4-chloro-2-methoxyphenyl)-6-(hydroxymethyl)oxane-3,4,5-triol

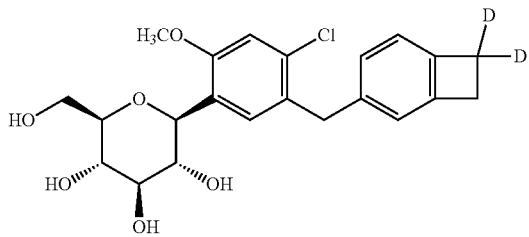 [SMILES: [2H]C1([2H])Cc2cc(Cc3cc([C@@H]4O[C@H](CO)[C@@H](O)[C@H](O)[C@H]4O)c(OC)cc3Cl)ccc21]

To a mixture of 2-chloro-4-hydroxybenzaldehyde (3 g, 19.161 mmol, 1.0 equiv) in DMF (50 mL) with potassium carbonate (6.6 g, 47.755 mmol, 2.5 equiv) was added iodomethane (6.0 g, 42.272 mmol, 2.2 equiv). Water was added and the mixture was extracted with ethyl acetate thrice. The combined extracts were washed with brine and dried over $Na_2SO_4$, then concentrated and purified by chromatography on silica gel (10:1 PE/EA) to yield 2-chloro-4-methoxybenzaldehyde as a white solid.

To a mixture of 2-chloro-4-methoxybenzaldehyde (2.8 g, 16.413 mmol, 1.0 equiv) in MeOH (30 mL) was added pyridinium bromide perbromide (7.9 g, 24.701 mmol, 1.5 equiv). The reaction mixture was stirred for 48 h at 55° C. Water was added and the mixture was extracted with ethyl acetate thrice. The combined extracts were washed with brine and dried over $Na_2SO_4$, then concentrated and purified by chromatography on silica gel (10:1 PE/EA) to yield 5-bromo-2-chloro-4-methoxybenzaldehyde as a white solid.

To a mixture of 3-bromospiro[bicyclo[4.2.0]octane-7,2'-[1,3]dioxolane]-1,3,5-triene (0.3 g, 1.244 mmol, 1.1 equiv) in THF (10 mL) was added n-BuLi (2.5 M in hexane, 0.5 mL, 1.25 mmol, 1.1 equiv) dropwise at −78° C. The reaction mixture was stirred for 30 min at −78° C. To the resulting mixture was then added a solution of 5-bromo-2-chloro-4-methoxybenzaldehyde (280 mg, 1.122 mmol, 1.0 equiv) in THF (1 mL) dropwise at −78° C. The reaction mixture was stirred for 2 h at −78° C. $NH_4Cl/H_2O$ was added and the mixture was extracted with EtOAc thrice. The combined extracts were washed with brine and dried over $Na_2SO_4$, then concentrated and purified by chromatography on silica gel (3:1 PE/EA) to yield (5-bromo-2-chloro-4-methoxyphenyl)({spiro[bicyclo[4.2.0]octane-7,2'-[1,3]dioxolane]-1(6),2,4-trien-3-yl})methanol as a yellow oil.

To a mixture of (5-bromo-2-chloro-4-methoxyphenyl)({spiro[bicyclo[4.2.0]octane-7,2'-[1,3]dioxolane]-1(6),2,4-trien-3-yl})methanol (240 mg, 0.583 mmol, 1.0 equiv) in dichloromethane (5 mL) with $Et_3SiH$ (250 mg, 2.15 mmol, 3.7 equiv) was added 2,2,2-trifluoroacetic acid (266 mg, 2.333 mmol, 4.0 equiv) dropwise at 25° C. The reaction mixture was stirred for 2 h at 25° C. Sodium bicarbonate was added and the mixture was extracted with DCM thrice. The combined extracts were washed with brine and dried over $Na_2SO_4$, then concentrated to yield 4-(5-bromo-2-chloro-4-methoxybenzyl)cyclobutabenzen-1(2H)-one as a yellow oil.

To a mixture of mercury (II) chloride (29 mg, 0.107 mmol, 0.3 equiv) in D2O (2 mL), were added deuterium chloride solution (35%, 0.1 mL) and Zn (0.1 g). The reaction mixture was stirred for 15 min at 25° C. The water was poured out. 4-(5-Bromo-2-chloro-4-methoxybenzyl)cyclobutabenzen-1 (2H)-one (110 mg, 0.303 mmol, 1.0 equiv), toluene (2 mL), and perdeuteroethanol (2 mL) were added to the solid. The resulting solution was stirred 16 h at 110° C. Water was added and the mixture was extracted with ethyl acetate thrice. The combined extracts were washed with brine and dried over $Na_2SO_4$, then concentrated and purified by chromatography on silica gel (5:1 PE/EA) to yield 3-[(5-bromo-2-chloro-4-methoxyphenyl)methyl](7,7-dideuterium)bicyclo[4.2.0]octa-1(6),2,4-triene as a yellow oil. $^1$H-NMR (400 MHz, Chloroform-d) δ 7.33 (s, 1H), 6.99-7.04 (m, 2H), 6.94 (s, 1H), 6.89 (s, 1H), 3.99 (s, 2H), 3.89 (s, 3H), 3.14 (s, 2H)

To a mixture of 3-[(5-bromo-2-chloro-4-methoxyphenyl)methyl](7,7-dideuterium)bicyclo[4.2.0]octa-1(6),2,4-triene (80 mg, 0.236 mmol, 1.0 equiv) in THF (5 mL) was added n-BuLi (2.5 M in hexane, 0.1 mL, 0.25 mmol, 1.1 equiv) dropwise at −78° C. The reaction mixture was stirred for 20 min at −78° C. To the resulting mixture was then added a solution of (3R,4S,5R,6R)-3,4,5-tris(benzyloxy)-6-[(benzyloxy)methyl]oxan-2-one (150 mg, 0.278 mmol, 1.2 equiv) in THF (1 mL) dropwise at −78° C. The reaction mixture was stirred for 2 h at −78° C. $NH_4Cl/H_2O$ was added and the mixture was extracted with EtOAc thrice. The combined extracts were washed with brine and dried over $Na_2SO_4$, then concentrated and purified by chromatography on silica gel (1:1 PE/EA) to yield (3R,4S,5R,6R)-3,4,5-tris(benzyloxy)-6-[(benzyloxy)methyl]-2-(5-{[(7,7-dideuterium)bicyclo[4.2.0]octa-1(6),2,4-trien-3-yl]methyl}-4-chloro-2-methoxyphenyl)oxan-2-ol as a yellow oil.

To a mixture of (3R,4S,5R,6R)-3,4,5-tris(benzyloxy)-6-[(benzyloxy)methyl]-2-(5-{[(7,7-dideuterium)bicyclo[4.2.0]octa-1(6),2,4-trien-3-yl]methyl}-4-chloro-2-methoxyphenyl)oxan-2-ol (150 mg, 0.188 mmol, 1.00 equiv) in dichloromethane (2 mL) with $Et_3SiH$ (60 mg, 0.516 mmol, 2.7 equiv) was added $BF_3.Et_2O$ (70 mg, 0.493 mmol, 2.6 equiv) dropwise at 0° C. The reaction mixture was stirred for 2 h at 0° C. Sodium bicarbonate was added and the mixture was extracted with DCM thrice. The combined extracts were washed with brine and dried over $Na_2SO_4$, then concentrated and purified by chromatography on silica gel (5:1 PE/EA) to yield (2R,3R,4R,5S,6S)-3,4,5-tris(benzyloxy)-2-[(benzyloxy)methyl]-6-(5-{[(7,7-dideuterium)bicyclo[4.2.0]octa-1(6),2,4-trien-3-yl]methyl}-4-chloro-2-methoxyphenyl)oxane as a yellow oil. MS (ES) m/z: 800.3 $[M+NH_4]^+$.

To a mixture of (2R,3R,4R,5S,6S)-3,4,5-tris(benzyloxy)-2-[(benzyloxy)methyl]-6-(5-{[(7,7-dideuterium)bicyclo[4.2.0]octa-1(6),2,4-trien-3-yl]methyl}-4-chloro-2-methoxyphenyl)oxane (80 mg, 0.102 mmol, 1.00 equiv) in dichloromethane (30 mL) with 1,2,3,4,5-pentamethylbenzene (160 mg, 1.079 mmol, 10.4 equiv) was added $BCl_3$ (1 M, in DCM, 1.6 mL, 1.60 mmol, 15.4 equiv) dropwise at −78° C. The reaction mixture was stirred for 1 h at −78° C. Methanol was added, and the resulting mixture was then concentrated and purified by chromatography on C18 (10%-50% $CH_3CN/H_2O$) to yield the title compound as a white solid.

$^1$H NMR (300 MHz, Methanol-$d_4$) δ 7.33 (s, 1H), 7.00-7.33 (m, 2H), 6.85-7.94 (m, 2H), 4.62 (d, J=9.3 Hz, 1H), 4.00 (d, J=3.1 Hz, 2H), 3.95 (s, 1H), 3.82 (s, 3H), 3.60-3.72 (m, 1H), 3.46 (d, J=6.4 Hz, 2H), 3.37 (d, J=4.7 Hz, 2H), 3.09 (s, 2H); MS (ES) m/z: 440.1 $[M+NH_4]^+$.

Example 70: Compound #84

(2S,3R,4R,5S,6R)-2-(5-{[(7,7-dideuterium)bicyclo[4.2.0]octa-1(6),2,4-trien-3-yl]methyl}-2,4-dimethoxyphenyl)-6-(hydroxymethyl)oxane-3,4,5-triol

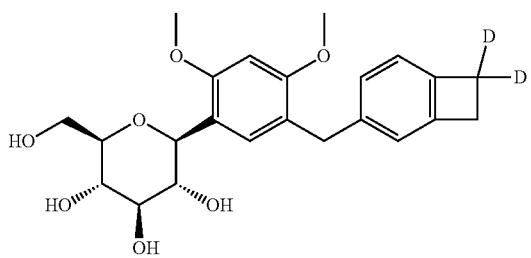 [SMILES: [2H]C1([2H])Cc2cc(Cc3cc([C@@H]4O[C@H](CO)[C@@H](O)[C@H](O)[C@H]4O)c(OC)cc3OC)ccc21]

To a mixture of 3-bromospiro[bicyclo[4.2.0]octane-7,2'-[1,3]dioxolane]-1,3,5-triene (300 mg, 1.244 mmol, 1.05 equiv) in THF (4 mL) was added n-BuLi (2.5 M in hexane, 0.55 ml, 1.375 mmol, 1.15 equiv) dropwise at −78° C. The reaction mixture was stirred for 30 min at −78° C. To the resulting mixture was then added a solution of 5-bromo-2,4-dimethoxybenzaldehyde (292 mg, 1.191 mmol, 1.00 equiv) in THF (2 mL) dropwise at −78° C. The reaction mixture was stirred for 1 h at −78° C. NH$_4$Cl/H$_2$O was added and the mixture was extracted with EtOAc thrice. The combined extracts were washed with brine and dried over Na$_2$SO$_4$, then concentrated and purified by chromatography on silica gel (1:1 PE/EA) to yield (5-bromo-2,4-dimethoxyphenyl)(spiro[bicyclo[4.2.0]octane-7,2'-[1,3]dioxolane]-1(6),2,4-trien-3-yl)methanol as a white solid.

To a mixture of (5-bromo-2,4-dimethoxyphenyl)(spiro[bicyclo[4.2.0]octane-7,2'-[1,3]dioxolane]-1(6),2,4-trien-3-yl)methanol (380 mg, 0.933 mmol, 1.00 equiv) in dichloromethane (8 mL) with Et$_3$SiH (326 mg, 2.804 mmol, 3.00 equiv) was added TFA (320 mg, 2.806 mmol, 3.00 equiv) dropwise at 0° C. The reaction mixture was stirred at 0° C. for 1 h. Sodium bicarbonate/H$_2$O was added and the mixture was extracted with dichloromethane thrice. The combined extracts were washed with brine and dried over Na$_2$SO$_4$, then concentrated and purified by chromatography on silica gel (4:1 PE/EA) to yield 4-(5-bromo-2,4-dimethoxybenzyl)cyclobutabenzen-1(2H)-one as a colorless oil.

To a mixture of HgCl$_2$ (521 mg, 0.077 mmol, 0.1 equiv)) and Zn (powder) (505 mg, 7.721 mmol, 10 equiv) in D$_2$O (2 mL) was added 2 drops of conc. DCl. The reaction mixture was stirred for 15 minutes at room temperature. D$_2$O was poured out and CH$_3$CH$_2$OD (2 mL), toluene (2 mL), conc. DCl (4 mL), and 4-(5-bromo-2,4-dimethoxybenzyl)cyclobutabenzen-1(2H)-one (270 mg, 0.778 mmol, 1.00 equiv) was added. The reaction mixture was stirred overnight at 110° C. The reaction mixture was cooled to room temperature and extracted with EA twice. The combined extracts were washed with brine and dried over Na$_2$SO$_4$, then concentrated and purified by chromatography on silica gel (4:1 PE/EA) to yield 3-[(5-bromo-2,4-dimethoxyphenyl)methyl](7,7-dideuterium)bicyclo[4.2.0]octa-1(6),2,4-triene as a white solid. $^1$H NMR δ 7.17 (s, 1H), 7.06-6.96 (m, 1H), 6.92 (dd, J=7.5, 1.0 Hz, 1H), 6.86 (t, J=1.3 Hz, 1H), 6.45 (s, 1H), 3.86 (s, 3H), 3.81 (s, 5H), 3.09 (s, 2H).

To a mixture of 3-[(5-bromo-2,4-dimethoxyphenyl)methyl](7,7-dideuterium)bicyclo[4.2.0]octa-1(6),2,4-triene (185 mg, 0.552 mmol, 1.05 mmol) in tetrahydrofuran (4 mL) was added n-BuLi (2.5M in hexane, 0.231 ml, 0.578 mmol, 1.10 equiv) dropwise at −78° C., the mixture was stirred at −78° C. for 30 min. (3R,4S,5R,6R)-3,4,5-Tris(benzyloxy)-6-[(benzyloxy)methyl]oxan-2-one (283 mg, 0.525 mmol, 1.00 equiv) in tetrahydrofuran (2 mL) was then added dropwise at −78° C. The reaction mixture was stirred at −78° C. for 1 h. NH$_4$Cl/H$_2$O was added and the mixture was extracted with EtOAc thrice. The combined extracts were washed with brine and dried over Na$_2$SO$_4$, then concentrated and purified by chromatography on silica gel (1:1 PE/EA) to yield (3R,4S,5R,6R)-3,4,5-tris(benzyloxy)-6-[(benzyloxy)methyl]-2-{5-[(7,7-dideuterium)bicyclo[4.2.0]octa-1(6),2,4-trien-3-ylmethyl]-2,4-dimethoxyphenyl}oxan-2-ol as a white solid. MS (ES) m/z: 777.4 [M−OH]$^+$.

To a mixture of (3R,4S,5R,6R)-3,4,5-tris(benzyloxy)-6-[(benzyloxy)methyl]-2-{5-[(7,7-dideuterium)bicyclo[4.2.0]octa-1(6),2,4-trien-3-ylmethyl]-2,4-dimethoxyphenyl}oxan-2-ol (240 mg, 0.302 mmol, 1.00 equiv) in dichloromethane (4 mL) with Et$_3$SiH (70 mg, 0.602 mmol, 2.00 equiv) was added BF$_3$.Et$_2$O (86 mg, 0.606 mmol, 2.00 equiv) dropwise at 0° C. The reaction mixture was stirred at 0° C. for 1 h. Sodium bicarbonate/HO was added and the mixture was extracted with dichloromethane thrice. The combined extracts were washed with brine and dried over Na$_2$SO$_4$, then concentrated and purified by chromatography on silica gel (4:1 PE/EA) to yield (2R,3R,4R,5S,6S)-3,4,5-tris(benzyloxy)-2-[(benzyloxy)methyl]-6-{5-[(7,7-dideuterium)bicyclo[4.2.0]octa-1(6),2,4-trien-3-ylmethyl]-2,4-dimethoxyphenyl}oxane as a white solid.

To a mixture of (2R,3R,4R,5S,6S)-3,4,5-tris(benzyloxy)-2-[(benzyloxy)methyl]-6-{5-[(7,7-dideuterium)bicyclo[4.2.0]octa-1(6),2,4-trien-3-ylmethyl]-2,4-dimethoxyphenyl}oxane (160 mg, 0.205 mmol, 1.00 equiv) in dichloromethane (8 mL) with 1,2,3,4,5-pentamethylbenzene (320 mg, 2.159 mmol, 10.5 equiv) was added BCl$_3$ (1 M in DCM, 3.2 ml, 3.2 mmol, 15.6 equiv) dropwise at −78° C. The reaction mixture was stirred at −78° C. for 1 h. 5 mL of methanol was added, and the resulting mixture was then concentrated and purified by chromatography on a C18 reversed phase column (0%-45% CH$_3$CN/H$_2$O) to yield the title compound as a white solid.

$^1$H NMR (300 MHz, CD$_3$OD): δ 7.11 (s, 1H), 6.97 (dd, J=6.8, 1.8 Hz, 1H), 6.79-6.85 (m, 2H), 6.56 (s, 1H), 4.55 (d, J=9.2 Hz, 1H), 3.73-3.86 (m, 9H), 3.56-3.64 (m, 1H), 3.38-3.56 (m, 2H), 3.31-3.36 (m, 2H), 3.03 (s, 2H); MS (ES) m/z: 436.1 [M+NH$_4$]$^+$.

Example 71: Compound #86

(2S,3R,4R,5S,6R)-(3-((1,1-dideuterium-1,2-dihydrocyclobutabenzen-4-yl)methyl)-4-methylphenyl)-6-(hydroxymethyl)-tetrahydro-2H-pyran-3,4,5-triol

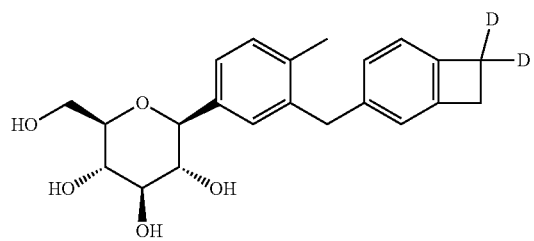 [SMILES: [2H]C1([2H])Cc2cc(Cc3cc([C@@H]4O[C@H](CO)[C@@H](O)[C@H](O)[C@H]4O)ccc3C)ccc21]

To a mixture of 3-bromospiro[bicyclo[4.2.0]octane-7,2'-[1,3]dioxolane]-1,3,5-triene (266 mg, 1.103 mmol, 1.10 equiv) in THF (4.5 mL) was added n-BuLi (0.44 mL, 1.100 mmol, 1.10 equiv, 2.5 M in hexane) dropwise at −78° C. under $N_2$, the mixture was stirred for 30 min at the temperature. Then a solution of 5-bromo-2-methylbenzaldehyde (200 mg, 1.005 mmol, 1.00 equiv) in THF (0.5 mL) was added at −78° C. dropwise, and the reaction mixture was stirred for 2h at the same temperature. $NH_4Cl/H_2O$ was added and the mixture was extracted with EtOAc thrice. The combined extracts were washed with brine and dried over $Na_2SO_4$, then concentrated to yield (5-bromo-2-methylphenyl)(spiro[bicyclo[4.2.0]-octane-7,2'-[1,3]dioxolane]-1(6),2,4-trien-3-yl)methanol as a yellow oil. MS (ES) m/z: 343.1 $[M-OH]^+$.

To a mixture of (5-bromo-2-methylphenyl)(spiro[bicyclo[4.2.0]-octane-7,2'-[1,3]dioxolane]-1(6),2,4-trien-3-yl) methanol (302.3 mg, 0.837 mmol, 1.00 equiv) in 8 mL of acetonitrile with chlorotrimethylsilane (365.1 mg, 3.361 mmol, 4.00 equiv) was added sodium iodide (502.4 mg, 3.352 mmol, 4.00 equiv), and the reaction mixture was stirred for 1 h at 50° C. under $N_2$. $H_2O$ was added and the mixture was extracted with EtOAc thrice. The combined extracts were washed with brine and dried over $Na_2SO_4$, then concentrated and purified by chromatography on silica gel (1:10 EA/PE) to yield 4-(5-bromo-2-methylbenzyl)cyclobutabenzen-1(2H)-one as a yellow oil. $^1$H NMR (400 MHz, Chloroform-d, ppm) δ: 7.27-7.34 (m, 2H), 7.25 (d, J=2.5 Hz, 2H), 7.19 (d, J=7.8 Hz, 1H), 7.06 (d, J=8.1 Hz, 1H), 4.02 (s, 2H), 3.92 (s, 2H), 2.19 (s, 3H).

To a mixture of mercury(II) chloride (40 mg, 0.147 mmol, 0.20 equiv) in $D_2O$ (1 mL) was added 2 drops of DCl (35% in $D_2O$) and zinc powder (483 mg, 7.384 mmol, 10.00 equiv) and stirred for 10 minutes. Then the $D_2O$ was poured out. A solution of 4-(5-bromo-2-methylbenzyl)cyclobutabenzen-1(2H)-one (223.8 mg, 0.743 mmol, 1.00 equiv) in $CH_3CH_2OD$ (1.2 mL) and toluene (1.2 mL) was added. DCl (35% in $D_2O$) was then added to the above solution and stirred for 16 h at 110° C. $H_2O$ was added and the mixture was extracted with EtOAc thrice. The combined extracts were washed with brine and dried over $Na_2SO_4$, then concentrated and purified by chromatography on silica gel (1:30 EA/PE) to yield 4-(5-bromo-2-methylbenzyl)-1,1-dideuterium-1,2-dihydrocyclobutabenzene as a light yellow oil. $^1$H NMR (300 MHz, Chloroform-d, ppm) δ: 7.18-7.23 (m, 2H), 6.99 (d, J=7.9 Hz, 1H), 6.93 (t, J=1.1 Hz, 2H), 6.77 (s, 1H), 3.87 (s, 2H), 3.09 (s, 2H), 2.17 (s, 3H).

To a mixture of 4-(5-bromo-2-methylbenzyl)-1,1-dideuterium-1,2-dihydrocyclobutabenzene (167.5 mg, 0.579 mmol, 1.10 equiv) in THF/toluene (1.6/3.2 mL) was added n-BuLi (0.23 mL, 0.575 mmol, 1.10 equiv, 2.5 M in hexane) dropwise at −78° C. The mixture was stirred for 30 min at that temperature. Then a solution of (3R,4S,5R,6R)-3,4,5-tris(trimethylsilyloxy)-6-((trimethylsilyloxy)methyl)-tetrahydropyran-2-one (246 mg, 0.527 mmol, 1.00 equiv) in THF/toluene (0.4/0.8 mL) was added dropwise, and the reaction mixture was stirred for 2 h at the same temperature. $NH_4Cl/H_2O$ was added and the mixture was extracted with EtOAc thrice. The combined extracts were washed with brine and dried over $Na_2SO_4$, then concentrated to yield (3R,4S,5R,6R)-2-(3-((1,1-dideuterium-1,2-dihydrocyclobut-abenzen-4-yl)methyl)-4-methylphenyl)-3,4,5-tris(trimethylsilyl-oxy)6-((trimethylsilyloxy)methyl)-tetrahydro-2H-pyran-2-ol as a light brown oil.

To a mixture of (3R,4S,5R,6R)-2-(3-((1,1-dideuterium-1,2-dihydrocyclobutabenzen-4-yl)methyl)-4-methylphenyl)-3,4,5-tris(trimethylsilyloxy)6-((trimethylsilyloxy)methyl)-tetrahydro-2H-pyran-2-ol (354 mg, 0.523 mmol, 1.00 equiv) in MeOH (5 mL) was added a solution of methanesulfonic acid (100.4 mg, 1.045 mmol, 2.00 equiv) in $CH_3OH$ (1 mL) dropwise at −78° C. under $N_2$. The reaction mixture was stirred at room temperature for 16 h. Sodium bicarbonate/$H_2O$ was added and the mixture was extracted with dichloromethane thrice. The combined extracts were washed with brine and dried over $Na_2SO_4$, then concentrated and purified by chromatography on silica gel (7% $CH_3OH$/DCM) to yield (3R,4S,5S,6R)-2-(3-((1,1-dideuterium-1,2-dihydrocyclobutabenzen-4-yl)methyl)-4-methylphenyl)-6-(hydroxymethyl)-2-methoxy-tetrahydro-2H-pyran-3,4,5-triol as an off-white oil. MS (ES) m/z: 371.3 $[M-OCH_3]^+$.

To a mixture of (3R,4S,5S,6R)-2-(3-((1,1-dideuterium-1,2-dihydrocyclobutabenzen-4-yl)methyl)-4-methylphenyl)-6-(hydroxymethyl)-2-methoxy-tetrahydro-2H-pyran-3,4,5-triol (139 mg, 0.345 mmol, 1.00 equiv) in dichloromethane (10 mL) with $Et_3SiH$ (80.2 mg, 0.690 mmol, 2.00 equiv) was added $BF_3.Et_2O$ (98 mg, 0.690 mmol, 2.00 equiv) dropwise at 0° C. The reaction mixture was stirred for 1.5 h at 0° C. Sodium bicarbonate/$H_2O$ was added and the mixture was extracted with dichloromethane thrice. The combined extracts were washed with brine and dried over $Na_2SO_4$, then concentrated and purified by chromatography on C18 reverse column (40% $CH_3CN/H_2O$) to yield the title compound as a white solid.
$^1$H NMR (300 MHz, $CD_3OD$): δ7.04-7.20 (m, 3H), 6.80-6.97 (m, 2H), 6.75 (s, 1H), 4.05 (d, J=9.2 Hz, 1H), 3.92 (s, 2H), 3.80-3.90 (m, 1H), 3.59-3.71 (m, 1H), 3.32-3.49 (m, 4H), 3.04 (s, 2H), 2.15 (s, 3H); MS (ES) m/z: 371.1 $[M-H]^-$.

Example 72: Compound #86

(2S,3R,4R,5S,6R)-2-(5-((1,1-dideuterium-1,2-dihydrocyclobutabenzen-4-yl)methyl)-2-methoxy-4-methylphenyl)-6-(hydroxymethyl)-tetrahydro-2H-pyran-3,4,5-triol

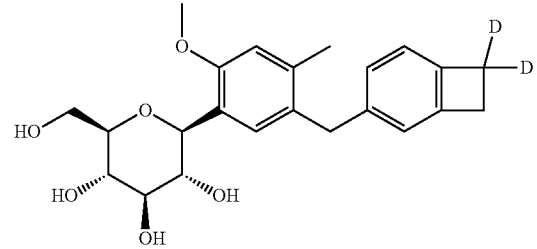 [SMILES: [2H]C1([2H])Cc2cc(Cc3cc([C@@H]4O[C@H](CO)[C@@H](O)[C@H](O)[C@H]4O)c(OC)cc3C)ccc21]

To a mixture of 3-bromospiro[bicyclo[4.2.0]octane-7,2'-[1,3]dioxolane]-1,3,5-triene (300 mg, 1.24 mmol, 1.00 equiv) in THF (5 mL) was added n-BuLi (2.5M in hexane, 0.52 mL, 1.05 equiv) dropwise at −78° C., the mixture was stirred at −78° C. for 30 min. 5-Bromo-4-methoxy-2-methylbenzaldehyde (271 mg, 1.18 mmol, 0.95 equiv) in THF (1 mL) was then added to the solution. The reaction mixture was stirred at −78° C. for 2 h. $NH_4Cl/H_2O$ was added and the mixture was extracted with EtOAc thrice. The combined extracts were washed with brine and dried over $Na_2SO_4$, then concentrated and purified by chromatography on silica gel (1:1 PE/EA) to yield (5-bromo-4-methoxy-2-methylphenyl)(spiro[bicyclo[4.2.0]octane-7,2'-[1,3]dioxolane]-1(6),2,4-trien-3-yl)methanol as a white solid. MS (ES) m/z: 373.0 $[M-OH]^+$ To a mixture of (5-bromo-4-methoxy-2-methylphenyl)(spiro[bicyclo[4.2.0]octane-7,2'-[1,3]dioxolane]-1(6),2,4-trien-3-yl)methanol (380 mg, 0.97 mmol, 1.00 equiv) in DCM (10 mL) with Et₃SiH (451 mg, 3.88 mmol, 4.00 equiv) was added TFA (443 mg, 3.88 mmol, 4.00 equiv) at 0° C. The reaction mixture was stirred at 0° C. for 2 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield 4-(5-bromo-4-methoxy-2-methylbenzyl)cyclobutabenzen-1 (2H)-one as a light yellow oil.

To a mixture of HgCl₂ (33 mg, 0.12 mmol, 0.20 equiv) and Zn (393 mg, 6.01 mmol, 10.03 equiv) in D₂O (3 mL) was added conc. DCl (0.1 mL). The mixture was stirred for 15 min at room temperature. The water was poured out. Then to the solid was added a solution of 4-(5-bromo-4-methoxy-2-methylbenzyl)cyclobutabenzen-1 (2H)-one (200 mg, 0.60 mmol, 1.00 equiv) in CH₃CH₂OD (2 mL) and toluene (2 mL), conc. DCl (3 mL). The reaction mixture was stirred overnight at 110° C. H₂O was added and the mixture was extracted with EtOAc thrice. The combined extracts were washed with brine and dried over Na₂SO₄, then concentrated and purified by chromatography on silica gel (5:1 PE/EA) to yield 4-(5-bromo-4-methoxy-2-methylbenzyl)-1,1-dideuterium-1,2-dihydrocyclobutabenzene as a light yellow oil. H-NMR (300 MHz, CD₃OD): δ 7.25 (s, 1H), 6.87-7.03 (m, 3H), 6.83 (s, 1H), 3.83 (s, 2H), 3.80 (s, 3H), 3.06 (s, 2H), 2.18 (s, 3H).

To a mixture of 4-(5-bromo-4-methoxy-2-methylbenzyl)-1,1-dideuterium-1,2-dihydrocyclobutabenzene (130 mg, 0.41 mmol, 1.10 equiv) in THF (5 mL) was added n-BuLi (2.5M in hexane, 0.17 mL, 1.10 equiv) dropwise at −78° C., the mixture was stirred at −78° C. for 30 min. (3R,4S,5R,6R)-3,4,5-Tris(benzyloxy)-6-[(benzyloxy)methyl]oxan-2-one (208 mg, 0.39 mmol, 0.95 equiv) in THF (1 mL) was then added to the solution. The reaction mixture was stirred at −78° C. for 2 h. NH₄Cl/H₂O was added and the mixture was extracted with EtOAc thrice. The combined extracts were washed with brine and dried over Na₂SO₄, then concentrated to yield (3R,4S,5R,6R)-3,4,5-tris(benzyloxy)-6-(benzyloxymethyl)-2-(5-((1,1-dideuterium-1,2-dihydrocyclobutabenzen-4-yl)methyl)-2-methoxy-4-methylphenyl)-tetrahydro-2H-pyran-2-ol as a light yellow oil.

To a mixture of (3R,4S,5R,6R)-3,4,5-tris(benzyloxy)-6-(benzyloxymethyl)-2-(5-((1,1-dideuterium-1,2-dihydrocyclobutabenzen-4-yl)methyl)-2-methoxy-4-methylphenyl)-tetrahydro-2H-pyran-2-ol (300 mg, 0.39 mmol, 1.00 equiv) in DCM (5 mL) with Et₃SiH (87 mg, 0.75 mmol, 2.00 equiv) was added BF₃.Et₂O (107 mg, 0.75 mmol, 2.00 equiv) at 0° C. The reaction mixture was stirred at 0° C. for 2 h. Sodium bicarbonate/H₂O was added and the mixture was extracted with dichloromethane thrice. The combined extracts were washed with brine and dried over Na₂SO₄, then concentrated and purified by chromatography on silica gel (5:1 PE/EA) to yield (2R,3R,4R,5S,6S)-3,4,5-tris(benzyloxy)-2-(benzyloxymethyl)-6-(5-((1,1-dideuterium-1,2-dihydrocyclobutabenzen-4-yl)methyl)-2-methoxy-4-methylphenyl)-tetrahydro-2H-pyran as a light yellow oil. MS (ES) m/z: 780.3 [M+NH₄]⁺

To a mixture of (2R,3R,4R,5S,6S)-3,4,5-tris(benzyloxy)-2-(benzyloxymethyl)-6-(5-((1,1-dideuterium-1,2-dihydrocyclobutabenzen-4-yl)methyl)-2-methoxy-4-methylphenyl)-tetrahydro-2H-pyran (80 mg, 0.11 mmol, 1.00 equiv) in dichloromethane (3 mL) with 1,2,3,4,5-pentamethylbenzene (100 mg, 0.68 mmol, 6.40 equiv) was added BCl₃ (1 M in DCM, 2 mL) dropwise at −78° C. The reaction mixture was stirred at −78° C. for 1 h. Methanol (15 mL) was added, and the resulting mixture was then concentrated and purified by chromatography on a C18 reversed phase column to yield the title compound as a white solid.

¹H NMR (300 MHz, CD₃OD): δ7.21 (s, 1H), 6.96 (d, J=7.3 Hz, 1H), 6.88 (d, J=7.7 Hz, 1H), 6.79 (s, 2H), 4.65 (d, J=9.3 Hz, 1H), 3.91 (s, 2H), 3.86 (d, J=11.6 Hz, 1H), 3.81 (s, 3H), 3.62-3.73 (m, 1H), 3.45-3.60 (m, 2H), 3.37-3.41 (m, 2H), 3.08 (s, 2H), 2.18 (s, 3H); MS (ES) m/z: 401.1 [M−H]⁻.

Example 73: Compound #87

(2S,3R,4R,5S,6R)-2-(3-((1,1-dideuterium-1,2-dihydrocyclo-butabenzen-4-yl)methyl)-4-ethylphenyl)-6-(hydroxymethyl)-tetrahydro-2H-pyran-3,4,5-triol

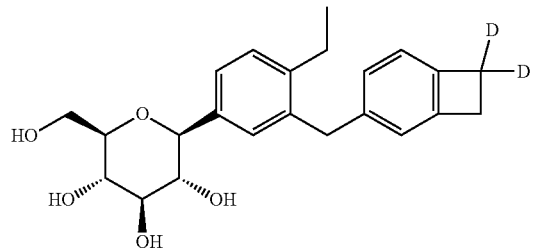 [SMILES: [2H]C1([2H])Cc2cc(Cc3cc([C@@H]4O[C@H](CO)[C@@H](O)[C@H](O)[C@H]4O)ccc3CC)ccc21]

To a mixture of 3-bromospiro[bicyclo[4.2.0]octane-7,2'-[1,3]dioxolane]-1,3,5-triene (150 mg, 0.622 mmol, 1.10 equiv) in THF (3 mL) was added n-BuLi (0.25 mL, 0.625 mmol, 1.10 equiv, 2.5 M in hexane) dropwise at −78° C. under N₂, the mixture was stirred for 30 min at the temperature. Then a solution of 5-bromo-2-ethylbenzaldehyde (120.6 mg, 0.566 mmol, 1.00 equiv) in THF (0.5 mL) was added at −78° C. dropwise, and the reaction mixture was stirred for 2 h at the same temperature. NH₄Cl/H₂O was added and the mixture was extracted with EtOAc thrice. The combined extracts were washed with brine and dried over Na₂SO₄, then concentrated to yield (5-bromo-2-ethylphenyl)(spiro-[bicyclo[4.2.0]octane-7,2'-[1,3]dioxolane]-1(6),2,4-trien-3-yl)methanol as a yellow oil. 375.0 [M+H]⁺.

To a mixture of (5-bromo-2-ethylphenyl)(spiro-[bicyclo[4.2.0]octane-7,2'-[1,3]dioxolane]-1(6),2,4-trien-3-yl)methanol (238 mg, 0.634 mmol, 1.00 equiv) in 8 mL of acetonitrile with chlorotrimethylsilane (276.7 mg, 2.547 mmol, 4.00 equiv) was added sodium iodide (380.8 mg, 2.540 mmol, 4.00 equiv), and the reaction mixture was stirred for 1 h at 50° C. under N₂. H₂O was added and the mixture was extracted with EtOAc thrice. The combined extracts were washed with brine and dried over Na₂SO₄, then concentrated and purified by chromatography on silica gel (1:10 EA/PE) to yield 4-(5-bromo-2-ethylbenzyl)cyclobutabenzen-1(2H)-one as a brown oil. ¹H NMR (400 MHz, Chloroform-d) δ: 7.38 (dd, J=8.2, 2.2 Hz, 1H), 7.24-7.32 (m, 3H), 7.21 (d, J=7.8 Hz, 1H), 7.13 (d, J=8.2 Hz, 1H), 4.08 (s, 2H), 3.95 (s, 2H), 2.57 (q, J=7.5 Hz, 2H), 1.16 (t, J=7.5 Hz, 3H).

To a mixture of mercury(II) chloride (29.4 mg, 0.108 mmol, 0.20 equiv) in D₂O (1 mL) in a 50-mL round-bottom flask was added 2 drops of DCl (35% in D₂O) and zincpowder (350.8 mg, 5.363 mmol, 10.00 equiv) and stirred for 10 minutes. Then the D₂O was poured out, and a solution of 4-(5-bromo-2-ethylbenzyl)cyclobutabenzen-1(2H)-one (170 mg, 0.539 mmol, 1.00 equiv) in CH₃CH₂OD/toluene (1.2/1.2 mL) was added. DCl (2 mL, 35% in D₂O) was then added to the above solution and stirred for 16 h at 110° C. Then the mixture was quenched with water, extracted with

143

EA thrice. The combined layers were washed with brine, then concentrated and purified by chromatography on silica gel (1:30 EA/PE) to yield 4-(5-bromo-2-ethylbenzyl)-1,1-dideuterium-1,2-dihydrocyclobutabenzene as a light yellow oil. ¹H NMR (400 MHz, Chloroform-d) δ: 7.32 (dd, J=8.2, 2.2 Hz, 1H), 7.24 (d, J=2.2 Hz, 1H), 7.08 (d, J=8.2 Hz, 1H), 6.95-7.02 (m, 2H), 6.82 (d, J=1.3 Hz, 1H), 3.96 (s, 2H), 3.14 (s, 2H), 2.60 (q, J=7.5 Hz, 2H), 1.16 (t, J=7.5 Hz, 3H).

To a mixture of 4-(5-bromo-2-ethylbenzyl)-1,1-dideuterium-1,2-dihydrocyclobutabenzene (110 mg, 0.363 mmol, 1.10 equiv) in THF/toluene (1.2/2.4 mL) was added n-BuLi (0.15 mL, 0.375 mmol, 1.10 equiv, 2.5 M in hexane) dropwise with stirring at −78° C. The mixture was stirred for 30 min at the temperature. Then a solution of (3R,4S,5R,6R)-3,4,5-tris(trimethylsilyloxy)-6-((trimethylsilyloxy)methyl)-tetrahydropyran-2-one (154 mg, 0.330 mmol, 1.00 equiv) in THF/toluene (0.3/0.6 mL) was added at −78° C. dropwise, and the reaction mixture was stirred for 2h at the same temperature. NH₄Cl/H₂O was added and the mixture was extracted with EtOAc thrice. The combined extracts were washed with brine and dried over Na₂SO₄, then concentrated to yield (3R,4S,5R,6R)-2-(3-((1,1-dideuterium-1,2-dihydrocyclobutabenzen-4-yl)methyl)-4-ethylphenyl)-3,4,5-tris(trimethylsilyloxy)-6-((trimethylsilyloxy)methyl)-tetrahydro-2H-pyran-2-ol as a light brown oil.

To a mixture of (3R,4S,5R,6R)-2-(3-((1,1-dideuterium-1,2-dihydrocyclobutabenzen-4-yl)methyl)-4-ethylphenyl)-3,4,5-tris(trimethylsilyloxy)-6-((trimethylsilyloxy)methyl)-tetrahydro-2H-pyran-2-ol (240 mg, 0.347 mmol, 1.00 equiv) in MeOH (4 mL) was added a solution of methanesulfonic acid (67 mg, 0.697 mmol, 2.00 equiv) in CH₃OH (1 mL) dropwise at −78° C. The reaction mixture was stirred at room temperature for 16 h. NaHCO₃/H₂O was added and the mixture was extracted with EtOAc thrice. The combined extracts were washed with brine and dried over Na₂SO₄, then concentrated and purified by chromatography on silica gel (8% CH₃OH/DCM) to yield (2S,3R,4S,5S,6R)-2-(3-((1,1-dideuterium-1,2-dihydrocyclobutabenzen-4-yl)methyl)-4-ethylphenyl)-6-(hydroxymethyl)-2-methoxy-tetrahydro-2H-pyran-3,4,5-triol as an off-white oil. MS (ES) m/z: 385.1 [M−OCH₃]⁺.

To a mixture of (2S,3R,4S,5S,6R)-2-(3-((1,1-dideuterium-1,2-dihydrocyclobutabenzen-4-yl)methyl)-4-ethylphenyl)-6-(hydroxymethyl)-2-methoxy-tetrahydro-2H-pyran-3,4,5-triol (78 mg, 0.187 mmol, 1.00 equiv) in dichloromethane (10 mL) with Et₃SiH (43.4 mg, 0.373 mmol, 2.00 equiv) was added BF₃.Et₂O (53.1 mg, 0.374 mmol, 2.00 equiv) dropwise at −10° C. The reaction mixture was stirred for 1 h at the temperature. NaHCO₃/H₂O was added and the mixture was extracted with EtOAc thrice. The combined extracts were washed with brine and dried over Na₂SO₄, then concentrated and purified by chromatography on C18 reverse column with (39% CH₃CN/H₂O) to yield the title compound as a white solid.

¹HNMR (400 MHz, CD₃OD): δ7.24 (dd, J=7.8, 1.9 Hz, 1H), 7.13-7.20 (m, 2H), 6.95 (dd, J=7.5, 1.3 Hz, 1H), 6.88 (dd, J=7.5, 1.0 Hz, 1H), 6.78 (s, 1H), 4.07 (d, J=9.3 Hz, 1H), 3.98 (d, J=3.3 Hz, 2H), 3.87 (dd, J=11.9, 1.5 Hz, 1H), 3.64-3.72 (m, 1H), 3.35-3.53 (m, 4H), 3.07 (s, 2H), 2.58 (q, J=7.5 Hz, 2H), 1.06 (t, J=7.5 Hz, 3H); MS (ES) m/z: 385.1 [M−H]⁻.

144

Example 74: Compound #91

(2S,3R,4R,6R)-2-(3-(bicyclo[4.2.0]octa-1(6),2,4-trien-3-ylmethyl)-4-methylphenyl)-5,5-difluoro-6-(hydroxymethyl)tetrahydro-2H-pyran-3,4-diol

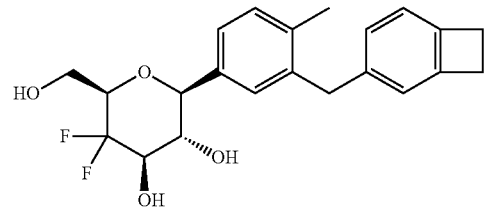 [SMILES: Cc1ccc([C@@H]2O[C@H](CO)C(F)(F)[C@H](O)[C@H]2O)cc1Cc1ccc2c(c1)CC2]

To a mixture of 3-bromobicyclo[4.2.0]octa-1,3,5-triene (1.09 g, 5.98 mmol) THF (4 mL) was added, cooled to −78° C. and the flask was evacuated, re-filled with nitrogen. To the mixture was added 3.7 ml of n-BuLi (3.74 ml, 5.98 mmol, 1.6 M in hexane) dropwise with stirring at −78° C. for 25 min. 5-Bromo-2-methylbenzaldehyde (1.19 g, 5.98 mmol) in THF (6 mL) was added to the solution and the mixture was kept stirring for 1 h at −78° C. The resulting mixture was quenched with aqueous NH₄Cl (15 ml), extracted with EtOAc three times (20 ml each time). The combined extracts were washed with brine, dried over Na₂SO₄, filtered and concentrated. The residue was purified by flash column chromatography on silica gel (40 g, EtOAc/heptane: 0>>>10%) to yield bicyclo[4.2.0]octa-1(6),2,4-trien-3-yl(5-bromo-2-methylphenyl)methanol as a colorless oil. MS (ES) m/z: 327.0 [M+Na]⁺.

To a mixture of bicyclo[4.2.0]octa-1(6),2,4-trien-3-yl(5-bromo-2-methylphenyl)methanol (820 mg, 2.70 mmol) in anhydrous DCM (20 mL) at 0° C. was added triethylsilane (1.30 ml, 8.11 mmol), followed by BF₃.Et₂O dropwised (0.68 ml, 5.41 mmol), and stirred at 0° C. for 1 h, then was quenched with aqueous NaHCO₃, extracted with DCM three times, concentrated and filtered. The filtrate was concentrated and the residue was purified by flash column chromatography on silica gel (40 g, EtOAc/heptane: 0>>>10%) to yield 3-(5-bromo-2-methylbenzyl)bicyclo[4.2.0]octa-1(6),2,4-triene as a colorless syrup. ¹H NMR (CHLOROFORM-d) δ: 7.21-7.25 (m, 1H), 6.99-7.05 (m, 1H), 6.96 (s, 2H), 6.76-6.82 (m, 1H), 3.90 (s, 2H), 3.13 (s, 4H), 2.20 (s, 3H).

To a mixture of 3-(5-bromo-2-methylbenzyl)bicyclo[4.2.0]octa-1(6),2,4-triene (233.1 mg, 0.81 mmol, 1.00 equiv) in THF (4 mL) was added n-BuLi (0.51 mL, 0.81 mmol, 1.00 equiv, 1.6 M in hexane) dropwise with stirring at −78° C., the mixture was stirred for 5 mins at −78° C., then warmed to 0° C. and stirred at that temperature for 35 mins. (3R,4R,6R)-3,4-Bis(benzyloxy)-6-((benzyloxy)methyl)-5,5-difluorotetrahydro-2H-pyran-2-one (380.2 mg, 0.81 mmol, 1.00 equiv) in tetrahydrofuran (6 mL) was then added to the solution. The reaction mixture was stirred at 0° C. for 1 h. NH₄Cl/H₂O was added and the mixture was extracted with EtOAc thrice. The combined extracts were dried over Na₂SO₄ and concentrated to yield (3R,4R,6R)-3,4-bis(benzyloxy)-2-(2-(benzyloxy)-5-(bicyclo[4.2.0]octa-1(6),2,4-trien-3-ylmethyl)-4-methylphenyl)-6-((benzyloxy)methyl)-5,5-difluorotetrahydro-2H-pyran-2-ol, which was used for next-step reaction without further purification.

To a mixture of (3R,4R,6R)-3,4-bis(benzyloxy)-2-(2-(benzyloxy)-5-(bicyclo[4.2.0]octa-1(6),2,4-trien-3-ylmethyl)-4-methylphenyl)-6-((benzyloxy)methyl)-5,5-difluorotetrahydro-2H-pyran-2-ol in DCM/acetonitrile (40 mL, v/v 1:1) with Et$_3$SiH (0.43 mL, 2.68 mmol, 3.30 equiv) was added BF$_3$.Et$_2$O (0.23 mL, 1.81 mmol, 2.2 equiv) dropwise at 0° C. The reaction mixture was stirred for 1 h at 0° C. NaHCO$_3$/water was added and the mixture was extracted with DCM thrice. The combined extracts were dried over Na$_2$SO$_4$, then concentrated and purified by chromatography on silica gel (EtOAc/heptane: 0>>>50%) to yield (2R,4R,5S,6S)-4,5-bis(benzyloxy)-6-(2-(benzyloxy)-5-(bicyclo[4.2.0]octa-1(6),2,4-trien-3-ylmethyl)-4-methylphenyl)-2-((benzyloxy)methyl)-3,3-difluorotetrahydro-2H-pyran as a white solid. MS (ES) m/z: 678.5 [M+NH$_4$]$^+$.

To a mixture of (2R,4R,5S,6S)-4,5-bis(benzyloxy)-6-(2-(benzyloxy)-5-(bicyclo[4.2.0]octa-1(6),2,4-trien-3-ylmethyl)-4-methylphenyl)-2-((benzyloxy)methyl)-3,3-difluorotetrahydro-2H-pyran (300.2 mg, 0.45 mmol, 1.00 equiv) in dichloromethane (15 mL) with 1,2,3,4,5-pentamethylbenzene (538.8 mg, 3.63 mmol, 8.00 equiv) was added BCl$_3$ (2.72 mL, 2.72 mmol, 6.00 equiv, 1 M in DCM) dropwise at −78° C. The reaction mixture was stirred for 1 h at −78° C. 2 mL of methanol was added, and the resulting mixture was then concentrated and purified by chromatography on a silica gel column to yield the title compound as a white solid.

$^1$H NMR (300 MHz, CD$_3$OD): δ 7.24-7.19 (br, 2H), 7.15 (d, J=7.58 Hz, 1H), 6.98 (d, J=7.58 Hz, 1H), 6.91 (d, J=7.58 Hz, 1H), 6.80 (s, 1H), 4.23 (d, J=9.09 Hz, 1H), 3.97 (s, 2H), 3.92 (d, J=10.11 Hz, 1H), 3.88-3.73 (m, 3H), 3.61 (d, J=8.59 Hz, 1H), 3.11 (s, 4H), 2.21 (s, 3H). MS (ES) m/z: 413.25 [M+Na]$^+$.

Example 75: Compound #92

(2S,3R,4R,6R)-2-(5-(bicyclo[4.2.0]octa-1(6),2,4-trien-3-ylmethyl)-2-hydroxy-4-methylphenyl)-5,5-difluoro-6-(hydroxymethyl)tetrahydro-2H-pyran-3,4-diol

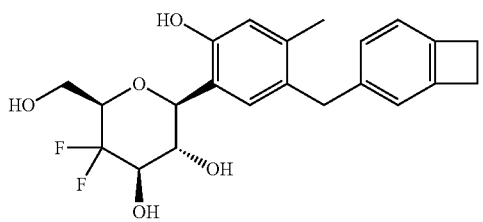 [SMILES: Cc1cc(O)c([C@@H]2O[C@H](CO)C(F)(F)[C@H](O)[C@H]2O)cc1Cc1ccc2c(c1)CC2]

To a mixture of 3-bromobicyclo[4.2.0]octa-1,3,5-triene (1092.9 mg, 5.97 mmol) THF (4 mL) was added, cooled to −78° C. and the flask was evacuated, re-filled with nitrogen. To the mixture was added 3.7 ml of n-BuLi (3.7 ml, 5.97 mmol, 1.6 M in hexane) dropwise with stirring at −78° C. for 25 min. 4-(Benzyloxy)-5-bromo-2-methylbenzaldehyde (1.82 g, 5.97 mmol) in THF (6 mL) was then added to the solution and the mixture was kept stirring for 1 h at −78° C. The resulting mixture was quenched with aqueous NH$_4$Cl (15 ml), extracted with EtOAc three times (20 ml each time). The combined extracts were washed with brine, dried over Na$_2$SO$_4$, filtered and concentrated. The residue was purified by flash column chromatography on silica gel (40 g, EtOAc/heptane: 0>>>10%) to yield (4-(benzyloxy)-5-bromo-2-methylphenyl)(bicyclo[4.2.0]octa-1(6),2,4-trien-3-yl)methanol as a colorless oil. MS (ES) m/z: 431.10 [M+Na]$^+$.

To a mixture of (4-(benzyloxy)-5-bromo-2-methylphenyl)(bicyclo[4.2.0]octa-1(6),2,4-trien-3-yl)methanol in anhydrous DCM at 0° C. was added triethylsilane (1.94 ml, 12.17 mmol), followed by BF$_3$.Et$_2$O dropwised (1.02 ml, 8.11 mmol), and stirred at 0° C. for 1 h, then quenched with aqueous NaHCO$_3$, extracted with DCM three times, concentrated and filtered. The filtrate was concentrated and the residue was purified by flash column chromatography on silica gel (40 g, EtOAc/heptane: 0>>>10%) to yield 3-(4-(benzyloxy)-5-bromo-2-methylbenzyl)bicyclo[4.2.0]octa-1(6),2,4-triene as a colorless syrup. MS (ES) m/z: 410.2 [M+NH$_4$]$^+$.

To a mixture of 3-(4-(benzyloxy)-5-bromo-2-methylbenzyl) bicyclo[4.2.0]octa-1(6),2,4-triene (371.1 mg, 0.94 mmol, 1.00 equiv) in THF (4 mL) was added n-BuLi (0.59 mL, 0.94 mmol, 1.00 equiv, 1.6M in hexane) dropwise with stirring at −78° C., the mixture was stirred for 5 mins at −78° C., then warmed to 0° C. and stirred at that temperature for 35 mins. (3R,4R,6R)-3,4-Bis(benzyloxy)-6-((benzyloxy)methyl)-5,5-difluorotetrahydro-2H-pyran-2-one (442 mg, 0.94 mmol, 1.00 equiv) in tetrahydrofuran (6 mL) was then added to the solution. The reaction mixture was stirred at 0° C. for 1 h. NH$_4$Cl/H$_2$O was added and the mixture was extracted with EtOAc thrice. The combined extracts were dried over Na$_2$SO$_4$ and concentrated to yield (3R,4R,6R)-3,4-bis(benzyloxy)-2-(2-(benzyloxy)-5-(bicyclo[4.2.0]octa-1(6),2,4-trien-3-ylmethyl)-4-methylphenyl)-6-((benzyloxy)methyl)-5,5-difluorotetrahydro-2H-pyran-2-ol, which was used for next-step reaction without further purification.

To a mixture of (3R,4R,6R)-3,4-bis(benzyloxy)-2-(2-(benzyloxy)-5-(bicyclo[4.2.0]octa-1(6),2,4-trien-3-ylmethyl)-4-methylphenyl)-6-((benzyloxy)methyl)-5,5-difluorotetrahydro-2H-pyran-2-ol in DCM (20 mL) with Et$_3$SiH (0.50 mL, 3.11 mmol, 3.30 equiv) was added BF$_3$.Et$_2$O (0.27 mL, 2.10 mmol, 2.2 equiv) dropwise at 0° C. The reaction mixture was stirred for 1 h at 0° C. NaHCO$_3$/water was added and the mixture was extracted with DCM thrice. The combined extracts were dried over Na$_2$SO$_4$, then concentrated and purified by chromatography on silica gel (EtOAc/heptane: 0>>>50%) to yield (2R,4R,5S,6S)-4,5-bis(benzyloxy)-6-(2-(benzyloxy)-5-(bicyclo[4.2.0]octa-1(6),2,4-trien-3-ylmethyl)-4-methylphenyl)-2-((benzyloxy)methyl)-3,3-difluorotetrahydro-2H-pyran as a white solid. MS (ES) m/z: 784.5 [M+NH$_4$].

To a mixture of (2R,4R,5S,6S)-4,5-bis(benzyloxy)-6-(2-(benzyloxy)-5-(bicyclo[4.2.0]octa-1(6),2,4-trien-3-ylmethyl)-4-methylphenyl)-2-((benzyloxy)methyl)-3,3-difluorotetrahydro-2H-pyran (145.5 mg, 0.19 mmol, 1.00 equiv) in dichloromethane (5 mL) with 1,2,3,4,5-pentamethylbenzene (225 mg, 1.52 mmol, 8.00 equiv) was added BCl$_3$ (1.14 mL, 1.14 mmol, 6.00 equiv, 1 M in DCM) dropwise at −78° C. The reaction mixture was stirred for 1 h at −78° C. 5 mL of methanol was added, and the resulting mixture was then concentrated and purified by chromatography on a silica gel column to yield the title compound as a white solid.

$^1$H NMR (300 MHz, CD$_3$OD): δ 7.11 (s, 1H), 6.93 (d, J=7.58 Hz, 1H), 6.86 (d, J=7.58 Hz, 1H), 6.76 (s, 1H), 6.63 (s, 1H), 4.69 (d, J=9.09 Hz, 1H), 3.93-3.69 (m, 7H), 3.08 (s, 4H), 2.09 (s, 3H); MS (ES) m/z: 429.15 [M+Na]$^+$.

Example 76: Compound #93

(2S,3R,4R,6R)-2-(5-(bicyclo[4.2.0]octa-1(6),2,4-trien-3-ylmethyl)-2-methoxy-4-methylphenyl)-5,5-difluoro-6-(hydroxymethyl)tetrahydro-2H-pyran-3,4-diol

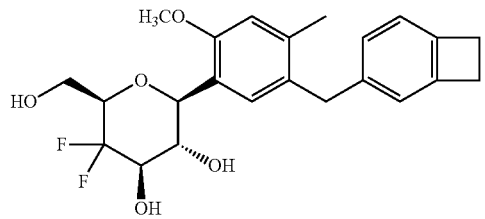 [SMILES: COc1cc(C)c(Cc2ccc3c(c2)CC3)cc1[C@@H]1O[C@H](CO)C(F)(F)[C@H](O)[C@H]1O]

To a solution of (2S,3R,4R,6R)-2-(5-(bicyclo[4.2.0]octa-1(6),2,4-trien-3-ylmethyl)-2-hydroxy-4-methylphenyl)-5,5-difluoro-6-(hydroxymethyl)tetrahydro-2H-pyran-3,4-diol (45 g, 0.11 mmol) in acetone (4 ml) was added 46 mg of $K_2CO_3$, followed by 21 μL of MeI and the mixture was kept stirring at room temperature for 16 hours. The solid was filtered off and the filtrate was concentrated. The residue was dissolved in 2 ml of MeOH, which was then subjected to Gilson HPLC purification to yield the title compound as a white solid.

$^1$H NMR (300 MHz, $CD_3OD$): δ 7.16 (s, 1H), 6.93 (d, J=7.58 Hz, 1H), 6.87 (d, J=7.58 Hz, 1H), 6.78 (s, 1H), 6.76 (s, 1H), 4.75 (d, J=9.09 Hz, 1H), 3.89 (s, 2H), 3.88 (m, 2H), 3.79 (s, 3H), 3.79-3.68 (m, 4H), 3.08 (s, 4H), 2.17 (s, 3H). MS (ES) m/z: 443.25 [M+Na]$^+$.

Biological Example 1: SGLT1 and SGLT2 Assay

The ability of the compounds of formula (I) of the present invention to treat an SGLT-mediated condition was determined using the following procedures:

SGLT1 and SGLT2 were cloned in form of cDNA from human small intestine (Genbank M24847), and from human kidney (Genbank M95549), respectively. Subsequently, each full cDNA was subcloned into pcDNA with each construct's integrity verified through follow-on sequencing. To generate CHO-K1 cells that stably express human SGLT1 or human SGLT2, CHO-K1 cells were transfected using DMRIE-C reagent (Life Technologies, Gaithersburg, Md.). Transfected cells were then selected in the presence of 500 μg/ml of the Geneticin (G418 Cellgro Catalog No. 30234-CI)

Individual clones were then characterized using the following cell-based assay for sodium-dependent glucose transport:

Inhibition of SGLT1 and SGLT2 activity was assessed in CHO K1 cells stably expressing either human SGLT1 or SGLT2, using the SGLT specific glucose analog methyl-glucopyranoside (Sigma Catalog No. M-9376). Cells were plated (45,000 cells/well) in white wall 96-well plates (CO-STAR, Cat#3903) for 24 hours in growth medium, then a final concentration of 10 mM Na-Butyrate (ALDRICH Cat#30341-0) was added. The cells were incubated for 24 hours. On the day of the assay, cells were rinsed and treated with test compounds (at concentrations of 0.001 μM to 10 μM) in assay buffer (50 mM HEPES, 20 mM Tris base, 5 mM KCl, 1 mM $MgCl_2$, 1 mM $CaCl_2$ and 137 mM NaCl, pH 7.4) for 10 minutes. Cells were then incubated with $^{14}$C-α-methyl-d-glucopyranoside (AMG, Amersham Catalog No. CFB 76), using 0.07 μCi per well in 500 μM AMG final concentration. The cells were incubated for 2 hours at 37° C. with 5% $CO_2$ and washed two times with ice-cold Phosphate Buffer Solution (Cellgro Catalog No. 21030-CV). The cells were then solubilized by adding 60 μl of MICROS-CINT™20 and the Na-dependent $^{14}$C-AMG uptake was quantified by measuring radioactivity. Plates were counted in a TopCount (Packard, Meriden, Conn.)

Representative compounds of the present invention were tested according to the procedures as described in Biological Example 1 above, with results as listed in Table BIO-1 below. Results are reported as the %-inhibition or $IC_{50}$ value. Variability for the functional assay was typically within 20%. The %-inhibition or $IC_{50}$ data were derived from the best curve fit as listed in BIO-1, below.

TABLE BIO-1

| | SGLT1 and SGLT2 Activity | |
|---|---|---|
| Cmpd No. | SGLT1 $IC_{50}$ (nM) | SGLT2 $IC_{50}$ (nM) |
| 1 | 33 | 1 |
| 2 | 45 | 1 |
| 3 | 39 | 3 |
| 4 | 18 | 3 |
| 5 | 32 | 5 |
| 6 | 4 | 1 |
| 7 | 48 | 1 |
| 8 | 5 | 1 |
| 9 | 53 | 1 |
| 10 | 5 | 1 |
| 11 | 58 | 1 |
| 12 | 3 | 2 |
| 13 | 32 | 1 |
| 14 | 3 | 6 |
| 15 | 67% at 0.3 μM | 31% at 0.03 μM |
| 16 | 0% at 0.3 μM | 43% at 0.03 μM |
| 17 | 192 | 1 |
| 18 | 25% at 0.3 μM | 74% at 0.03 μM |
| 19 | 62% at 0.3 μM | 38% at 0.03 μM |
| 20 | 24% at 0.3 μM | 77% at 0.03 μM |
| 21 | 67% at 0.3 μM | 35% at 0.03 μM |
| 22 | 12 | 3 |
| 23 | 24% at 0.3 μM | 39% at 0.03 μM |
| 24 | 5% at 0.3 μM | 23% at 0.03 μM |
| 25 | 36% at 0.3 μM | 71% at 0.03 μM |
| 26 | 5% at 0.3 μM | 58% at 0.03 μM |
| 27 | 29 | 1 |
| 28 | 50% at 0.3 μM | 40% at 0.03 μM |
| 29 | 92 | 3 |
| 30 | 206 | 3 |
| 31 | 84 | 10 |
| 32 | 10 | 3 |
| 33 | 23% at 0.3 μM | 57% at 0.03 μM |
| 34 | 24% at 0.3 μM | 72% at 0.03 μM |
| 35 | 29% at 0.3 μM | 45% at 0.03 μM |
| 36 | 26% at 0.3 μM | 84% at 0.03 μM |
| 37 | 20% at 0.3 μM | 84% at 0.03 μM |
| 38 | 20% at 0.3 μM | 78% at 0.03 μM |
| 39 | 27 | 13 |
| 40 | 149 | 1 |
| 41 | 106 | 18 |
| 42 | 34 | 2 |
| 51 | 35 | 1 |
| 52 | 4 | 1 |
| 53 | 80 | 1 |
| 54 | 63 | 1 |
| 55 | 7 | 1 |
| 56 | 93 | 2 |
| 57 | 44 | 6 |
| 58 | 25 | 2 |
| 59 | 140 | 3 |
| 60 | 83 | 3 |
| 61 | 7 | 4 |
| 62 | 168 | 9 |
| 63 | 84 | 1 |

TABLE BIO-1-continued

SGLT1 and SGLT2 Activity

| Cmpd No. | SGLT1 IC$_{50}$ (nM) | SGLT2 IC$_{50}$ (nM) |
| --- | --- | --- |
| 64 | 93 | 4 |
| 65 | 24 | 3 |
| 66 | 32 | 3 |
| 67 | 48 | 2 |
| 68 | 41 | 2 |
| 69 | 50 | 5 |
| 70 | 85% at 0.3 µM | 35% at 0.03 µM |
| 71 | 71 | 3 |
| 72 | 24 | 3 |
| 73 | 16 | 3 |
| 74 | 12 | 10 |
| 81 | 62 | 1 |
| 82 | 30 | 8 |
| 83 | 64 | 1 |
| 84 | 63 | 2 |
| 85 | 46 | 2 |
| 86 | 68 | 2 |
| 87 | 18 | 2 |
| 91 | 49 | 1 |
| 92 | 14 | 2 |
| 93 | 95 | 3 |
| 100 | NT | NT |
| 101 | 22% at 0.3 µM | 70% at 0.03 µM |
| 102 | 12 | 2 |
| 103 | 13 | 2 |
| 104 | 14 | 1 |
| 105 | 32 | 1 |
| 106 | 41% at 0.3 µM | 26% at 0.03 µM |
| 107 | 10 | 1 |
| 108 | 27 | 1 |
| 109 | 158 | 5 |
| 110 | 15 | 1 |
| 111 | 13 | 3 |
| 112 | 24 | 2 |
| 113 | 84 | 1 |
| 114 | 37 | 2 |
| 115 | 22 | 1 |
| 116 | 13 | 2 |
| 117 | 50 | 2 |
| 118 | 22 | 1 |
| 119 | 41 | 1 |
| 120 | 14 | 7 |
| 121 | 11 | 2 |
| 122 | 53% at 0.3 µM | 55.5% at 0.03 µM |
| 123 | 80 | 1 |
| 125 | 29% at 0.3 µM | 54% at 0.03 µM |
| 126 | 52 | 4 |
| 127 | 1 | 2 |
| 128 | 47 | 8 |
| 129 | 4 | 1 |
| 130 | 15 | 1 |
| 131 | 49 | 1 |
| 132 | 18 | 1 |
| 133 | 15 | 1 |
| 134 | 36 | 2 |
| 135 | 3 | 3 |
| 136 | 9 | 1 |
| 137 | 20 | 1 |
| 139 | 9% at 0.3 µM | 49.5% at 0.03 µM |
| 140 | 50 | 2 |
| 141 | 33 | 2 |
| 142 | 133 | 23 |
| 143 | 72% at 0.3 µM | 27% at 0.03 µM |
| 144 | NT | NT |

*NT indicates that the compound was not testes.

Formulation Example 1

Solid, Oral Dosage Form—Prophetic Example

As a specific embodiment of an oral composition, 100 mg of the Compound #6, prepared as in Example 6 or Compound #12, prepared as in Example 12 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

We claim:

1. A compound of formula (I)

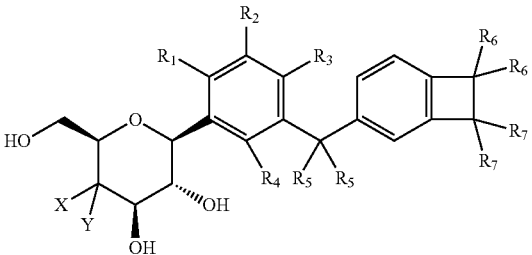

(I)

wherein

X is hydrogen and Y is selected from the group consisting of fluoro and (S)—OH; alternatively, X is fluoro and Y is fluoro;

$R^1$ is selected from the group consisting of hydrogen, halogen, —OH, $C_{1-4}$alkyl, fluorinated $C_{1-4}$alkyl, $C_{1-4}$alkoxy, fluorinated $C_{1-2}$alkoxy, —O-cylopropyl, —O-phenyl and —O-benzyl;

$R^2$ is selected from the group consisting of hydrogen, halogen and $C_{1-4}$alkyl;

$R^3$ is selected from the group consisting of hydrogen, halogen, $C_{1-4}$alkyl, $C_{1-4}$alkoxy, cyano, $NR^A R^B$, and $C_{3-5}$ cycloalkyl, wherein $R^A$ and $R^B$ are each independently selected from the group consisting of hydrogen, methyl and ethyl;

$R^4$ is selected from the group consisting of hydrogen and $C_{1-4}$alkyl, the two $R^5$ groups are the same and are selected from the group consisting of hydrogen and fluoro; alternatively, the two $R^5$ groups are taken together with the carbon atom to which they are bound to form carbonyl;

each $R^6$ is hydrogen;

each $R^7$ is hydrogen;

or an isotopologue or pharmaceutically acceptable salt thereof.

2. A compound as in claim 1, wherein $R^1$ is selected from the group consisting of hydrogen, halogen, —OH, $C_{1-2}$alkyl, fluorinated $C_{1-2}$ alkyl, $C_{1-4}$alkoxy, fluorinated $C_{1-2}$ alkoxy, —O-cylopropyl and —O-benzyl;

$R^3$ is selected from the group consisting of hydrogen, halogen, $C_{1-4}$alkyl, $C_{1-4}$alkoxy, cyano, $NR^A R^B$, and $C_{3-4}$cycloalkyl, wherein $R^A$ and $R^B$ are each independently selected from the group consisting of hydrogen, methyl and ethyl;

$R^4$ is selected from the group consisting of hydrogen and $C_{1-4}$alkyl, or an isotopologue or pharmaceutically acceptable salt thereof.

3. A compound as in claim 2, wherein
$R^1$ is selected from the group consisting of hydrogen, halogen, —OH, $C_{1-2}$alkoxy, fluorinated $C_{1-2}$ alkoxy, —O-cyclopropyl and —O-benzyl;
$R^2$ is selected from the group consisting of hydrogen, halogen and $C_{1-2}$alkyl,
$R^3$ is selected from the group consisting of hydrogen, halogen, $C_{1-2}$ alkyl, $C_{1-2}$ alkoxy, cyclopropyl, cyano, and $NR^AR^B$; wherein $R^A$ and $R^B$ are each independently selected from the group consisting of hydrogen and methyl;
$R^4$ is selected from the group consisting of hydrogen and $C_{1-2}$alkyl,
or an isotopologue or pharmaceutically acceptable salt thereof.

4. A compound as in claim 3, wherein
$R^1$ is selected from the group consisting of hydrogen, fluoro, —OH, methoxy, ethoxy, fluoromethoxy, difluoromethoxy, trifluoromethoxy, —O-cyclopropyl and —O-benzyl;
$R^2$ is selected from the group consisting of hydrogen, bromo, iodo and methyl;
$R^3$ is selected from the group consisting of hydrogen, fluoro, chloro, methyl, ethyl, methoxy, cyano, dimethylamino and cyclopropyl;
$R^4$ is selected from the group consisting of hydrogen and methyl;
or an isotopologue or pharmaceutically acceptable salt thereof.

5. A compound as in claim 3, wherein
$R^1$ is selected from the group consisting of hydrogen, fluoro, —OH, methoxy, —OCD$_3$, ethoxy, fluoromethoxy, difluoromethoxy, trifluoromethoxy, —O-cyclopropyl and —O-benzyl;
$R^2$ is selected from the group consisting of hydrogen, deuterium, bromo, iodo and methyl;
$R^3$ is selected from the group consisting of hydrogen, fluoro, chloro, methyl, ethyl, methoxy, cyano, dimethylamino and cyclopropyl;
$R^4$ is selected from the group consisting of hydrogen and methyl;
the two $R^5$ groups are the same and are selected from the group consisting of hydrogen, deuterium and fluoro; alternatively, the two $R^5$ groups are taken together with the carbon atom to which they are bound to form carbonyl;
the two $R^6$ groups are the same and are selected from the group consisting of hydrogen and deuterium;
the two $R^7$ groups are the same and are selected from the group consisting of hydrogen and deuterium;
or a pharmaceutically acceptable salt thereof.

6. A compound as in claim 5, wherein
$R^1$ is selected from the group consisting of hydrogen, fluoro, —OH, methoxy, —OCD$_3$, ethoxy, fluoromethoxy and —O-cyclopropyl,
$R^2$ is selected from the group consisting of hydrogen, deuterium, iodo and methyl;
$R^4$ is hydrogen;
the two $R^5$ groups are the same and are selected from the group consisting of hydrogen, deuterium and fluoro;
or a pharmaceutically acceptable salt thereof.

7. A compound as in claim 5, wherein
$R^1$ is selected from the group consisting of hydrogen, fluoro, —OH, methoxy, —OCD$_3$, ethoxy, fluoromethoxy and —O-cyclopropyl,
$R^2$ is selected from the group consisting of hydrogen, deuterium, iodo and methyl;
$R^3$ is selected from the group consisting of hydrogen, chloro, methyl, ethyl, methoxy, dimethylamino and cyclopropyl;
$R^4$ is hydrogen;
the two $R^5$ groups are the same and are selected from the group consisting of hydrogen, deuterium and fluoro;
or a pharmaceutically acceptable salt thereof.

8. A compound as in claim 5, wherein
$R^1$ is selected from the group consisting of hydrogen, fluoro, —OH, methoxy, —OCD$_3$, ethoxy and —O-cyclopropyl,
$R^2$ is selected from the group consisting of hydrogen, deuterium and iodo;
$R^3$ is selected from the group consisting of chloro, methyl, ethyl, methoxy, dimethylamino and cyclopropyl;
$R^4$ is hydrogen;
the two $R^5$ groups are the same and are selected from the group consisting of hydrogen and deuterium;
or a pharmaceutically acceptable salt thereof.

9. A compound as in claim 4, wherein
X is hydrogen and Y is (S)—OH;
$R^1$ is selected from the group consisting of hydrogen, —OH and methoxy;
$R^2$ is hydrogen;
$R^3$ is selected from the group consisting of chloro, methyl, ethyl and methoxy;
$R^4$ is hydrogen;
each $R^5$ is hydrogen;
or an isotopologue or pharmaceutically acceptable salt thereof.

10. A compound as in claim 4, selected from the group consisting of
(2S,3R,4R,5S,6R)-2-(3-((1,2-dihydrocyclobutabenzen-4-yl)methyl)-4-methylphenyl)-6-(hydroxymethyl)-tetrahydro-2H-pyran-3,4,5-triol,
(2S,3R,4R,5S,6R)-2-(4-chloro-3-((1,2-dihydrocyclobutabenzen-4-yl)methyl)phenyl)-6-(hydroxymethyl)-tetrahydro-2H-pyran-3,4,5-triol;
(2S,3R,4R,5S,6R)-2-(3-((1,2-dihydrocyclobutabenzen-4-yl)methyl)-4-methoxyphenyl)-6-(hydroxymethyl)-tetrahydro-2H-pyran-3,4,5-triol;
(2S,3R,4R,5S,6R)-2-(5-((1,2-dihydrocyclobutabenzen-4-yl)methyl)-2-hydroxy-4-methylphenyl)-6-(hydroxymethyl)-tetrahydro-2H-pyran-3,4,5-triol;
2S,3R,4R,5S,6R)-2-(4-chloro-5-((1,2-dihydrocyclobutabenzen-4-yl)methyl)-2-methoxyphenyl)-6-(hydroxymethyl)-tetrahydro-2H-pyran-3,4,5-triol;
(2S,3R,4R,5S,6R)-2-(5-((1,2-dihydrocyclobutabenzen-4-yl)methyl)-2,4-dimethoxyphenyl)-6-(hydroxymethyl)-tetrahydro-2H-pyran-3,4,5-triol;
(2S,3R,4R,5S,6R)-2-(5-{bicyclo[4.2.0]octa-1(6),2,4-trien-3-ylmethyl}-4-ethyl-2-hydroxyphenyl)-6-(hydroxymethyl)oxane-3,4,5-triol;
(2S,3R,4R,5S,6R)-2-(5-((1,2-dihydrocyclobutabenzen-4-yl)methyl)-4-ethyl-2-methoxyphenyl)-6-(hydroxymethyl)-tetrahydro-2H-pyran-3,4,5-triol;
and isotopologues and pharmaceutically acceptable salts thereof.

11. A pharmaceutical composition comprising a pharmaceutically acceptable carrier and a compound of claim 1.

12. A pharmaceutical composition made by mixing a compound of claim 1 and a pharmaceutically acceptable carrier.

13. A process for making a pharmaceutical composition comprising mixing a compound of claim 1 and a pharmaceutically acceptable carrier.

14. A method of treating a disorder selected from the group consisting of impaired glucose tolerance (IGT), impaired fasting glucose (IFT), gestational diabetes, Type I diabetes mellitus, and Type II diabetes mellitus, comprising administering to a subject in need thereof a therapeutically effective amount of the compound of claim 1.

* * * * *